(12) United States Patent
Gin et al.

(10) Patent No.: US 8,466,142 B2
(45) Date of Patent: Jun. 18, 2013

(54) CEPHALOTAXUS ESTERS, METHODS OF SYNTHESIS, AND USES THEREOF

(75) Inventors: David Gin, Pelham, NY (US); Jeremy Wilmot, Indianapolis, IN (US); Hakim Djaballah, Scarsdale, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 141 days.

(21) Appl. No.: 12/920,227

(22) PCT Filed: Mar. 3, 2009

(86) PCT No.: PCT/US2009/035868
§ 371 (c)(1),
(2), (4) Date: Dec. 8, 2010

(87) PCT Pub. No.: WO2009/148654
PCT Pub. Date: Dec. 10, 2009

(65) Prior Publication Data
US 2011/0071097 A1    Mar. 24, 2011

Related U.S. Application Data

(60) Provisional application No. 61/033,187, filed on Mar. 3, 2008.

(51) Int. Cl.
*A61K 31/55*    (2006.01)
*C07D 223/00*   (2006.01)
*C07D 491/00*   (2006.01)

(52) U.S. Cl.
USPC ................ 514/214.01; 540/543; 540/581

(58) Field of Classification Search
USPC ............... 536/17.4; 514/214.01; 540/543, 540/581
See application file for complete search history.

(56) References Cited

U.S. PATENT DOCUMENTS

| | | | |
|---|---|---|---|
| 4,152,214 A | 5/1979 | Delfel et al. | |
| 4,152,333 A | 5/1979 | Mikolajczak et al. | |
| 4,203,996 A | 5/1980 | Mikolajczak et al. | |
| 4,206,221 A | 6/1980 | Miller et al. | |
| 6,579,869 B1 | 6/2003 | Robin et al. | |
| 6,613,900 B2 | 9/2003 | Robin et al. | |
| 6,734,178 B2 | 5/2004 | Brown | |
| 6,831,180 B1 | 12/2004 | Robin et al. | |
| 7,169,774 B2 | 1/2007 | Robin et al. | |
| 7,285,546 B2 | 10/2007 | Robin et al. | |
| 2006/0234999 A1 | 10/2006 | Robin et al. | |

FOREIGN PATENT DOCUMENTS

| | | |
|---|---|---|
| JP | 57 064695 A | 4/1982 |
| WO | WO 99/48894 A1 | 9/1999 |
| WO | WO 02/32904 A1 | 4/2002 |
| WO | WO 02/074776 A2 | 9/2002 |
| WO | WO 2004/009030 A2 | 1/2004 |
| WO | WO 2004/009092 A1 | 1/2004 |

OTHER PUBLICATIONS

International Search Report and Written Opinion for PCT/US2009/035868 mailed Jan. 5, 2010.
International Preliminary Report on Patentability for PCT/US2009/035868 mailed Sep. 16, 2010.
[No Author Listed] Cancer multidrug resistance. Nat Biotechnol. Oct. 2000;18 Suppl:IT18-20.
Abraham et al., Single crystal x-ray structures of chemotherapeutic agents II, The structure of Cephalotaxine methiodide. Tetrahedron Lett. 1969:4085-6.
Ali et al., Efficient enantioselective syntheses of carbocyclic nucleoside and prostaglandin synthons. Tetrahedron Lett. 1990;31:1509-12.
Antczak et al., High-throughput identification of inhibitors of human mitochondrial peptide deformylase. J Biomol Screen. Jun. 2007;12(4):521-35. Epub Apr. 13, 2007.
Arora et al., Crystal and Molecular Structure of Cephalotaxine p-bromobenzoate. J Org Chem. May 3, 1974;39(9):1269-71.
Arora et al., Crystal and Molecular Structure of Cephalotaxine. J Org Chem. Feb. 6, 1976;41(3):551-4.
Auerbach et al., Synthesis of the diacid sidechain of deoxyharringtonine. Tetrahedron Lett. 1973:4561-4.
Auerbach et al., The Total Synthesis of Cephalotaxine. J Am Chem Soc. Oct. 4, 1972;94(20):7172-3.
Baraznenok et al., 3-Trifloxy-3-triflouromethylpropeniminium Triflate: Reaction with Aromatic Amines—An Efficient Synthesis of 2-Trifluoromethylquinolines. Eur J Org Chem. 1999:937-41.
Baraznenok et al., Efficient Synthesis of (E)-3-Trifluoromethy1-3-Aryl(Hetaryl)acroleins. Tetrahedron. 1998;54:119-28.
Beall et al., An Approach to the Cephalotaxine Ring Skeleton Using an Ammonium Ylide/Stevens [1,2]-Rearrangement. Tetrahedron Lett. 1998;39:4159-62.
Benderra et al., Characterization of H+-ATPase-dependent activity of multidrug resistance—associated protein in homoharringtonine-resistant, human leukemic K562 cells. Leukemia. Oct. 1998;12(10):1539-44.
Berge et al., Pharmaceutical Salts. J Pharm Sci. Jan. 1977;66(1):1-19.
Berhal et al., Stereoselective synthesis of enantiopure analogues of (−)-cephalotaxine. Tetrahedron: Asymmetry. 2010;21:325-332.
Berhal et al., Synthesis of Optically Active Monoacid Side-Chains of *Cephalotaxus* Alkaloids. Eur J Org Chem. 2009:437-43.

(Continued)

*Primary Examiner* — Elli Peselev
(74) *Attorney, Agent, or Firm* — Wolf, Greenfield & Sacks, P.C.; C. Hunter Baker

(57) ABSTRACT

The present invention provides novel cephalotaxus esters, syntheses thereof, and intermediates thereto. The invention also provides pharmaceutical compositions comprising a compound of the present invention and methods of using said compounds or compositions in the treatment of proliferative diseases (e.g., benign neoplasm, cancer, inflammatory disease, autoimmune disease, diabetic retinopathy) and infectious disease. The invention further provides methods of using said compounds or compositions in the treatment of multidrug resistant cancer.

14 Claims, 6 Drawing Sheets

OTHER PUBLICATIONS

Blaser et al., A Selective α-L-Fucosidase Inhibitor Based on an Aminocyclopentane Framework. Helv Chim Acta. 1999;82:760-8.

Bocar et al., New alkaloids from *Cephalotaxus fortunei*. J Nat Prod. Jan. 2003;66(1):152-4.

Booker-Milburn et al., Formal intramolecular [5+2] photocycloaddition reactions of maleimides: a novel approach to the CDE ring skeleton of (−)-cephalotaxine. Org Lett. Sep. 20, 2001;3(19):3005-8.

Brumfield et al., Intramolecular photoarylations of haloarylethyl-β- and -α- enaminoketones. A correction and further results. Tetrahedron Lett. 1983;24(50):5567-70.

Burkholder et al., Total Synthesis of dl-Cephalotaxine. The First Example of an Intramolecular 4+2 Cycloaddition When the Dienophile Has Been Delivered from the Face Opposite to the Tethering Moiety. J Am Chem Soc. 1988;110:2341-42.

Burkholder et al., Total Synthesis of the *Cephalotaxus* Alkaloids dl-Cephalotaxine, dl-11-Hydroxycephalotaxine. J Am Chem Soc. 1990;112:9601-13.

Cenac et al., Ring Opening of Lactones and Anhydrides Induced by $[Cp_2ZrHCl]_n$. J Org Chem. Jan. 26, 1996;61(2):796-798.

Chatterjee et al., A general model for selectivity in olefin cross metathesis. J Am Chem Soc. Sep. 17, 2003;125(37):11360-70.

Chen et al., Inhibitory effects of omacetaxine on leukemic stem cells and BCR-ABL-induced chronic myeloid leukemia and acute lymphoblastic leukemia in mice. Leukemia. Aug. 2009;23(8):1446-54. Epub Mar. 26, 2009.

Chu et al., Antiviral activity of cyclopentenyl nucleosides against orthopox viruses (Smallpox, monkeypox and cowpox). Bioorg Med Chem Lett. Jan. 6, 2003;13(1):9-12.

Clarke et al., A one-step procedure for the monoacylation of symmetrical 1,2-diols. J Org Chem. Jul. 26, 2002;67(15):5226-31.

Clarke et al., Direct one step mono-functionisation of symmetrical 1,2-diolas. Tetrahedron Lett. 2000;41:2687-90.

Clarke et al., Mechanistic insight into the lanthanide(III) salt catalysed monoacylation of symmetrical diols from structural models. Chem Commun (Camb). Oct. 21, 2003;(20):2588-9.

Coldham et al., Intramolecular dipolar cycloaddition reactions of azomethine ylides. Chem Rev. Jul. 2005;105(7):2765-809.

Conway et al., Vincristine- and cisplatin-induced apoptosis in human retinoblastoma. Potentiation by sodium butyrate. Eur J Cancer. Oct. 1998;34(11):1741-8.

Craig et al., Synthesis of 2,5-Disubstituted 3-(Phenylsulfonyl)pyrrolidines via 5-Endo-Trig Cyclisation Reactions. Synlett. 1997:1423-5.

Dauksas et al., Relative reactivity of the aromatic ring in benzo-1,3-dioxole, its cyclohomologues and veratrole. Heterocycles. 1981;15:1395-404.

Dixon, The role of sigma electrons in aromatic substitution. Tetrahedron Lett. 1968:189-92.

Eckelbarger et al., Strain-release rearrangement of N-vinyl-2-arylaziridines. Total synthesis of the anti-leukemia alkaloid (−)-deoxyharringtonine. J Am Chem Soc. Aug. 16, 2006;128(32):10370-1.

Eckelbarger et al., Synthesis of antiproliferative *Cephalotaxus* esters and their evaluation against several human hematopoietic and solid tumor cell lines: uncovering differential susceptibilities to multidrug resistance. Chemistry. 2008;14(14):4293-306.

Effenberger et al., The First Unequivocal Evidence of the Reacting Electrophile in Aromatic Acylation Reactions. J Am Chem Soc. 1996;118:12572-9.

El Bialy et al., Efficient Formal Total Synthesis of (−)-Cephalotaxine Using Reductive Intramolecular Heck Reaction and Optical Resolution (Part II). Med Chem Res. 2002;11(5):293-300.

El Bialy et al., Enantioselective Synthesis of α-Alkylmalates as the Pharmacophoric Group of Several Natural Alkaloids and Glycosides. Eur J Org Chem. 2005:2965-72.

Epperson et al., Enantiospecific synthesis of the bridged pyrrolizidine core of asparagamine A: dipolar cycloadditions of azomethine ylides derived from the sulfonylation of vinylogous amides. Angew Chem Int Ed Engl. May 17, 2002;41(10):1778-80.

Esmieu et al., A formal synthesis of (−)-cephalotaxine. Org Lett. Jul. 17, 2008;10(14):3045-8. Epub Jun. 13, 2008.

Ess et al., Distortion/interaction energy control of 1,3-dipolar cycloaddition reactivity. J Am Chem Soc. Sep. 5, 2007;129(35):10646-7. Epub Aug. 9, 2007.

Figeys et al., A kinetic investigation of the thermal rearrangement of N-pyridino-2-vinyl-aziridines. Tetrahedron Lett. 1981;22:637-40.

Figeys et al., Rearrangements of N-heteroaromatic-2-vinyl-aziridines. Synthesis of isothiazolo-, pyrido- and thieno-azepines. Tetrahedron Lett. 1980;21:2995-8.

Fresno et al., Inhibition of translation in eukaryotic systems by harringtonine. Eur J Biochem. Jan. 1977;72(2):323-30.

Gilmore et al., Discovery and x-ray crystal structure of a new host compound: 1,2,4-tris (phenylthio) [1]benzothieno [3,2-c] pyridine. Tetrahedron Lett. 1984;25(38):4303-6.

Gitterman et al., Biosynthesis of the *Cephalotaxus* Alkaloids. Investigations of the Biosynthesis of Deoxyharringtonine, Isoharringtonine, and Harringtonine. J Am Chem Soc. 1980;102(6):2074-81.

Gothelf et al., Asymmetric 1,3-Dipolar Cycloaddition Reactions. Chem Rev. Apr. 2, 1998;98(2):863-909.

Gottesman et al., Multidrug resistance in cancer: role of ATP-dependent transporters. Nat Rev Cancer. Jan. 2002;2(1):48-58.

Grubbs, Olefin metathesis. Tetrahedron. 2004;60:7117-40.

Hameed et al., A second generation formal synthesis of (−)-cephalotaxine. Org Chem. Oct. 17, 2008;73(20):8045-8. Epub Sep. 12, 2008.

Harada et al., The Catalytic Friedel-Crafts Acylation Reaction and the Catalytic Beckmann Rearrangement Promoted by a Gallium (III) or an Antimony (V) Cationic Species. Synthesis. 1991:1216-20.

Hassner et al., cycloaddition of vinyl aziridines with unsaturated substrates. A novel rearrangement of an unsaturated nitro compound. Tetrahedron Lett. 1981;22:3691-4.

Hiranuma et al., Studies in *Cephalotaxus* Alkaloids. Stereospecific Total Synthesis of Homoharringtonine. J Org Chem. 1983;48:5321-6.

Hiranuma et al., Synthesis of homoharringtonine and its derivative by partial esterification of cephalotaxine. Tetrahedron Lett. 1982;23:3431-34.

Huang et al., Asymmetric synthesis of (S)-homocitric acid lactone. Tetrahedron: Asymmetry. 2005;16:3367-70.

Huang et al., Chapter 3. *Cephalotaxus* alkaloids. In: The Alkaloids. Academic Press, Inc. 1984;23:157-226.

Huang, Harringtonine, an inhibitor of initiation of protein biosynthesis. Mol Pharmacol. Sep. 1975;11(5):511-9.

Hudlicky et al., Chapter 1. Divinylcyclopropane-cycloheptadiene Rearrangement. In: Org React. Paquette et al., eds. John Wiley & Sons, Inc. New York, New York. 1992;41:1-133.

Ikeda et al., A Formal Total Synthesis of (−)-Cephalotaxine. Chem Pharm Bull (Tokyo). Jul. 1999;47(7):983-7.

Ikeda et al., Synthetic Studies on *Cephalotaxus* Alkaloids. A Synthesis of (±)-Cephalotaxine. Chem Pharm Bull. 1993;41:276-81.

Inanaga et al., A Rapid Esterification by Means of Mixed Anhydride and Its Application to Large-ring Lactonization. Bull Chem Soc Jpn. 1979;52:1989-93.

Ishibashi et al., Total Synthesis of (±)-Cephalotaxine. J Chem Soc, Chem Commun. 1990:1436-7.

Isono et al., Total Synthesis of (−)-Cephalotaxine. J Org Chem. 1995;60:115-19.

Jin et al., Palladium[0]-Mediated Aminospirocyclization of Tertiary Allylic Sulfones. Stereospecific Construction of the Azabicyclic Ring System of Cephalotaxine. Tetrahedron Lett. 1996;37(30):5253-6.

Jin et al., Practical synthesis of D- and L-2-cyclopentenone and their utility for the synthesis of carbocyclic antiviral nucleosides against orthopox viruses (smallpox, monkeypox, and cowpox virus). J Org Chem. Nov. 14, 2003;68(23):9012-8.

Kantarjian et al., Homoharringtonine: history, current research, and future direction. Cancer. Sep. 15, 2001;92(6):1591-605.

Keller et al., Enantioselective Synthesis of the Ester Side Chain of Homoharringtonine. Eur J Org Chem. 2003:2488-97.

Kelly et al., Preparation of Harringtonine from Cephalotaxine. J Org Chem. 1979;44:63-7.

Kolb et al., The growing impact of click chemistry on drug discovery. Drug Discov Today. Dec. 15, 2003;8(24):1128-37.

Koseki et al., A formal total synthesis of (±)-cephalotaxine using sequential N-acyliminium ion reactions. Org Lett. Mar. 21, 2002;4(6):885-8.

Kuehne et al., Total Synthesis of (±)-Cephalotaxine and (±)-8-Oxocephalotaxine. J Org Chem. 1988;53:3439-50.

Kunzer et al., Reductive desulfonylation of phenyl sulfones by samarium(II) iodide-hexamethylphosphoric triamide. Tetrahedron Lett. 1991;32:1949-52.

Legha et al., Phase I clinical investigation of homoharringtonine. Cancer Treat Rep. Sep. 1984;68(9):1085-91.

Legros et al., BCR-ABL(T315I) transcript disappearance in an imatinib-resistant CML patient treated with homoharringtonine: a new therapeutic challenge? Leukemia. Oct. 2007;21(10):2204-6. Epub May 31, 2007.

Li et al., A novel and efficient total synthesis of cephalotaxine. Org Lett. Aug. 7, 2003;5(16):2931-4.

Li et al., A novel formal total synthesis of cephalotaxine. J Org Chem. Apr. 15, 2005;70(8):3277-80.

Lin et al., A Cephalotaxine Synthesis Founded on a Mechanistically Interesting, Quasi-biomimetic Strategy. J Am Chem Soc. 1994;116:9791-92.

Lin et al., Two Interrelated Strategies for Cephalotaxine Synthesis. J Org Chem. Oct. 18, 1996;61(21):7335-7347.

Lindstrom et al., A Highly Stereoseletive Aza-[3,3]-Claisen Rearrangement of Vinylaziridines as a Novel Entry to Seven-Membered Lactams. J Am Chem Soc. 1997;119:8385-6.

Liu et al., Convergency and divergency as strategic elements in total synthesis: the total synthesis of (−)-drupacine and the formal total synthesis of (+/−)-cephalotaxine, (−)-cephalotaxine, and (+)-cephalotaxine. J Org Chem. Sep. 14, 2007;72(19):7352-8. Epub Aug. 18, 2007.

Lwowski et al., Carbethoxynitrene. J Am Chem Soc. 1963;85:1200-2.

Mai et al., Induction of apoptosis by homoharringtonine in G1 phase human chronic myeloid leukemic cells. Chin Med J (Engl). Mar. 20, 2005;118(6):487-92.

Miah et al., Chapter 2. *Cephalotaxus* Alkaloids. In: The Alkaloids. Academic Press. 1998;51:199-269.

Mikolajczak et al., Deoxyharringtonine, a new antitumor alkaloid from *Cephalotaxus*: Structure and synthetic studies. Tetrahedron. 1972;28:1995-2001.

Mikolajczak et al., Synthesis of Deoxyharringtonine. Tetrahedron Lett. 1974;(3):283-6.

Mikolajczak et al., Synthesis of Harringtonine, a *Cephalotaxus* Antitumor Alkaloid. J Org Chem. 1978;43(25):4762-5.

Morita et al., Cephalezomines A-F, Potent Cytotoxic Alkaloids from *Cephalotaxus harringtonia* var. nana. Tetrahedron. 2000;56:2929-34.

Moses et al., The growing applications of click chemistry. Chem Soc Rev. Aug. 2007;36(8):1249-62. Epub May 3, 2007.

Najera et al., Azomethine Ylides in Organic Synthesis. Curr Org Chem. 2003;7:1105-50.

Padwa et al., Cesium fluoride induced desilylation reaction of immonium salts derived from vinylogous amides. Tetrahedron Lett. 1984;24(40):4303-6.

Paudler et al., The Alkaloids of *Cephalotaxus drupacea* and *Cephalotaxus fortunei*. J Org Chem. 1963;28:2194-7.

Pearson et al., Cycloadditions of Nonstabilized 2-Azaallyllithiums (2-Azaallyl Anions) and Azomethine Ylides with Alkenes: [3+2] Approaches to Pyrrolidines and Application to Alkaloid Total Synthesis. Synlett. 2003:903-21.

Pilcher et al., Utilization of Tetrabutylammonium (Triphenylsilyl) difluorosilicate as a Fluoride Source for Nucleophilic Fluorination. J Am Chem Soc. 1995;117:5166-7.

Planas et al., Stereoselective synthesis of (−)-cephalotaxine and C-7 alkylated analogues. J Org Chem. Apr. 30, 2004;69(9):3087-92.

Pommelet et al., Synthesis and thermal isomerization of cis N-methyl-2,3-divinyl aziridine. Tetrahedron Lett. 1974;(44):3897-8.

Powell et al., Antitumor alkaloids for *Cephalotaxus harringtonia*: structure and activity. J Pharm Sci. Aug. 1972;61(8):1227-30.

Powell et al., Structure of Cephalotaxine and related alkaloids. Tetrahedron Lett. 1969;(46):4081-4.

Powell et al., Structures of harringtonine, isoharringtonine, and homoharringtonine. Tetrahedron Lett. Mar. 1970;11;(11):815-8.

Powell, Structures of homoerythrina alkaloids from *Cephalotaxus harringtonia*. Phytochemistry. 1972;11:1467-72.

Quintás-Cardama et al., Homoharringtonine, omacetaxine mepesuccinate, and chronic myeloid leukemia circa 2009. Cancer. Dec. 1, 2009;115(23):5382-93.

Robin et al., The First Semi-synthesis of Enantiopure Homoharringtonine via Anhydrohomoharringtonine from a Preformed Chiral Acyl Moiety. Tetrahedron Lett. 1999;40:2931-4.

Salomon et al., Ruthenium (II) Catalysis in Redox Fragmentation of Allyl Ethers. Am Chem Soc. 1977;99(13):4372-9.

Scheiner, Rearrangements of a 2-Vinylaziridine. J Org Chem. 1967;32:2628-30.

Schwartz et al., Hydrozirconation: A New Transition Metal Reagent for Organic Synthesis. Angew Chem Int Ed. 1976;15:333-40.

Seebach et al., α-Alkylation of α-heterosubstituted carboxylic acids without racemization. Tetrahedron. 1984;40(8):1313-24.

Seigel et al., Human embryonic and neuronal stem cell markers in 0. Mol Vis. Jun. 8, 2007;13:823-32.

Semmelhack et al., Total synthesis of the *Cephalotaxus* alkaloids. A problem in nucleophilic aromatic substitution. J Am Chem Soc. Apr. 30, 1975;97(9):2507-16.

Shum et al., A high density assay format for the detection of novel cytotoxic agents in large chemical libraries. J Enzyme Inhib Med Chem. Dec. 2008;23(6):931-45.

Stewart et al., Increased efficiency in cross-metathesis reactions of sterically hindered olefins. Org Lett. Feb. 7, 2008;10(3):441-4. Epub Jan. 5, 2008.

Stogryn et al., Valence Tautomerism of Vinyl-Substituted Three-Membered Heterocycles. II. Conversion of N-Ethyl-2,3-divinylaziridine to N-ethyl-4,5-dihydroazepine. J Org Chem. 1965;30:88-91.

Suga et al., Electroauxiliary-assisted sequential introduction of two carbon nucleophiles on the same alpha-carbon of nitrogen: application to the synthesis of spiro compounds. J Am Chem Soc. Dec. 18, 2002;124(50):14824-5.

Sun et at, Highly efficient formal synthesis of cephalotaxine, using the Stevens rearrangement—acid lactonization sequence as a key transformation. J Org Chem. Mar. 6, 2009;74(5):2213-6.

Takano et al., Drupangtonine, a novel antileukemic alkaloid from *Cephalotaxus harringtonia* var. drupacea. Bioorg Med Chem Lett. 1996;6(14):1689-90.

Takano et al., New *Cephalotaxus* Alkaloids from *Cephalotaxus harringtonia* var. drupacea. J Nat Prod. 1996;59:965-7.

Tanida et al., Kinetics and Mechanism of Aziridine Synthesis from Ketoxime with Lithium Aluminum Hydride. Bull Chem Soc Jpn. 1973;46(3):934-8.

Taniguchi et al., 7-endo selective aryl radical cyclization onto enamides leading to 3-benzazepines: concise construction of a cephalotaxine skeleton. J Org Chem. Mar. 4, 2005;70(5):1922-5.

Tietze et al., A Domino Spirocyclization to Form Lactams. Eur J Org Chem 2001:4353-6.

Tietze et al., Efficient synthesis of cephalotaxine- and deoxyharringtonine analogues by a trimethylaluminium-mediated domino reaction. Tetrahedron. 2007;63:6437-45.

Tietze et al., Efficient Synthesis of Six-Membered Ring D Analogues of the Pentacyclic Alkaloid Cephalotaxine by Two Palladium-Catalyzed Reactions. Eur J Org Chem. 2000:2433-44.

Tietze et al., Enantioselective Highly Efficient Synthesis of (−)-Cephalotaxine Using Two Palladium-Catalyzed Transformations. J Am Chem Soc. 1999;121:10264-9.

Tietze et al., Highly Efficient Synthesis of Cephalotaxine by Two Palladium-Catalyzed Cyclizations. Angew Chem Int Ed. 1997;36:1124-5.

Tiner-Harding et al., Intramolecular Photoarylations of N-(Haloaryl)ethyl β-Enaminoes. J Org Chem. 1982;47:482-5.

Ullrich et al., Electron-Transfer-Initiated Photospirocyclization Reaction of β-Enaminone-Derived Allyliminium Salts. J Org Chem. 1984;49:220-8.

Vedejs et al., Methylides from Trimethylsilylmethylsulfonium, -ammonium, -immonium, and -phosphonium Salts. J Am Chem Soc. 1979:101:6452-4.

Vedejs et al., Ylides by the Desilylation of α-Silyl Onium Salts. Chem Rev. 1986;86:941-55.

Viallon et al., Synthesis of Tetrahydroazocino- and Dihydroazepino -1,2-Benzoquinones via Amino-Claisen Rearrangement of 4-(2-Vinyl-Azetidino and Aziridino)-1,2-Benzoquinones. Tetrahedron Lett. 1995;36:4787-90.

Wang et al., [Studies on the alkaloids of *Cephalotaxus*. IX. Semi-synthesis of cephalotaxine esters and their anti-leukemic activity]. Yao Xue Xue Bao. 1992;27(3):178-84. Chinese.

Wang et al., [Studies on the alkaloids of *Cephalotaxus*. VII. Structures and semi-synthesis of two anticancer cephalotaxine esters]. Yao Xue Xue Bao. 1992;27(3):173-7. Chinese.

Worden et al., Towards a total synthesis of (−)-cephalotaxine: contruction of the BCDE-tetracyclic core. Tetrahedron Lett. 2002;43:6011-4.

Yadav et al., Formal Total Synthesis of Ovalcin by Carbohydrate Approach. Synlett. 2007;(6):992-4.

Yasuda et al., A novel and stereoselective synthesis of (±)-Cephalotaxine and its analogue. Tetrahedron Lett. 1986;27(18):2023-26.

Yasuda et al., A total synthesis of (±)-Cephalotaxinamide. Chem Pharm Bull. 1988;36(10):4229-31.

Yu et al., The Combination of Diallylboration and Ring-Closing Metathesis in the Synthesis of Spiro-β-Amino Alcohols and (±)-Cephalotaxine. Eur J Org Chem. 2008:5647-55.

Zhang et al., A facile total synthesis of hainanensine via an unusual rearrangement—annulation cascade. Org Lett. Apr. 16, 2010;12(8):1649-51.

Zhao et al., Application of the photocyclization reaction of 1,2-cyclopenta-fused pyridinium perchlorate to formal total syntheses of (−)-cephalotaxine. Tetrahedron. 2006;62:7266-73.

Zheng et al., Synthesis of fluorine-18 labeled fluoromethyl iodide, a synthetic precursor for fluoromethylation of radiopharmaceuticals. J Nucl Med. 1997;38:177P. Abstract No. 761.

Zora, A comparison of the Cope rearrangements of cis-1,2-divinylcyclopropane, cis-2,3-divinylaziridine, cis-2,3-divinyloxirane, cis-2,3-divinylphosphirane, and cis-2,3-divinylthiirane: a DFT study. J Org Chem. Jul. 22, 2005;70(15):6018-26.

Extended European Search Report for EP 09758817.2, dated Mar. 26, 2012.

Mikolajczak et al., Partial synthesis of harringtonine analogs. J Pharm Sci. Aug. 1974;63(8):1280-3.

Takano et al., Ester-type *Cephalotaxus* alkaloids from *Cephalotaxus harringtonia* var. drupacea. Phytochemistry. Feb. 1997;44(4):735-8.

Mikolajczak et al., Synthesis of cephalotaxine esters and correlation of their structures with antitumor activity. J Med Chem. Mar. 1977;20(3):328-32.

Paudler et al., The structures of some of the minor alkaloids of *Cephalotaxus fortunei*. J Org Chem. Jun. 1, 1973;38(71):2110-2.

Takano et al., Alkaloids from *Cephalotaxus harringtonia*. Phytochemistry. 1996;43(1):299-303.

CEPHALOTAXUS ESTERS, METHODS OF SYNTHESIS, AND USES THEREOF

CROSS REFERENCE TO RELATED APPLICATIONS

The present application is a national stage filing under 35 U.S.C. §371 of international PCT application, PCT/US2009/035868, filed Mar. 3, 2009, which claims priority under 35 U.S.C. §119(e) to U.S. provisional application, U.S. Ser. No. 61/033,187, filed Mar. 3, 2008, the contents of each of which are incorporated herein by reference.

GOVERNMENT SUPPORT

This invention was made with United States government support under grant GM67659 awarded by the National Institutes of Health—National Institute of General Medical Sciences, and a predoctoral fellowship awarded by the National Science Foundation. The United States government has certain rights in the invention.

FIELD OF THE INVENTION

The present invention relates to cephalotaxus esters, syntheses thereof, and intermediates thereto. The invention also provides pharmaceutical compositions comprising compounds of the present invention and methods of using said compounds or compositions in the treatment of proliferative diseases (e.g., benign neoplasm, cancer, inflammatory disease, autoimmune disease, diabetic retinopathy) and infectious disease.

BACKGROUND OF THE INVENTION

*Cephalotaxus harringtonia*, commonly known as the Japanese plum-yew, is a small evergreen shrub native to Eastern Asia. Alcoholic extracts of the powdered leaves and stems of *Cephalotaxus* genera yielded cephalotaxine as the most abundant alkaloid constituent (L. Huang and Z. Xue, *Alkaloids* 1984, 23, 157-226; W. W. Paudler, J. McKay and G. I. Kerley, *J. Org. Chem.* 1963, 28, 2194). While cephalotaxine accounts for approximately 50% of the mass of the crude alkaloid extract mixture, several minor constituents have also been identified. Among these are several rare C3-ester derivatives (K. L. Mikolajczak, C. R. Smith and R. G. Powell, *Tetrahedron* 1972, 28, 1995; R. G. Powell, D. Weisleder, C. R. Smith, Jr. and W. K. Rohwedder, *Tetrahedron Lett.* 1970, 815-818; I. Takano, I. Yasuda, M. Nishijima, Y. Hitotsuyanagi, K. Takeya and H. Itokawa, *J. Nat. Prod.* 1996, 59, 965-967; D. Z. Wang, G. E. Ma and R. S. Xu, *Acta pharmaceutica Sinica* 1992, 27, 173-177).

(1)

R = H Cephalotaxine

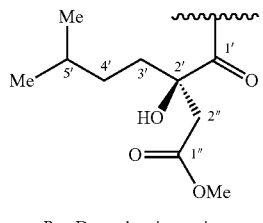

(2)

R = Deoxyharringtonine

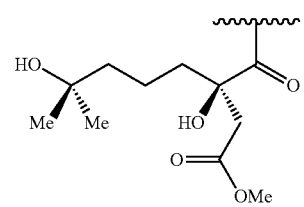

(3)

R = Homoharringtonine

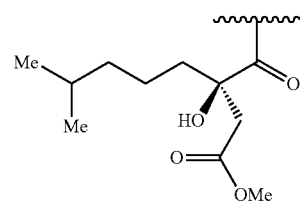

(4)

R = Homodeoxyharringtonine

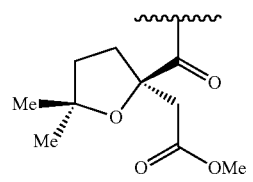

(5)

R = Anhydroharringtonine

The cytotoxic properties of the cephalotaxus esters arise from reversible inhibition of protein synthesis (M. T. Huang, *Mol. Pharmacol.* 1975, 11, 511-519) via induction of rapid breakdown of the polyribosome, with concomitant release of the polypeptide chain (M. Fresno, A. Jimenez and D. Vazquez, *Eur. J. Biochem.* 1977, 72, 323-330). The remarkable anti-leukemia activity of several *Cephalotaxus* esters spawned intense investigations into their therapeutic potential. Several *Cephalotaxus* esters demonstrate acute toxicity toward various murine leukemia, murine lymphoma, and human epidermoid carcinoma cells (H. Morita, M. Arisaka, N. Yoshida and J. Kobayashi, *Tetrahedron* 2000, 56, 2929-2934; Powell, et al., supra). Homoharringtonine (HHT) has advanced through clinical studies and is now used for the treatment of chronic myeloid leukemia. However, difficulties in production, hematologic toxicity, and susceptibility to multidrug resistance (MDR) have hindered its clinical development (Z. Benderra, H. Morjani, A. Trussardi and M. Manfait, *Leukemia* 1998, 12, 1539-1544).

Cephalotaxine itself has been found to be biologically inactive (M. A. J. Miah, T. Hudlicky and J. W. Reed, *Alkaloids* 1998, 51, 199-269), highlighting the necessity for an elaborate C3 ester side chain for anticancer activity. However, the naturally occurring ester derivatives are typically attainable in only <0.1% of the plant dry weight. While certain cephalotaxus ester derivatives, namely HHT, are available through semisynthetic methods, such approaches are not appropriate for other bioactive members of the family. A versatile and streamlined synthetic approach will allow for the chemical synthesis of virtually any cephalotaxus ester, and will enable cytotoxic profile evaluation of cephalotaxine derivatives in efforts to combat multidrug resistance.

SUMMARY OF THE INVENTION

The present invention encompasses the recognition that homoharringtonine, the clinically favored cephalotaxus ester, is highly susceptible to multidrug resistance (MDR), thus inherently limiting its therapeutic potential. Novel non-natural cephalotaxus ester compounds are provided that are cytotoxic against both hematological and solid tumor cell lines.

In one aspect, the invention provides compounds of formula I:

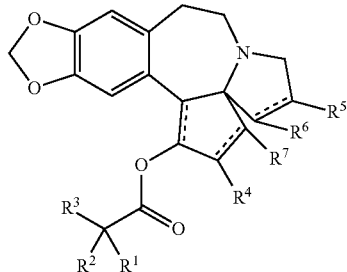

or a pharmaceutically acceptable salt thereof, wherein:
each ----- independently designates a single or double bond;
$R^1$ is hydrogen, optionally substituted $C_{1-6}$ aliphatic, —$(CH_2)_nCO_2R^8$, —$(CH_2)_nCON(R^8)_2$, —$(CH_2)_nCOSR^8$, or taken together with $R^2$ to form an optionally substituted, saturated or unsaturated 3-7-membered ring having 0-2 heteroatoms independently selected from nitrogen, oxygen, or sulfur; and
each $R^8$ is independently hydrogen, an optionally substituted group selected from cephalotaxine, $C_{1-6}$ aliphatic, 6-10-membered aryl, or $C_{1-6}$ heteroaliphatic having 1-2 heteroatoms independently selected from nitrogen, oxygen, or sulfur;
n is an integer from 0-4;
$R^2$ is hydrogen, —$NR_2$, —OR, or an optionally substituted group selected from acyl, $C_{1-6}$ aliphatic, or $C_{1-6}$ heteroaliphatic having 1-2 heteroatoms independently selected from nitrogen, oxygen, or sulfur;
$R^3$ is -T-$R^z$, wherein:
T is a covalent bond or a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—; and
$R^z$ is hydrogen, halogen, a monosaccharide, a disaccharide, —OR, —SR, —$NR_2$, —$N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur; or a hydrogen radical on $R^z$ is replaced with a substituent of the formula:

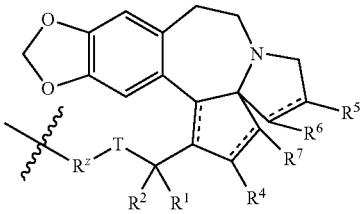

wherein each occurrence of $R^1$, $R^2$, $R^4$, $R^5$, $R^6$, $R^7$, T, and $R^z$ may be the same or different;
$R^4$ is hydrogen, —OR, or =O;
$R^5$ and $R^6$ are each independently selected from hydrogen, $C_{1-6}$ aliphatic, —$SO_2R$, —$CO_2R$; or $R^5$ and $R^6$ are taken together with their intervening atoms to form an optionally substituted 5-7-membered ring having 0-2 heteroatoms independently selected from nitrogen, oxygen, or sulfur;
$R^7$ is hydrogen, —OR, —$OCO_2R$, —OCOR, —OCOSR, or —$OCONR_2$; and
each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; or:
two R on the same nitrogen atom are taken with the nitrogen to form a 4-7-membered heterocyclic ring having 1-2 heteroatoms independently selected from nitrogen, oxygen, or sulfur.

According to one aspect, inventive compounds have been shown to be useful as antiproliferative agents against multiple cancer cell lines, including those of hematopoietic malignancies, acute promyelocytic leukemia, T cell leukemia, acute lymphoblastic leukemia, Mantle cell lymphoma, B cell lymphoma, acute lymphoblastic T cell leukemia, neuroblastoma, adenocarcinoma, Ewing's sarcoma, glioblastoma, epithelial carcinoma, cervical adenocarcinoma, or well-differentiated liposarcoma cancers, to name but a few. In certain embodiments, compounds of formula I are useful against cancer cell lines that are multidrug resistant. In some embodiments, the cells are HL-60/RV+ cells. In some embodiments, the cells are resistant to homoharringtonine. In some embodiments, compounds of formula I are useful for treating cancer in a subject suffering therefrom. In certain embodiments, compounds of formula I are useful for treating refractory cancers in a subject suffering therefrom. In some embodiments, compounds of formula I are useful for treating drug-resistant cancers in a subject suffering therefrom.

In another aspect, the invention provides pharmaceutical compositions comprising compounds of the invention and pharmaceutically acceptable excipients.

In another aspect, the invention provides kits comprising pharmaceutical compositions of inventive compounds. In some embodiments, the kits comprise prescribing information. In some embodiments, such kits include the combination of an inventive compound and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. In certain embodiments, the kit includes one cycle of chemotherapy. In certain embodiments, the kit includes multiple cycles of chemotherapy.

In another aspect, the invention provides a method of treating infectious disease in a subject comprising administering to the subject a therapeutically effective amount of an inventive compound. In some embodiments, the subject is human. In certain embodiments, the infection is caused by a bacterium. In certain embodiments, the infection is caused by a fungus. In certain embodiments, the infection is caused by a parasite.

In yet another aspect, the invention provides a method for synthesizing cephalotaxus ester derivatives through a cross metathesis strategy, the method comprising the steps of:
(a) providing a compound of formula A:

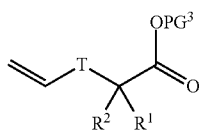

A wherein:
$R^1$ is hydrogen, optionally substituted $C_{1-6}$ aliphatic, —$(CH_2)_nCO_2R^8$, —$(CH_2)_nCON(R^8)_2$, —$(CH_2)_nCOSR^8$, or taken together with $R^2$ to form an optionally substituted, saturated or unsaturated 3-7-membered ring having 0-2 heteroatoms independently selected from nitrogen, oxygen, or sulfur; and
each $R^8$ is independently hydrogen, an optionally substituted group selected from cephalotaxine, $C_{1-6}$ aliphatic or $C_{1-6}$ heteroaliphatic having 1-2 heteroatoms independently selected from nitrogen, oxygen, or sulfur;
n is an integer from 0-4;
$R^2$ is hydrogen, —$NR_2$, —OR, or an optionally substituted group selected from acyl, $C_{1-6}$ aliphatic, or $C_{1-6}$ heteroaliphatic having 1-2 heteroatoms independently selected from nitrogen, oxygen, or sulfur;
T is a covalent bond or a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—;
$PG^3$ is a suitable protecting group; and
each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; or:
two R on the same nitrogen atom are taken with the nitrogen to form a 4-7-membered heterocyclic ring having 1-2 heteroatoms independently selected from nitrogen, oxygen, or sulfur;
and
(b) treating said compound of formula A under suitable conditions with a compound of formula B:

B wherein:
$R^y$ is hydrogen, halogen, a monosaccharide, a disaccharide, —OR, —SR, —$NR_2$, —$N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen, or sulfur;
in the presence a suitable cross metathesis catalyst, to form a compound of formula C:

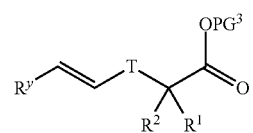

C

In certain embodiments, a suitable cross metathesis catalyst is Grubbs $2^{nd}$ generation catalyst.

The invention further provides compounds of formulae III-A, III-B, III-C, or III-D:

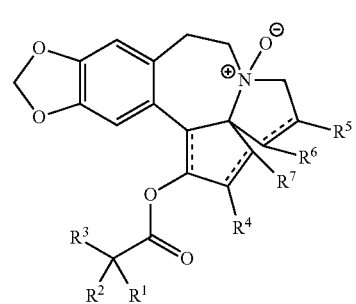

III-A

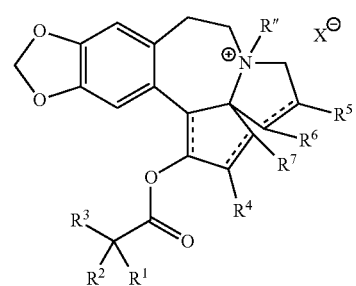

III-B

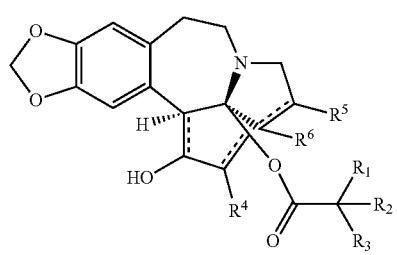

III-C

-continued

III-D

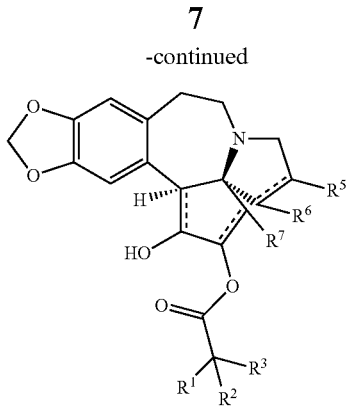

or a pharmaceutically acceptable salt thereof, wherein:

each ---- independently designates a single or double bond;

$R^1$ is hydrogen, optionally substituted $C_{1-6}$ aliphatic, $-(CH_2)_nCO_2R^8$, $-(CH_2)_nCON(R^8)_2$, $-(CH_2)_nCOSR^8$, or taken together with $R^2$ to form an optionally substituted, saturated or unsaturated 3-7-membered ring having 0-2 heteroatoms independently selected from nitrogen, oxygen, or sulfur; and each $R^8$ is independently hydrogen, an optionally substituted group selected from cephalotaxine, $C_{1-6}$ aliphatic, 6-10-membered aryl, or $C_{1-6}$ heteroaliphatic having 1-2 heteroatoms independently selected from nitrogen, oxygen, or sulfur;

n is an integer from 0-4;

$R^2$ is hydrogen, $-NR_2$, $-OR$, or an optionally substituted group selected from acyl, $C_{1-6}$ aliphatic, or $C_{1-6}$ heteroaliphatic having 1-2 heteroatoms independently selected from nitrogen, oxygen, or sulfur;

$R^3$ is -T-$R^z$, wherein:

T is a covalent bond or a bivalent $C_{1-12}$ saturated or unsaturated, straight or branched, hydrocarbon chain, wherein one or two methylene units of T are optionally and independently replaced by $-O-$, $-S-$, $-N(R)-$, $-C(O)-$, $-C(O)O-$, $-OC(O)-$, $-N(R)C(O)-$, $-C(O)N(R)-$, $-S(O)$, $-S(O)_2-$, $-N(R)SO_2-$, or $-SO_2N(R)-$; and $R^z$ is hydrogen, halogen, a monosaccharide, a disaccharide, $-OR$, $-SR$, $-NR_2$, $-N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur; or a hydrogen radical on $R^z$ is replaced with a substituent of the formula:

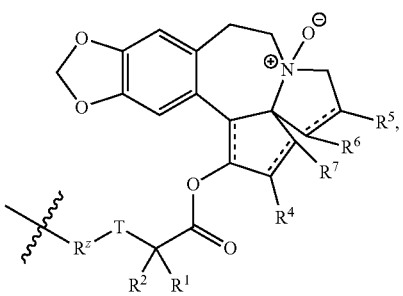

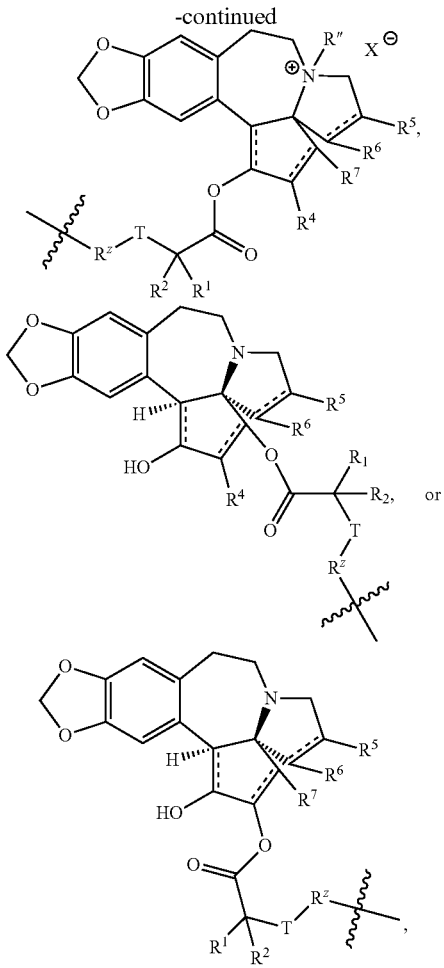

wherein each occurrence of $R^1$, $R^2$, $R^4$, $R^5$, $R^6$, $R^7$, T, X, and $R^z$ may be the same or different;

$R^4$ is hydrogen, $-OR$, or $=O$;

$R^5$ and $R^6$ are each independently selected from hydrogen, $C_{1-6}$ aliphatic, $-SO_2R$, $-CO_2R$; or $R^5$ and $R^6$ are taken together with their intervening atoms to form an optionally substituted 5-7-membered ring having 0-2 heteroatoms independently selected from nitrogen, oxygen, or sulfur;

$R^7$ is hydrogen, $-OR$, $-OCO_2R$, $-OCOR$, $-OCOSR$, or $-OCONR_2$; and each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; or:

two R on the same nitrogen atom are taken with the nitrogen to form a 4-7-membered heterocyclic ring having 1-2 heteroatoms independently selected from nitrogen, oxygen, or sulfur;

R" is hydrogen or an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; and X is a suitable counter ion.

DETAILED DESCRIPTION OF CERTAIN EMBODIMENTS

Figure 1:
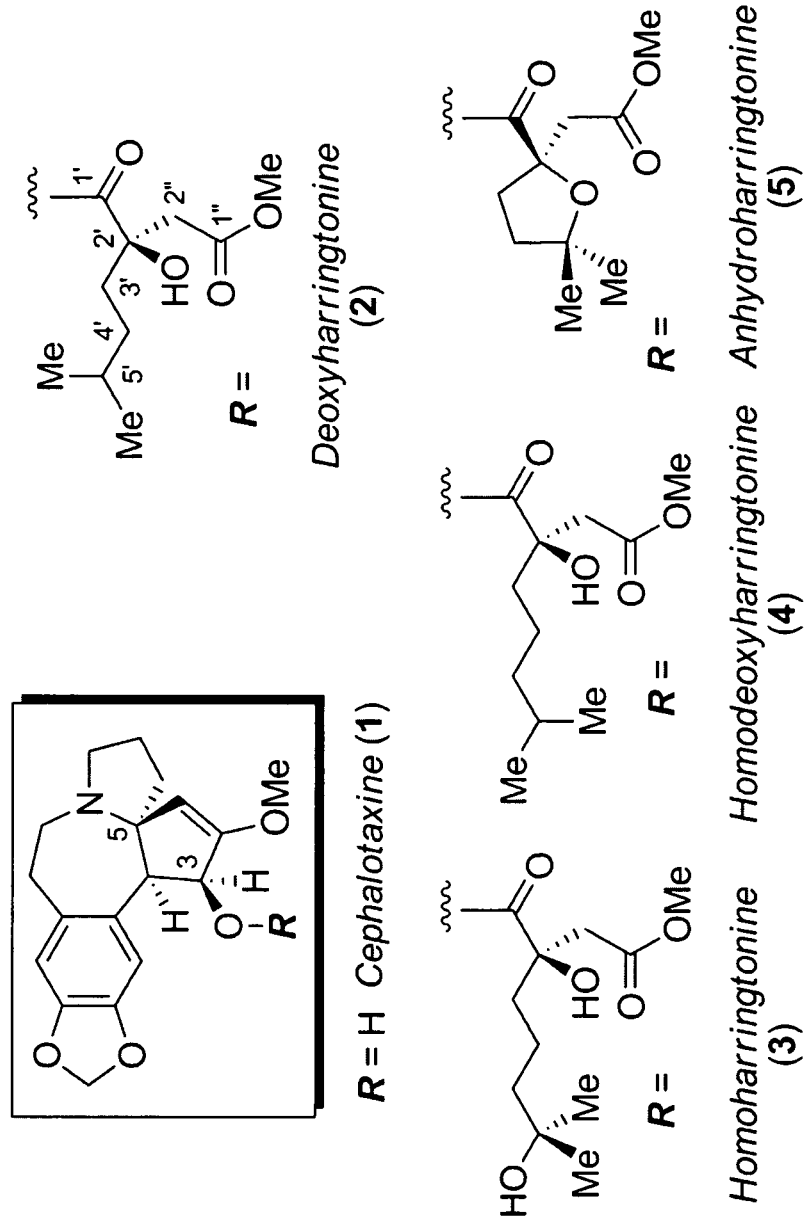
FIG. 1 depicts the chemical structures of cephalotaxine and related esters.
Figure 2:
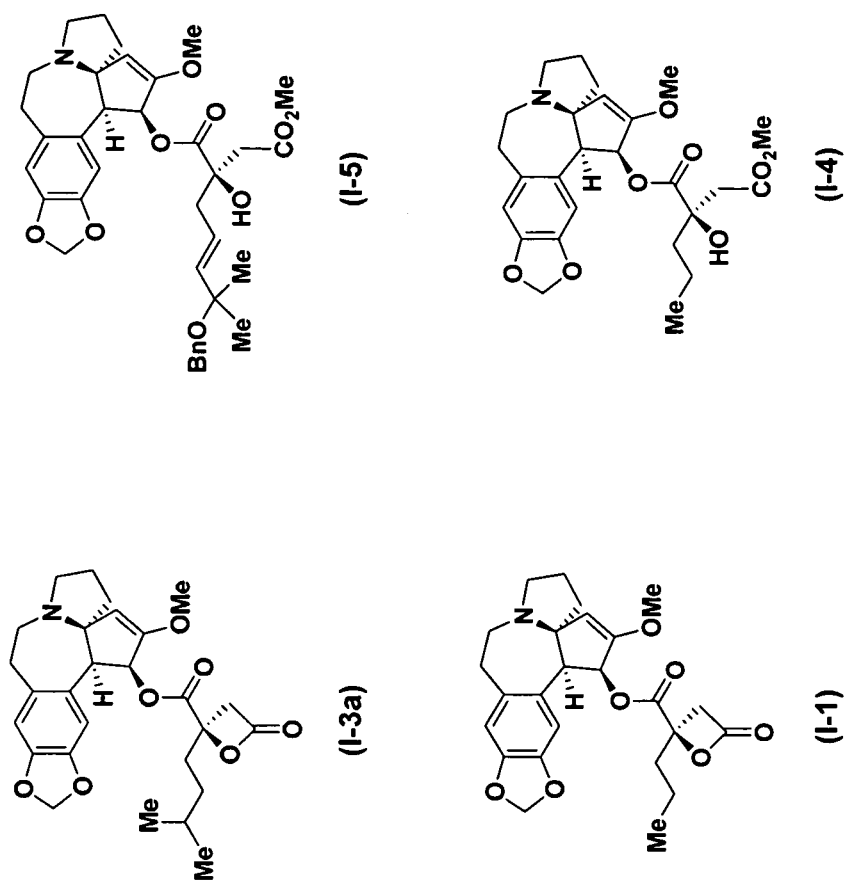
FIG. 2 depicts selected non-natural cephalotaxus esters of formula I.

Cephalotaxine has received considerable and enduring attention in the arena of total synthesis. Several syntheses of cephalotaxine have been reported over the past three decades. The significance of the complex cephalotaxus esters (e.g., deoxyharringtonine, homoharringtonine, homodeoxyharringtonine, and anhydroharringtonine, see FIG. 1) extends beyond that of cephalotaxine on several levels, the most prominent of which being their exceedingly potent anti-proliferative properties. Moreover, the scarcity of these complex ester derivatives from the natural source is far more pronounced than that of cephalotaxine, wherein complex cephalotaxus esters are typically attainable in only <0.1% of the plant dry weight. Thus, in one aspect the invention described herein provides a novel synthetic approach to bioactive cephalotaxus esters that is markedly different from prior approaches.

In another aspect, the invention described herein enables extensive cytotoxicity evaluation of several advanced natural and non-natural compounds with an array of well established human hematopoietic and solid tumor cell lines. In certain embodiments, the inventive compounds are cytotoxic. In some embodiments, the inventive compounds are cytotoxic when tested against these cell lines. Structure-activity relationships based on these natural and non-natural cephalotaxus esters suggests modifications to modulate multidrug resistant (MDR) cancer susceptibility. In some embodiments, those modifications include a hydrogen bond donating group at the C7 position of the ester side chain. In certain embodiments, the lipophilicity of the ester side chain is correlated with low susceptibility to MDR. In some embodiments, the placement of more lipophilic groups at the C6' position of the ester side chain, relative to that of homoharringtonine, is correlated with low susceptibility to MDR.

In certain embodiments, potent cytotoxicity is observed in several cell lines previously not challenged with these alkaloids. In some embodiments, comparative cytotoxicity assays reveal the potential of synthetic structural modification of this family of alkaloids to modulate susceptibility to multi-drug resistance.

Compounds

Compounds of this invention include those described generally above, and are further illustrated by the classes, subclasses, and species disclosed herein. For purposes of this invention, the chemical elements are identified in accordance with the Periodic Table of the Elements, CAS version, *Handbook of Chemistry and Physics*, 75th Ed. Additionally, general principles of organic chemistry are described in *Organic Chemistry*, Thomas Sorrell, University Science Books, Sausalito: 1999, and *March's Advanced Organic Chemistry*, 5th Ed., Ed.: Smith, M. B. and March, J., John Wiley & Sons, New York: 2001, the entire contents of which are hereby incorporated by reference.

Description of Exemplary Compounds

In certain embodiments, the present invention provides a compound of formula I:

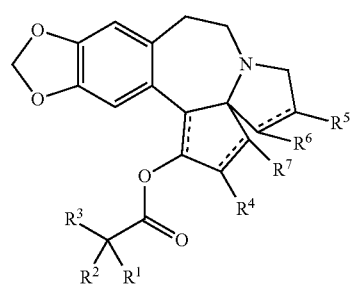

I or a pharmaceutically acceptable salt thereof, wherein:
each ----- independently designates a single or double bond;
$R^1$ is hydrogen, optionally substituted $C_{1-6}$ aliphatic, $-(CH_2)_nCO_2R^8$, $-(CH_2)_nCON(R^8)_2$, $-(CH_2)_nCOSR^8$, or taken together with $R^2$ to form an optionally substituted, saturated or unsaturated 3-7-membered ring having 0-2 heteroatoms independently selected from nitrogen, oxygen, or sulfur; and
each $R^8$ is independently hydrogen, an optionally substituted group selected from cephalotaxine, $C_{1-6}$ aliphatic, 6-10-membered aryl, or $C_{1-6}$ heteroaliphatic having 1-2 heteroatoms independently selected from nitrogen, oxygen, or sulfur;
n is an integer from 0-4;
$R^2$ is hydrogen, $-NR_2$, $-OR$, or an optionally substituted group selected from acyl, $C_{1-6}$ aliphatic, or $C_{1-6}$ heteroaliphatic having 1-2 heteroatoms independently selected from nitrogen, oxygen, or sulfur;
$R^3$ is -T-$R^z$, wherein:
T is a covalent bond or a bivalent $C_{1-12}$ saturated or unsaturated, straight or branched, hydrocarbon chain, wherein one or two methylene units of T are optionally and independently replaced by $-O-$, $-S-$, $-N(R)-$, $-C(O)-$, $-C(O)O-$, $-OC(O)-$, $-N(R)C(O)-$, $-C(O)N(R)-$, $-S(O)$, $-S(O)_2-$, $-N(R)SO_2-$, or $-SO_2N(R)-$; and
$R^z$ is hydrogen, halogen, a monosaccharide, a disaccharide, $-OR$, $-SR$, $-NR_2$, $-N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur; or
a hydrogen radical on $R^z$ is replaced with a substituent of the formula:

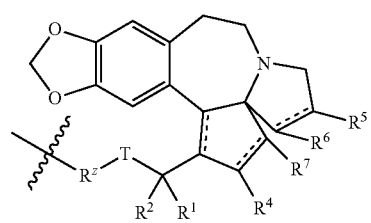

wherein each occurrence of $R^1$, $R^2$, $R^4$, $R^5$, $R^6$, $R^7$, T, and $R^z$ may be the same or different;

$R^4$ is hydrogen, —OR, or =O;

$R^5$ and $R^6$ are each independently selected from hydrogen, $C_{1-6}$ aliphatic, —SO$_2$R, —CO$_2$R; or $R^5$ and $R^6$ are taken together with their intervening atoms to form an optionally substituted 5-7-membered ring having 0-2 heteroatoms independently selected from nitrogen, oxygen, or sulfur;

$R^7$ is hydrogen, —OR, —OCO$_2$R, —OCOR, —OCOSR, or —OCONR$_2$; and each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur, or:

two R on the same nitrogen atom are taken with the nitrogen to form a 4-7-membered heterocyclic ring having 1-2 heteroatoms independently selected from nitrogen, oxygen, or sulfur.

In certain embodiments, $R^1$ is optionally substituted $C_{1-6}$ aliphatic, —(CH$_2$)$_n$C(O)OR$^8$, —(CH$_2$)$_n$C(O)N(R$^8$)$_2$, —(CH$_2$)$_n$C(O)SR$^8$, or taken together with $R^2$ to form an optionally substituted, saturated or unsaturated 3-7-membered ring having 0-2 heteroatoms independently selected from nitrogen, oxygen, or sulfur.

In some embodiments, $R^1$ is —(CH$_2$)$_n$C(O)OR$^8$, wherein $R^8$ is hydrogen, an optionally substituted group selected from $C_{1-6}$ aliphatic or $C_{1-6}$ heteroaliphatic having 1-2 heteroatoms independently selected from nitrogen, oxygen, or sulfur; and n is an integer from 0-4, inclusive.

In some embodiments, $R^8$ is an optionally substituted $C_{1-6}$ aliphatic group. In some embodiments, $R^8$ is an optionally substituted $C_{1-3}$ aliphatic group. In some embodiments, $R^8$ is methyl. In some embodiments, $R^8$ is ethyl. In some embodiments, $R^8$ is CH$_2$F. In some embodiments, $R^8$ is aryl. In some embodiments, $R^8$ is

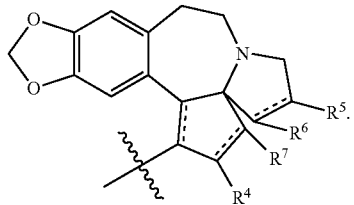

In some embodiments, $R^1$ is —(CH$_2$)$_n$C(O)N(R$^8$)$_2$, and wherein each $R^8$ is independently hydrogen, an optionally substituted group selected from $C_{1-6}$ aliphatic or $C_{1-6}$ heteroaliphatic having 1-2 heteroatoms independently selected from nitrogen, oxygen, or sulfur; and n is an integer from 0-4, inclusive.

In some embodiments, $R^1$ is —(CH$_2$)$_n$C(O)N(R$^8$)$_2$, and $R^8$ is methyl.

In some embodiments, $R^1$ is —(CH$_2$)$_n$C(O)SR$^8$, and wherein each $R^8$ is independently hydrogen, an optionally substituted group selected from $C_{1-6}$ aliphatic or $C_{1-6}$ heteroaliphatic having 1-2 heteroatoms independently selected from nitrogen, oxygen, or sulfur; and n is an integer from 0-4, inclusive.

In some embodiments, $R^1$ is —(CH$_2$)$_n$C(O)SR$^8$, and $R^8$ is ethyl.

In some embodiments, n is 0. In certain embodiments, n is 1 or 2. In some embodiments, n is 1. In certain embodiments, n is 2. In some embodiments, n is 3. In some embodiments, n is 4.

In certain embodiments, $R^1$ is taken together with $R^2$ to form an optionally substituted, saturated or unsaturated 3-7-membered ring having 0-2 heteroatoms independently selected from nitrogen, oxygen, or sulfur.

In some embodiments, $R^1$ and $R^2$ are taken together to form a saturated 3-5-membered ring having 1-2 heteroatoms independently selected from nitrogen or oxygen. In some embodiments, $R^1$ and $R^2$ are taken together to form a saturated 4-membered ring having 1 oxygen atom. In some embodiments, $R^1$ and $R^2$ are taken together to form:

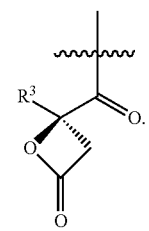

In some embodiments, $R^1$ and $R^2$ are taken together to form:

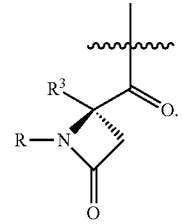

In certain embodiments, $R^2$ is hydrogen, —SR, —NR$_2$, —OR, or an optionally substituted group selected from $C_{1-6}$ aliphatic, or $C_{1-6}$ heteroaliphatic having 1-2 heteroatoms independently selected from nitrogen, oxygen, or sulfur.

In certain embodiments, $R^2$ is —NR$_2$ or —OR, wherein each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur, or two R on the same nitrogen atom are taken together with the nitrogen to form a 4-7-membered heterocyclic ring having 1-2 heteroatoms independently selected from nitrogen, oxygen, or sulfur.

In some embodiments, $R^2$ is —OR, wherein R is H. In some embodiments, $R^2$ is —OR, wherein R is acyl. In some embodiments, $R^2$ is —OR, wherein R is optionally substituted $C_{1-6}$ aliphatic. In some embodiments, $R^2$ is —OR, wherein R is methyl.

In some embodiments, $R^2$ is —NR$_2$, wherein each R is independently hydrogen or optionally substituted $C_{1-6}$ aliphatic. In some embodiments, $R^2$ is —NR$_2$, wherein each R is hydrogen.

As generally described above, $R^3$ is -T-R$^z$, wherein:

T is a covalent bond or a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—; and $R^z$ is hydrogen, halogen, a monosaccharide, a disaccharide, —OR, —SR, —NR$_2$, —N$_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur; 4-7-membered heterocyclyl having 1-2 heteroatoms independently selected from nitrogen, oxygen or sulfur; or a hydrogen radical on $R^z$ is replaced with a substituent of the formula:

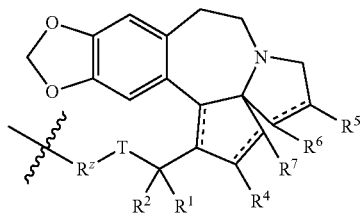

wherein each occurrence of $R^1$, $R^2$, $R^4$, $R^5$, $R^6$, $R^7$, T, and $R^z$ may be the same or different.

In certain embodiments, T is a bivalent $C_{1-12}$ saturated or unsaturated, straight or branched, hydrocarbon chain, wherein one methylene unit of T is optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—. In certain embodiments, T is a bivalent $C_{3-12}$ saturated or unsaturated, straight or branched, hydrocarbon chain. In some embodiments, T is selected from:

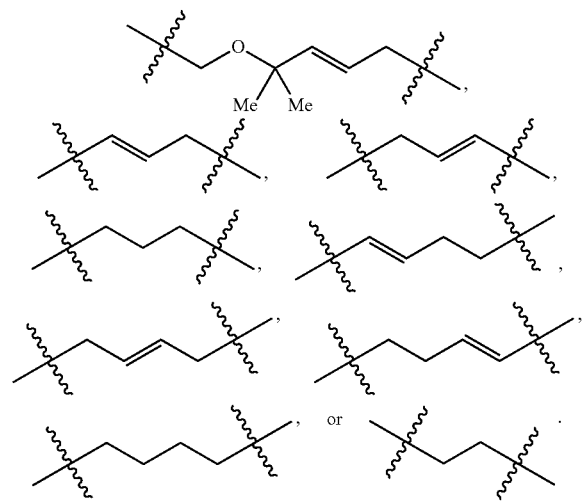

In certain embodiments, T is a bivalent $C_{1-12}$ saturated hydrocarbon chain, wherein one methylene unit of T is optionally and independently replaced by —O—. In certain embodiments, T is a bivalent $C_{1-12}$ unsaturated hydrocarbon chain, wherein one methylene unit of T is optionally and independently replaced by —O—. In certain embodiments, T is a bivalent $C_{1-10}$ saturated hydrocarbon chain, wherein one methylene unit of T is optionally and independently replaced by —O—.

In some embodiments $R^z$ is hydrogen, halogen, —OR, —SR, —NR$_2$, —N$_3$, a monosaccharide, a disaccharide, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur; 4-7-membered heterocyclyl having 1-2 heteroatoms independently selected from nitrogen, oxygen or sulfur; wherein each R is independently hydrogen or an optionally substituted group selected from acyl, arylalkyl, or $C_{1-6}$ aliphatic.

In some embodiments, $R^z$ is hydrogen or an optionally substituted group selected from —OR, —NR$_2$, arylalkyl, heteroarylalkyl, $C_{1-6}$ aliphatic, or 6-10-membered aryl. In some embodiments, $R^z$ is —OR and R is benzyl. In some embodiments, $R^z$ is —OR and R is methyl. In some embodiments, $R^z$ is arylalkyl. In other embodiments, $R^z$ is hetroarylalkyl. In some embodiments, $R^z$ is —N$_3$. In other embodiments, $R^z$ is $C_{1-6}$ aliphatic. In other embodiments, $R^z$ is hydrogen. In other embodiments, $R^z$ is fluoro.

In some embodiments, a hydrogen radical on $R^z$ is replaced with a substituent corresponding to another unit of a compound of formula I, thereby forming a dimer. Exemplary dimer compounds are depicted in Table 1, below.

In some embodiments, $R^z$ is a saccharide group. In other embodiments, $R^z$ is a disaccharide group. In some embodiments, $R^z$ is

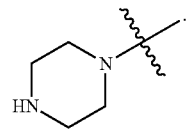

In some embodiments, $R^z$ is

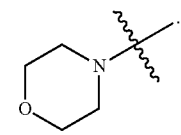 [SMILES: *N1CCOCC1]

In certain embodiments, $R^4$ is —OR, or =O. In some embodiments, $R^4$ is —OR, wherein R is hydrogen, acyl or $C_{1-6}$ aliphatic. In some embodiments, $R^4$ is —OR, wherein R is $C_{1-6}$ aliphatic. In some embodiments, $R^4$ is —OR, wherein R is methyl. In other embodiments, $R^4$ is =O. In some embodiments, $R^4$ is OH.

In certain embodiments, $R^5$ and $R^6$ are each independently selected from hydrogen, $C_{1-6}$ aliphatic, —S(O)$_2$R, or —C(O) OR. In some embodiments, $R^5$ and $R^6$ are both hydrogen. In certain embodiments, at least one of $R^5$ or $R^6$ is hydrogen. In other embodiments, $R^5$ and $R^6$ are —C(O)OR, wherein R is selected from hydrogen or $C_{1-6}$ aliphatic. In other embodiments, $R^5$ is —S(O)$_2$R and $R^6$ is hydrogen. In other embodiments, $R^6$ is —S(O)$_2$R and $R^5$ is hydrogen. In some embodiments, $R^6$ is —S(O)$_2$R, and R is phenyl.

In certain embodiments, $R^5$ and $R^6$ are taken together with their intervening atoms to form an optionally substituted 5-7-membered ring having 0-2 heteroatoms independently selected from nitrogen, oxygen, or sulfur. In some embodiments, $R^5$ and $R^6$ are taken together with their intervening atoms to form a $C_{5-6}$-membered ring having 1 heteroatom selected from nitrogen, oxygen, or sulfur. In some embodiments, $R^5$ and $R^6$ are both $C_{1-6}$ aliphatic and taken together with their intervening atoms to form an optionally substituted 5-7 membered ring.

In certain embodiments, $R^7$ is hydrogen, —OR, —OC(O) OR, —OC(O)R, —OC(O)SR, or —OC(O)NR$_2$. In certain embodiments, $R^7$ is hydrogen. In other embodiments, $R^7$ is —OC(O)OR, wherein R is selected from hydrogen or $C_{1-6}$ aliphatic. In some embodiments, $R^7$ is —OC(O)OR, wherein R is methyl.

In some embodiments, the invention provides compounds with increased or decreased lipophilicity through the attachment of certain functional groups.

In some embodiments, the invention provides compounds with increased cell permeability through the attachment of certain functional groups. Exemplary functional groups include, without limitation,

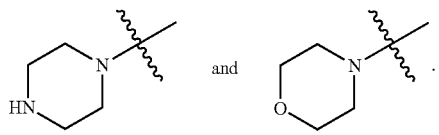 [SMILES: *N1CCNCC1 ; *N1CCOCC1]

As described above for compounds of formula I, each ⁃⁃⁃⁃ independently designates a single or double bond. In certain embodiments, such compounds of are formulae II-1, II-2, and II-3:

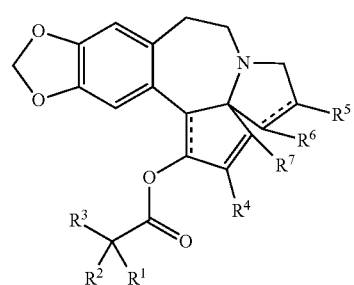

II-1

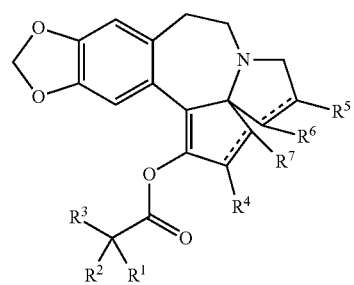

II-2

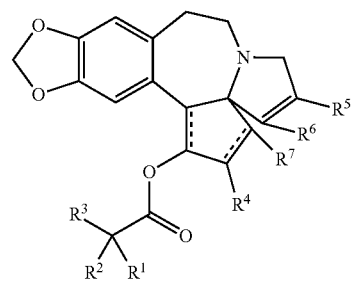

II-3

One of ordinary skill in the art will appreciate that compounds of formula I may possess a number of stereogenic centers. Unless otherwise stated, all stereoisomers of the compounds of the invention are within the scope of the invention. In certain embodiments, such compounds of formulae II-4, II-5, II-6 and II-7:

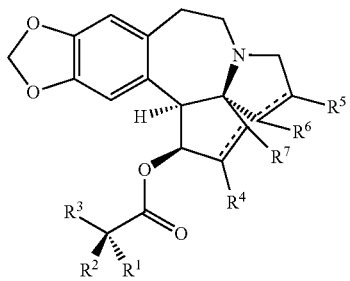

II-4

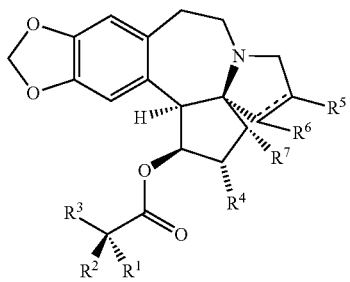

II-5

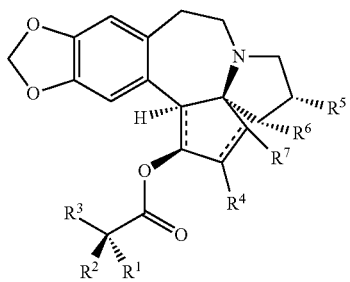

II-6

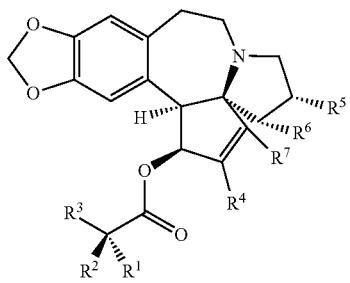

II-7

As described above and herein for compounds of formula I, $R^1$ may be taken together with $R^2$ to form an optionally substituted, saturated or unsaturated 3-7-membered ring having 0-2 heteroatoms independently selected from nitrogen, oxygen, or sulfur. In certain embodiments, such compounds are of formula II-8:

II-8

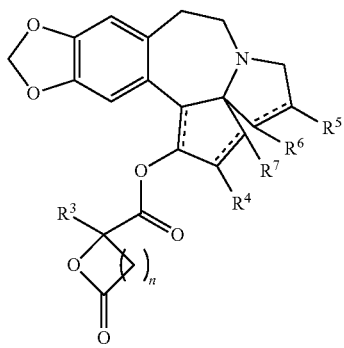

One of ordinary skill in the art will appreciate that the tertiary amine present in compounds of formula I may be further derivitized into a salt, tertiary amine, or N-oxide. Such derivatives are comtemplated by the invention and are within its scope. In some embodiments, such compounds are of formulae III-A and III-B:

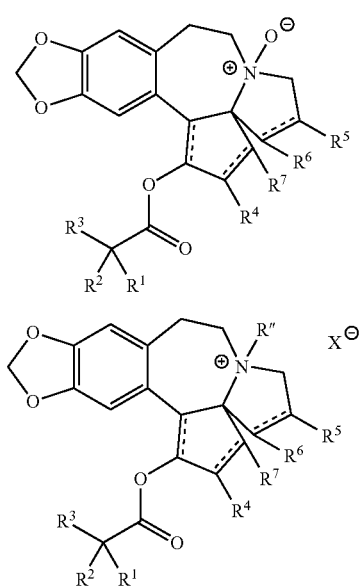

III-A

III-B or a pharmaceutically acceptable salt thereof, wherein:
each ----- independently designates a single or double bond;
$R^1$ is hydrogen, optionally substituted $C_{1-6}$ aliphatic, $-(CH_2)_nCO_2R^8$, $-(CH_2)_nCON(R^8)_2$, $-(CH_2)_nCOSR^8$, or taken together with $R^2$ to form an optionally substituted, saturated or unsaturated 3-7-membered ring having 0-2 heteroatoms independently selected from nitrogen, oxygen, or sulfur; and
each $R^8$ is independently hydrogen, an optionally substituted group selected from cephalotaxine, $C_{1-6}$ aliphatic, 6-10-membered aryl, or $C_{1-6}$ heteroaliphatic having 1-2 heteroatoms independently selected from nitrogen, oxygen, or sulfur;
n is an integer from 0-4;
$R^2$ is hydrogen, $-NR_2$, $-OR$, or an optionally substituted group selected from acyl, $C_{1-6}$ aliphatic, or $C_{1-6}$ heteroaliphatic having 1-2 heteroatoms independently selected from nitrogen, oxygen, or sulfur;

$R^3$ is -T-$R^z$, wherein:
T is a covalent bond or a bivalent $C_{1-12}$ saturated or unsaturated, straight or branched, hydrocarbon chain, wherein one or two methylene units of T are optionally and independently replaced by $-O-$, $-S-$, $-N(R)-$, $-C(O)-$, $-C(O)O-$, $-OC(O)-$, $-N(R)C(O)-$, $-C(O)N(R)-$, $-S(O)$, $-S(O)_2-$, $-N(R)SO_2-$, or $-SO_2N(R)-$; and
$R^z$ is hydrogen, halogen, a monosaccharide, a disaccharide, $-OR$, $-SR$, $-NR_2$, $-N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur; or
a hydrogen radical on $R^z$ is replaced with a substituent of the formula:

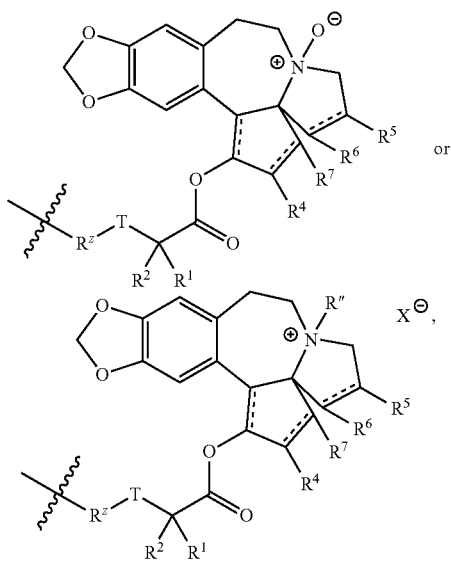

or wherein each occurrence of $R^1$, $R^2$, $R^4$, $R^5$, $R^6$, $R^7$, T, X, and $R^z$ may be the same or different;
$R^4$ is hydrogen, $-OR$, or $=O$;
$R^5$ and $R^6$ are each independently selected from hydrogen, $C_{1-6}$ aliphatic, $-SO_2R$, $-CO_2R$; or $R^5$ and $R^6$ are taken together with their intervening atoms to form an optionally substituted 5-7-membered ring having 0-2 heteroatoms independently selected from nitrogen, oxygen, or sulfur;
$R^7$ is hydrogen, $-OR$, $-OCO_2R$, $-OCOR$, $-OCOSR$, or $-OCONR_2$; and
each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; or:
two R on the same nitrogen atom are taken with the nitrogen to form a 4-7-membered heterocyclic ring having 1-2 heteroatoms independently selected from nitrogen, oxygen, or sulfur;
R" is hydrogen or an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; and
X is a suitable counter ion.

The ester side chain of natural cephalotaxus esters is appended off of the C3 carbon. One of ordinary skill will recognize that the ester side chain may also be appended to other carbons on the cephalotaxine core skeleton. In certain embodiments, such compounds are of formulae III-C and III-D:

III-C

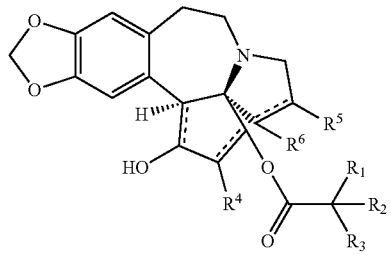

III-D

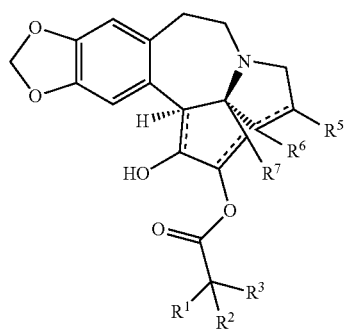

or a pharmaceutically acceptable salt thereof, wherein:
each ---- independently designates a single or double bond;
$R^1$ is hydrogen, optionally substituted $C_{1-6}$ aliphatic, —$(CH_2)_nCO_2R^8$, —$(CH_2)_nCON(R^8)_2$, —$(CH_2)_nCOSR^8$, or taken together with $R^2$ to form an optionally substituted, saturated or unsaturated 3-7-membered ring having 0-2 heteroatoms independently selected from nitrogen, oxygen, or sulfur; and
  each $R^8$ is independently hydrogen, an optionally substituted group selected from cephalotaxine, $C_{1-6}$ aliphatic, 6-10-membered aryl, or $C_{1-6}$ heteroaliphatic having 1-2 heteroatoms independently selected from nitrogen, oxygen, or sulfur;
  n is an integer from 0-4;
$R^2$ is hydrogen, —$NR_2$, —OR, or an optionally substituted group selected from acyl, $C_{1-6}$ aliphatic, or $C_{1-6}$ heteroaliphatic having 1-2 heteroatoms independently selected from nitrogen, oxygen, or sulfur;
$R^3$ is -T-$R^z$, wherein:
  T is a covalent bond or a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—; and
  $R^z$ is hydrogen, halogen, a monosaccharide, a disaccharide, —OR, —SR, —$NR_2$, —$N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur; or a hydrogen radical on $R^z$ is replaced with a substituent of the formula:

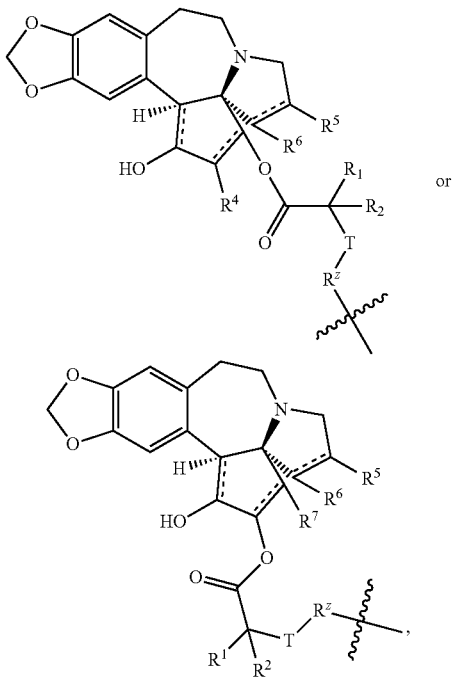

wherein each occurrence of $R^1$, $R^2$, $R^4$, $R^5$, $R^6$, $R^7$, T, X, and $R^z$ may be the same or different;
$R^4$ is hydrogen, —OR, or =O;
$R^5$ and $R^6$ are each independently selected from hydrogen, $C_{1-6}$ aliphatic, —$SO_2R$, —$CO_2R$; or $R^5$ and $R^6$ are taken together with their intervening atoms to form an optionally substituted 5-7-membered ring having 0-2 heteroatoms independently selected from nitrogen, oxygen, or sulfur;
$R^7$ is hydrogen, —OR, —$OCO_2R$, —OCOR, —OCOSR, or —$OCONR_2$; and
each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; or:
  two R on the same nitrogen atom are taken with the nitrogen to form a 4-7-membered heterocyclic ring having 1-2 heteroatoms independently selected from nitrogen, oxygen, or sulfur.

In certain embodiments, the synthesis of compound of formulae III-C and III-D is carried out using suitable protecting groups as known in the art and as described by Greene, et al. (infra). Such protecting group strategies allow the placement of the ester side chain on different carbons of the cephalotaxine core at the discretion of one of ordinary skill in the art.

In certain embodiments, compounds of formulae I, III-A, III-B, III-C, or III-D have a c-logP value that may increase their multidrug resistance ratio. In certain embodiments, the c-logP value is at least about 0.95. In certain embodiments, the c-logP value is at least about 0.96. In certain embodiments, the c-logP value is at least about 0.97. In certain embodiments, the c-logP value is at least about 0.98. In certain embodiments, the c-logP value is at least about 0.99. In certain embodiments, the c-logP value is at least about 1.0. In certain embodiments, the c-logP value is at least about 1.1. In certain embodiments, the c-logP value is at least about 1.2. In certain embodiments, the c-logP value is at least about 1.3.

In certain embodiments, the c-logP value is about 0.95 to about 3.0. In certain embodiments, the c-logP value is about 1.0 to about 3.0. In certain embodiments, the c-logP value is about 1.2 to about 2.8. In certain embodiments, the c-logP value is about 1.2 to about 2.4. In certain embodiments, the c-logP value is about 1.9 to about 2.4. In certain embodiments, the c-logP value is about 1.2 to about 1.3. In certain embodiments, the c-logP value is about 1.9 to about 2.0. In certain embodiments, the c-logP value is about 2.3 to about 2.4. In certain embodiments, the c-logP value is about 2.75 to about 2.85.

Exemplary compounds of formula I are set forth in Table 1 below.

TABLE 1

Exemplary compounds of formula I

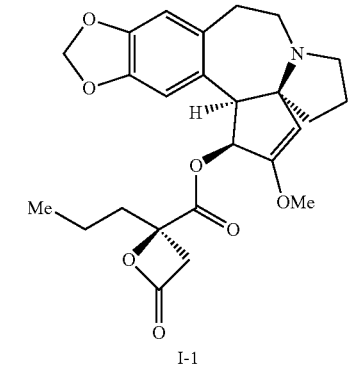

I-1

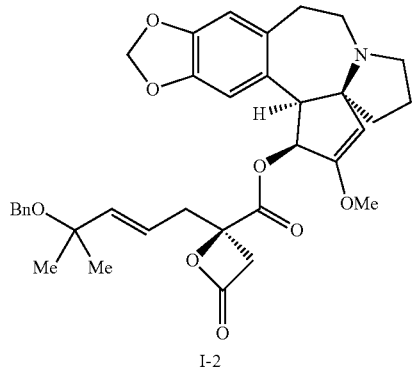

I-2

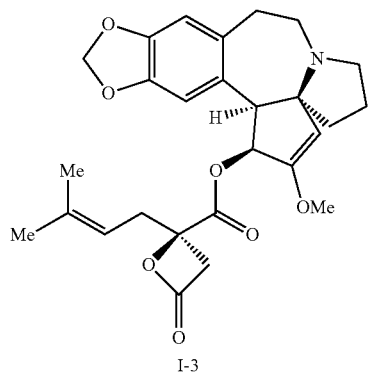

I-3

TABLE 1-continued

Exemplary compounds of formula I

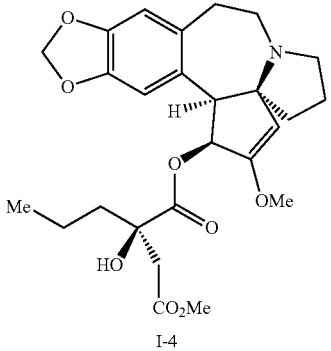

I-4

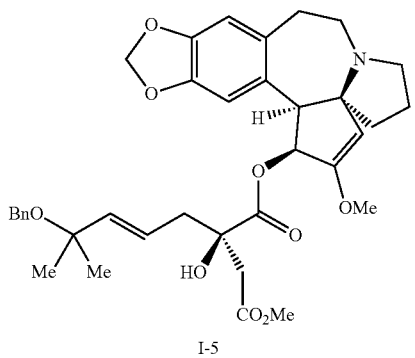

I-5

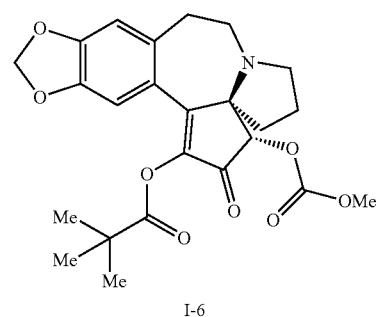

I-6

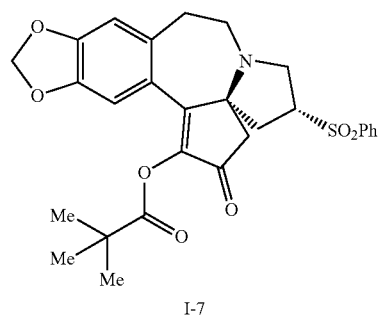

I-7

TABLE 1-continued
Exemplary compounds of formula I
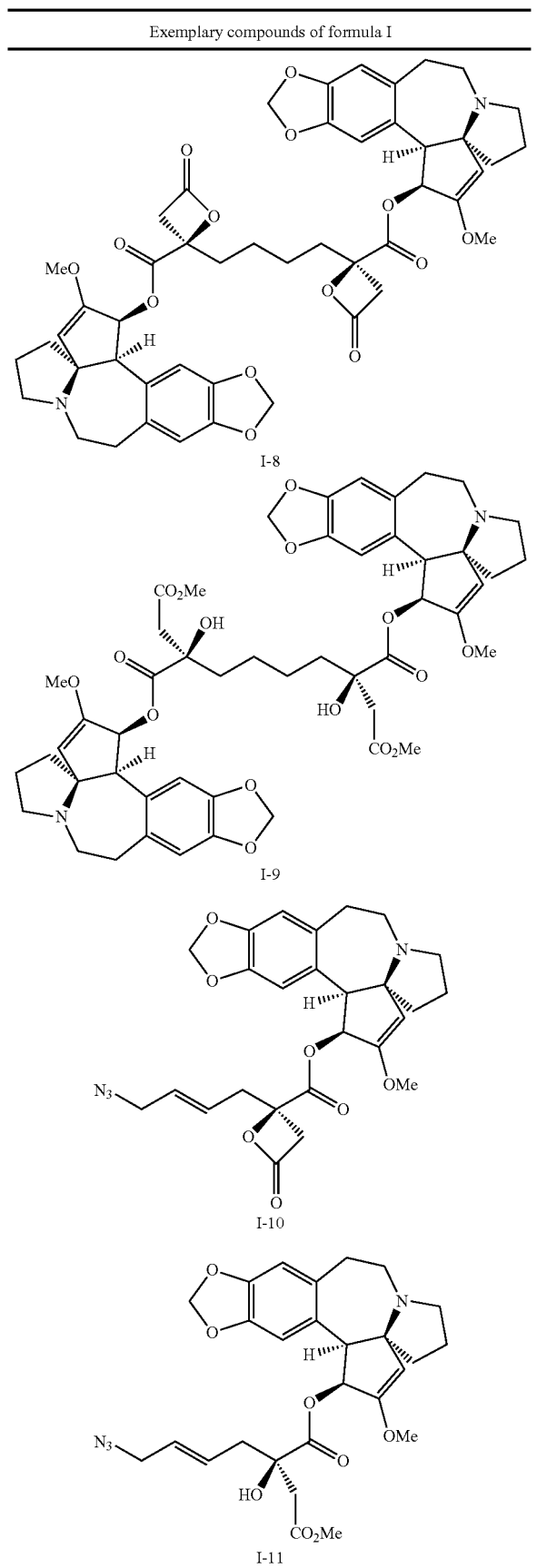
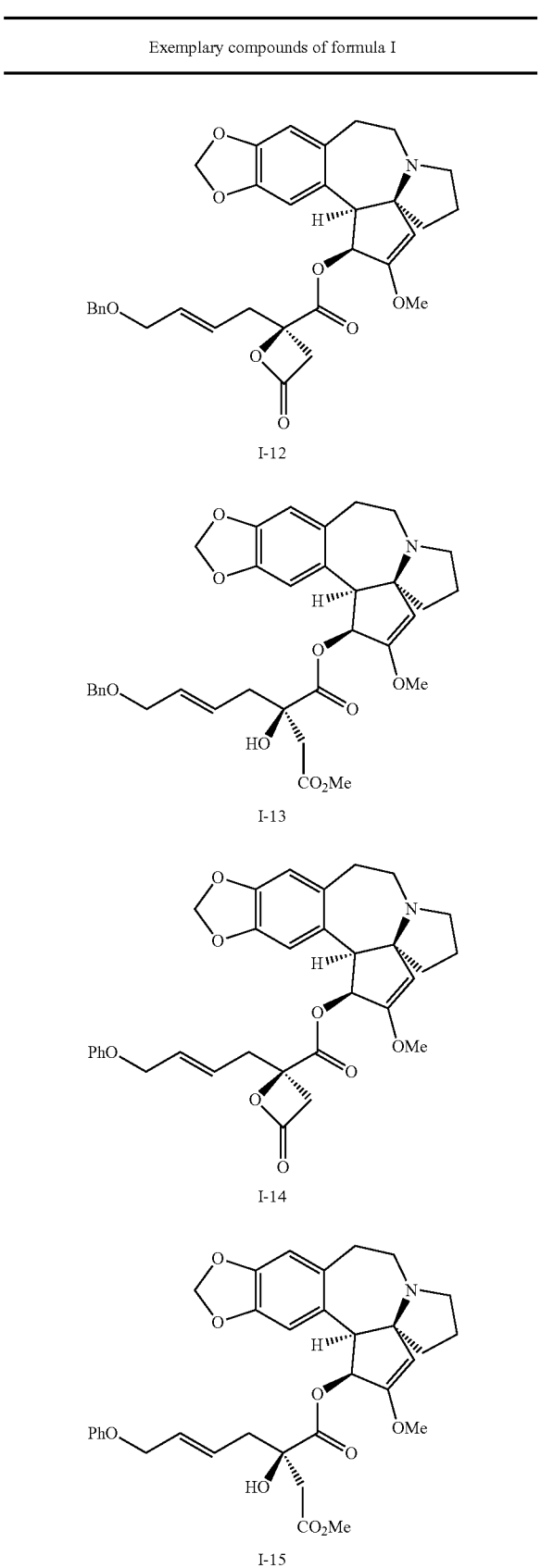

TABLE 1-continued
Exemplary compounds of formula I
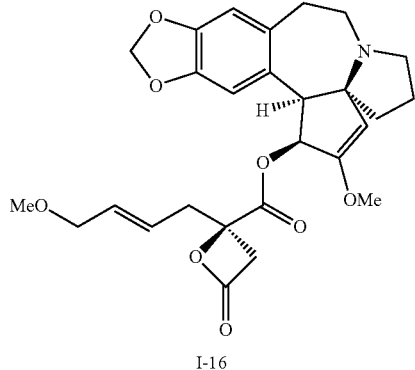
I-16
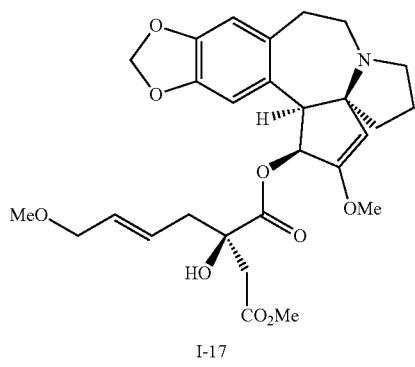
I-17
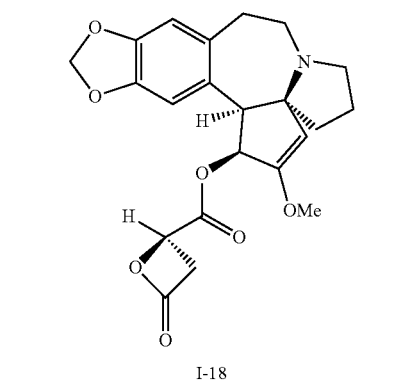
I-18
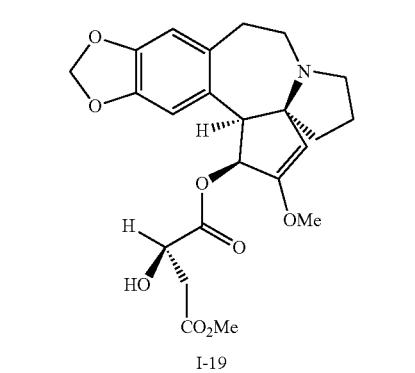
I-19
TABLE 1-continued
Exemplary compounds of formula I
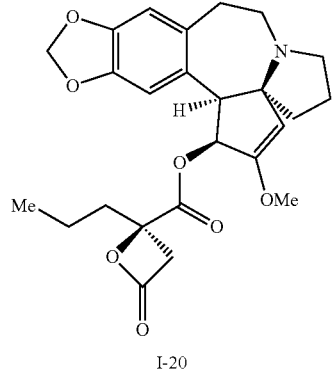
I-20
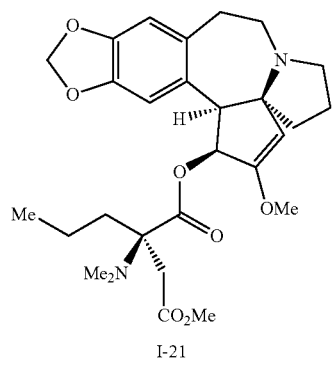
I-21
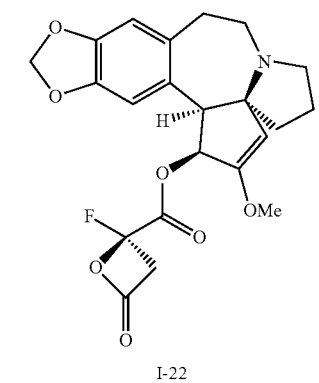
I-22
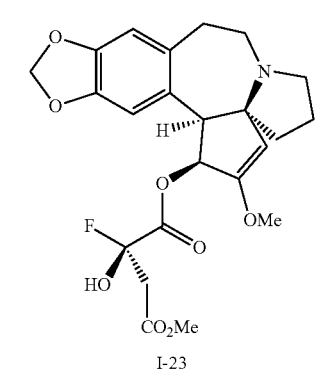
I-23

TABLE 1-continued
Exemplary compounds of formula I
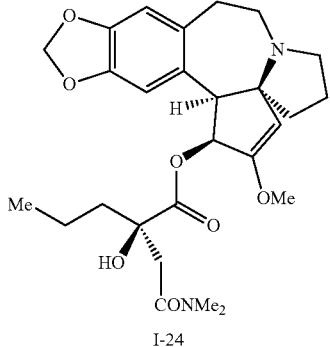
I-24
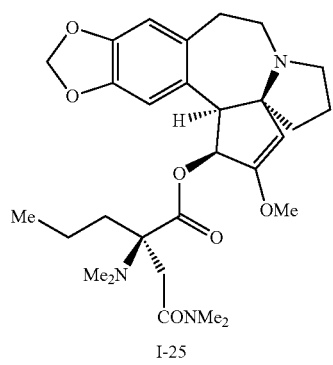
I-25
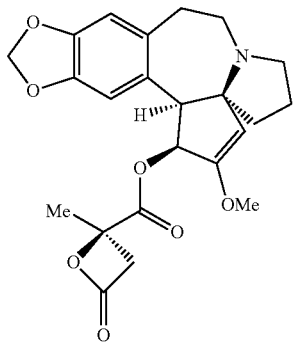 [SMILES: COC1=C[C@]23CCCN2CCc2cc4c(cc2[C@@H]3[C@@H]1OC(=O)[C@@]1(C)CC(=O)O1)OCO4]
I-26
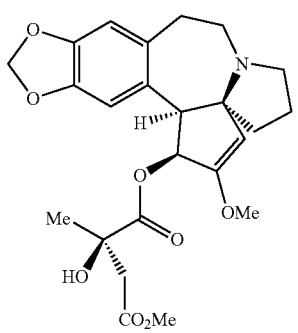 [SMILES: COC(=O)C[C@@](C)(O)C(=O)O[C@@H]1C(OC)=C[C@]23CCCN2CCc2cc4c(cc2[C@H]13)OCO4]
I-27
TABLE 1-continued
Exemplary compounds of formula I
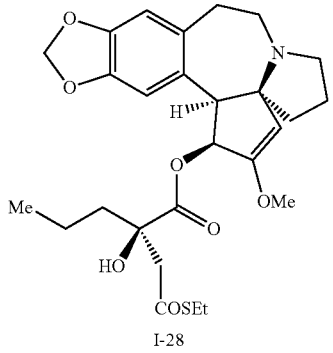
I-28
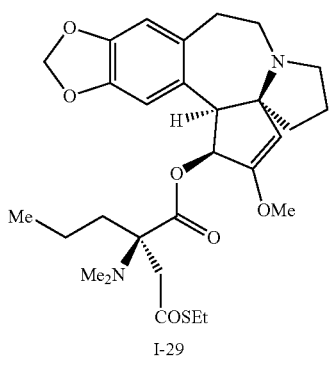
I-29
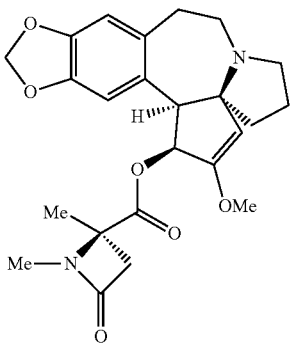 [SMILES: COC1=C[C@]23CCCN2CCc2cc4c(cc2[C@@H]3[C@@H]1OC(=O)[C@@]1(C)CC(=O)N1C)OCO4]
I-30
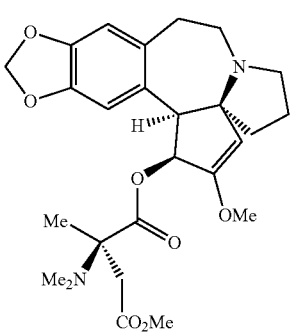 [SMILES: COC(=O)C[C@](C)(C(=O)O[C@@H]1C(OC)=C[C@]23CCCN2CCc2cc4c(cc2[C@H]13)OCO4)N(C)C]
I-31

TABLE 1-continued
Exemplary compounds of formula I
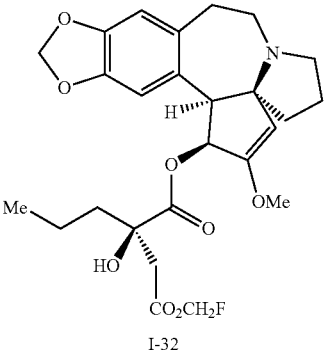
I-32
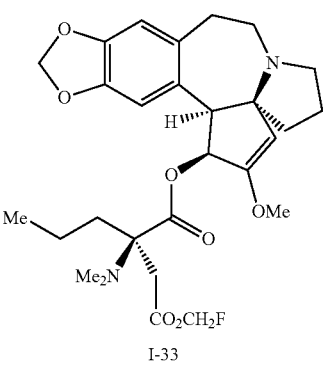
I-33
TABLE 1-continued
Exemplary compounds of formula I
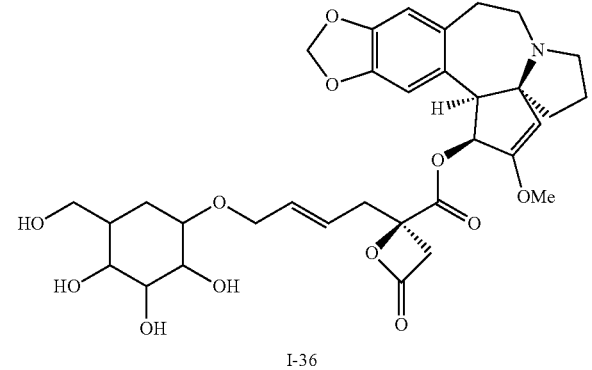
I-36
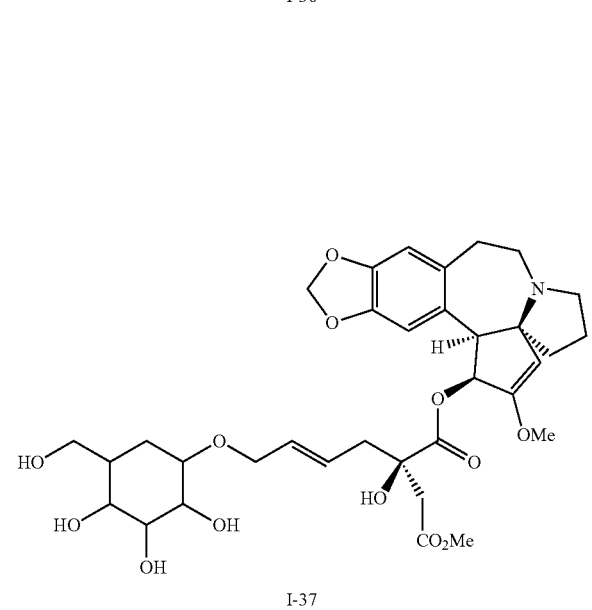
I-37
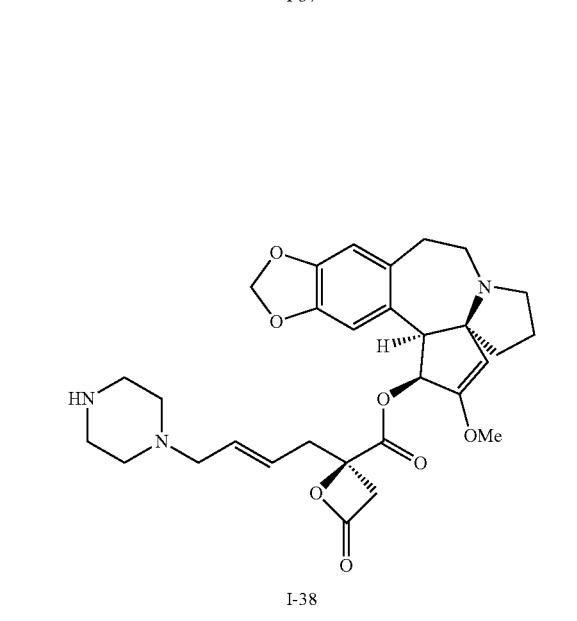
I-38

TABLE 1-continued

Exemplary compounds of formula I

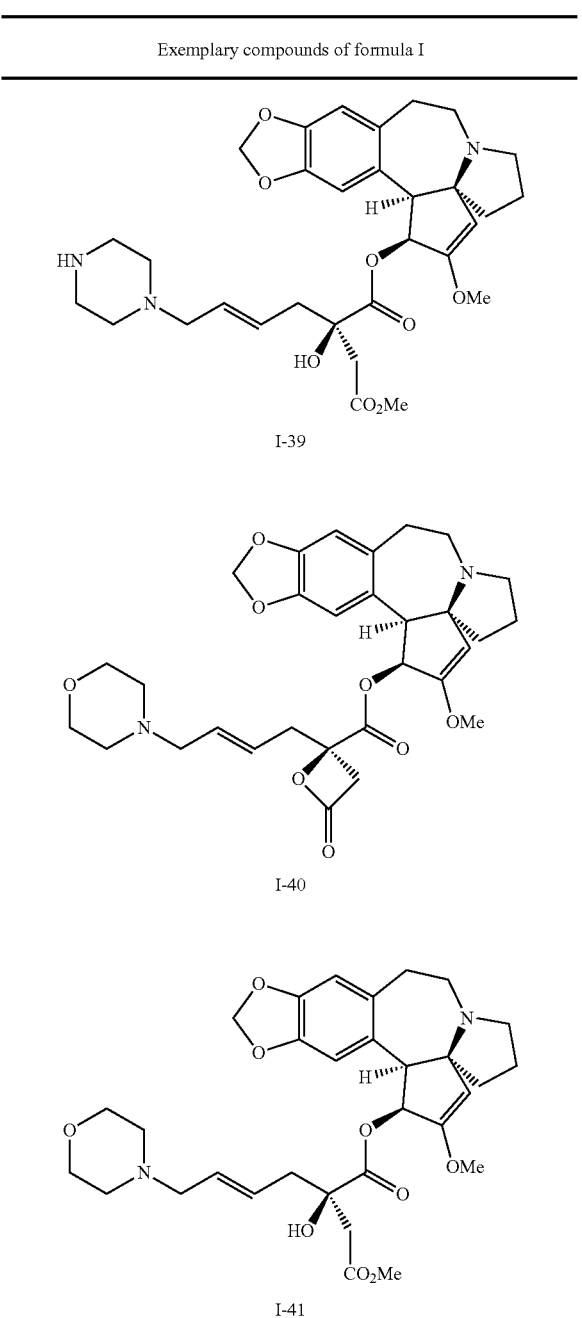

I-39

I-40

I-41

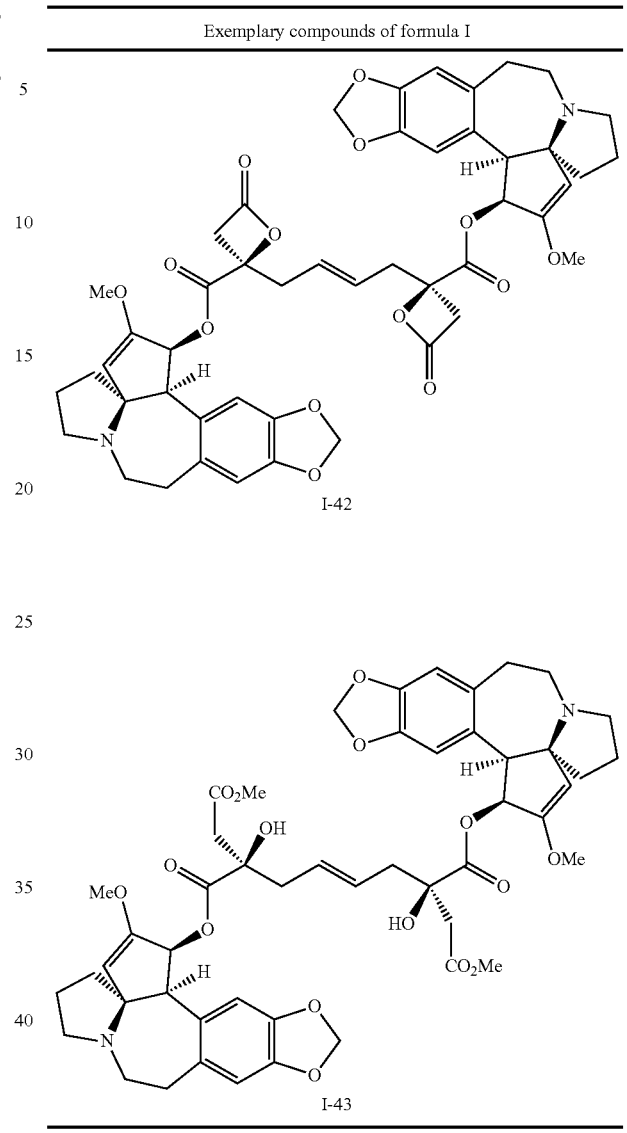

I-42

I-43

Synthesis of Compounds

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.)

Scheme 1.

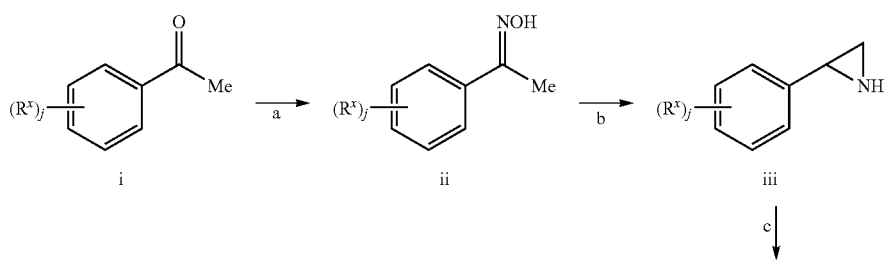

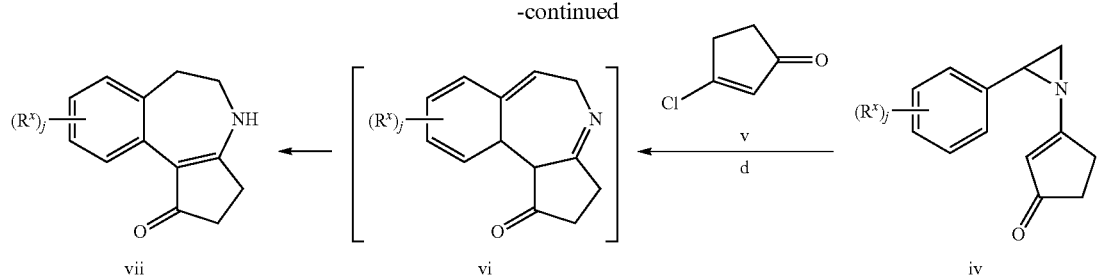

(a) HONH₂·HCl, NaOH, EtOH, H₂O, 60-80° C.; (b) i-Pr₂NH, LiAlH₄, THF, 60° C.; (c) Et₃N, THF, 23-60° C.; (d) Cs₂CO₃, 1,4-dioxane, 100-150° C.

In one aspect, the present invention provides methods for the synthesis of intermediates as shown in Scheme 1, wherein each $R^x$ is independently halogen, —OR, or —NR₂; two $R^x$ on adjacent carbon atoms may be taken together to form a 5-7-membered ring;

each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur, or:

two R on the same nitrogen atom are taken with the nitrogen to form a 4-7-membered heterocyclic ring having 1-2 heteroatoms independently selected from nitrogen, oxygen, or sulfur;

j is an integer from 0 to 4.

Scheme 2.

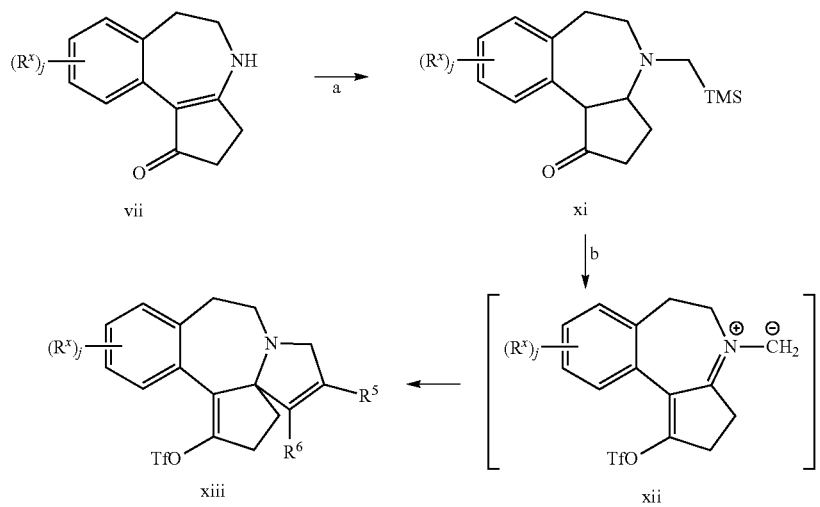

(a) TMSCH₂I, NaH, THF, 50° C.; (b) Tf₂O; DMAD; TBAT, CH₂Cl₂, 23° C.

According to another aspect, the invention provides methods of synthesizing intermediates as shown in Scheme 2, wherein $R^x$, $R^5$, $R^6$, and j are defined as described above and herein.

Scheme 3.

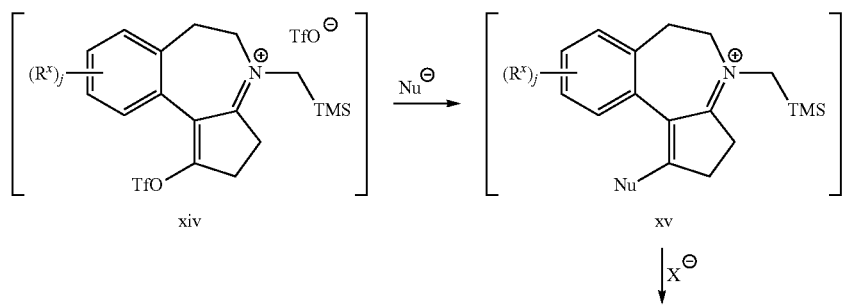

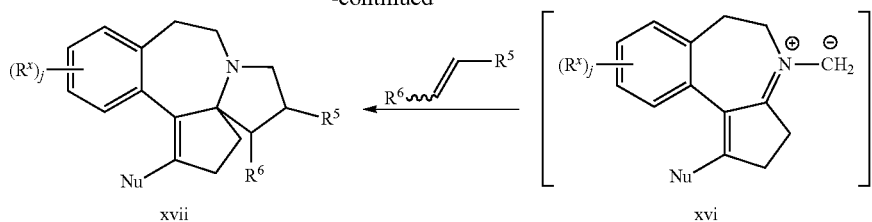

As described in Scheme 3, compounds of formula xvii may be synthesized by reacting a compound of formula xiv with a suitable nucleophile, such as a tetraalkylammonium halide, to give a compound of formula xv. Compound of formula xv may be transformed into compound of formula xvii by reaction with a halide such as fluorine, followed by cycloaddition of a dipolarophile to azomethine ylide intermediate xvi.

Scheme 4.

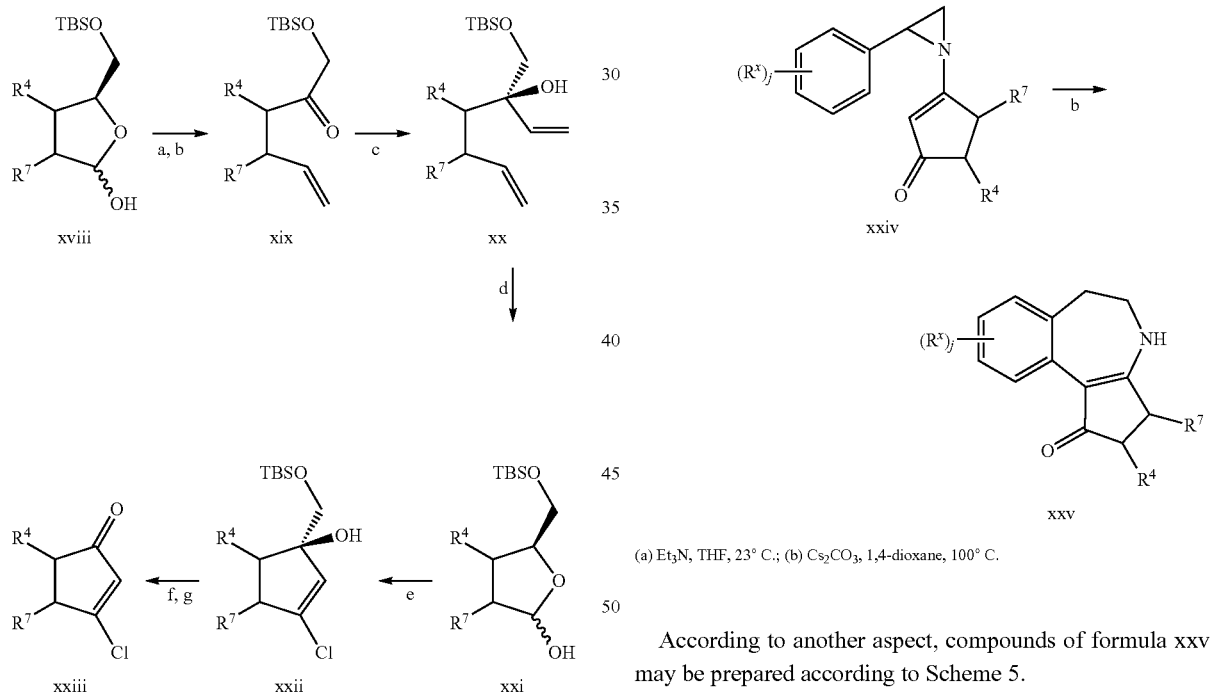

(a) KHMDS, Ph₃PMeBr, THF, 60° C.; (b) DMSO, Et₃N, SO₃•Pyr, CH₂Cl₂, 23° C.; (c) CH₂═CHMgBr, THF, -78 → 23° C., dr 8:1; (d) Grubbs-II, CH₂Cl₂, 23° C.; (e) PhSeCl, MeCN, 0° C.; m-CPBA, Et₃N, CH₂Cl₂, 0 → 23° C.; (f) TBAF, THF, 23° C.; (g) NaIO₄, CH₂Cl₂, H₂O, 23° C.

Chloroeneones of formula xxiii may be prepared according to Scheme 4, wherein $R^4$ and $R^7$ are defined as described above and herein.

Scheme 5.

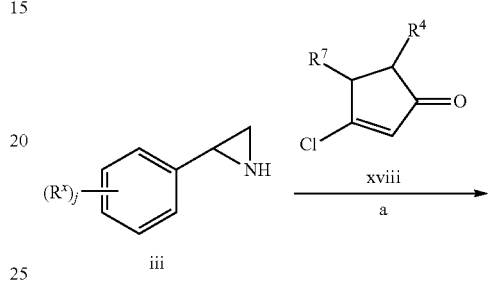

(a) Et₃N, THF, 23° C.; (b) Cs₂CO₃, 1,4-dioxane, 100° C.

According to another aspect, compounds of formula xxv may be prepared according to Scheme 5.

Scheme 6.

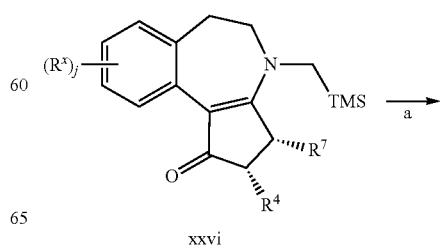

-continued

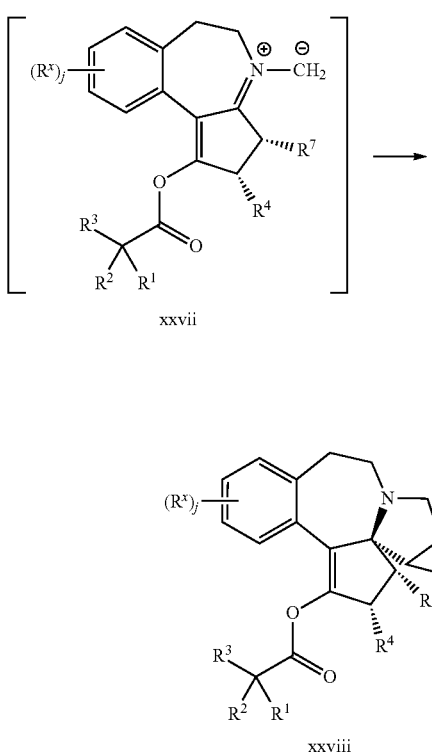

(a) Me₃CCOCl, AgOTf; PhSO₂CH=CH₂; TBAT, CH₂Cl₂, -45 → 23° C.

In some embodiments, compounds of formula xxviii are prepared according to Scheme 6.

Scheme 7.

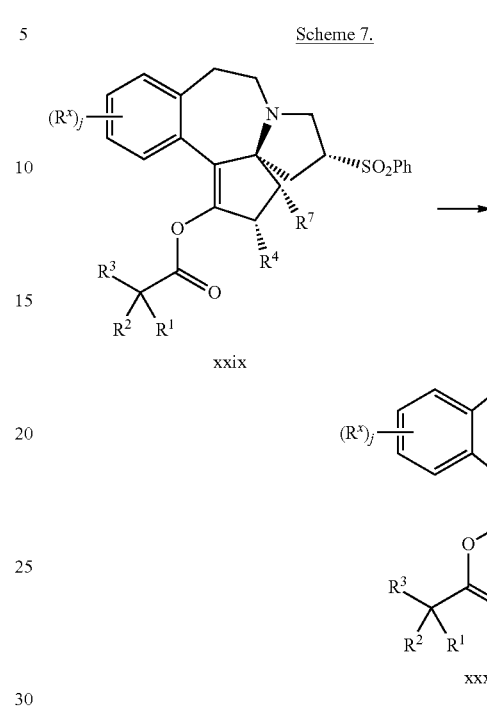

In some embodiments, compounds of formula xxx are prepared by reacting a compound of formula xxix under suitable desulfurization conditions to form a compound of formula xxx. Suitable desulfurization conditions are known in the art and are described in *March's Advanced Organic Chemistry* (supra).

Scheme 8.

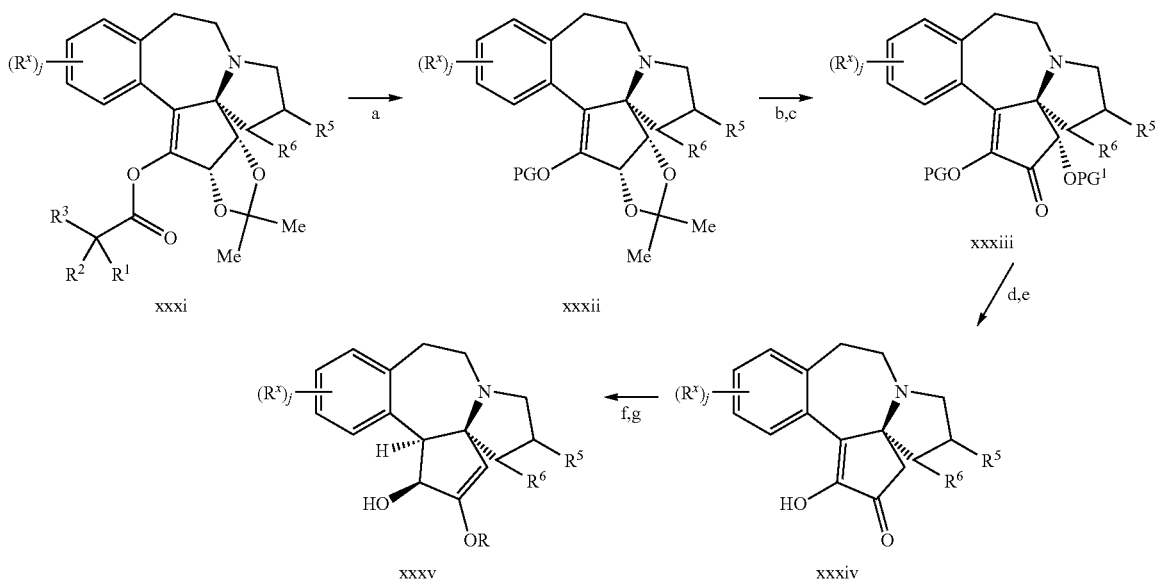

(a) KHMDS, CbzCl, THF, 0° C.; Cp₂ZrHCl, THF, 40° C., 99%; (b) 2N HCl, MeOH, 23° C.; Boc₂O, Yb(OTf)₃·xH₂O, CH₂Cl₂, 0° C.; (c) IBX, DMSO, 23° C. (d) CrCl₂, acetone, H₂O 23° C.; (e) H₂, Pd-C, EtOAc, 23° C.; (f) HC(OMe)₃, p-TsOH, CH₂Cl₂, 55° C.; (g) NaBH₄, MeOH, -78→23° C.

According to another aspect, compounds of formula xxxv may be synthesized as described in Scheme 8, wherein PG and $PG^1$ are suitable protecting groups. While certain protecting groups are described in Scheme 8, one of ordinary skill in the art will recognize that other protecting groups may be utilized.

Scheme 9.

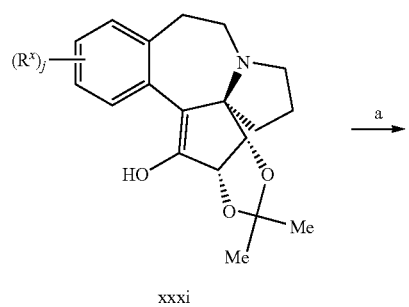

xxxi

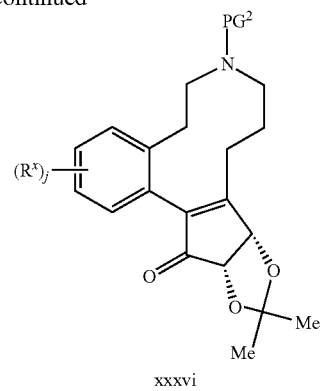

xxxvi (a) $Et_3N$, CbzCl, $CH_2Cl_2$, 23° C.

Scheme 9 depicts the synthesis of compounds of formula xxxvi, wherein $PG^2$ represents a suitable protecting group. While certain protecting groups are described, one of ordinary skill in the art will recognize that other protecting groups may be utilized.

Scheme 10.

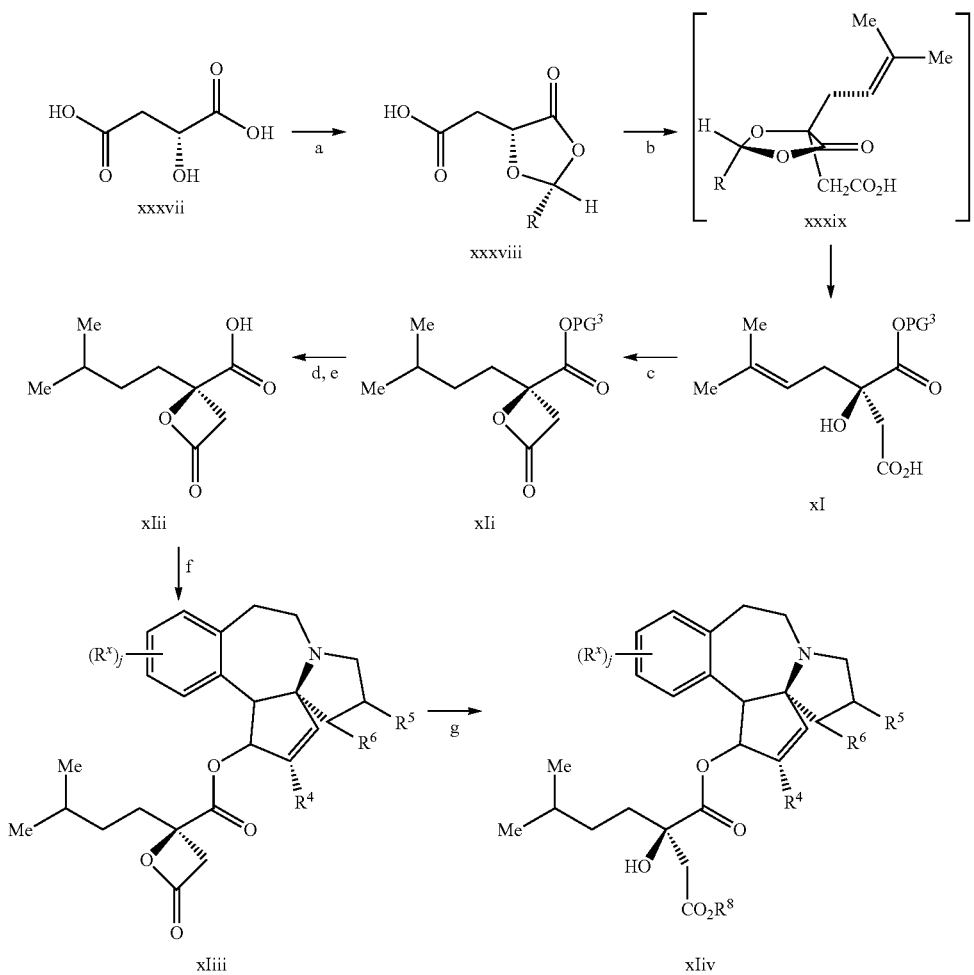

(a) TMSCl, $TMS_2NH$, $CH_2Cl_2$, 23° C.; $Me_3CCHO$, TMSOTf, $CH_2Cl_2$, -25° C.; (b) LHMDS, $Me_2C$=$CHCH_2Br$, THF, -78° C.; (c) NaH, BnOH, THF, 0° C.; (d) 2,4,6-$Cl_3C_6H_2COCl$, DMAP, $CH_2Cl_2$, 23° C.; (e) $H_2$, Pd-C, EtOAc, 23° C.; (f) 2,4,6-$Cl_3C_6H_2COCl$, DMAP, 1, $CH_2Cl_2$, 23° C.; (g) NaOMe, MeOH, 23° C.

Scheme 10 depicts the synthesis of compounds of formulae xliii and xliv, wherein $PG^3$ is a suitable protecting group and $R^8$ is defined as described above and herein. While certain protecting groups are described, one of ordinary skill in the art will recognize that other protecting groups may be utilized.

protecting groups, taken with the —NH— moiety to which it is attached, include, but are not limited to, aralkylamines, carbamates, allyl amines, amides, and the like. Examples of other protecting groups include t-butyloxycarbonyl (BOC), ethyloxycarbonyl, methyloxycarbonyl, trichloroethyloxycarbonyl, allyloxycarbonyl (Alloc), benzyloxocarbonyl

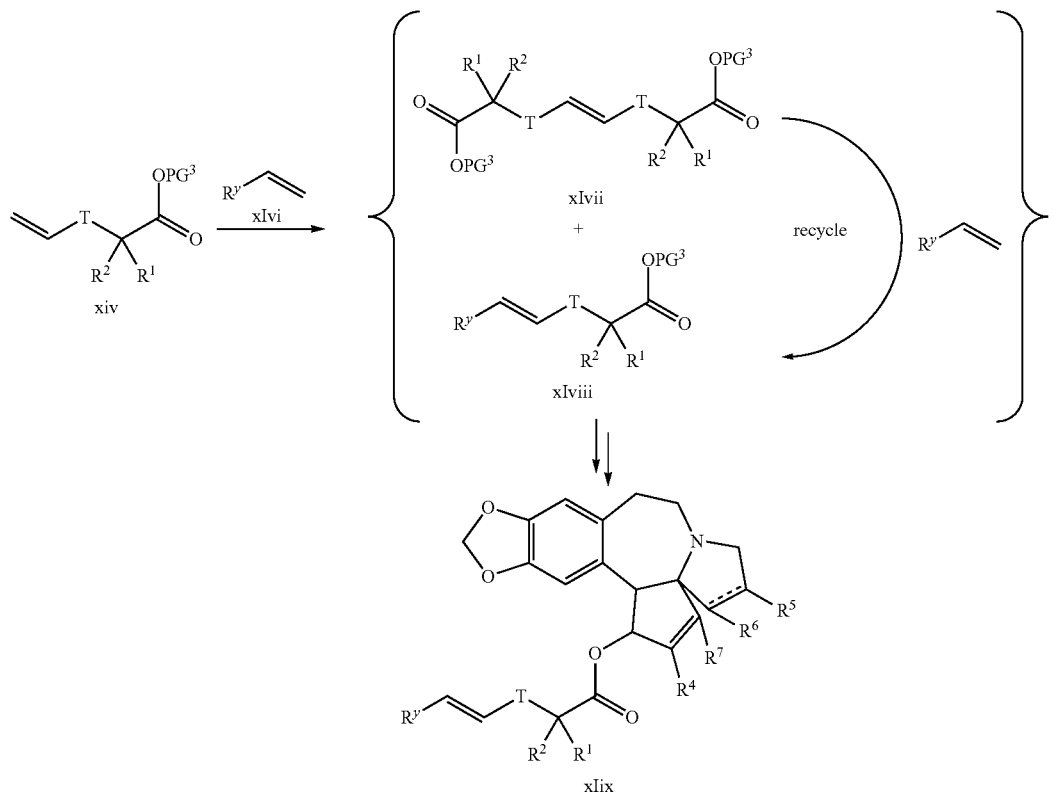

Scheme 11 depicts the synthesis of compounds of formulae xlvii, xlviii, and xlix, wherein T is a covalent bond or a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—;

$PG^3$ is a suitable protecting group;

$R^y$ is hydrogen, halogen, a monosaccharide, a disaccharide, —OR, —SR, —NR$_2$, —N$_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur.

The PG, $PG^1$, $PG^2$, and $PG^3$ groups on the formulae described above and herein are suitable protecting groups. Suitable amino and hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino (CBZ), allyl, benzyl (Bn), fluorenylmethylcarbonyl (Fmoc), acetyl, chloroacetyl, dichloroacetyl, trichloroacetyl, phenylacetyl, trifluoroacetyl, benzoyl, and the like.

Suitable protecting groups may be removed under conditions known in the art (see, for example, Greene, supra). One of ordinary skill in the art will recognize that, under certain conditions, a protecting group may be removed concomitantly with another chemical transformation. In some embodiments, the protecting group may be removed in a stepwise fashion either before or after the other chemical transformation.

As described in Scheme 11, one aspect of the invention is to provide a method of synthesizing compounds of formula I using a cross metathesis reaction. Thus, in certain embodiments, a method is provided comprising the steps of:

(a) providing a compound of formula A:

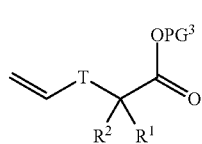

wherein:

R[1] is hydrogen, optionally substituted $C_{1-6}$ aliphatic, —$(CH_2)_nCO_2R^8$, —$(CH_2)_6CON(R^8)_2$, —$(CH_2)_6COSR^8$, or taken together with R[2] to form an optionally substituted, saturated or unsaturated 3-7-membered ring having 0-2 heteroatoms independently selected from nitrogen, oxygen, or sulfur; and each R[8] is independently hydrogen, an optionally substituted group selected from $C_{1-6}$ aliphatic or $C_{1-6}$ heteroaliphatic having 1-2 heteroatoms independently selected from nitrogen, oxygen, or sulfur;

n is an integer from 0-4;

R[2] is hydrogen, —$NR_2$, —OR, or an optionally substituted group selected from acyl, $C_{1-6}$ aliphatic, or $C_{1-6}$ heteroaliphatic having 1-2 heteroatoms independently selected from nitrogen, oxygen, or sulfur;

T is a covalent bond or a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —S(O)$_2$—, —N(R)SO$_2$—, or —SO$_2$N(R)—;

PG[3] is a suitable protecting group; and each R is independently hydrogen, an optionally substituted group selected from acyl, arylalkyl, $C_{1-6}$ aliphatic, or $C_{1-6}$ heteroaliphatic having 1-2 heteroatoms independently selected from nitrogen, oxygen, or sulfur; or:

two R on the same nitrogen atom are taken with the nitrogen to form a 4-7-membered heterocyclic ring having 1-2 heteroatoms independently selected from nitrogen, oxygen, or sulfur; and (b) treating said compound of formula A under suitable conditions with a compound of formula B:

B wherein:

R[y] is hydrogen, halogen, a monosaccharide, a disaccharide, —OR, —SR, —$NR_2$, —$N_3$, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from nitrogen, oxygen or sulfur;

in the presence a suitable cross metathesis catalyst, to form a compound of formula C:

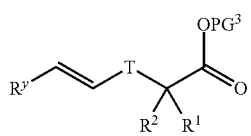

C

In certain embodiments, step (b) provides a compound of formula A':

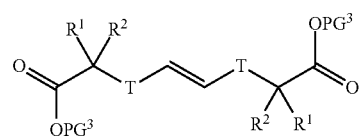

A'

One of ordinary skill in the art will recognize that a compound of formula A' may be resubjected to cross metathesis conditions to provide additional quantities of a compound of formula C. Thus, in certain embodiments, the present invention provides a method of treating said compound of formula A' with a compound of formula B in the presence a suitable cross metathesis catalyst, to form a compound of formula C.

In another aspect, the present invention provides a method comprising the steps of (a) providing a compound of formula C; and

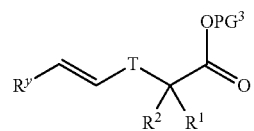

C (b) removing the PG[3] moiety from a compound of formula C under suitable conditions; and (c) treating said compound of formula C under suitable conditions with a compound of formula I-A:

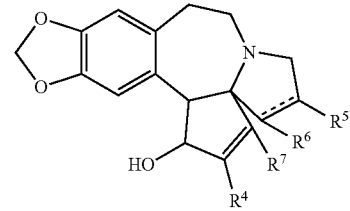

I-A wherein:

R[5] and R[6] are each independently selected from hydrogen, $C_{1-6}$ aliphatic, —$SO_2R$, —$CO_2R$, or R[5] and R[6] are taken together with their intervening atoms to form an optionally substituted 5-7-membered ring having 0-2 heteroatoms independently selected from nitrogen, oxygen, or sulfur;

R[7] is hydrogen, —OR, —$OCO_2R$, —OCOR, —OCOSR, or —$OCONR_2$;

to form a compound of formula I-B:

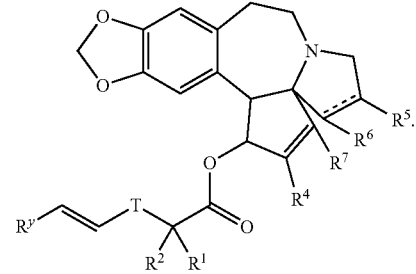

I-B

In certain embodiments, the present invention provides a method comprising the steps of:
(a) providing a compound of formula A'; and

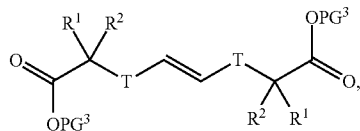

(b) removing the PG³ moiety from a compound of formula A' under suitable conditions; and
(c) treating said compound of formula A' under suitable conditions with a compound of formula I-A:

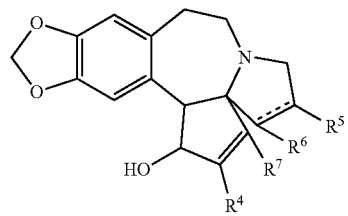

wherein:
R⁵ and R⁶ are each independently selected from hydrogen, C₁₋₆ aliphatic, —SO₂R, —CO₂R, or R⁵ and R⁶ are taken together with their intervening atoms to form an optionally substituted 5-7-membered ring having 0-2 heteroatoms independently selected from nitrogen, oxygen, or sulfur;
R⁷ is hydrogen, —OR, —OCO₂R, —OCOR, —OCOSR, or —OCONR₂;
to form a compound of formula I-B':

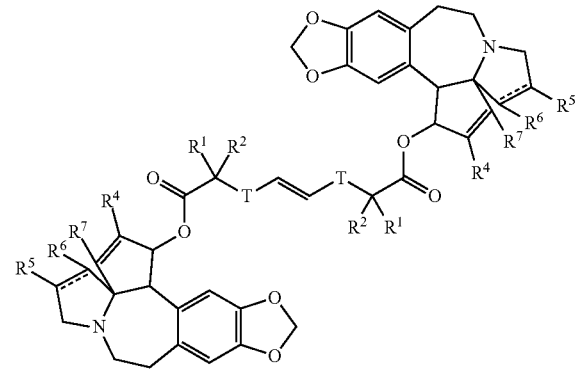

In some embodiments, suitable conditions for the cross metathesis reaction may comprise the use of a suitable solvent. Suitable solvents include, but are not limited to, halogenated hydrocarbons and aromatic hydrocarbons. In some embodiments, the solvent is dichloromethane. In some embodiments, the solvent is benzene. In some embodiments, the solvent is toluene.
In some embodiments, suitable conditions for the cross metathesis reaction are in the temperature range of about 10° C. to about 120° C. In some embodiments, the reaction proceeds at a temperature of about 25° C. to about 80° C. In some embodiments, the reaction proceeds at a temperature of about 10° C. to about 25° C. In some embodiments, the reaction proceeds at a temperature of about 25° C. to about 40° C. In some embodiments, the reaction proceeds at reflux temperature reaction mixture.

One of ordinary skill in the art will recognize that compounds of formulae I-B and I-B' may be subjected to suitable hydrogenation conditions (e.g., Pd/C, H₂; Wilkinson's catalyst; etc.) to provide compounds of formulae I-C and I-C'. Thus, in certain embodiments, the present invention provides a method of subjecting a compound of formulae I-B or I-B' to suitable hydrogenation conditions to provide a compound of formulae I-C or I-C':

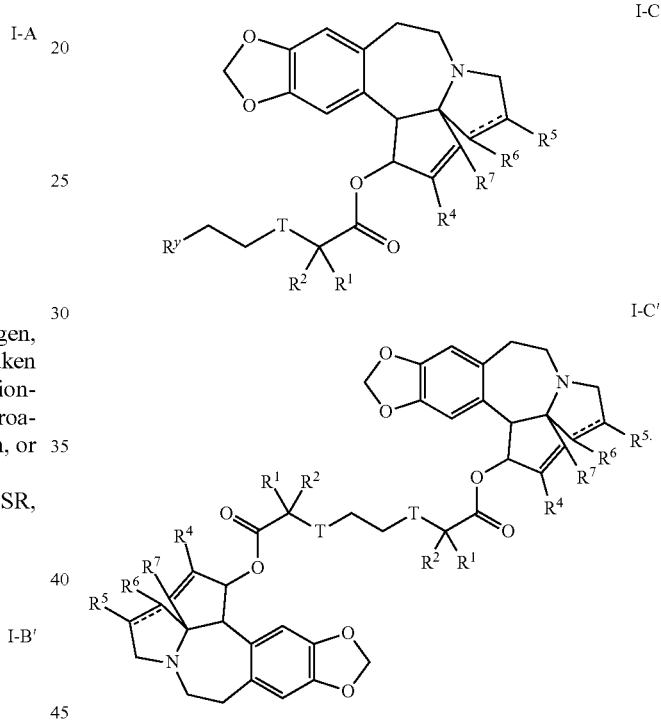

As used herein, the term "suitable cross metathesis catalyst" refers to any catalyst known in the art to act as a catalyst for the cross metathesis reaction of two olefin moieties. In certain embodiments, the catalyst is a ruthenium alkylidene or ruthenium carbene. In some embodiments, the catalyst is a molybdenum-based species. In some embodiments, the catalyst is Grubbs 1ˢᵗ generation. In some embodiments, the catalyst is Grubbs 2ⁿᵈ generation. In some embodiments, the catalyst is Hoveyda-Grubbs 1ˢᵗ generation. In some embodiments, the catalyst is Hoveyda-Grubbs 2ⁿᵈ generation. In some embodiments, the catalyst is dichloro(3-methyl-2-butenylidene)bis(tricyclopentylphosphine) ruthenium(II). In some embodiments, the catalyst is dichloro(3-methyl-2-butenylidene)bis(tricyclohexylphosphine) ruthenium(II). In some embodiments, the catalyst is a chiral ruthenium catalyst.

Methods of using and general descriptions of suitable cross metathesis catalysts are described in Grubbs, R. H.; *Tetrahedron*, 2004, 7117-7140; Grubbs, R. H., et al.; *Org. Lett.*, 2008, 441-444; the entire contents of each are hereby incorporated by reference.

Synthesis and Attachment of the Acyl Chain of Antitumor *Cephalotaxus* Esters

The bulk of the synthetic reports concerning the cephalotaxus alkaloids have focused on cephalotaxine. On the other hand, reports on the synthesis of natural anti-leukemia cephalotaxus esters have been relatively scarce, likely a result of the difficulties associated with appending a fully intact acyl side chain onto the C3-OH of cephalotaxine. The challenge of such an acylation arises from extensive steric obstruction, marked by the secondary C3-hydroxyl nucleophile buried within the concave face of cephalotaxine, and exacerbated by a fully α-substituted acyl electrophile in the side chain. Indeed, the difficulty of this acylation event is highlighted in numerous semi-syntheses of the cephalotaxus esters from cephalotaxine, wherein the bulk of these efforts employed a less hindered prochiral C2'-sp$^2$ hybridized side chain derivative in the acylation event, followed by subsequent non-stereoselective functional group manipulation. (K. L. Mikolajczak, C. R. Smith, Weislede. D, T. R. Kelly, J. C. McKenna and Christen. Pa, *Tetrahedron Lett.* 1974, 283-286; K. L. Mikolajczak and C. R. Smith, *J. Org. Chem.* 1978, 43, 4762-4765; S. Hiranuma and T. Hudlicky, *Tetrahedron Lett.* 1982, 23, 3431-3434; S. Hiranuma, M. Shibata and T. Hudlicky, *J. Org. Chem.* 1983, 48, 5321-5326) A notable exception to this strategy used an acyl chain substrate specifically appropriate for homoharringtonine in which the C1"-ester moiety was constrained as a cyclic derivative to allow for acylation with the C1'-electrophile. (T. R. Kelly, R. W. McNutt, M. Montury, N. P. Tosches, K. L. Mikolajczak, C. R. Smith and D. Weisleder, *J. Org. Chem.* 1979, 44, 63-67) This approach was introduced with racemic substrates and has recently evolved to non-racemic examples wherein enantio-enriched side chain substrates were prepared in >10-step sequences. (J. P. Robin, R. Dhal, G. Dujardin, L. Girodier, L. Mevellec and S. Poutot, *Tetrahedron Lett.* 1999, 40, 2931-2934)

Since the most pressing late-stage challenge in the synthesis of the cephalotaxus esters is the efficient attachment of hindered acyl chain derivatives, the present invention employs novel bond angle strain elements to these substrates to enable their use in high yielding acylations of cephalotaxine. Without wishing to be bound by any particular theory, it is believed that constraining a fully α-substituted acyl electrophile to a β-lactone relieves local steric congestion at the electrophilic site; it may also engender greater electrophilicity through induction by imparting higher hybrid orbital s-character.

In certain embodiments, this strategy initially provides a synthesis of deoxyharringtonine. In some embodiments, the synthesis of other members of this alkaloid class, namely anyhydroharringtonine, homoharringtonine, and homodeoxyharringtonine is provided. In other embodiments, the synthesis of novel non-natural cephalotaxus esters is provided.

Anti Proliferative Activity

The completion of the synthesis of deoxyharringtonine and anhydroharringtonine permitted, for the first time, an expanded evaluation of their in vitro cytotoxicity. Following the early screening of the cephalotaxus esters against murine P388 and L1210 cell lines (R. G. Powell, Weislede. D and C. R. Smith, *J. Pharm. Sci.* 1972, 61, 1227), many of the cytotoxic evaluations focused on leukemia and lymphoma, with comparatively fewer reports on activity profiles against solid tumor cell lines. (H. M. Kantarjian, M. Talpaz, V. Santini, A. Murgo, B. Cheson and S. M. O'Brien, *Cancer* 2001, 92, 1591-1605) As a result, deoxyharringtonine, anhydroharringtonine, and various non-natural cephalotaxus ester derivatives were evaluated against a variety of human hematopoietic and solid tumor cell lines (Table 2). (C. Antczak, D. Shum, S. Escobar, B. Bassit, E. Kim, V. E. Seshan, N. Wu, G. L. Yang, O. Ouerfelli, Y. M. Li, D. A. Scheinberg and H. Djaballah, *J. Biomol. Screening* 2007, 12, 521-535; D. Shum, C. Radu, E. Kim, M. Cajuste, Y. Shao, V. E. Seshan and H. Djaballah, *Journal of Enzyme Inhibition and Medicinal Chemistry* (in press)) These include HL-60 (acute promyelocytic leukemia), HL-60/RV+ (a P-glycoprotein over-expressing multidrug resistant HL-60 variant which was selected by continuous exposure to the vinca alkaloid vincristine), JURKAT (T cell leukemia), ALL3 (acute lymphoblastic leukemia recently isolated from a patient treated at MSKCC and characterized as Philadelphia chromosome positive), NCEB1 (Mantle cell lymphoma), JEKO (B cell lymphoma), MOLT-3 (acute lymphoblastic T-cell), SKNLP (neuroblastoma), Y79 (retinoblastoma), PC9 (adenocarcinoma), H1650 (adenocarcinoma), H1975 (adenocarcinoma), H2030 (adenocarcinoma), H3255 (adenocarcinoma), TC71 (Ewing's sarcoma), HTB-15 (glioblastoma), A431 (epithelial carcinoma), HeLa (cervical adenocarcinoma), and WD0082 (well-differentiated liposarcoma).

Several general features are evident in the cytotoxicity data accumulated in the screening campaigns (Table 2). As expected, evaluation of deoxyharringtonine revealed exceedingly potent cytotoxic activity against all of the hematopoietic cell lines tested (HL-60, HL-60/RV+, JURKAT, ALL3, NCEB1, JEKO, MOLT-3); moreover, the alkaloid exhibited similarly high activity against most of the solid tumor cell lines tested (SKNLP, PC9, H1650, H1975, H2030, H3255, A431, HeLa, TC71, HTB-15, WD0082). Interestingly, the late-stage β-lactone variant I-3a (see also Scheme 13-1) exhibited significant cytotoxicity, yet at attenuated levels compared to the parent alkaloid 2, revealing the importance of a hydroxyl group or an H-bond donor functionality at the C2'-position. Surprisingly, the cytotoxicity profile of anhydroharringtonine revealed fairly poor antitumor activity. While an early report noted comparable cytotoxic activity of anhydroharringtonine to that of deoxyharringtonine against murine P388, (Wang, 1992, supra) the present result indicates that the activity of anhydroharringtonine is generally several orders of magnitude lower in human HL-60 tumor cells. This unimpressive potency level of anhydroharringtonine is consistent with the desire for a 2'-hydroxy group or other suitable H-bond donor in the acyl chain to confer adequate activity (vide supra).

TABLE 2

Cytotoxicity of deoxyharringtonine, β-lactone I-3a and anhydroharringtonine.

| | Cmpd | | |
|---|---|---|---|
| Cell Line | 2 IC$_{50}$(μM) | I-3a IC$_{50}$(μM) | 5 IC$_{50}$(μM) |
| HL-60 | 0.02 | 2.68 | 22.7 |
| HL-60/RV+ | 0.22 | 21.8 | >100 |
| JURKAT | 0.04 | 5.71 | 42.99 |
| ALL3 | <0.1** | 1.47 | >100 |
| NCEB1 | 0.07 | 8.62 | >100 |
| JEKO | 0.08 | 10.48 | >100 |
| MOLT-3 | 0.02 | 2.68 | 26.83 |
| SKNLP | <0.1** | 6.46 | 5.34 |
| Y79 | 70.59 | >100 | >100 |
| PC9 | 0.03 | 4.23 | 29.08 |
| H1650 | 0.04 | 4.53 | N.A. |
| H1975 | 0.06 | 8.42 | N.A. |
| H2030 | 0.10 | 7.72 | N.A. |
| H3255 | 0.08 | 5.55 | N.A. |
| A431 | 0.06 | N.A. | N.A. |
| HeLa | 0.04 | N.A. | N.A. |

TABLE 2-continued

Cytotoxicity of deoxyharringtonine, β-lactone
I-3a and anhydroharringtonine.

| Cell Line | Cmpd | | |
|---|---|---|---|
| | 2 IC$_{50}$(μM) | I-3a IC$_{50}$(μM) | 5 IC$_{50}$(μM) |
| TC71 | 0.06 | 12 | >100 |
| HTB-15 | 0.20 | 52 | >100 |
| WD0082 | 0.10 | 5 | >100 |

*Highest compound concentration tested.
**Lowest compound concentration tested and yielding 100% cellular killing.

Multidrug Resistant Cancer

The development of vincristine-resistance in cancer cells, such as HL-60/RV+ (Table 2), is believed to arise from classic multidrug resistance (MDR). This involves the overexpression of ATP-dependent efflux pumps, such as P-glycoprotein (Pgp) and multidrug resistance-associated protein (MRP), leading to expulsion of natural product hydrophobic drugs (e.g., vinca alkaloids, anthracyclines, actinomycin-D, paclitaxel) from the cell. (M. M. Gottesman, T. Fojo and S. E. Bates, *Nat. Rev. Cancer* 2002, 2, 48-58) Previous reports have noted that the activity of homoharringtonine (HHT), the cephalotaxus ester currently being evaluated in clinical trials, is also compromised in MDR human leukemia cells. (Benderra, supra) The susceptibility of MDR cancer cells to different cephalotaxus esters has not been systematically probed previously. Prevention of MDR would significantly improve therapeutic response to this family of chemotherapeutics and extend their use in the clinic. One possible way to achieve this would be to develop anticancer agents that are not substrates for these ATP-dependent transporters, thus overcoming their efflux from cells.

In examining variations in potencies of deoxyharringtonine against this extensive panel of cell lines (Table 2), it is worth noting that its activity against vincristine-resistant HL-60/RV+ cells (IC$_{50}$ 0.22 μM), relative to its non-resistant counterpart HL-60 (IC$_{50}$ 0.02 μM), shows only a ~10-fold decrease in potency. This trend is also reflected in the β-lactone derivative I-3a (albeit with lower absolute cytotoxicity levels). This rather low observed 10-fold resistance index spawned an interest in probing potential molecular design criteria that may offset MDR susceptibility in this class of alkaloids. The current synthetic approach to deoxyharringtonine permits the rapid and versatile attachment of sterically demanding acyl chains onto the cephalotaxine core. Thus, the synthetic strategy to deoxyharringtonine was further extended to the construction of two additional anti-leukemia cephalotaxus ester natural products, namely homoharringtonine and homodeoxyharringtonine, all reported to be potent anti-leukemia alkaloids.

Figure 3:
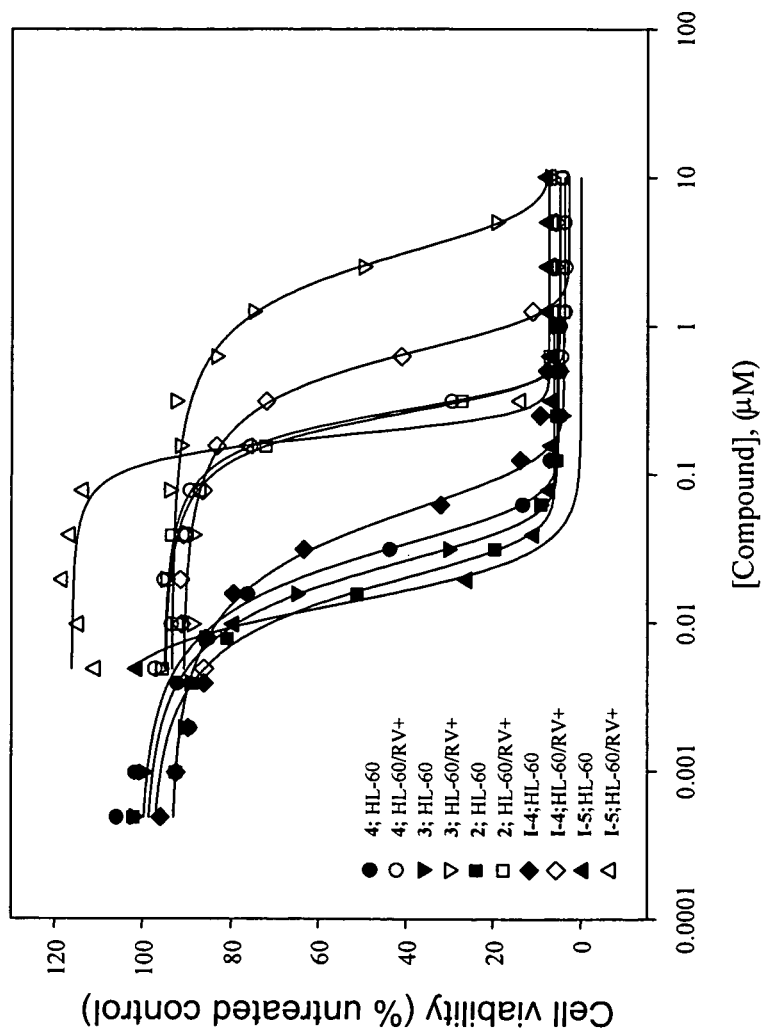
FIGS. 3 and 4 show comparative antitumor effects of cephalotaxus esters against sensitive and vincristine-resistant HL-60 cells.
Figure 4:
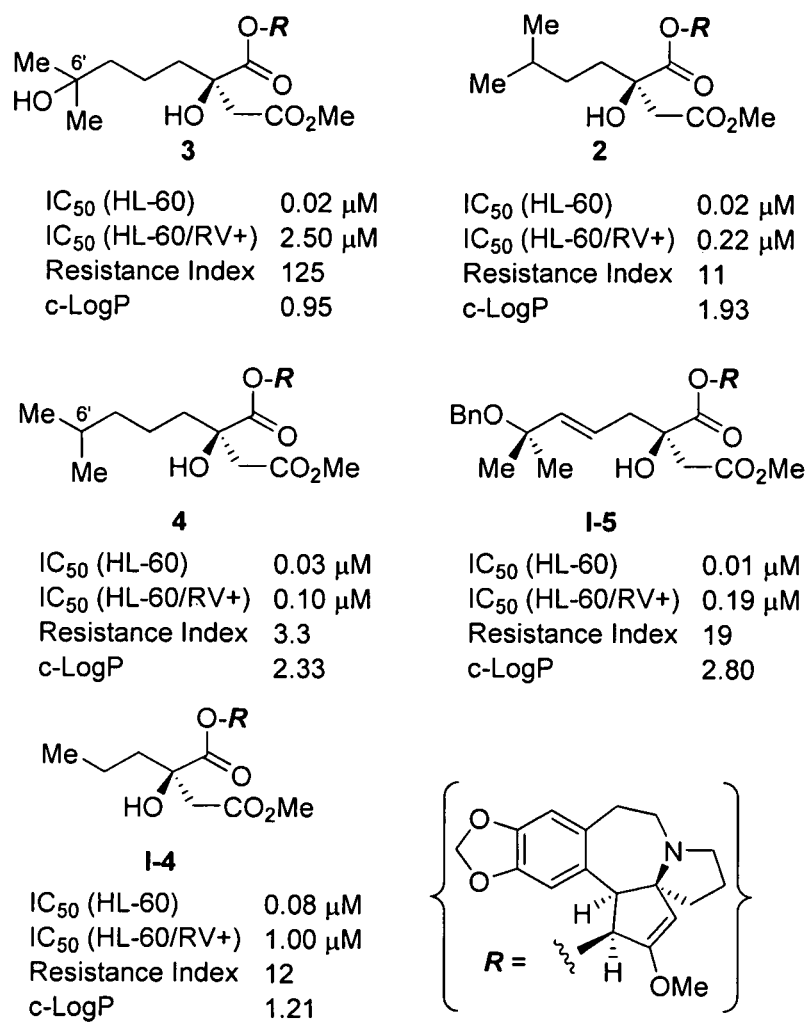

As described above and herein, certain aspects of the present invention provide the syntheses of the natural cephalotaxus esters 2-4 (see FIG. 1) together with two non-natural synthetic analogues, such as benzyldehydrohomoharringtonine I-5 and bis(demethyl)deoxyharringtonine I-4, and further permits their comparative biological evaluation against "sensitive" and MDR tumor cell lines (see FIGS. 3 and 4). When tested against the "sensitive" HL-60 cell line, all were found to be exceedingly potent (IC$_{50}$<0.08 μM). When evaluated against the "resistant" HL60/RV+ cell line, stark differential response levels were observed within this collection of cephalotaxus esters (FIG. 4). Interestingly homoharringtonine (3) displayed a 125-fold decrease in activity toward HL-60/RV+ relative to that of HL-60 (resistance index=125).

By contrast, much lower resistance indices of 11, 3, 12, and 19 were observed with the esters 2, 4, I-5, and I-4, respectively, indicating that these latter natural and non-natural products are significantly less susceptible to MDR. While not wishing to be bound by any particular theory, one possible explanation for the high MDR susceptibility of homoharringtonine (3) is its decreased lipophilicity as a consequence of its acyl chain structure, thereby rendering it a good substrate for the efflux pumps.

The relationship of the calculated lipophilicity values (c-logP) to the resistance indices for the highly potent cephalotaxus esters 2-4, I-5, and I-4 is presented in FIG. 4, wherein compounds with c-logP values greater than 1.2 lead to generally low susceptibility to MDR (i.e., resistance indices ≦19 for the cephalotaxus esters 2, 4, I-5, and I-4). The exception is homoharringtonine (3), exhibiting a relatively low c-logP value (0.95, relatively more polar) to reflect an increased susceptibility to MDR (i.e., resistance index 125). Thus, in certain aspects, the present invention provides for the first time new insights into the contribution of acyl chain structure modification toward overcoming MDR resistance for this class of compounds.

Figure 5:
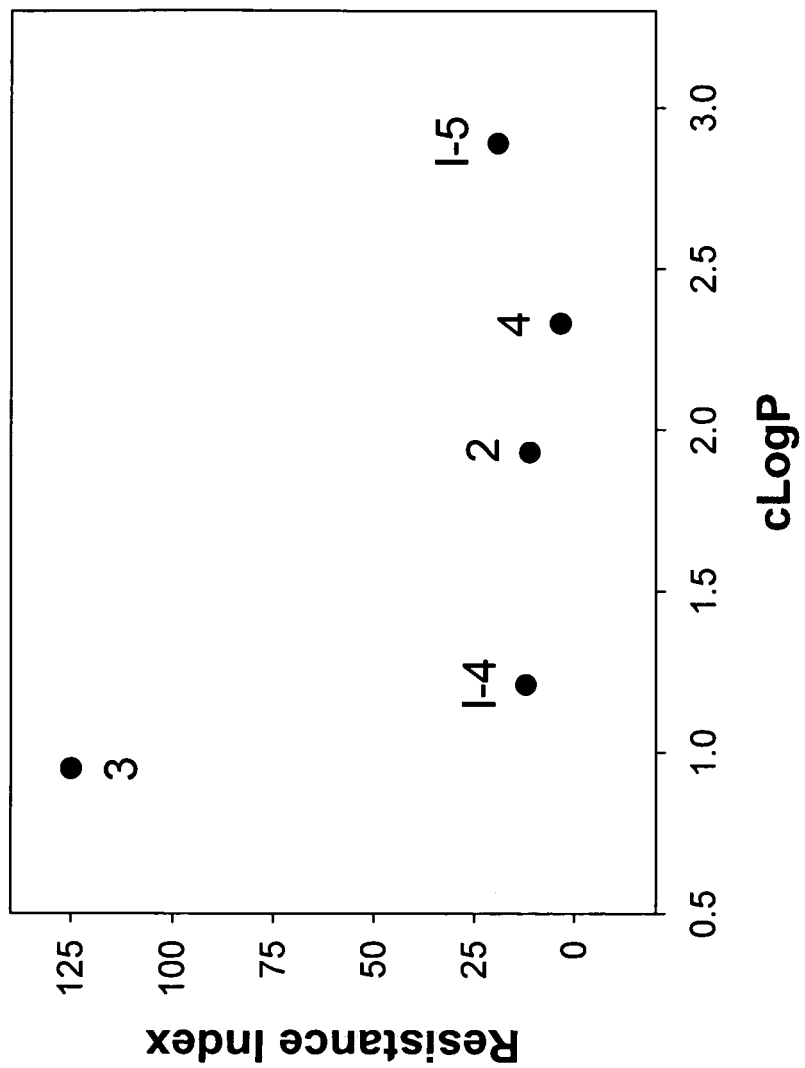
FIG. 5 depicts the correlation of calculated log P values and MDR resistance ratio for selected cephalotaxus esters.

It is worth emphasizing that the only structural difference on the acyl chain between homoharringtonine (3) and homodeoxyharringtonine (4) is a hydroxyl group at the 6'-position (FIG. 4). While only a minor structural perturbation, this 6'-substitution difference drastically affects the lipophilicity of the molecules, ranging from a c-logP value of 0.95 (polar) for 3 to a more hydrophobic compound 4 with a c-logP value of 2.33 (i.e., FIG. 5). Importantly, with a resistance index of only 3 (as in the case with homodeoxyharringtonine 4), both comparative cell lines can be "sensitive" to the compound of interest. As a consequence, this minor structural variation from 3 to 4 has allowed for effective quelling of MDR resistance in this cell line. Given this finding, it is thus surprising that despite its MDR liability, homoharringtonine (3) is employed as the favored cephalotaxus ester for advancement in the clinic, exemplified by a current phase III clinic prospective trial with 3 for use as a combination therapy for chronic myeloid leukemia. (L. Legros, S. Hayette, F. E. Nicolini, S. Raynaud, K. Chabane, J. P. Magaud, J. P. Cassuto and M. Michallet, *Leukemia* 2007, 21, 2204-2206) One practical reason for this may lie in the increased natural abundance of homoharringtonine (3) relative to other cephalotaxus esters. (R. G. Powell, *Phytochemistry* 1972, 11, 1467) Moreover, semisynthetic sources of homoharringtonine have built on the seminal work of Kelly, wherein the 6'-oxygen functionality is a prerequisite for efficient acyl chain attachment to cephalotaxine. (Kelly, 1989, supra) Notably, this semi-synthetic approach is uniquely suited for homoharringtonine (3). Fortunately, the synthetic strategies described herein enable unfettered access to other, more therapeutically viable cephalotaxus esters, for the development of additional compounds for the treatment of leukemia and other proliferative diseases.

Resistance of Vincristine-Sensitive Y79 Retinoblastoma to *Cephalotaxus* Esters

In the initial cytotoxicity evaluation (Table 1), it is also worth highlighting that the Y79 retinoblastoma cell line uniquely showed significant resistance to both deoxyharringtonine (2) and its β-lactone derivative I-3a. Indeed, this selective resistance of Y79 may be a general phenomenon (Table 3) as evaluation with a few other active cytotoxic non-natural synthetic cephalotaxus ester analogues, including the benzyldehydrohomoharringtonine I-5, the β-lactone ester I-1, and bis(demethyl)deoxyharringtonine I-4. All of these compounds behaved similarly to that of deoxyharringtonine (2) and its β-lactone derivative I-3a (cf. Table 2), exhibiting broad spectrum cytoxicity with the exception of the Y79 cell line, to which the molecules were essentially impotent.

TABLE 3

| Cell Line | Cmpd | | |
|---|---|---|---|
| | I-5 IC$_{50}$(μM) | I-1 IC$_{50}$(μM) | I-4 IC$_{50}$(μM) |
| HL-60 | 0.01 | 5.73 | 0.08 |
| HL-60/RV+ | 0.19 | 40.30 | 0.80 |
| JURKAT | 0.03 | 12.01 | 0.19 |
| ALL3 | <0.01 | 4.24 | 0.16 |
| NCEB1 | 0.06 | 39.24 | 0.50 |
| JEKO | 0.08 | 25.1 | 0.56 |
| MOLT3 | 0.01 | 6.41 | 0.06 |
| SKNLP | <0.01 | 10.04 | 0.11 |
| Y79 | >100 | >100 | >100 |
| PC9 | 0.04 | 11.29 | 0.13 |
| TC71 | 0.03 | 24 | 0.20 |
| HTB-15 | 0.10 | 58 | 0.50 |
| WD0082 | 0.05 | 11 | 0.20 |

Though this specific lack of cytotoxicity in Y79 could also be attributed to the overexpression of multidrug resistance genes (MDR), Conway and co-workers have reported the Y79 cell line to be sensitive to vincristine with an IC$_{50}$ value of approx 0.8 μM. (R. M. Conway, M. C. Madigan, F. A. Billson and P. L. Penfold, *Eur. J. Cancer* 1998, 34, 1741-1748) Furthermore, a comparative microarray analysis of the Y79 cell line with normal retinal tissue detected up-regulation of several genes typically found to be markers of stem cell-like characteristics including the mdr gene ABCG2. (G. M. Seigel, A. S. Hackam, A. Ganguly, L. M. Mandell and F. Gonzalez-Fernandez, *Mol. Vis.* 2007, 13, 823-832) Without wishing to be bound by any particular theory, we postulate that perhaps the mechanism of resistance to cephalotaxus esters by Y79 is not entirely mediated through the classical ATP-dependent efflux pumps alone but rather through an as yet unknown mechanism involving stem cell-like characteristics. This is consistent with the hypothesis that the appearance of subsequent tumors in leukemias, brain tumors, breast cancer, lung cancer, as well as many other cancers, is linked to the persistence of cancer stem cells. This observation suggests that designed cephalotaxus esters have the potential to serve as small molecule probes for interrogating the genetic basis of this highly resilient retinoblastoma cell line as well as potentially shedding some light on how to overcome this persistence phenomena in these dormant progenitor cancer stem cells.

The development, optimization, and application of novel synthetic strategies have enabled the synthesis of the potent anti-leukemia agents (−)-deoxyharringtonine (2), (−)-homoharringtonine (3), (−)-homodeoxyharringtonine (4), and (−)-anhydroharringtonine (5). Several advances served as key elements in the preparation of (−)-cephalotaxine (1) and should find general applicability in complex N-heterocycle synthesis. Efforts to advance these synthetic pursuits beyond that of (−)-1 to that of the rare anti-neoplastic C3-O-ester derivatives have led to an efficient non-racemic synthesis of novel cephalotaxus acyl chains. Construction of strained β-lactone intermediates enabled late-stage C3-O-acylation of cephalotaxine, a long-standing challenge in the synthesis of sterically congested bioactive cephalotaxus esters. This technology enabled cytotoxicity screening of natural and non-natural cephalotaxus esters against an expansive array of human hematopoietic and solid tumor cell lines. These evaluations were instrumental in discovering novel non-natural cephalotaxus esters with potent antitumor effects. Moreover, these efforts have uncovered the potential of specific members of this family of alkaloids to overcome resistance in MDR HL-60/RV+ tumor cells through the preparation of acyl chain variants, uniquely made available with by the invention's acyl chain attachment approach. Thus, in one aspect, the present invention provides new avenues for molecular design of these alkaloids to offset multi-drug resistance, offering new lines of chemotherapeutic defense against leukemia and other cancers.

Radiolabeling

It has been found that $^{18}$F-fluoroiodomethane ($^{18}$FCH$_2$I) is a useful intermediate for the fluorination of organic intermediates. See Zheng et al., *J. Nucl. Med.*, 38: 177P (Abs. 761) (1997), the entire contents of which are hereby incorporated by reference. The resulting $^{18}$F-labeled molecules are useful in imaging targeted tissue by clinical positron emission tomography. In certain embodiments, compounds of formulae I, III-A, III-B, III-C, or III-D may be derivatized for radiolabeling via the incorporation of one or more —CH$_2$$^{18}$F groups, or derivatives thereof.

Click Chemistry

"Click chemistry" is well known in the art and is useful in some aspects of the present invention. Click chemistry embodies versatile cycloaddition reactions between azides and alkynes that enable a number of useful applications. Methods of carrying out click chemistry are known in the art, and are described by Kolb, H. C.; Sharpless, K. B., Drug Disc. Today, 2003, 1128-1137; Moses, J. E.; Moorhouse, A. D.; *Chem. Soc. Rev.*, 2007, 1249-1262; the entire contents of each are hereby incorporated by reference. In some embodiments, compounds of formulae I, III-A, III-B, III-C, or III-D contain a azide moiety that may be reacted with an alkyne under conditions suitable for click chemistry. In some embodiments, compounds of formulae I, III-A, III-B, III-C, or III-D contain an alkyne moiety that may be reacted with an azide under conditions suitable for click chemistry. In certain embodiments, the click chemistry reaction appends a functional group to a compound of formulae I, III-A, III-B, III-C, or III-D. In certain embodiments, the click chemistry reaction appends a targeting moiety to a compound of formulae I, III-A, III-B, III-C, or III-D. In certain embodiments, the click chemistry reaction appends a labeling moiety to a compound of formulae I, III-A, III-B, III-C, or III-D.

DEFINITIONS

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C$_3$-C$_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-12}$ (or $C_{1-10}$, $C_{3-12}$) or saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "alkynylene" refers to a bivalent alkynyl group. A substituted alkynylene chain is a polymethylene group containing at least one double bond in which one or more hydrogen atoms are replaced with a substituent. Suitable substituents include those described below for a substituted aliphatic group.

The term "acyl," used alone or a part of a larger moiety, refers to groups formed by removing a hydroxy group from a carboxylic acid. Exemplary acyl groups include, without limitation, $-C(=O)Me$, $-C(=O)Et$, $-C(=O)i$-Pr, $-C(=O)aryl$, and $-C(=O)CH_2F$.

The term "halogen" means F, Cl, Br, or I.

The terms "aralkyl" and "arylalkyl" are used interchangably and refer to alkyl groups in which a hydrogen atom has been replaced with an aryl group. Such groups include, without limitation, benzyl, cinnamyl, and dihyrocinnamyl.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The terms "heteroaralkyl" and "heteroarylalkyl" refer to an alkyl group substituted by a heteroaryl moiety, wherein the alkyl and heteroaryl portions independently are optionally substituted.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary, tertiary, or quaternary amine Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Representative organic amines useful for the formation of base addition salts include ethylamine, diethylamine, ethylenediamine, ethanolamine, diethanolamine, piperazine and the like. (See, for example, Berge et al., supra).

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —$O$—$(CH_2)_{0-4}C(O)OR^\circ$; —$(CH_2)_{0-4}$—$CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ C(O)R^\circ)$; —$N(R^\circ)C(S)R^\circ$; —$(CH_2)_{0-4}N(R^\circ C(O)NR^\circ_2$; —$N(R^\circ)C(S)NR^\circ_2$; —$(CH_2)_{0-4}N(R^\circ)C(O)OR^\circ$; —$N(R^\circ N(R^\circ C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ)_2$; or —$(C_{1-4}$ straight or branched)alkylene)C(O) O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, —(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)$ $OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR'_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)O R^\dagger$, —$C(O)C(O)R^\dagger$, —$C(O)CH_2C(O)$ $R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of $R^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "multidrug resistant" as used herein refers to cells, cell lines, cell states, tumors, neoplasms, cancers of a subject's body, and microbes that are resistant to a particular pharmaceutical agent. Such multidrug resistant cells and/or neoplasms may consist of mixed populations of malignant cells, some of which are drug-sensitive while others are drug-resistant. Chemotherapy may kill drug-sensitive cells, leaving behind a higher proportion of drug-resistant cells which may propogate. Similarly, subpopulations of multidrug resistant microbes may survive chemotherapy and multiply, in some cases passing genetic information to neighboring microbes to confer resistance.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Uses

Compounds of formulae I, III-A, III-B, III-C, or III-D may be used in vitro or in vivo. The inventive compounds may be particularly useful in the treatment of neoplasms or other proliferative diseases in vivo. However, inventive compounds described above may also be used in vitro for research or clinical purposes (e.g., determining the susceptibility of a patient's disease to a compound of formulae I, III-A, III-B, III-C, or III-D, researching the mechanism of action, elucidating a cellular pathway or process). In certain embodiments, the neoplasm is a benign neoplasm. In other embodiments, the neoplasm is a malignant neoplasm. Any cancer may be treated using compounds of formulae I, III-A, III-B, III-C, or III-D. Other proliferative diseases that may be treated using compounds of formulae I, III-A, III-B, III-C, or III-D include inflammatory disease, autoimmune disease, diabetic retinopathy, and infectious disease.

In certain embodiments, the malignancy is a hematological malignancy. Hematological malignancies are types of cancers that affect the blood, bone marrow, and/or lymph nodes. Examples of hematological malignancies that may be treated using compounds of formulae I, III-A, III-B, III-C, or III-D include, but are not limited to, acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma. In certain embodiments, compounds of formulae I, III-A, III-B, III-C, or III-D are used to treat multiple myeloma, glioblastoma, epithelial carcinoma, cervical adenocarcinoma, or well-differentiated liposarcoma. In certain particular embodiments, the cancer is relapsed and/or refractory multiple myeloma. In other embodiments, compounds of formula I are used to treat chronic lymphocytic leukemia (CLL). In certain embodiments, compounds of formulae I, III-A, III-B, III-C, or III-D are used to treat acute lymphoblastic leukemia (ALL). In certain embodiments, compounds of formulae I, III-A, III-B, III-C, or III-D are used to treat acute myelogenous leukemia (AML). In certain embodiments, the cancer is a chronic myeloid leukemia (CML). In certain embodiments, the cancer is cutaneous T-cell lymphoma. In other embodiments, the cancer is peripheral T-cell lymphoma. Compounds of formulae I, III-A, III-B, III-C, or III-D may also be used to treat a refractory or relapsed malignancy. In certain embodiments, the cancer is a refractory and/or relapsed hematological malignancy. In certain embodiments, the cancer is multidrug resistant. For example, the cancer may be resistant to a particular chemotherapeutic agent.

Other cancers besides hematological malignancies may also be treated using compounds of formulae I, III-A, III-B, III-C, or III-D. In certain embodiments, the cancer is a solid tumor. Exemplary cancers that may be treated using compounds of formulae I, III-A, III-B, III-C, or III-D include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few. In certain embodiments, compounds of formulae I, III-A, III-B, III-C, or III-D are used to treat pancreatic cancer. In certain embodiments, compounds of formulae I, III-A, III-B, III-C, or III-D are used to treat prostate cancer. In certain specific embodiments, the prostate cancer is hormone refractory prostate cancer.

Compounds of formulae I, III-A, III-B, III-C, or III-D may also be used to treat and/or kill cells in vitro. In certain embodiments, a cytotoxic concentration of a compound of formulae I, III-A, III-B, III-C, or III-D is contacted with the cells in order to kill them. In other embodiments, a sublethal concentration of a compound of formulae I, III-A, III-B, III-C, or III-D is used to treat the cells. In certain embodiments, the concentration of a compound of formulae I, III-A, III-B, III-C, or III-D ranges from 0.01 nM to 100 nM. In certain embodiments, the concentration of a compound of formulae I, III-A, III-B, III-C, or III-D ranges from 0.1 nM to 50 nM. In certain embodiments, the concentration of a compound of formulae I, III-A, III-B, III-C, or III-D ranges from 1 nM to 10 nM. In certain embodiments, the concentration of a compound of formulae I, III-A, III-B, III-C, or III-D ranges from 1 nM to 10 nM, more particularly 1 nM to 5 nM.

Any type of cell may be tested or killed with a compound of formulae I, III-A, III-B, III-C, or III-D. The cells may be derived from any animal, plant, bacterial, or fungal source. The cells may be at any stage of differentiation or development. In certain embodiments, the cells are animal cells. In certain embodiments, the cells are vertebrate cells. In certain embodiments, the cells are mammalian cells. In certain embodiments, the cells are human cells. The cells may be derived from a male or female human in any stage of development. In certain embodiments, the cells are primate cells. In other embodiments, the cells are derived from a rodent (e.g., mouse, rat, guinea pig, hamster, gerbil). In certain embodiments, the cells are derived from a domesticated animal such as a dog, cat, cow, goat, pig, etc. The cells may also be derived from a genetically engineered animal or plant, such as a transgenic mouse.

The cells used may be wild type or mutant cells. The cells may be genetically engineered. In certain embodiments, the cells are normal cells. In certain embodiments, the cells are hematological cells. In certain embodiments, the cells are white blood cells. In certain particular embodiments, the cells are precursors of white blood cells (e.g., stem cells, progenitor cells, blast cells). In certain embodiments, the cells are neoplastic cells. In certain embodiments, the cells are cancer cells. In certain embodiments, the cells are derived from a hematological malignancy. In other embodiments, the cells are derived from a solid tumor. For example, the cells may be derived from a patient's tumor (e.g., from a biopsy or surgical excision). In certain embodiments, the cells are derived from a blood sample from the subject or from a bone marrow biopsy. In certain embodiments, the cells are derived from a lymph node biopsy. Such testing for cytotoxicity may be useful in determining whether a patient's disease will respond to a particular therapy. Such testing may also be useful in determining the dosage needed to treat the malignancy. This testing of the susceptibility of a patient's cancer to a compound of formulae I, III-A, III-B, III-C, or III-D would prevent the unnecessary administration of drugs with no effect to the patient. The testing may also allow the use of lower dose of an inventive compound If the patient's cancer is particularly susceptible to the compound.

In other embodiments, the cells are derived from cancer cells lines. In certain embodiments, the cells are from hematological malignancies such as those discussed herein. Human leukemia cell lines include U937, HL-60, HL-60/RV+ (a P-glycoprotein over-expressing multidrug resistant HL-60 variant which was selected by continuous exposure to the vinca alkaloid vincristine), THP-1, Raji, CCRF-CEM, ALL3 (acute lymphoblastic leukemia recently isolated from a patient treated at Memorial Sloan Kettering Cancer Center and characterized as Philadelphia chromosome positive), and Jurkat. Exemplary CLL cell lines include JVM-3 and MEC-2. Exemplary myeloma cells lines include MM1.S, MM1.R (dexamethasone-resistant), RPMI8226, NCI-H929, and U266. Exemplary lymphoma cell lines include NCEB1 (Mantle cell lymphoma), JEKO (B cell lymphoma), Karpas, SUDH-6, SUDH-16, L428, KMH2, and Granta mantle lymphoma cell line. In certain embodiments, the cells are AML cells or multiple myeloma (CD138$^+$) cells. In certain embodiments, the cells are hematopoietic stem or progenitor cells. For example, in certain embodiments, the cells are hematopoietic progenitor cells such as CD34$^+$ bone marrow cells. In certain embodiments, the cells are MOLT-3 (acute lymphoblastic T-cell), SKNLP (neuroblastoma), PC9 (adenocarcinoma), H1650 (adeocarcinoma), H1975 (adeocarcinoma), H2030 (adeocarcinoma), H3255 (adeocarcinoma), TC71 (Ewing's sarcoma), HTP-15 (glioblastoma), A431 (epithelial carcinoma), HeLa (cervical adenocarcinoma), or WD0082 (well-differentiated liposarcoma) cells. In some embodiments, the cells are HL-60/RV+ cells. In certain embodiments, the cell lines are resistant to a particular chemotherapeutic agent. In certain particular embodiments, the cell line is resistant to homoharringtonine.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In certain embodiments, inventive compounds are useful in treating a subject in clinical remission, where the subject has been treated by surgery or has limited unresected disease.

In certain embodiments, inventive compounds are useful in treating multidrug resistant cancer. In some embodiments, such compounds are selected from:

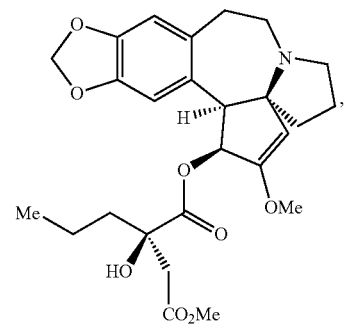

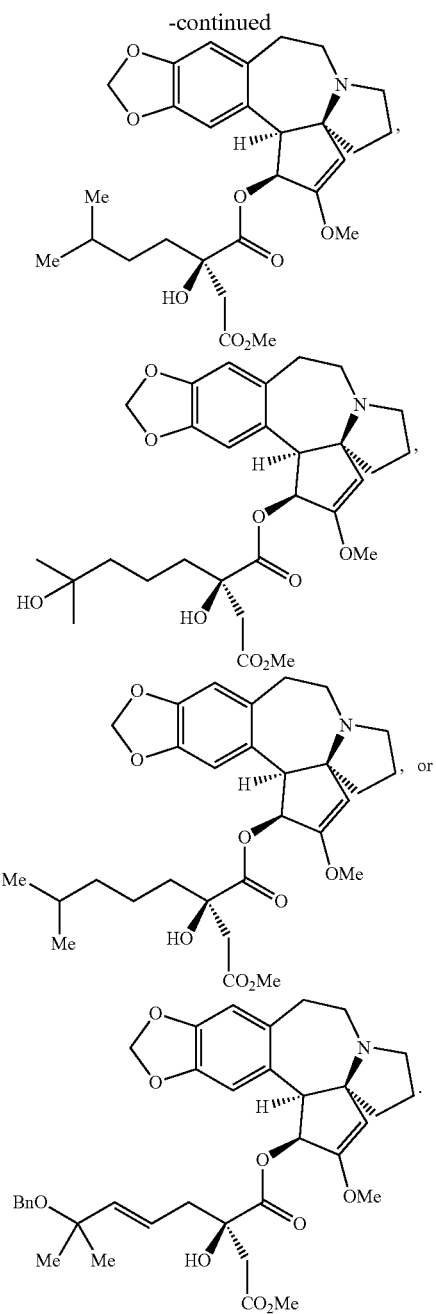

It will be appreciated that, as natural products, cephalotaxus esters may possess antimicrobial activity. In certain embodiments, compounds of formulae I, III-A, III-B, III-C, or III-D are useful in treating microbial infection. In some embodiments, compounds of formulae I, III-A, III-B, III-C, or III-D induce antimicrobial activity in a subject with a pathological microbe infection. In certain embodiments, the subject is an animal. In certain embodiments, the subject is human. In some embodiments, compounds of formulae I, III-A, III-B, III-C, or III-D induce antimicrobial in cells of a biological sample. In certain embodiments, the microbe is bacterial. In certain embodiments, the microbe is fungal.

In another aspect, the invention provides a method of treating infectious disease in a subject comprising administering to the subject a therapeutically effective amount of a compound of formulae I, III-A, III-B, III-C, or III-D. In some embodiments, the subject is human. In certain embodiments, the infection is caused by a bacterium. In certain embodiments, the infection is caused by a fungus. In certain embodiments, the infection is caused by a parasite.

Formulations

Inventive compounds may be combined with a pharmaceutically acceptable excipient to form a pharmaceutical composition. In certain embodiments, the pharmaceutical composition includes a pharmaceutically acceptable amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits including the combination of a compound of formulae I, III-A, III-B, III-C, or III-D and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

The entire contents of all references cited above and herein are hereby incorporated by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

EXEMPLIFICATION

Unless otherwise noted, operations related to synthetic chemistry were carried out as described under general procedures.
General Procedures.

All reactions were performed in flame-dried modified Schlenk (Kjeldahl shape) flasks fitted with a glass stopper under a positive pressure of argon, unless otherwise noted. Air- and moisture-sensitive liquids and solutions were transferred via syringe. Organic solutions were concentrated by rotary evaporation below 30° C. Flash column chromatography was performed employing 230-400 mesh silica gel. Thin-layer chromatography (analytical and preparative) was performed using glass plates pre-coated to a depth of 0.25 mm with 230-400 mesh silica gel impregnated with a fluorescent indicator (254 nm).
Materials Dichloromethane (DCM), tetrahydrofuran (THF), acetonitrile, diethyl ether, hexane, toluene, and benzene were purified by passage through two packed columns of neutral alumina under an argon atmosphere. Methanol was distilled from magnesium at 760 Torr. Dimethylformamide (DMF), isopropanol (IPA), and ethanol were dried over 4 Å molecular sieves. Trifluoromethanesulfonic anhydride ($Tf_2O$) was distilled from phosphorus pentoxide at 760 Ton.
Instrumentation Infrared (IR) spectra were obtained using a Perkin Elmer Spectrum BX spectrophotometer or a Bruker Tensor 27 referenced to a polystyrene standard. Data are presented as the frequency of absorption ($cm^{-1}$). Proton and carbon-13 nuclear magnetic resonance ('H NMR or $^{13}C$ NMR) spectra were recorded on a Varian 400, a Varian 500, Varian Inova 500 NMR, or a Bruker Avance III spectrometer; chemical shifts are expressed in parts per million ($\delta$ scale) downfield from tetramethylsilane and are referenced to the residual protium in the NMR solvent ($CHCl_3$: $\delta$ 7.26 for $^1H$ NMR, $\delta$ 77.16 for $^{13}C$ NMR; $CD_3OD$: $\delta$ 3.30 for $^1H$ NMR, $\delta$ 49.00 for $^{13}C$ NMR). Data are presented as follows: chemical shift, multiplicity (s=singlet, bs=broad singlet, d=doublet, bd=broad doublet, t=triplet, m=multiplet and/or multiple resonances), coupling constant in Hertz (Hz), integration, assignment.

Example 1

Alcoholic extracts of the powdered leaves and stems of *Cephalotaxus* genera yield cephalotaxine (1, FIG. 1) as the most abundant alkaloid constituent, (L. Huang and Z. Xue, *Alkaloids* 1984, 23, 157-226; W. W. Paudler, J. McKay and G. I. Kerley, *J. Org. Chem.* 1963, 28, 2194) whose structure was unambiguously verified by X-ray crystallographic analysis. (R. G. Powell, Weislede. D, C. R. Smith and I. A. Wolff, *Tetrahedron Lett.* 1969, 4081; D. J. Abraham, Rosenste. Rd and E. L. McGandy, *Tetrahedron Lett.* 1969, 4085; S. K. Arora, R. B. Bates and R. A. Grady, *J. Org. Chem.* 1974, 39, 1269-1271; S. K. Arora, R. B. Bates, R. A. Grady, G. Germain, J. P. Declercq and R. G. Powell, *J. Org. Chem.* 1976, 41, 551-554) While cephalotaxine (1) accounts for approximately 50% of the mass of the crude alkaloid extract mixture, many minor constituents have also been identified. Among these are several rare C3-ester derivatives, including complex variants such as deoxyharringtonine (2) (K. L. Mikolajczak, C. R. Smith and R. G. Powell, *Tetrahedron* 1972, 28, 1995), homoharringtonine (3) (R. G. Powell, D. Weisleder, C. R. Smith, Jr. and W. K. Rohwedder, *Tetrahedron Lett.* 1970, 815-818), homodeoxyharringtonine (4) (I. Takano, I. Yasuda, M. Nishijima, Y. Hitotsuyanagi, K. Takeya and H. Itokawa, *J. Nat. Prod.* 1996, 59, 965-967), and anhydroharringtonine (5) (D. Z. Wang, G. E. Ma and R. S. Xu, *Acta pharmaceutica Sinica* 1992, 27, 173-177).

Early biological evaluations of these alkaloids revealed that several *Cephalotaxus* esters demonstrate acute toxicity toward various murine leukemia, murine lymphoma, and human epidermoid carcinoma cells. (H. Morita, M. Arisaka, N. Yoshida and J. Kobayashi, *Tetrahedron* 2000, 56, 2929-2934; Powell, et al., supra) Deoxyharringtonine (2), homoharringtonine (3), and homodeoxyharringtonine (4) exhibit $IC_{50}$ levels of 7.5, 17, and 56 ng/mL, respectively, against P388 leukemia cells. Likewise, anhydroharringtonine (5) was reported to induce 98% growth inhibition of P388 leukemia cells at 1 µg/mL, a level comparable to that of deoxyharringtonine (2). (D. Z. Wang, G. E. Ma and R. S. Xu, *Acta pharmaceutica Sinica* 1992, 27, 178-184) By contrast, cephalotaxine (1) itself was found to be biologically inactive. (M. A. J. Miah, T. Hudlicky and J. W. Reed, *Alkaloids* 1998, 51, 199-269) The cytotoxic properties of the cephalotaxus esters arise from reversible inhibition of protein synthesis (M. T. Huang, *Mol. Pharmacol.* 1975, 11, 511-519) via induction of rapid breakdown of the polyribosome, with concomitant release of the polypeptide chain. (M. Fresno, A. Jimenez and D. Vazquez, *Eur. J. Biochem.* 1977, 72, 323-330) The remarkable anti-leukemia activity of several *Cephalotaxus* esters spawned intense investigations into their therapeutic potential. Clinical studies were first performed in the mid-1970s in China, where the seeds of *Cephalotaxus* plants had long been used in traditional medicine. These results prompted Phase I clinical evaluation of homoharringtonine (3) in the US in 1981, (S. S. Legha, M. Keating, S. Picket, J. A. Ajani, M. Ewer and G. P. Bodey, *Cancer Treatment Reports* 1984, 68, 1085-1091) advancing to more recent Phase II studies. (H. M. Kantarjian, M. Talpaz, V. Santini, A. Murgo, B. Cheson and S. M. O'Brien, *Cancer* 2001, 92, 1591-1605) While difficulties in production, coupled with its hematologic toxicity and susceptibility to multidrug resistance (MDR), (Z. Benderra, H. Morjani, A. Trussardi and M. Manfait, *Leukemia* 1998, 12, 1539-1544) have hindered the development of 3, it is still viewed as a useful drug for the treatment of chronic myeloid leukemia in combination therapy. (Kantarjian, et al., supra)

Cephalotaxine (1) has received considerable and enduring attention in the arena of total synthesis. Several elegant syntheses of 1 have been reported over the past three decades. The racemic approaches have embodied several key transformations, including Nazarov cyclization, (J. Auerbach and S. M. Weinreb, *J. Am. Chem. Soc.* 1972, 94, 7172) photo-stimulated $S_{RN}1$ cyclization, (M. F. Semmelhack, B. P. Chong, R. D. Stauffer, T. D. Rogerson, A. Chong and L. D. Jones, *J. Am. Chem. Soc.* 1975, 97, 2507-2516) Claisen rearrangement, (S. Yasuda, T. Yamada and M. Hanaoka, *Tetrahedron Lett.* 1986, 27, 2023-2026; S. Yasuda, Y. Yamamoto, S. Yoshida and M. Hanaoka, *Chem. Pharm. Bull.* 1988, 36, 4229-4231) oxidative ring contraction, (M. E. Kuehne, W. G. Bornmann, W. H. Parsons, T. D. Spitzer, J. F. Blount and J. Zubieta, *J. Org. Chem.* 1988, 53, 3439-3450) acylnitroso Diels-Alder cycloaddition, (T. P. Burkholder and P. L. Fuchs, *J. Am. Chem. Soc.* 1988, 110, 2341-2342; T. P. Burkholder and P. L. Fuchs, *J. Am. Chem. Soc.* 1990, 112, 9601-9613) trans-annular N-conjugate addition, (X. D. Lin, R. W. Kavash and P. S. Mariano, *J. Am. Chem. Soc.* 1994, 116, 9791-9792; X. D. Lin, R. W. Kavash and P. S. Mariano, *J. Org. Chem.* 1996, 61, 7335-7347) intramolecular alkyne hydroamination, (Y. Koseki, H. Sato, Y. Watanabe and T. Nagasaka, *Org. Lett.* 2002, 4, 885-888) and reductive ring expansion of tetrahydroisoquinoline intermediates. (W. D. Z. Li and Y. Q. Wang, *Org. Lett.* 2003, 5, 2931-2934; W. D. Z. Li and B. C. Ma, *J. Org. Chem.* 2005, 70, 3277-3280) Non-racemic routes have featured electrophilic aromatic substitution, (N. Isono and M. Mori, *J. Org. Chem.* 1995, 60, 115-119) Heck arylation, (L. F. Tietze and H. Schirok, *Angew. Chem. Int. Ed.* 1997, 36, 1124-1125; L. F. Tietze and H. Schirok, *J. Am. Chem. Soc.* 1999, 121, 10264-10269) Pummerer-electrophilic aromatic substitution cascade, (H. Ishibashi, M. Okano, H. Tamaki, K. Maruyama, T. Yakura and M. Ikeda, *J. Chem. Soc., Chem. Commun.* 1990, 1436-1437; M. Ikeda, M. Okano, K. Kosaka, M. Kido and H. Ishibashi, *Chem. Pharm. Bull.* 1993, 41, 276-281; M. Ikeda, S. A. A. El Bialy, K. Hirose, M. Kotake, T. Sato, S. M. M. Bayomi, I. A. Shehata, A. M. Abdelal, L. M. Gad and T. Yakura, *Chem. Pharm. Bull.* 1999, 47, 983-987) and acid catalyzed ring expansion of cyclobutanol derivatives. (L. Planas, J. Perard-Viret and J. Royer, *J. Org. Chem.* 2004, 69, 3087-3092)

Figure 6:
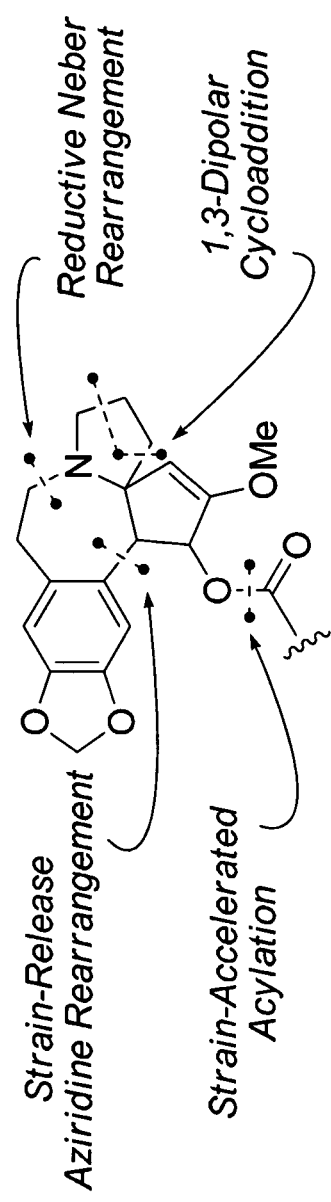
FIG. 6 depicts a retrosynthetic analysis and summary of key steps in the synthesis of cephalotaxus esters.

On the other hand, the significance of the complex cephalotaxus esters (e.g., 2-5) extends beyond that of 1 on several levels, the most prominent of which being their exceedingly potent anti-proliferative properties. Moreover, the scarcity of these complex ester derivatives from the natural source is far more pronounced than that of 1, wherein complex cephalotaxus esters are typically attainable in only <0.1% of the plant dry weight. Thus, a goal in the work described herein was the establishment of a synthetic approach to the bioactive cephalotaxus esters by a route completely distinct from previous efforts. (J. D. Eckelbarger, J. T. Wilmot and D. Y. Gin, *J. Am. Chem. Soc.* 2006, 128, 10370-10371) Several key elements in the synthetic strategy include (FIG. 6): (1) introduction of the nitrogen atom via Neber rearrangement; (2) construction of the benzazepine core via the strain-release rearrangement of N-vinyl-2-aryl aziridines; (3) assembly of the spiro-fused pyrrolidine core via 1,3-dipolar cycloaddition of azomethine ylides derived from vinylogous amides; and (4) synthesis of strained variants of advanced side chain intermediates to facilitate late-stage cephalotaxine acylation. Notably, the latter three elements had not been applied to complex natural product synthesis, yet ultimately played critical roles in the non-racemic syntheses of the cephalotaxus esters 2-5.

The success of the synthetic endeavors described herein enabled extensive cytotoxicity evaluation of several advanced natural and non-natural compounds with an array of well established human hematopoietic and solid tumor cell lines. Potent cytotoxicity was observed in several cell lines previously not challenged with these alkaloids. Moreover, comparative cytotoxicity assays reveal the potential of synthetic structural modification of this family of alkaloids to modulate susceptibility to multi-drug resistance.

Results and Discussion

Dihydro[3]benzazepine construction Via Strain-Release Rearrangement.

The first challenge addressed in the synthesis of cephalotaxine (1) focused on construction of its seven-membered N-heterocycle. Strain-release [3,3]-sigmatropic rearrangements, in which a high energy three-membered ring is incorporated into the 1,5-diene system of the substrate, have been widely used for the construction of 7-membered rings. Although the all-carbon divinyl cyclopropane rearrangement has received the most attention, the heterocyclic epoxide-, thiirane-, and aziridine-containing variants are also documented. (T. Hudlicky, R. Fan, J. W. Reed and K. G. Gadamasetti, *Org. React.* 1992, 41, 1-133) However, the aziridine-to-azepine version of this transformation (W. Lwowski, T. J. Maricich and T. W. Mattingly, Jr., *J. Am. Chem. Soc.* 1963, 85, 1200-1202; E. L. Stogryn and S. J. Brois, *J. Org. Chem.* 1965, 30, 88; J. C. Pommelet and J. Chuche, *Tetrahedron Lett.* 1974, 3897-3898; M. Zora, *J. Org. Chem.* 2005, 70, 6018-6026; A. Hassner, R. Dcosta, A. T. McPhail and W. Butler, *Tetrahedron Lett.* 1981, 22, 3691-3694; L. Viallon, O. Reinaud, P. Capdevielle and M. Maumy, *Tetrahedron Lett.* 1995, 36, 4787-4790; U. M. Lindstrom and P. Somfai, *J. Am. Chem. Soc.* 1997, 119, 8385-8386) has only been sporadically used in target-directed synthesis. In this context, adaptation to the synthesis of benzazepines and heterocyclic variants thereof have focused on N-aryl-2-vinyl aziridines to form dihydro[1]benzazepines. (P. Scheiner, *J. Org. Chem.* 1967, 32, 2628; H. P. Figeys and R. Jammar, *Tetrahedron Lett.* 1980, 21, 2995-2998; H. P. Figeys and R. Jammar, *Tetrahedron Lett.* 1981, 22, 637-640)

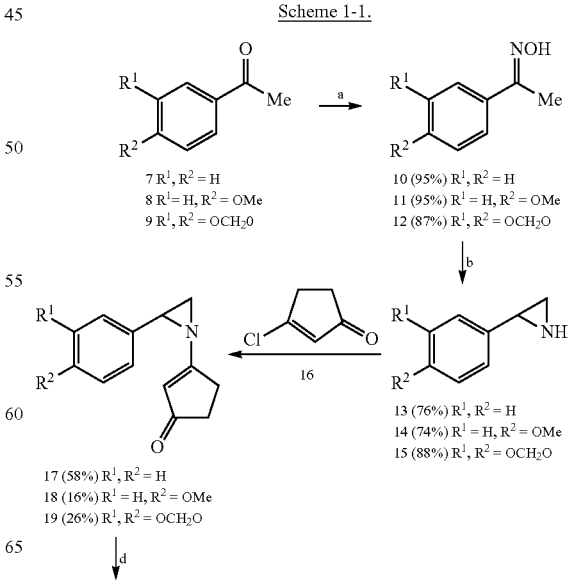

Scheme 1-1.

-continued

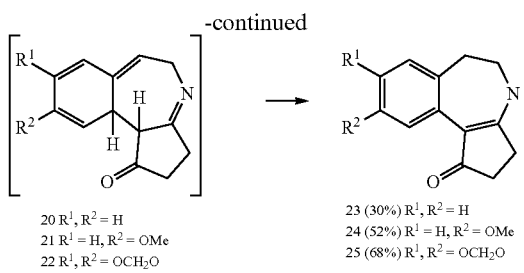

20 R¹, R² = H
21 R¹ = H, R² = OMe
22 R¹, R² = OCH₂O 23 (30%) R¹, R² = H
24 (52%) R¹ = H, R² = OMe
25 (68%) R¹, R² = OCH₂O (a) HONH₂•HCl, NaOH, EtOH, H₂O, 60-80° C.; (b) i-Pr₂NH, LiAlH₄, THF, 60° C.;
(c) Et₃N, THF, 23-60° C.; (d) Cs₂CO₃, 1,4-dioxane, 100-150° C.

However, the [3,3]-sigmatropic rearrangement of N-vinyl-2-aryl aziridines to form dihydro[3]benzazepines, such as that present in 1, had not been reported. Thus, investigations into this reaction commenced with the synthesis of a few N-vinyl-2-aryl aziridines (Scheme 1-1) via the condensation of acetophenone derivatives 7/8/9 with hydroxylamine hydrochloride to provide the corresponding oximes (10/11/12) in high yields (95%/95%/87%), respectively. (T. Harada, T. Ohno, S. Kobayashi and T. Mukaiyama, *Synthesis* 1991, 1216-1220) Each of these oximes was exposed to LiAlH₄ and i-Pr₂NH at elevated temperatures to induce reductive Neber rearrangement, (H. Tanida, T. Okada and K. Kotera, *Bull. Chem. Soc. Jpn.* 1973, 46, 934-938) furnishing the corresponding aziridines (13/14/15) in good yields (76%/74%/88%), and providing a series of substituted 2-aryl aziridines available for N-vinylation. This was most conveniently accomplished via addition-elimination with the readily available alkene electrophile 3-chloro-2-cyclopentenone (16), prepared in one step from the reaction of 1,3-cyclopentanedione with oxalyl chloride. (J. W. Ullrich, F. T. Chiu, T. Tinerharding and P. S. Mariano, *J. Org. Chem.* 1984, 49, 220-228) Condensation of the two substrates 13 and 16 with expulsion of HCl provided the vinyl aziridine 17 in moderate yield (58%). By comparison, coupling of aziridine 14 or 15 with chloroenone 16 proceeded with significantly diminished efficiency, resulting in only a 16% and 26% isolated yield of vinyl aziridines 18 and 19, respectively.

Nevertheless, access to these three 2-aryl-N-vinyl aziridines 17-19 allowed for investigations into the feasibility of the ring expansion rearrangement. An optimized procedure for the thermal rearrangement of aziridine 17 involved its heating in a dilute [10 mM] solution in 1,4-dioxane at 180° C., in the presence of Cs₂CO₃, to provide the desired dihydro[3]benzazepine 23 in low yield (30%). Variation in the aromatic substituents within the aziridine substrates was found to have a significant effect on the efficiency of the rearrangement. For example, the p-methoxyacetophenone-derived aziridine 18 was subjected to the same thermal rearrangement conditions, resulting in its transformation to the dihydro[3]benzazepine 24 with significantly increased efficiency (52%) compared to that of its predecessor 17→23. Likewise, rearrangement of aziridine 19, incorporating the 3,4-methylenedioxy-substituted aryl group, resulted in the formation of dihydro[3]benzazepine 25 in the most efficient example of the rearrangement thus far (68%). As expected, the rearrangement proceeded with complete regioselectivity. (W. T. Dixon, *Tetrahedron Lett.* 1968, 189; V. K. Dauksas, G. V. Purvaneckas, E. B. Udrenaite, V. L. Gineityte and A. V. Barauskaite, *Heterocycles* 1981, 15, 1395-1404) Rationales for the favorable effect of electronically activating groups on the aromatic ring in the rearrangement (i.e., 18/19→24/25) may arise from compression of the HOMO-LUMO gap in a concerted [3,3]-sigmatropic rearrangement. Conversely, a stepwise ionic mechanism for rearrangement might also be enhanced by initial aziridine opening to form a stabilized benzylic cation (vide infra).

Scheme 2-1.

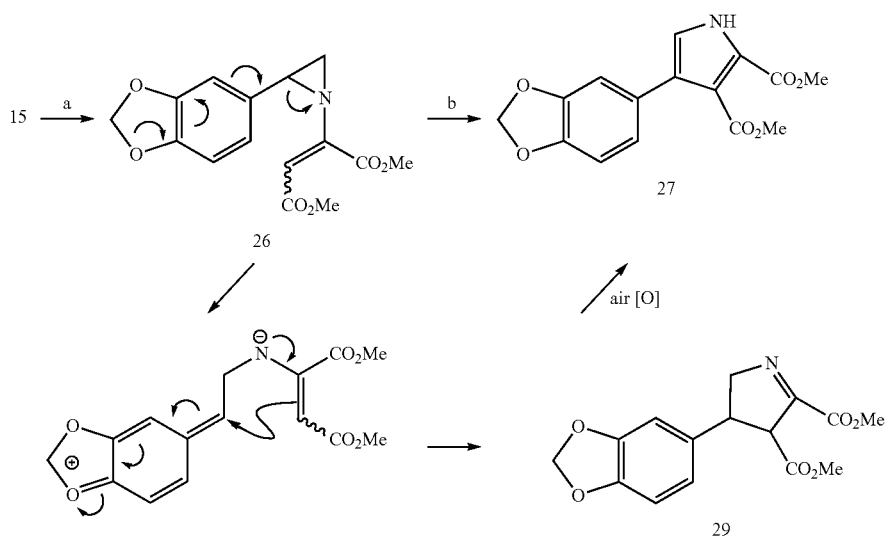

(a) DMAD, PhH, 23° C., 57%; (b) Cs₂CO₃, 1,4-dioxane, 100° C., 92%.

Although the rearrangements of aziridines 17-19 all provided the corresponding dihydro[3]benzazepine products, one exception to this trend was uncovered with the N-vinyl-2-arylaziridine substrate 26 (Scheme 2-1), derived from the conjugate addition of aziridine 15 into DMAD (57%). This substrate exhibited a clear propensity for a stepwise rearrangement pathway, as heating led exclusively to the formation of the pyrrole 27. Its formation can be rationalized by initial aziridine opening in 26 to form the highly reactive p-quininone methide zwitterion 28, presumably due to the enhanced electron-deficient character of its N-vinyl substituent. Subsequent 5-exo cyclization by the C-nucleophile onto the benzylic position provided the dihydropyrrole 29, which underwent facile air oxidation to provide the substituted pyrrole 27.

Scheme 3-1.

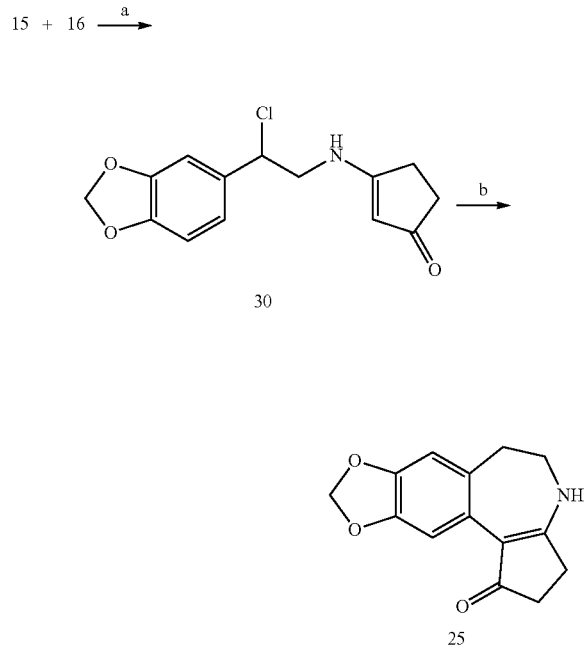

(a) Et₃N, THF, 60° C., 64%; (b) Cs₂CO₃, 1,4-dioxane, 100° C., 68%.

Despite this final example of pyrrole formation (27, Scheme 2-1), the majority of examples of successful dihydro [3]benzazepine formation (23-25, Scheme 1-1) boded well for the synthesis of cephalotaxine (1). However, access to the tricyclic dihydro[3]benzazepine 25 was compromised by the low yielding condensation of aziridine 15 with β-chloroenone 16, reflecting a trend in which π-donor substituents on the aromatic ring elicit a detrimental effect on the addition-elimination step. Further investigation of this transformation revealed that the N-vinylaziridine adduct 19 has an increased susceptibility to nucleophilic attack at its benzylic position, resulting in post-coupling chloride-mediated aziridine cleavage. Thus, a minor variation in the protocol to prepare dihydro [3]benzazepine 25 was implemented (Scheme 3-1). The addition of aziridine 15 into chloroenone 16 was conducted at elevated temperature, resulting in the isolation of benzylic chloride 30 (64%). Treatment of β-chloroamine 30 with Cs₂CO₃ in THF led to the generation of the desired dihydro [3]benzazepine 25 (68%), presumably via reformation of the aziridine functionality in situ and subsequent rearrangement. This sequence provided a means for large scale access to dihydro[3]benzazepine 25, facilitating investigation into the challenge of pyrrolidine construction.

Pyrrolidine Construction Via azomethine ylide 1,3-dipolar cycloaddition.

The azomethine ylide 1,3-dipolar cycloaddition is a powerful tool for the synthesis of highly substituted pyrrolidine rings within many complex alkaloid targets. (E. Vedejs and F. G. West, Chem. Rev. 1986, 86, 941-955; K. V. Gothelf and K. A. Jorgensen, Chem. Rev. 1998, 98, 863-909; C. Najera and J. M. Sansano, Curr. Org. Chem. 2003, 7, 1105-1150; W. H. Pearson and P. Stoy, Synlett 2003, 903-921; I. Coldham and R. Hufton, Chem. Rev. 2005, 105, 2765-2809) Many methods exist for the generation of these transient 4π-electron dipoles, both in stabilized and non-stabilized forms, wherein a common approach to the formation of the latter involves the desilylation of iminium salt intermediates. This strategy, first developed by Vedejs, (Vedejs, 1986, supra; E. Vedejs and G. R. Martinez, J. Am. Chem. Soc. 1979, 101, 6452-6454) has seen use in a variety of complex molecule syntheses and has spawned a number of variants. In particular, a method of Padwa involves N-alkylation of vinylogous imidates with trimethylsilylmethyl electrophiles followed by desilylation. (A. Padwa, G. Haffmanns and M. Tomas, Tetrahedron Lett. 1983, 24, 4303-4306) Recently, we disclosed a complementary strategy to generate non-stabilized azomethine ylides from N—CH₂TMS substituted tertiary vinylogous amides via initial O-activation followed by desilylation. (M. T. Epperson and D. Y. Gin, Angew. Chem. Int. Ed. 2002, 41, 1778)

This method was found to be suitable for the generation of pyrrolidine structures bearing a fully substituted carbon at the α-position, a structure that directly maps onto the C5-spiro-fused pyrrolidine substructure within cephalotaxine (1). These efforts commenced with N-alkylation of dihydro[3] benzazepine 25 (Scheme 4-1), accomplished with TMSCH₂I to afford the tertiary vinylogous amide 31 (62%). Carbonyl O-activation of vinylogous amide 31 was performed by treatment with Tf₂O. This was followed by the sequential addition of DMAD as an activated dipolarophile and tetrabutylammonium triphenylsilyldifluorosilicate (TBAT) (A. S. Pilcher, H. L. Ammon and P. Deshong, J. Am. Chem. Soc. 1995, 117, 5166-5167) as the desilylating agent. The cycloadduct 33, incorporating the C5-spiro-fused pyrrolidine core of cephalotaxine, was isolated in 53% yield, indicating successful generation and cycloaddition of the azomethine ylide 32.

Scheme 4-1.

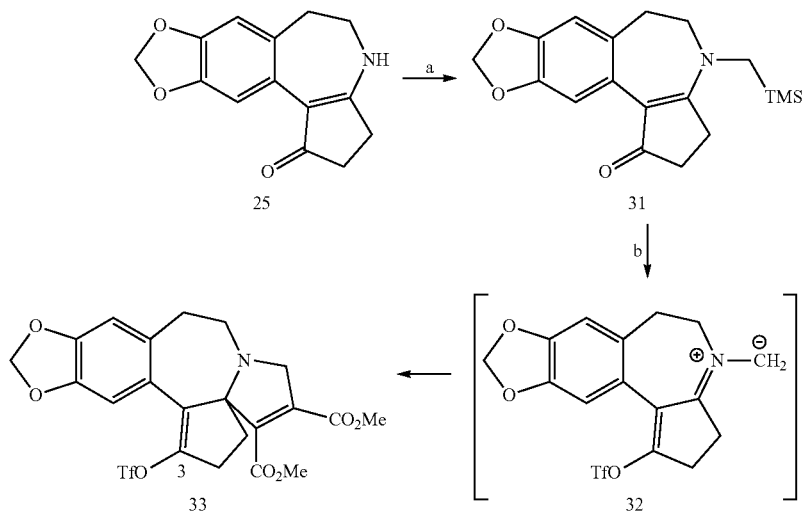

(a) TMSCH$_2$I, NaH, THF, 50° C., 62%; (b) Tf$_2$O; DMAD; TBAT, CH$_2$Cl$_2$, 23° C., 53%.

Azomethine Ylide Generation from vinylogous amides Via Sequential O-sulfonylation and Nucleophilic Exchange.

The successful synthesis of pyrrolidine 33 provided rapid access to the complete pentacyclic core of cephalotaxine. Moreover, a vinyl triflate moiety was installed at C3, the position of acyl chain attachment in the cephalotaxus esters. While a number of avenues could have been pursued to use this functionality as a direct precursor for installation of the acyl side chain, there existed the possibility of adapting this key cycloaddition step not only to pyrrolidine formation, but also for concomitant installation of the acyl chain.

onstrated to engage in electrophilic aromatic substitution reactions at the enol triflate carbon center. (I. L. Baraznenok, V. G. Nenajdenko and E. S. Balenkova, *Tetrahedron* 1998, 54, 119-128; I. L. Baraznenok, V. G. Nenajdenko and E. S. Balenkova, *Eur. J. Org. Chem.* 1999, 937-941) That intermediates such as 34 are susceptible to nucleophilic attack suggested the possibility of its interception with an external nucleophile (Nu) prior to azomethine ylide formation and cycloaddition (34→35→36→38). This presented the prospect of directly introducing the cephalotaxus ester side chain in the pyrroli- Scheme 5-1.

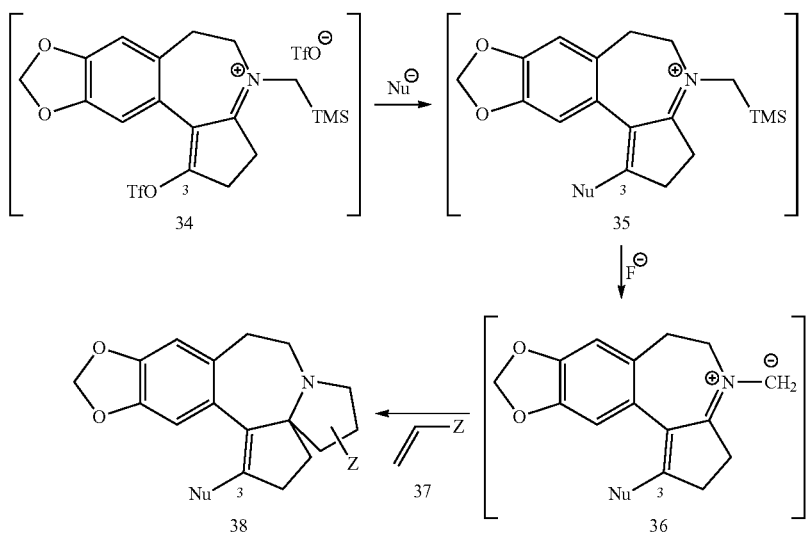

Implicit in this vinylogous amide activation protocol is the initial formation of the C3-vinylogous iminium triflate 34 (Scheme 5-1). Vinylogous iminium triflates have been demdine-forming event. Additionally, this pursuit may find general utility in the preparation of differentially functionalized pyrrolidines from vinylogous amide precursors.

TABLE 1-1

Azomethine ylide generation from vinylogous amides via sequential O-sulfonylation and nucleophilic exchange.

| Entry | Nu⁻ | Cycloadduct | Yield (%) |
|---|---|---|---|
| 1 | Bu₄NI | 40 (Nu = I) | 52 |
| 2 | Bu₄NBr | 41 (Nu = Br) | 45 |
| 3 | Bu₄NCl | 42 (Nu = Cl) | 52 |

The hypothesis was evaluated with a simple model vinylogous amide 39 (Table 1-1), which was activated with Tf$_2$O, Subsequent introduction of an activated dipolarophile (DMAD), a variety of halide nucleophiles, and TBAT, led to rapid cycloaddition at 23° C. Importantly, the external halide nucleophiles were successfully incorporated into the cycloadducts 40-42 (entries I-3), thereby validating the feasibility of this in situ nucleophilic exchange protocol for azomethine ylide cycloadditions.

Scheme 6-1.

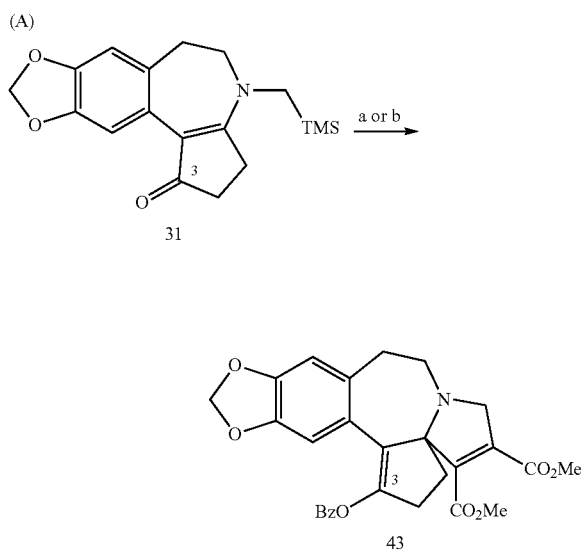

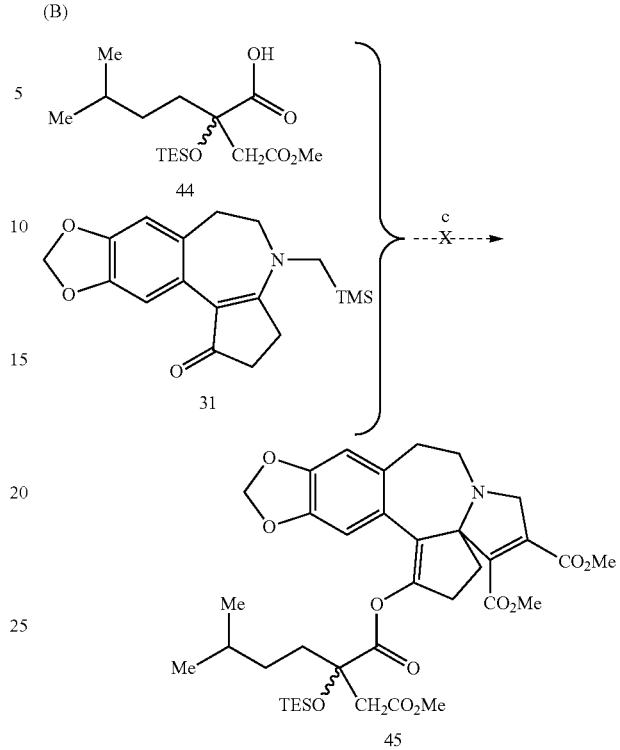

(a) Tf$_2$O; PhCO$_2$H•NEt$_3$; DMAD; TBAT, CH$_2$Cl$_2$, 23° C., 35%; (b) Tf$_2$O; PhCO$_2$Cs; DMAD; TBAT, CH$_2$Cl$_2$, 23° C., 64%; (c) 31, Tf$_2$O; 44, Cs$_2$CO$_3$; DMAD; TBAT, CH$_2$Cl$_2$, 23° C.

The concept was further extended to that of the cephalotaxus esters, involving exchange with external carboxylate nucleophiles. Activation of the dihydro[3]benzazepine-derived vinylogous amide 31 (Scheme 6-1A) with Tf$_2$O was performed to provide the corresponding transient triflyl-imidate. Prior to ylide formation via desilylation, triethylammonium benzoate was introduced to generate the corresponding acyl-imidate, which underwent subsequent azomethine ylide formation with TBAT and cycloaddition with DMAD to provide the C3-substituted cycloadduct 43 in 35% yield. A significantly improved efficiency for this reaction was achieved with cesium benzoate as the nucleophilic species, affording the cycloadduct 43 in 64% yield. While this promising result presented a convenient method for transient nucleophilic exchange in an azomethine ylide cycloaddition, the ultimate purpose for which it was developed, that of introduction of an intact cephalotaxus ester side chain in the cycloaddition event, met with no success. For example, the racemic cesium carboxylate 44 (Scheme 6-1B) was prepared from itaconic acid via a modification of the sequence of Weinreb (J. Auerbach, T. Ipaktchi and S. M. Weinreb, *Tetrahedron Lett.* 1973, 4561-4564), and was introduced as a nucleophilic exchange reagent for the azomethine ylide cycloaddition with vinylogous amide precursor 31. Unfortunately, none of the desired cycloadduct 45, incorporating the deoxyharringtonine acyl chain, was detected in this operation, despite extensive attempts at optimization.

Asymmetric Synthesis of (−)-cephalotaxine (1). Azomethine ylide Generation and cycloaddition Via O-acylation of vinylogous amides.

While the aziridine-rearrangement/dipolar-cycloaddition reactions (Schemes 5-1 and 10-1) remained at the heart of the synthetic plan, the goal of installing the acyl chain in an operation concomitant with azomethine ylide cycloaddition was set aside in favor of pursuing an asymmetric construction of the cephalotaxine core 1 as the initial target. Investigations on this front were initiated to determine the responsiveness of the 1,3-dipolar cycloaddition reaction to elements of relative stereochemical control in the formation of the C5-spiro ring fusion. Thus, a chiral azomethine ylide such as 46 (Scheme 7-1), incorporating proximal C1 and C2 substituents, was anticipated to bias facial-selective approach of the dipolarophile. (Exhaustive investigation of azomethine ylide precursors incorporating only a C2 group led to no diastereoselectivity in the cycloaddition.) Such a substrate was envisioned to take the form of β-chloroenone 53 (Scheme 8-1), which could be prepared in non-racemic form from D-ribose.

The early incarnation of the synthesis of chloro-enone 53 relied on a key olefination sequence first reported by Borchardt and coworkers, (S. M. Ali, K. Ramesh and R. T. Borchardt, *Tetrahedron Lett.* 1990, 31, 1509-1512; A. Blaser and J. L. Reymond, *Helv. Chim. Acta* 1999, 82, 760-768; C. K. Chu, Y. H. Jin, R. O. Baker and J. Huggins, *Bioorg. Med. Chem. Lett.* 2003, 13, 9-12) and indeed provided initial quantities of β-chloroenone 53 for investigation. (Eckelbarger, supra) However, we found the above-mentioned olefination reaction to be unreliable in efforts to secure larger workable quantities of this intermediate. As a result, a second generation synthesis of 53 was developed (Scheme 8-1). The selectively protected D-ribofuranose 48 (J. S. Yadav, S. Pamu, D. C. Bhunia and S. Pabbaraja, *Synlett* 2007, 992-994) was treated with triphenylphosphonium methylide to effect C1 olefination (75%). This was followed by C4 oxidation (SO$_3$.Pyr) to afford enone 49 (88%). Addition of vinyl magnesium bromine to ketone 49 proceeded stereoselectively (8:1 dr) via Cram chelation control to provide the allylic alcohol 50 (93%), whose 1,6-diene functionality underwent ring closing olefin metathesis (Grubbs-II) to afford the cyclopentene 51 (95%). (Y. H. Jin, P. Liu, J. N. Wang, R. Baker, J. Huggins and C. K. Chu, *J. Org. Chem.* 2003, 68, 9012-9018) Regioselective chloroselenylation of the alkene within 51 followed by selenide oxidation and elimination afforded the chlorocyclopentene 52 (98%). Finally, silyl ether deprotection revealed a vicinal diol (99%), which underwent periodate-mediated oxidative cleavage to furnish the chiral β-chloroenone 53 (90%) in a robust and scalable synthetic sequence.

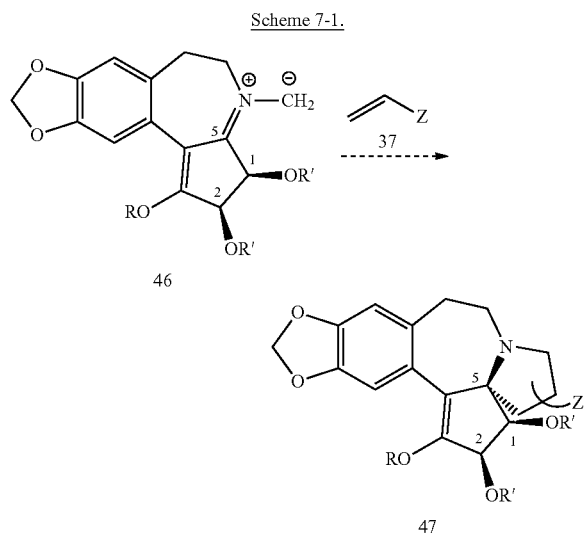

Scheme 7-1.

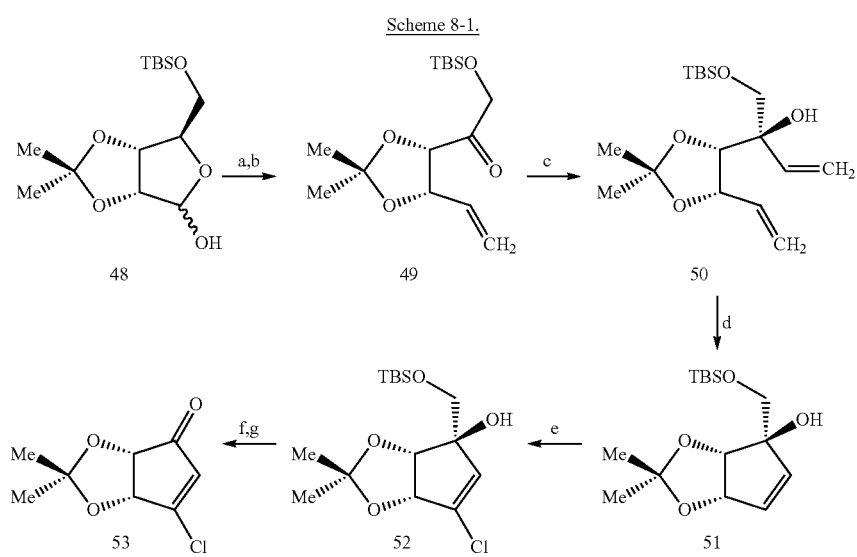

Scheme 8-1.

(a) KHMDS, Ph$_3$PMeBr, THF, 60° C., 75%; (b) DMSO, Et$_3$N, SO$_3$•Pyr, CH$_2$Cl$_2$, 23° C., 88%; (c) CH$_2$=CHMgBr, THF, -78→23° C., 93%, dr 8:1; (d) Grubbs-II, CH$_2$Cl$_2$, 23° C., 95%; (e) PhSeCl, MeCN, 0° C.; m-CPBA, Et$_3$N, CH$_2$Cl$_2$, 0→23° C.; 98%; (f) TBAF, THF, 23° C., 99%; (g) NaIO$_4$, CH$_2$Cl$_2$, H$_2$O, 23° C., 90%.

Scheme 9-1.

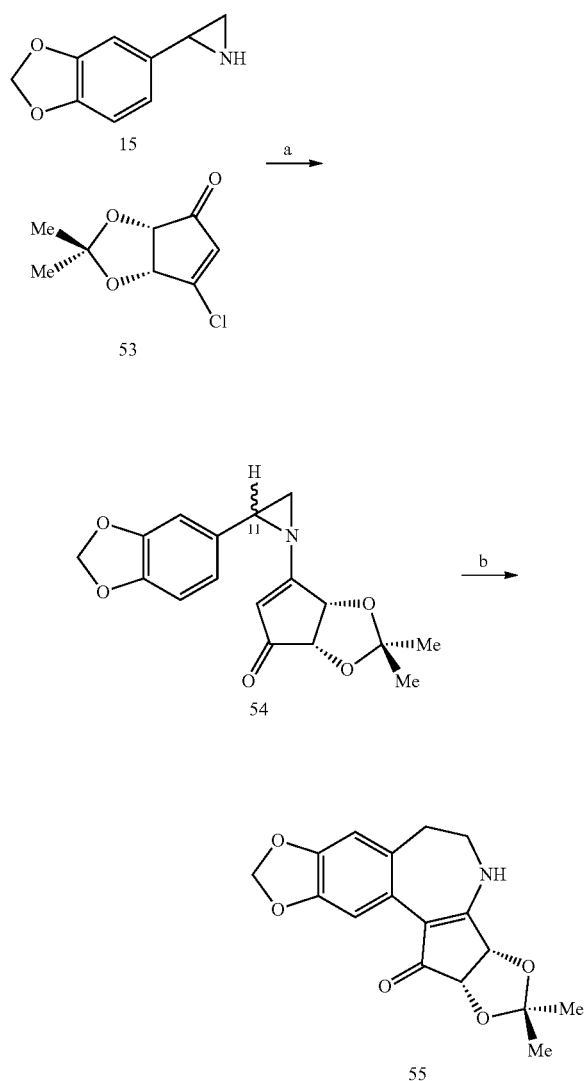

a Et₃N, THF, 23° C., 85%;
b Cs₂CO₃, 1,4-dioxane, 100° C., 76%.

Use of β-chloroenone 53 in the synthesis of the dihydro[3]benzazepine core of cephalotaxine (1) involved addition-elimination with the racemic aziridine nucleophile 15 at ambient temperature (Scheme 9-1). This afforded a 1:1 diastereomeric mixture of the N-vinyl aziridine 54 (85%), interestingly with no evidence of chloride induced aziridine opening (cf. 30, Scheme 3-1). Heating of a dilute solution of 54 in 1,4-dioxane led to efficient rearrangement to afford the dihydro[3]benzazepine 55 (76%).

It is worth noting that although the rearrangement precursor 54 existed as a 1:1 mixture of diastereomers, the formation of 55 proceeded in >50% yield. This implies that the C11-R diastereomer 54a (Scheme 10-1) likely proceeded through an aziridine rupture step prior to azepine formation. For example, if the rearrangement occurred in a concerted fashion, a strain-release variant involving an internal aziridine ring would necessitate an endo-disposed boat-like transition state (Scheme 10-1), such as 56a for the C11-R-diastereomer 54a, or 56b for the C11-S-diastereomer 54b. While the concerted conversion of the C11-S-diastereomer 54b to 57 via the transition state 56b appears reasonable, direct rearrangement of the C11-R-diastereomer 54a is unlikely, given the severe steric interaction between the aryl ring and the isopropylidene ketal in transition state 56a. As a consequence, the C11-R-diastereomer 54a could relieve this strain by first forming the p-quinone methide zwitterion 58 followed by re-closure to the C11-S-diastereomer 54b prior to sigmatropic rearrangement via 56b. Conversely, if a stepwise ionic mechanism is invoked, both aziridine diastereomers may open to the common p-quinone methide zwitterion 58, followed by 7-exo-trig cyclization to afford the azepine 57.

Scheme 10-1.

85 86
-continued
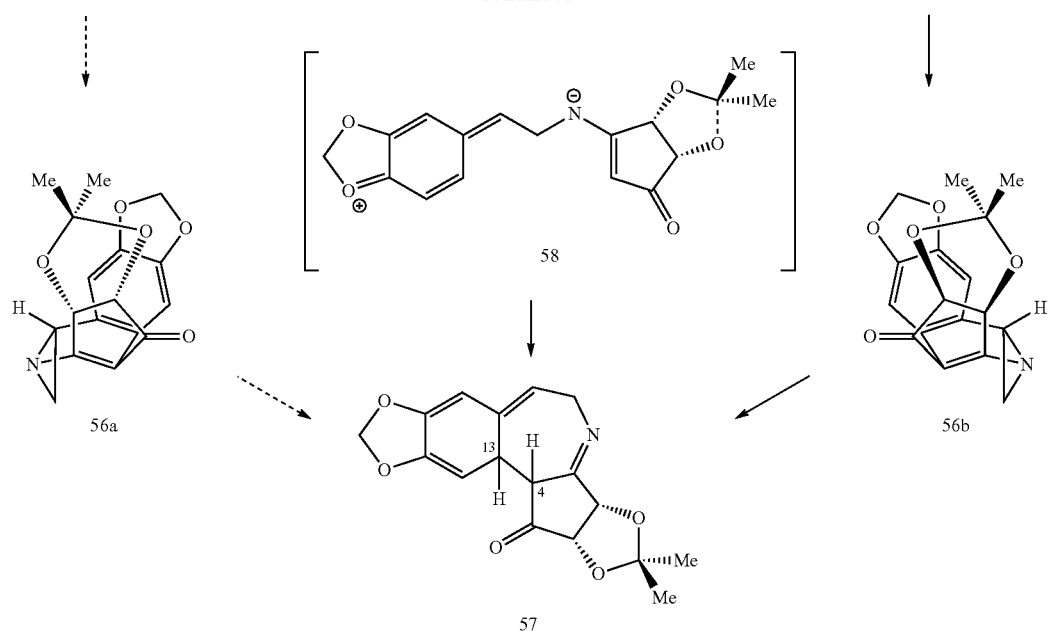
Scheme 11-1.
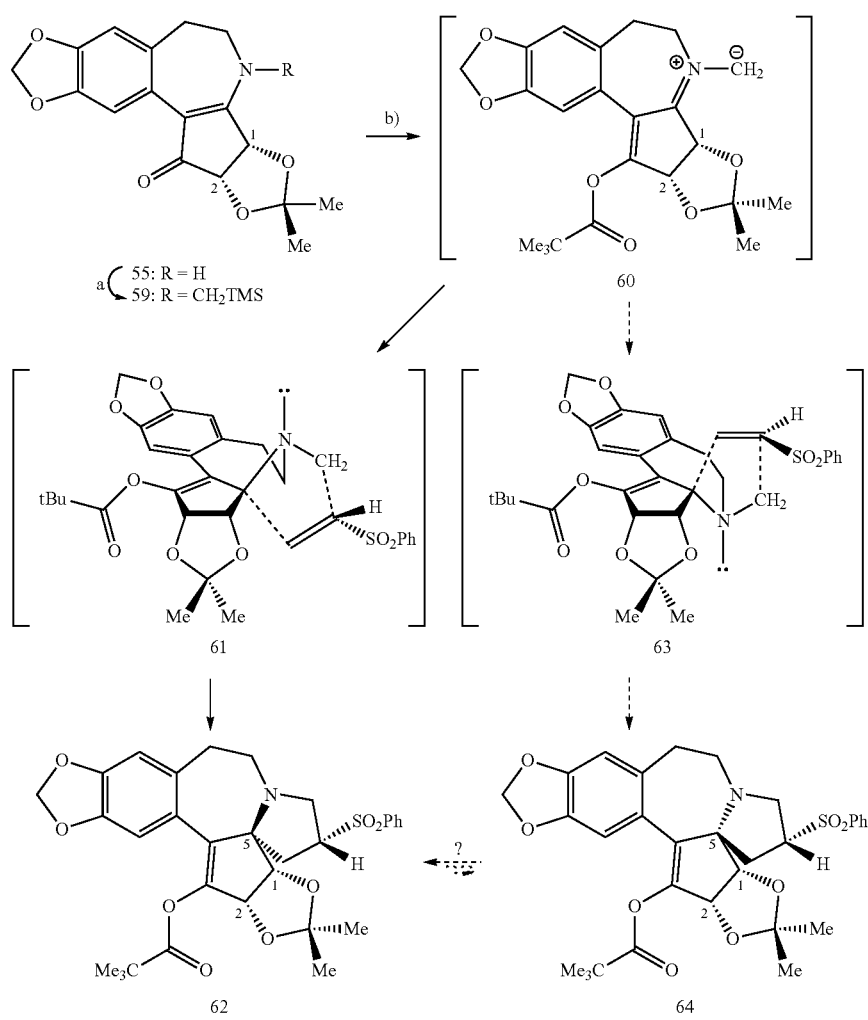

-continued

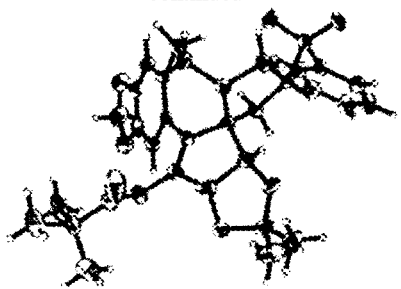

62 (X-ray)

a Cs$_2$CO$_3$, TMSCH$_2$I, MeCN, 23° C., 75%;

b Me$_3$CCOCl, AgOTf; PhSO$_2$CH═CH$_2$; TBAT, CH$_2$Cl$_2$, -45 → 23° C., 77%.

At this stage, advancement of the pentacyclic dihydro[3]benzazepine 55 to cephalotaxine (1) relied on the 1,2-di-O-isopropylidene substituent to serve as a chiral controller in establishing the stereoselectivity of the key azomethine ylide cycloaddition. The dihydro[3]benzazepine 55 (Scheme 11-1) was N-alkylated with TMSCH$_2$I to afford the tertiary vinylogous amide 59. O-Activation of the vinylogous amide group in 59 was then investigated with an electrophilic agent distinct from Tf$_2$O in order to preclude any possibility of nucleophilic exchange involving the transient iminium intermediate (vide supra). As a result, the highly reactive acyl electrophile, pivaloyl triflate, generated in situ by the reagent combination of pivaloyl chloride and AgOTf, (F. Effenberger, J. K. Eberhard and A. H. Maier, J. Am. Chem. Soc. 1996, 118, 12572-12579) proved suitable for this purpose. Subsequent desilylation with TBAT led to azomethine ylide formation (60) and cycloaddition with phenyl vinyl sulfone, affording the spiro-fused pyrrolidine 62 (77%) as a single constitutional stereoisomer. This high level of stereoselectivity in the cycloaddition signals the effectiveness of the C$_1$-C$_2$ isopropylidene ketal as a stereodetermining element, albeit with an unanticipated result.

With the formation of the putative non-stabilized azomethine ylide 60, the phenylvinyl sulfone dipolarophile was initially thought to approach the dipole face distal to the isopropylidene ketal (i.e., 63) in an early transition state. This would lead to the generation of a C5-S cycloadduct 64, which would be appropriate for the synthesis of ent-(1) as an enantiomeric model system. However, the sole product of cycloaddition, 62, possessed the C5-R configuration, verified by single crystal X-ray analysis. While this unexpected outcome provided a convenient means to access the natural enantiomer of cephalotaxine from naturally abundant D-ribose, the reason for the stereochemical outcome is unclear. Favorable bias for transition state 61 over 63 could be rationalized in a late transition state model where the nitrogen atom is significantly pyramidalized. (D. H. Ess and K. N. Houk, J. Am. Chem. Soc. 2007, 129, 10646) As a consequence, transition structure 61, with α-approach of the dipolarophile, would lead to a smaller net dipole given that the developing nitrogen lone pair is oriented opposite to that of the electronegative oxygen atoms of the isopropylidene ketal. By contrast, β-approach of the dipolarophile (63) would lead to an enhancement of a net dipole, despite a more sterically forgiving arrangement of atoms. This dipole moment rationalization, be it in a concerted cycloaddition or a stepwise ionic mechanism, is of course predicated on a kinetically controlled reaction. Indeed, one cannot discount the possibility of thermodynamic selection via either a reversible cycloaddition process, or post-cycloaddition C5-epimerization pathways such as reversible trans-annular ring fragmentation. Unfortunately, these hypotheses could not be explored since the C5-S diastereomer 64 could not be detected.

The remaining sequence in the non-racemic synthesis of (−)-cephalotaxine (1) involved functional group manipulations of hexacyclic cycloadduct 62 (Scheme 12-1). Reductive desulfurization of 62 to produce pyrrolidine 65 (74%) proceeded with SmI$_2$ in the presence of HMPA (H. Kunzer, M. Stahnke, G. Sauer and R. Wiechert, Tetrahedron Lett. 1991, 32, 1949-1952; D. Craig, P. S. Jones and G. J. Rowlands, Synlett 1997, 1423-1425) with 10 equiv of t-BuOH as a proton source to avoid rupture of the pyrrolidine ring via elimination. Subsequent experimentation revealed that the pivaloate enol ester moiety in 65 was recalcitrant to both hydrolysis and hydrogenation. As a result, reductive cleavage of the enol ester in 65 was performed with Schwartz' reagent (J. Schwartz and J. A. Labinger, Angew. Chem. Int. Ed. 1976, 15, 333-340; N. Cenac, M. Zablocka, A. Igau, J. P. Majoral and A. Skowronska, J. Org. Chem. 1996, 61, 796-798) to provide the enol 66 (99%), which was then re-acylated with benzyl chloroformate and KHMDS to provide the enol benzyl carbonate 67 (86%). Interestingly, when Et$_3$N was used as base for this transformation, N-acylation occurred with concomitant 13-elimination to afford enone 68. Differentiation of the C1 and C2 oxygen substituents in 67 was then initiated with isopropylidene removal (99%). Regioselective derivatization of the corresponding diol proved challenging, as several attempts at regioselective silylation, acylation, and alkylation with numerous reagent combinations were unsuccessful. The only suitable derivatization protocol involved the Lewis acid catalyzed acylation procedure of Clarke and co-workers, (P. A. Clarke, R. A. Holton and N. E. Kayaleh, Tetrahedron Lett. 2000, 41, 2687-2690; P. A. Clarke, N. E. Kayaleh, M. A. Smith, J. R. Baker, S. J. Bird and C. Chan, J. Org. Chem. 2002, 67, 5226-5231; P. A. Clarke, P. L. Arnold, M. A. Smith, L. S. Natrajan, C. Wilson and C. Chan, Chem. Commun. 2003, 2588-2589) in which treatment of the C1, C2-diol with Boc$_2$O and Yb(OTf)$_3$, necessarily in its polyhydrated form, led to selective C1-O-acylation. Subsequent C2-oxidation using IBX furnished enone 69 (50%, from 67), allowing for CrCl$_2$-mediated reductive deoxygenation of the Boc carbonate and benzylcarbonate hydrogenolysis to provide the enol 70 (42%, 2 steps). Sequential methyl enol ether derivatization of the C2 ketone and stereoselective reduction of the C3 enol functionality with NaBH$_4$ (Isono, supra) concluded the synthesis of (−)-cephalotaxine (1) (Eckelbarger, supra).

Scheme 12-1.

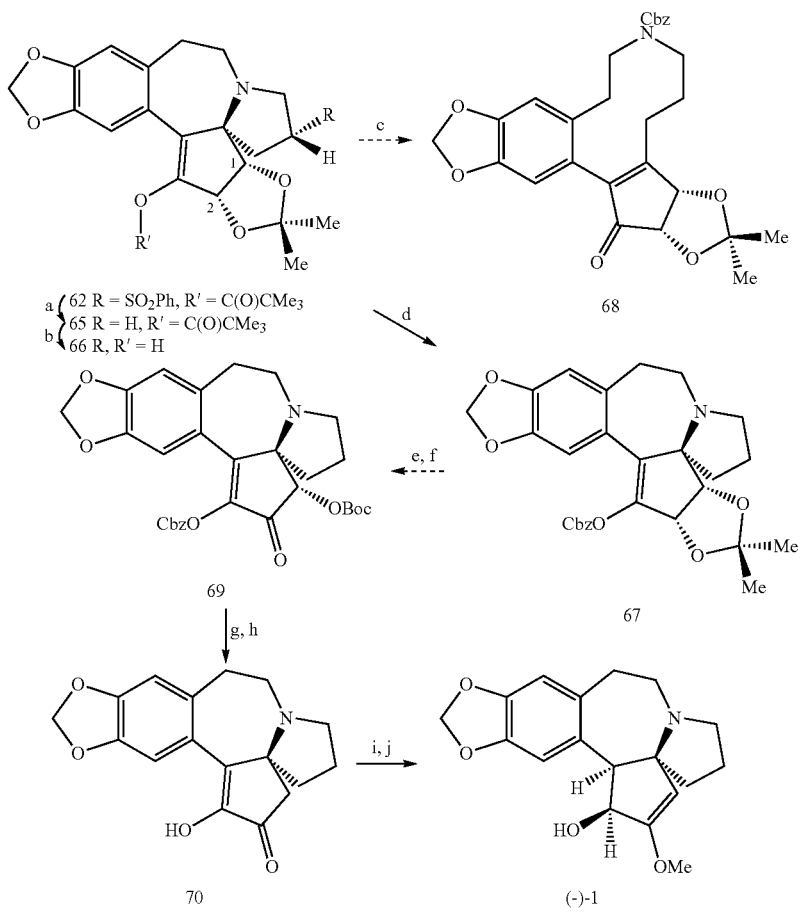

a SmI$_2$, HMPA, t-BuOH, THF, -45° C., 74%;
b Cp$_2$ZrHCl, THF, 40° C., 99%;
c Et$_3$N, CbzCl, CH$_2$Cl$_2$, 23° C., 50%;
d KHMDS, CbzCl, THF, 0° C., 86%Pd—C,
e 2N HCl, MeOH, 23° C., Boc$_2$O, Yb(OTf)$_3$•xH$_2$O, CH$_2$Cl$_2$, 0° C.;
f IBX, DMSO, 23° C., 50% (2 steps)
g CrCl$_2$, acetone, H$_2$O, 23° C.;
h H$_2$, EtOAc, 23° C., 42% (2 steps);
i HC(OMe)$_3$, p-TsOH, CH$_2$Cl$_2$, 55° C., 90%;
j NaBH$_4$, MeOH, -78 → 23° C., 95%.

Synthesis and Attachment of the Acyl Chain of Antitumor *Cephalotaxus* Esters.

The bulk of the synthetic reports concerning the cephalotaxus alkaloids have focused on cephalotaxine (1). On the other hand, reports on the synthesis of natural anti-leukemia cephalotaxus esters have been relatively scarce, likely a result of the difficulties associated with appending a fully intact acyl side chain onto the C3-OH of cephalotaxine. The challenge of such an acylation arises from extensive steric obstruction, marked by the secondary C3-hydroxyl nucleophile buried within the concave face of cephalotaxine, and exacerbated by a fully α-substituted acyl electrophile in the side chain. Indeed, the difficulty of this acylation event is highlighted in numerous semi-syntheses of the cephalotaxus esters from cephalotaxine (1, see Chart 1), wherein the bulk of these efforts employed a less hindered prochiral C2'-sp$^2$ hybridized side chain derivative in the acylation event, followed by subsequent non-stereoselective functional group manipulation. (K. L. Mikolajczak, C. R. Smith, Weislede. D, T. R. Kelly, J. C. McKenna and Christen. Pa, *Tetrahedron Lett.* 1974, 283-286; K. L. Mikolajczak and C. R. Smith, *J. Org. Chem.* 1978, 43, 4762-4765; S. Hiranuma and T. Hudlicky, *Tetrahedron Lett.* 1982, 23, 3431-3434; S. Hiranuma, M. Shibata and T. Hudlicky, *J. Org. Chem.* 1983, 48, 5321-5326) A notable exception to this strategy used an acyl chain substrate specifically appropriate for homoharringtonine in which the C1"-ester moiety was constrained as a cyclic derivative to allow for acylation with the C1'-electrophile. (T. R. Kelly, R. W. McNutt, M. Montury, N. P. Tosches, K. L. Mikolajczak, C. R. Smith and D. Weisleder, *J. Org. Chem.* 1979, 44, 63-67) This approach was introduced with racemic substrates and has recently evolved to non-racemic examples wherein enantio-enriched side chain substrates were prepared in >10-step sequences. (J. P. Robin, R. Dhal, G. Dujardin, L. Girodier, L. Mevellec and S. Poutot, *Tetrahedron Lett.* 1999, 40, 2931-2934)

Since the most pressing late-stage challenge in the synthesis of the cephalotaxus esters is the efficient attachment of hindered acyl chain derivatives, an approach was explored whereby novel bond angle strain elements were imparted to these substrates to enable their use in high yielding acylations of cephalotaxine (1). This strategy initially led to the facile synthesis deoxyharringtonine (2), and subsequently to other members of this alkaloid class, namely anyhydroharringtonine (5), homoharringtonine (3), and homodeoxyharringtonine (4) (i.e., see FIG. 1).

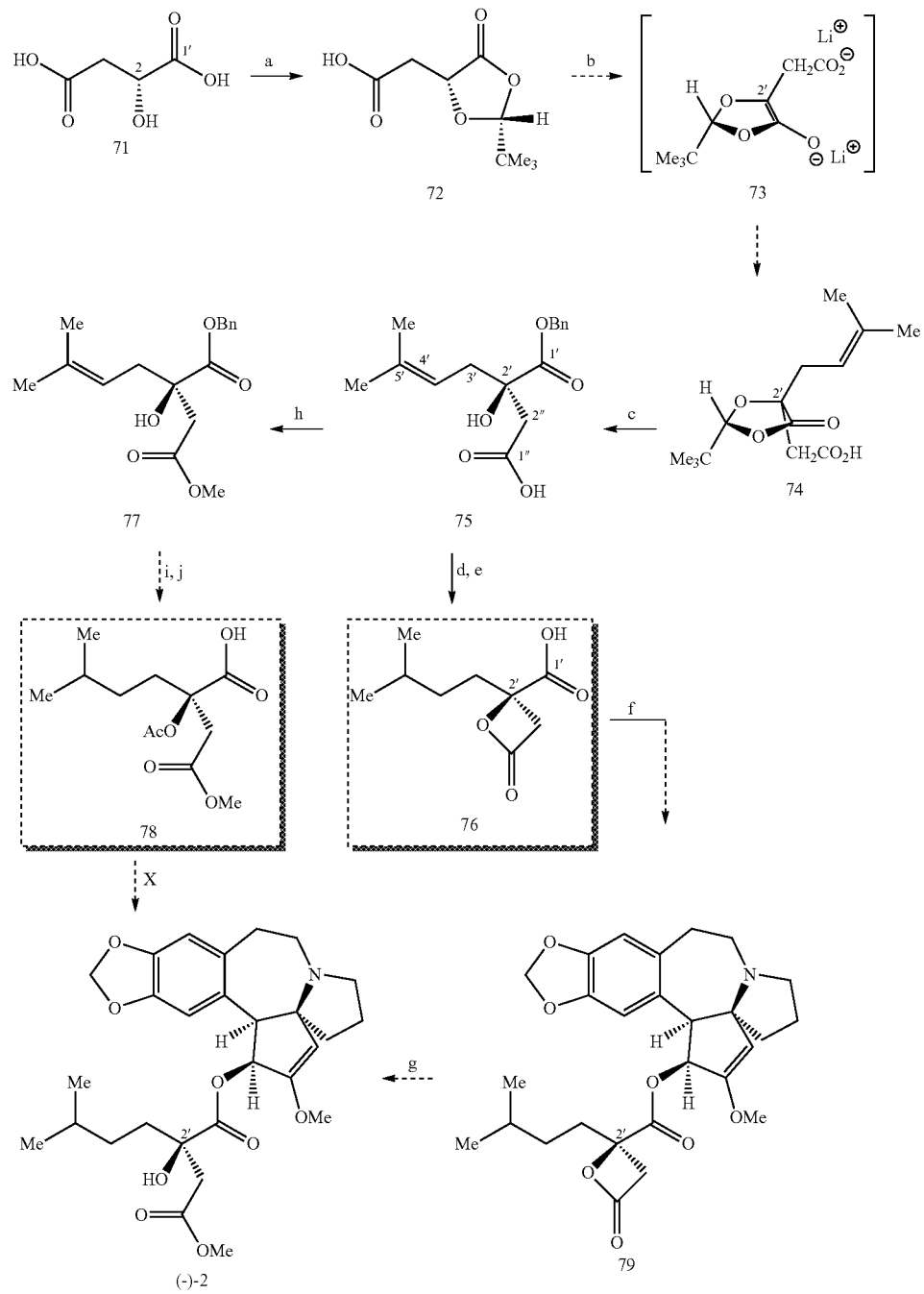

Scheme 13-1.

a TMSCl, TMS$_2$NH, CH$_2$Cl$_2$, 23° C.; Me$_3$CCHO, TMSOTf, CH$_2$Cl$_2$, -25° C.,82%;
b LHMDS, Me$_2$C=CHCH$_2$Br, THF, -78° C., 66%;
c NaH, BnOH, THF, 0° C.; 88%;
d 2,4,6-Cl$_3$C$_6$H$_2$COCl, DMAP, CH$_2$Cl$_2$, 23° C., 50%;
e H$_2$, Pd—C, EtOAc, 23° C., 99%;
f 2,4,6-Cl$_3$C$_6$H$_2$COCl, DMAP, 1, CH$_2$Cl$_2$, 23° C., 81%;
g NaOMe, MeOH, 23° C., 76%;
h TMSCHN$_2$, 7:2 PhH:MeOH, 23° C., 100%;
i Ac$_2$O, DMAP, pyr, 23° C., 74%;
j Pd/C, H$_2$, EtOAc, 23° C., >99%.

The initial steps in the synthesis of several cephalotaxus acyl chains involved the application of the Seebach concept of "self-reproduction of chirality," (D. Seebach, R. Naef and G. Calderari, *Tetrahedron* 1984, 40, 1313-1324) an approach that has shown promise in the preparation of chiral non-racemic α-alkylmalates. (S. A. A. El Bialy, H. Braun and L. F. Tietze, *Eur. J. Org. Chem.* 2005, 2965-2972; P. Q. Huang and Z. Y. Li, *Tetrahedron: Asymmetry* 2005, 16, 3367-3370) Beginning with R-malic acid (71, Scheme 13-1) as a readily available chiral starting material, its C1' carboxylic acid and CT hydroxyl were tethered by a t-butyl acetal upon treatment with pivaldehyde and TMSOTf. Only a single diastereomer of the acetal 72 was observed (82%), after which double deprotonation was induced with excess LHMDS. Although the formation of dilithium carboxylate-enolate 73 resulted in destruction of the CT stereocenter, its stereochemical information was preserved in the chiral acetal carbon bearing the t-butyl group. This sterically demanding substituent forced enolate alkylation with prenyl bromide from the distal face, thereby securing the C2'-R configuration in 74 (66%). Trans-esterification of 74 with NaOBn removed the acetal to afford benzyl ester 75 (88%) as a single enantiomer.

In an effort to facilitate the esterification of cephalotaxine (1), the strategy of constraining both the C2'-hydroxyl and the C1''-carboxylic acid in 75 into a β-lactone functionality such as 76 appeared attractive. The strain energy arising from endocyclic bond angle compression within β-lactone ring in 76 would necessarily induce exocyclic bond angle expansion, thereby relieving local steric congestion at the electrophilic C1' site. Moreover, the angle strain in a four-membered ring imparts higher hybrid orbital s-character in the exocyclic bonds, an effect that could result in increased C1' electrophilicity through induction. In addition, the increased p-character of the endocyclic bonds within the β-lactone may also aid in stabilizing the formation of C1'-acylium like intermediates in activated ester derivatives of 76 through vicinal π-delocalization. Despite these potential advantages, however, the strain associated with the β-lactone moiety in 76 could also serve to be a liability, as undesired ring expansion reaction manifolds may ensue upon C1'-ester activation.

Nevertheless, these aspects were investigated by the treatment of hydroxy acid 75 with 2,4,6-$C_{13}C_6H_2$COCl (J. Inanaga, K. Hirata, H. Saeki, T. Katsuki and M. Yamaguchi, *Bull. Chem. Soc. Jpn.* 1979, 52, 1989-1993) to afford the corresponding β-lactone, which was subsequently treated with $H_2$ and Pd to reduce both the alkene and the benzyl ester to afford the carboxylic acid 76 (50%, 2 steps). Fortunately, activation of the acid 76 as the Yamaguchi mixed anhydride allowed for efficient acylation of cephalotaxine to form the ester I-3a (81%, 23° C., <1 min) without compromising the integrity of the β-lactone. Subsequent methanolysis of the β-lactone provided (–)-deoxyharringtonine (2, 76%), whose spectral data was identical to that of the natural product. To get a better measure of the beneficial effects of the β-lactone moiety in the acylation step, an analogous acyclic acyl electrophile 78 was prepared, beginning with trimethylsilyldiazomethane treatment of hydroxy acid 75 to afford the methyl ester 77 (>99%). Acetylation of the CT hydroxyl group in 77 followed by benzyl ester hydrogenolysis and alkene hydrogenation provided the carboxylic acid 78 (74%, 2 steps), which was devoid of the ring strain elements present in the β-lactone 76. Attempts at cephalotaxine acylation with 78 under otherwise identical conditions led to only trace quantities of protected deoxyharringtonine. Furthermore, heating of the reaction for several hours was also unsuccessful, signaling the critical beneficial effect of the β-lactone moiety in 76 in the synthesis of the bioactive cephalotaxus esters.

The successful synthesis of deoxyharringtonine (2) also allowed for rapid access to the anti-leukemia alkaloid anhydroharringtonine (5) through interception of the chiral hydroxy diester 77 (Scheme 14-1), previously prepared in the acylation studies toward 2 (see Scheme 13-1). This substrate was subjected to intramolecular alkene alkoxymercuration and reduction (Scheme 14-1) to furnish the corresponding tetrahydrofuran (77%). Subsequent benzyl ester hydrogenolysis provided the acylation precursor 80 (99%). Although the strain imparted by the tetrahydrofuran ring in 80 is significantly less than that of β-lactone 76 in the synthesis of 2, the use of 80 in the acylation of cephalotaxine produced (–)-anhydroharringtonine (5) in excellent yield (99%, 23° C., 1 hr), yet with a significantly extended reaction time (i.e., 1 hr for 80 as opposed to <1 min for 76). This effort furnished two natural product cephalotaxus esters (2 and 5), as well as a host of non-natural synthetic intermediates for expansive antitumor evaluation.

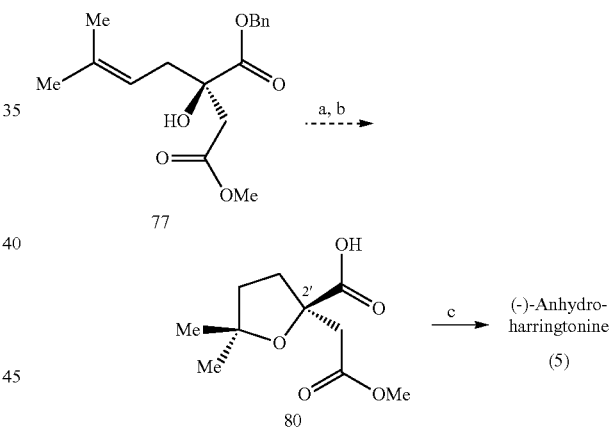

Scheme 14-1.

a Hg(OAc)$_2$, NaBH$_4$, 1:1 THF:H$_2$O, 23° C., 77%;
b Pd/C, H$_2$, EtOAc, 23° C., 99%;
c 2,4,6-trichlorobenzoyl chloride, DMAP, TEA, 1, CH$_2$Cl$_2$, 23° C., 99%.

Anti-Proliferative Activity of deoxyharringtonine (2), β-lactone I-3a, and anhydroharringtonine (5).

The completion of the synthesis of deoxyharringtonine (2) and anhydroharringtonine (5) permitted, for the first time, an expanded evaluation of their in vitro cytotoxicity. Following the early screening of the cephalotaxus esters against murine P388 and L1210 cell lines, (R. G. Powell, Weislede. D and C. R. Smith, *J. Pharm. Sci.* 1972, 61, 1227) many of the cytotoxic evaluations focused on leukemia and lymphoma, with comparatively fewer reports on activity profiles against solid tumor cell lines. (Kantarjian, supra) As a result, deoxyharringtonine (2), anhydroharringtonine (5), and the β-lactone intermediate I-3a (generated in the synthesis of 2, Scheme 13-1) were evaluated against a variety of human hematopoietic and solid tumor cell lines (Table 2). (C. Antczak, D.

Shum, S. Escobar, B. Bassit, E. Kim, V. E. Seshan, N. Wu, G. L. Yang, O. Ouerfelli, Y. M. Li, D. A. Scheinberg and H. Djaballah, *J. Biomol. Screening* 2007, 12, 521-535; D. Shum, C. Radu, E. Kim, M. Cajuste, Y. Shao, V. E. Seshan and H. Djaballah, *Journal of Enzyme Inhibition and Medicinal Chemistry* (in press)) These include HL-60 (acute promyelocytic leukemia), HL-60/RV+ (a P-glycoprotein over-expressing multidrug resistant HL-60 variant which was selected by continuous exposure to the vinca alkaloid vincristine), JURKAT (T cell leukemia), ALL3 (acute lymphoblastic leukemia recently isolated from a patient treated at MSKCC and characterized as Philadelphia chromosome positive), NCEB1 (Mantle cell lymphoma), JEKO (B cell lymphoma), MOLT-3 (acute lymphoblastic T-cell), SKNLP (neuroblastoma), Y79 (retinoblastoma), PC9 (adenocarcinoma), H1650 (adenocarcinoma), H1975 (adenocarcinoma), H2030 (adenocarcinoma), H3255 (adenocarcinoma), TC71 (Ewing's sarcoma), HTB-15 (glioblastoma), A431 (epithelial carcinoma), HeLa (cervical adenocarcinoma), and WD0082 (well-differentiated liposarcoma).

Several general features are evident in the cytoxicity data accumulated in the initial screening campaigns (Table 2). As expected, evaluation of deoxyharringtonine (2) revealed exceedingly potent cytotoxic activity against all of the hematopoietic cell lines tested (HL-60, HL-60/RV+, JURKAT, ALL3, NCEB1, JEKO, MOLT-3); moreover, the alkaloid exhibited similarly high activity against most of the solid tumor cell lines tested (SKNLP, PC9, H1650, H1975, H2030, H3255, A431, HeLa, TC71, HTB-15, WD0082). Interestingly, the late-stage β-lactone variant I-3a (see also Scheme 13-1) exhibited significant cytotoxicity, yet at attenuated levels compared to the parent alkaloid 2, revealing the likely necessity of a hydroxyl group or an H-bond donor functionality at the CT-position. Surprisingly, the cytotoxicity profile of anhydroharringtonine (5) revealed fairly poor antitumor activity. While an early report noted comparable cytotoxic activity of anhydroharringtonine (5) to that of deoxyharringtonine (2) against murine P388, (Wang, 1992, supra) the present result indicates that the activity of 5 is generally several orders of magnitude lower in human HL-60 tumor cells. This unimpressive potency level of 5 thus effectively disqualifies it as a potential therapeutic agent despite previous cytotoxicity data, and is consistent with the proposed need for a 2'-hydroxy group in the acyl chain to confer adequate activity (vide supra).

Synthesis of Additional *Cephalotaxus* Ester Natural Products and Variants to Probe Susceptibility to Multidrug Resistant Cancer.

The development of vincristine-resistance in cancer cells, such as HL-60/RV+ (Table 2) is believed to arise from classic multidrug resistance (MDR). This involves the overexpression of ATP-dependent efflux pumps, such as P-glycoprotein (Pgp) and multidrug resistance-associated protein (MRP), leading to expulsion of natural product hydrophobic drugs (e.g., vinca alkaloids, anthracyclines, actinomycin-D, paclitaxel) from the transformed cell. (M. M. Gottesman, T. Fojo and S. E. Bates, *Nat. Rev. Cancer* 2002, 2, 48-58) Previous reports have noted that the activity of homoharringtonine (3), the cephalotaxus ester currently being evaluated in clinical trials, is also compromised in MDR human leukemia cells. (Benderra, supra) Remarkably, the susceptibility of MDR cancer cells to different cephalotaxus esters has not been systematically probed. Prevention of MDR would significantly improve therapeutic response to this family of chemotherapeutics and extend their use in the clinic. One possible way to achieve this would be to develop anticancer agents that are not substrates for these ATP-dependent transporters, thus overcoming their efflux from cells.

In examining variations in potencies of deoxyharringtonine (2) against this extensive panel of cell lines (Table 2), it is worth noting that its activity against vincristine-resistant HL-60/RV+ cells ($IC_{50}$ 0.22 μM), relative to its non-resistant counterpart HL-60 ($IC_{50}$ 0.02 μM), shows only a ~10-fold decrease in potency. This trend is also reflected in the β-lactone derivative I-3a (albeit with lower absolute cytotoxicity levels). This rather low observed 10-fold resistance index spawned an interest in probing potential molecular design criteria that may offset MDR susceptibility in this class of alkaloids. Fortunately, our current synthetic approach to deoxyharringtonine (2) permits the rapid and versatile attachment of sterically demanding acyl chains onto the cephalotaxine core. Thus, the synthetic strategy to deoxyharringtonine (2) was further extended to the construction of two additional anti-leukemia cephalotaxus ester natural products, namely homoharringtonine (3) and homodeoxyharringtonine (4), all reported to be potent antileukemia alkaloids.

Scheme 15-1.

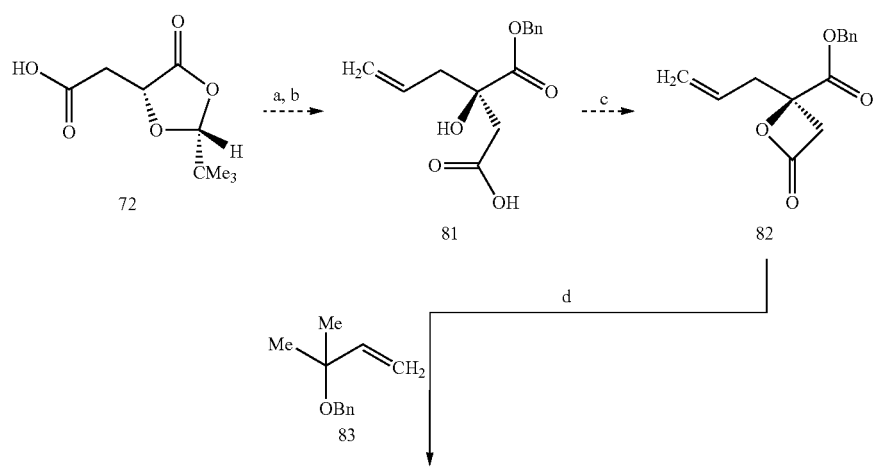

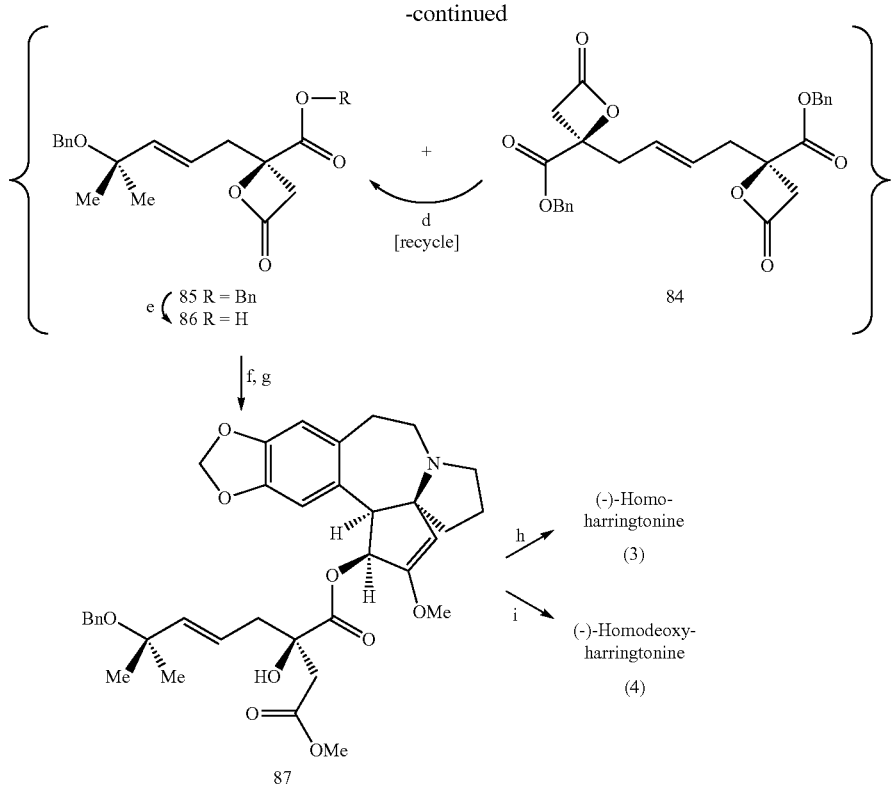

a LHMDS, allyl bromide, THF, -78° C., 59%;
b BnOH, NaH, THF, 0 → 23° C., 85%;
c 2,4,6-trichlorbenzoyl chloride, DMAP, Et₃N, CH₂Cl₂, 23° C., 67%;
d Grubbs II, 23° C., 61%;
e Pd(OAc)₂, Et₃SiH, Et₃N, CH₂Cl₂, 23° C., 85%;
f 2,4,6-trichlorobenzoyl chloride, DMAP, Et₃N, 1, CH₂Cl₂, 23° C., 97%;
g NaOMe, MeOH, 0° C., 79%;
h Pd/C, H₂, MeOH then 9:1 MeOH:HOAc, 23° C., 79%;
i Pd/C, H₂, HOAc, 23° C., 69%.

The syntheses of homoharringtonine 3 and homodeoxyharringtonine 4 involved a common early sequence (Scheme 15-1) beginning with the R-malic acid derived acetal 72, which underwent double deprotonation and diastereoselective enolate alkylation with allyl bromide (59%). (Seebach, supra) Following NaOBn-mediated transesterification of the resultant acetal-ester to afford the R-α-hydroxy benzyl ester 81 (85%), β-lactone formation was accomplished via the Yamaguchi mixed anhydride to provide the strained intermediate 82 (67%). Subsequent alkene cross metathesis (Grubbs-II) with excess alkene 83 (R. G. Salomon and J. M. Reuter, *J. Am. Chem. Soc.* 1977, 99, 4372-4379; A. K. Chatterjee, T. L. Choi, D. P. Sanders and R. H. Grubbs, *J. Am. Chem. Soc.* 2003, 125, 11360-11370) provided disubstituted alkene 85 (61%) along with the dimeric bis(lactone) 84 (22%) as an equilibrium mixture. Although the direct conversion of 82 to 85 was moderate, the recovered dimer 84 could be re-equilibrated under olefin metathesis conditions with excess 83 to accumulate additional quantities of 85. Following selective transfer hydrosilylation of 85, the resultant acid 86 (85%) was employed in a highly efficient cephalotaxine acylation to prepare the corresponding ester (97%), whose β-lactone was then subjected to methanolysis to furnish I-5 (79%). This intermediate was then diverged to both of the natural products homoharringtonine (3) and deoxyhomoharringtonine (4). When the allylic benzyl ether in I-5 was subjected to Pd/C-catalyzed hydrogenolysis/hydrogenation in MeOH, followed by the addition of AcOH in the latter stages of the reaction, (−)-homoharringtonine (3, 79%) was isolated (presumably through initial alkene hydrogenation followed by benzyl ether hydrogenolysis). On the other hand, when the Pd/C-catalyzed reduction was performed in glacial AcOH solvent at the outset, deoxygenation preceded alkene reduction (presumably through E1 elimination of the allylic benzyl ether prior to hydrogenation) to afford (−)-homodeoxyharringtonine (4, 69%).

Scheme 16-1.

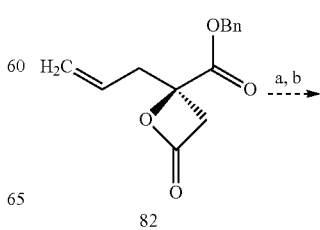

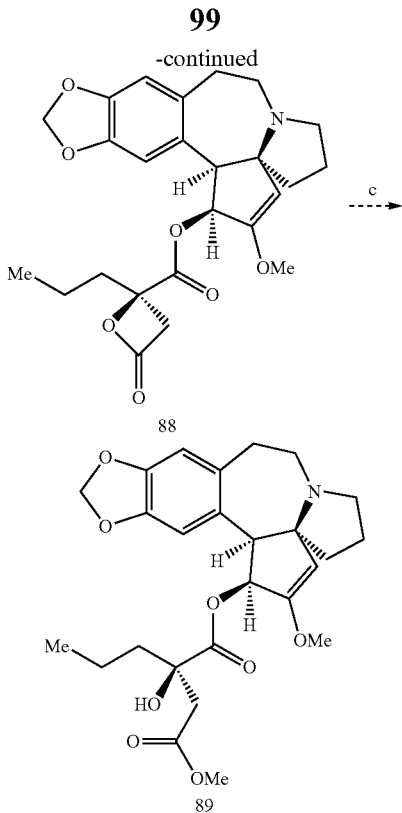

a Pd/C, H₂, EtOAc, 23° C., 97%;
b 2,4,6-trichlorobenzoyl chloride, DMAP, TEA, 1, CH₂Cl₂, 23° C., 81%;
c NaOMe, MeOH, 23° C., 93%.

The efficient synthesis of the acyl chain precursors in the preparation of the natural product cephalotaxus esters 3 and 4 also presented the opportunity to prepare a non-natural analogue for biological evaluation with only a minor variation in the synthetic sequence. This analogue took the form of bis(demethyl)deoxyharringtonine I-4 (Scheme 16-1), also anticipated to exhibit potent anti-proliferative activity, although much simpler in structure and more easily prepared than 3 or 4. The synthesis of cephalotaxus ester I-4 (Scheme 16-1) involved interception of the β-lactone acyl chain 82, derived from R-malic acid in three steps (refer to Scheme 15-1). Following hydrogenolysis/hydrogenation of the alkenyl ester 82 (97%), the resulting carboxylic acid was activated as the Yamaguchi mixed anhydride to effect the acylation of cephalotaxine (1), providing the ester-β-lactone I-1 (81%). Methanolysis of the β-lactone in I-1 proceeded efficiently to afford the non-natural bis(demethyl)deoxyharringtonine analogue I-4 (93%).

The completion of the syntheses of the natural cephalotaxus esters 2-4 together with two non-natural synthetic analogues, namely benzyldehydrohomoharringtonine I-5 and bis(demethyl)deoxyharringtonine I-4, permitted their comparative biological evaluation against "sensitive" and MDR tumor cell lines (FIG. 3). When tested against the "sensitive" HL-60 cell line, all were found to be exceedingly potent (IC₅₀<0.08 μM). When evaluated against the "resistant" HL60/RV+ cell line, stark differential response levels were observed within this collection of cephalotaxus esters (FIG. 4). Interestingly homoharringtonine (3) displayed a 125-fold decrease in activity toward HL-60/RV+ relative to that of HL-60 (resistance index=125). By contrast, much lower resistance indices of 11, 3, 12, and 19 were observed with the esters 2, 4, I-5, and I-4, respectively, indicating that these latter natural and non-natural products are significantly less susceptible to MDR. One possible explanation for the high MDR susceptibility of homoharringtonine (3) is its decreased lipophilicity as a consequence of its acyl chain structure, thereby rendering it a good substrate for the efflux pumps.

The relationship of the calculated lipophilicity values (c-logP) to the resistance indices for the highly potent cephalotaxus esters 2-4, I-5, and I-4 is presented in FIG. 4, wherein compounds with c-logP values greater than 1.2 lead to generally low susceptibility to MDR (i.e., resistance indices≦19 for the cephalotaxus esters 2, 4, I-5, and I-4). The exception is homoharringtonine (3), exhibiting a relatively low c-logP value (0.95, relatively more polar) to reflect an increased susceptibility to MDR (i.e., resistance index 125). Although these data were obtained on a limited set of analogs, they provide for the first time new insights into the contribution of acyl chain structure modification toward overcoming MDR resistance for this class of compounds.

It is worth emphasizing that the only structural difference on the acyl chain between homoharringtonine (3) and homodeoxyharringtonine (4) is a hydroxyl group on the 6'-position (FIG. 4). While only a minor structural perturbation, this 6'-substitution difference drastically affects the lipophilicity of the molecules, ranging from a c-logP value of 0.95 (polar) for 3 to a more hydrophobic compound 4 with a c-logP value of 2.33 (i.e., FIG. 5). Importantly, with a resistance index of only 3 (as in the case with homodeoxyharringtonine 4), both comparative cell lines can be considered as "sensitive" to the compound of interest. As a consequence, this minor structural variation from 3 to 4 has allowed for effective quelling of MDR resistance in this cell line. Given this finding, it is thus surprising that despite its MDR liability, homoharringtonine (3) is employed as the favored cephalotaxus ester for advancement in the clinic, exemplified by a current phase III clinic prospective trial with 3 for use as a combination therapy for chronic myeloid leukemia. (L. Legros, S. Hayette, F. E. Nicolini, S. Raynaud, K. Chabane, J. P. Magaud, J. P. Cassuto and M. Michallet, *Leukemia* 2007, 21, 2204-2206) One practical reason for this may lie in the increased natural abundance of homoharringtonine (3) relative to other cephalotaxus esters. (R. G. Powell, *Phytochemistry* 1972, 11, 1467) Moreover, semisynthetic sources of homoharringtonine have built on the seminal work of Kelly, wherein the 6'-oxygen functionality is a prerequisite for efficient acyl chain attachment to cephalotaxine. (Kelly, 1989, supra) Notably, this semi-synthetic approach is uniquely suited for homoharringtonine (3). Fortunately, the synthetic strategies described herein enable unfettered access to other, more therapeutically viable cephalotaxus esters, such as 2, 4, I-5, and I-4, for the development of additional lines of chemotherapeutic defense against leukemia.

Resistance of Vincristine-Sensitive Y79 Retinoblastoma to *Cephalotaxus* Esters.

In the initial cytotoxicity evaluation (Table 2), it is also worth highlighting that the Y79 retinoblastoma cell line uniquely showed significant resistance to both deoxyharringtonine (2) and its β-lactone derivative I-3a. Indeed, this selective resistance of Y79 appears to be a general phenomenon (Table 3) upon evaluation with a few of our active cytotoxic non-natural synthetic cephalotaxus ester analogues, including the benzyldehydrohomoharringtonine I-5, the β-lactone ester I-1, and bis(demethyl)deoxyharringtonine I-4. All of these compounds behaved similarly to that of deoxyharringtonine (2) and its β-lactone derivative I-3a (cf.

Table 2), exhibiting broad spectrum cytotoxicity with the exception of the Y79 cell line, to which the molecules were essentially impotent.

Though this specific lack of cytotoxicity in Y79 could also be attributed to the overexpression of multidrug resistance genes (MDR), Conway and co-workers have reported the Y79 cell line to be sensitive to vincristine with an $IC_{50}$ value of approx 0.8 μM. (R. M. Conway, M. C. Madigan, F. A. Billson and P. L. Penfold, *Eur. J. Cancer* 1998, 34, 1741-1748) Furthermore, a comparative microarray analysis of the Y79 cell line with normal retinal tissue detected upregulation of several genes typically found to be markers of stem cell like characteristics including the mdr gene ABCG2. (G. M. Seigel, A. S. Hackam, A. Ganguly, L. M. Mandell and F. Gonzalez-Fernandez, *Mol. Vis.* 2007, 13, 823-832) Based on this, we postulate that perhaps the mechanism of resistance to cephalotaxus esters by Y79 is not entirely mediated through the classical ATP-dependent efflux pumps alone but rather through an as yet unknown mechanism involving stem cell like characteristics. This is consistent with the hypothesis that the appearance of subsequent tumors in leukemias, brain tumors, breast cancer, lung cancer, as well as many other cancers, is linked to the persistence of cancer stem cells. This observation suggests that designed cephalotaxus esters have the potential to serve as small molecule probes for interrogating the genetic basis of this highly resilient retinoblastoma cell line as well as potentially shedding some light on how to overcome this persistence phenomena in these dormant progenitor cancer stem cells.

CONCLUSION

The development, optimization, and application of novel synthetic strategies have enabled the synthesis of the potent anti-leukemia agents (−)-deoxyharringtonine (2), (−)-homoharringtonine (3), (−)-homodeoxyharringtonine (4), and (−)-anhydroharringtonine (5). Several advances served as key elements in the preparation of (−)-cephalotaxine (1) and should find general applicability in complex N-heterocycle synthesis. These included (1) a strain-release aziridine rearrangement of 2-aryl-N-vinyl aziridines for dihydro[3]benzazepine synthesis, and (2) a vinylogous amide-derived azomethine ylide cycloaddition which takes an unusual and unexpected stereochemical course. Efforts to advance these synthetic pursuits beyond that of (−)-1 to that of the rare anti-neoplastic C3-O-ester derivatives (i.e., 2-5) have led to an efficient non-racemic synthesis of several cephalotaxus acyl chains. Construction of strained β-lactone intermediates enabled late-stage C3-O-acylation of cephalotaxine, a long-standing challenge in the synthesis of sterically congested bioactive cephalotaxus esters. This technology enabled cytotoxicity screening of several natural and non-natural cephalotaxus esters against an expansive array of human hematopoietic and solid tumor cell lines. These evaluations were instrumental in discovering novel non-natural cephalotaxus esters with potent antitumor effects. Moreover, these efforts have uncovered the potential of specific members of this family of alkaloids to overcome resistance in MDR HL-60/RV+tumor cells through the preparation of acyl chain variants, uniquely made available with our acyl chain attachment approach. This presents new avenues for molecular design of these alkaloids to offset multi-drug resistance, offering new lines of chemotherapeutic defense against leukemia and other cancers.

EXPERIMENTALS

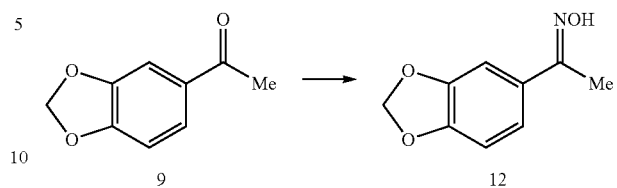

General Procedure for the Preparation of Oximes 10, 11, 12

1-Benzo[1,3]dioxol-5-yl-ethanone oxime (12)

Powdered sodium hydroxide (6.6 g, 170 mmol, 9.0 equiv) and hydroxylamine hydrochloride (3.8 g, 55 mmol, 3.0 equiv) were sequentially added to a stirred suspension of and 3,4-(methylenedioxy)acetophenone (9) (3.0 g, 18 mmol, 1.0 equiv) in ethanol (32 mL) and distilled water (13 mL) at 25° C. The reaction vessel was equipped with a reflux condenser and heated to 80° C. via oil bath for 3 h. The reaction mixture was cooled to 25° C., diluted with saturated aqueous ammonium chloride (400 mL), and the product was extracted with dichloromethane (5×125 mL). The combined organic layers were dried (sodium sulfate), gravity filtered, and concentrated by rotary evaporation. The residue was purified by rinsing with cold dichloromethane followed by vacuum filtration to afford 12 (2.9 g, 87% yield) as an off-white crystalline solid. $R_f$=0.41 (25% ethyl acetate in hexane); $^1$H NMR (500 MHz, CDCl$_3$) δ 7.77 (s, 1H, OH), 7.18 (d, 1H, J=1.5 Hz, ArH), 7.10 (dd, 1H, J=6, 1.5 Hz, ArH), 6.81 (d, 1H, J=6 Hz, ArH), 5.99 (s, 2H, OCH$_2$O), 2.24 (s, 3H, CH$_3$); IR (neat film) 3296 (w, br), 3228 (w, br), 2907 (w), 1505 (s), 1266 (s), 1227 (s), 1037 (s) cm$^{-1}$; HRMS (EI) m/z: Calcd for C$_9$H$_9$NO$_3$ (M$^+$) 179.0582; observed 179.0584.

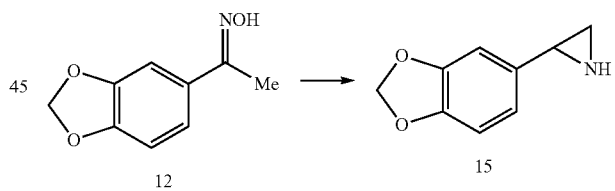

General Procedure for the Preparation of Aziridines 13, 14, 15

2-Benzo[1,3]dioxol-5-yl-aziridine (15)

A solution of oxime 12 (2.7 g, 15 mmol, 1.0 equiv) in tetrahydrofuran (60 mL) at 25° C. was transferred via cannula to a stirred suspension of lithium aluminum hydride (3.5 g, 61 mmol, 4.0 equiv) and di-iso-propyl amine (8.5 mL, 61 mmol, 4.0 equiv) in tetrahydrofuran (70 mL) at 25° C. The emptied reaction vessel was rinsed with tetrahydrofuran (22 mL) and the resulting solution was also transferred via cannula. The reaction vessel was equipped with a reflux condenser under nitrogen atmosphere and heated to 60° C. via oil bath for 4 h. The mixture was cooled to 25° C., diluted with ice water (400 mL), and the product was extracted with dichloromethane (5×200 mL). The combined organic layers were dried (sodium sulfate), gravity filtered, and concentrated by rotary evaporation. The residue was purified by silica gel column chromatography (5% triethylamine in ethyl acetate) to afford 15 (2.17 g, 88% yield) as a pale yellow oil. $R_f$=0.40 (5% triethylamine in ethyl acetate); $^1$H NMR (500 MHz, CDCl$_3$) δ 6.75 (br s, 2H, ArH), 6.70 (br s, 1H, ArH), 5.93 (s, 2H, OCH$_2$O), 2.97 (br s, 1H, ArCH), 2.17 (br s, 1H, CH$_2$), 1.67 (br s, 1H, CH$_2$).

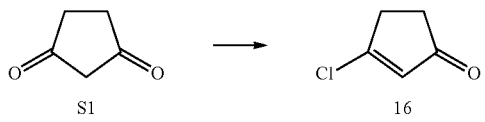

3-Chloro-cyclopent-2-enone (16)

A solution of oxalyl chloride (0.17 mL, 2.0 mmol, 2.0 equiv) in dichloromethane (2.5 mL) at 0° C. was transferred via cannula to a stirred suspension of 1,3-cyclopentanedione (S1) (98 mg, 1.0 mmol, 1.0 equiv) in dichloromethane (2.5 mL) at 0° C. The resulting yellow solution was stirred at 0° C. for 2 h, allowed to warm to 25° C., and stirred for 1 h. The reaction mixture was diluted with ice water (100 mL) and the product was extracted with dichloromethane (4×75 mL). The combined organic layers were dried (sodium sulfate), gravity filtered, and concentrated by rotary evaporation to afford 16 (115 mg, 99% yield) as a brown oil. Rf=0.75 (25% hexane in ethyl acetate); $^1$H NMR (500 MHz, CDCl$_3$) δ 6.23 (t, 1H, J=2 Hz, vinyl H), 2.88 (m, 2H, CH2), 2.57 (m, 2H, CH2); IR (neat film) 3089 (w), 2927 (w), 1716 (s), 1592 (s), 1259 (m), 1229 (m), 1036 (m), 824 (w) cm$^{-1}$; HRMS (EI) m/z: Calcd for C$_5$H$_5$OCl (MH$^+$) 116.0029; observed 116.0029.

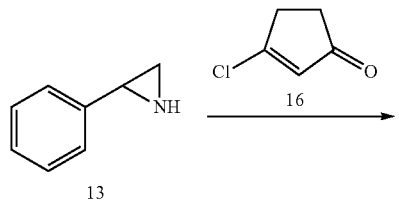

3-(2-phenyl-aziridin-1-yl)-cyclopent-2-enone (17)

A solution of chloroenone 16 (140 mg, 1.2 mmol, 1.1 equiv) in tetrahydrofuran (3.5 mL) at 25° C. was transferred via cannula to a stirred solution of aziridine 13 (130 mg, 1.1 mmol, 1.0 equiv) and triethylamine (0.19 mL, 1.4 mmol, 1.2 equiv) in tetrahydrofuran (4.0 mL) at 25° C. The reaction vessel was sealed under argon and heated to 60° C. via oil bath for 24 h. The reaction mixture was cooled to 25° C. and concentrated by rotary evaporation. The residue was purified by silica gel column chromatography (5% triethylamine in ethyl acetate) to afford 17 (130 mg, 58% yield) as a brown oil. $R_f$=0.56 (5% triethylamine in ethyl acetate); $^1$H NMR (500 MHz, C$_6$D$_6$) δ 7.05-7.15 (m, 5H, ArH), 5.39 (t, 1H, J=1.5 Hz, vinyl H), 2.41 (dd, 1H, J=6, 3 Hz, ArCHN), 2.08 (m, 2H, CH$_2$), 1.85-1.95 (m, 2H, CH$_2$), 1.73 (dd, 1H, J=3, 1 Hz, CH$_2$N), 1.60 (dd, 1H, J=6, 1 Hz, CH$_2$N).

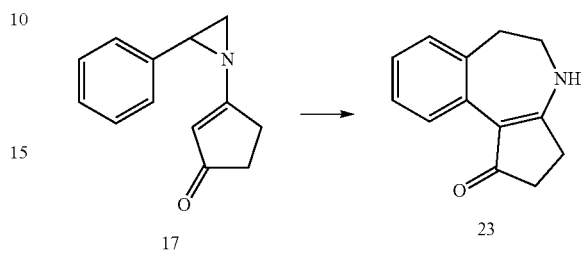

Tetracyclic benzazepine 23

Cesium carbonate (66 mg, 0.20 mmol, 4.0 equiv) was added to a stirred solution of aziridine 17 (10 mg, 50 μmol, 1.0 equiv) in 1,4-dioxane (7.2 mL) at 25° C. The reaction vessel was sealed under argon and heated to 150° C. via oil bath for 4 d. The reaction mixture was cooled to 25° C., gravity filtered, and concentrated by rotary evaporation. The residue was purified by silica gel column chromatography (5% triethylamine in ethyl acetate) to afford 23 (3.0 mg, 30% yield) as a white film. $R_f$=0.21 (5% triethylamine in ethyl acetate); $^1$H NMR (500 MHz, CD$_3$S(O)CD$_3$) δ 8.20-8.26 (m, 2H, ArH, NH), 7.13 (m, 1H, ArH), 6.97-7.05 (m, 2H, ArH), 3.40-3.50 (m, 2H, CH$_2$), 2.88-2.94 (m, 2H, CH$_2$), 2.52-2.56 (m, 2H, CH$_2$), 2.31-2.35 (m, 2H, CH$_2$); $^{13}$C NMR (125 MHz, CD$_3$S(O)CD$_3$) δ 200.32, 171.22, 138.55, 133.48, 128.62, 127.20, 125.50, 124.47, 107.40, 46.52, 36.98, 33.51, 26.05; IR (neat film) 3251 (w, br), 2925 (w), 1574 (s), 1350 (w) cm$^{-1}$; HRMS (ESI) m/z: Calcd for C$_{13}$H$_{14}$NO (MH$^+$) 200.1075; observed 200.1084.

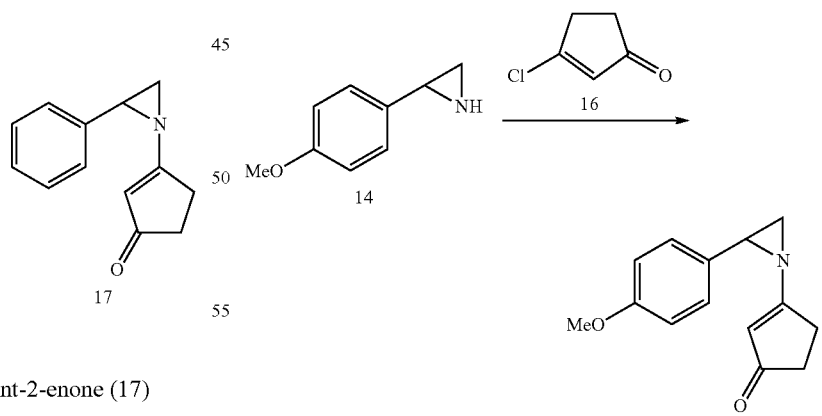

3-[2-(4-methoxy-phenyl)-aziridin-1-yl]-cyclopent-2-enone (18)

A solution of chloroenone 16 (16 mg, 0.14 mmol, 1.0 equiv) in tetrahydrofuran (1.0 mL) at 25° C. was transferred via cannula to a stirred solution of aziridine 14 (25 mg, 0.17 mmol, 1.2 equiv) and triethylamine (35 μL, 0.25 mmol, 1.5 equiv) in tetrahydrofuran (1.0 mL) at 25° C. The resulting brown solution was stirred at 25° C. for 24 h. The reaction mixture was concentrated by rotary evaporation. The residue was purified by silica gel column chromatography (5% triethylamine and 20% ethyl acetate in benzene) to afford 18 (5 mg, 16% yield) as a yellow film. $R_f$=0.29 (5% triethylamine and 20% ethyl acetate in benzene); $^1$H NMR (500 MHz, C$_6$D$_6$) δ 7.00 (m, 2H, ArH), 6.76 (m, 2H, ArH), 5.43 (t, 1H, J=1.5 Hz, vinyl H), 3.28 (s, 3H, OCH$_3$), 2.45 (dd, 1H, J=6, 3 Hz, ArCHN), 2.11 (m, 2H, CH$_2$), 1.85-2.00 (m, 2H, CH$_2$), 1.77 (dd, 1H, J=3, 1 Hz, CH$_2$N), 1.63 (dd, 1H, J=6, 1 Hz, CH$_2$N).

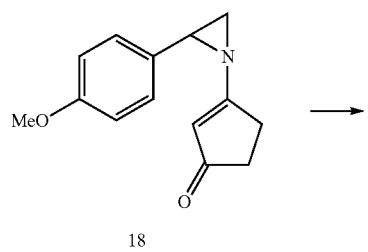

18

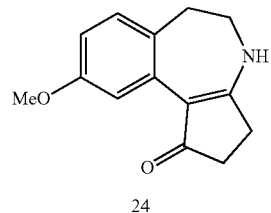

24

Tetracyclic benzazepine 24

Cesium carbonate (30 mg, 87 μmol, 4.0 equiv) was added to a stirred solution of aziridine 18 (5.0 mg, 22 μmol, 1.0 equiv) in 1,4-dioxane (3.0 mL) at 25° C. The reaction vessel was sealed under argon and heated to 150° C. via oil bath for 4 d. The reaction mixture was cooled to 25° C., gravity filtered, and concentrated by rotary evaporation. The residue was purified by silica gel column chromatography (10% methanol in chloroform) to afford 24 (2.6 mg, 52% yield) as a yellow film. $R_f$=0.28 (10% methanol in chloroform); $^1$H NMR (500 MHz, CDCl$_3$) δ 8.00 (d, 1H, J=3 Hz, ArH), 6.90 (d, 1H, J=8 Hz, ArH), 6.64 (dd, 1H, J=8, 3 Hz, ArH), 5.79 (br s, 1H, NH), 3.82 (s, 3H, OCH$_3$), 3.58 (m, 2H, CH$_2$), 2.95 (m, 2H, CH$_2$), 2.50-2.60 (m, 4H, CH$_2$); $^{13}$C NMR (125 MHz, CDCl$_3$) δ 202.31, 170.54, 158.31, 153.19, 133.90, 131.05, 129.64, 112.60, 112.04, 55.41, 48.10, 36.58, 34.03, 27.20; IR (neat film) 3256 (w, br), 3086 (w), 2927 (w), 1576 (s), 1512 (m), 1248 (m) cm$^{-1}$; HRMS (ESI) m/z: Calcd for C$_{14}$H$_{16}$NO$_2$ (MH$^+$) 230.1181; observed 230.1188.

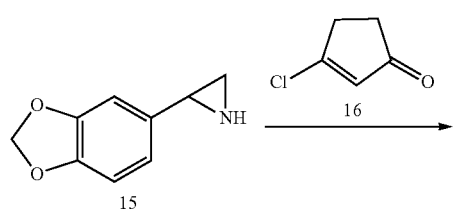

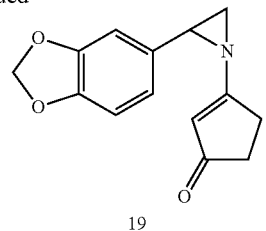

19

Aziridine 19

A solution of chloroenone 16 (98 mg, 0.84 mmol, 1.2 equiv) in tetrahydrofuran (2.5 mL) at 25° C. was transferred via cannula to a stirred solution of aziridine 15 (110 mg, 0.70 mmol, 1.0 equiv) and triethylamine (0.20 mL, 1.4 mmol, 2.0 equiv) in tetrahydrofuran (2.5 mL) at 25° C. The resulting brown solution was stirred at 25° C. for 24 h. The reaction mixture was concentrated by rotary evaporation. The residue was purified by silica gel column chromatography (5% triethylamine and 20% ethyl acetate in benzene) to afford 19 (32 mg, 26% yield) as a yellow film. $R_f$=0.28 (10% methanol in chloroform); $^1$H NMR (500 MHz, CDCl$_3$) δ 8.00 (d, 1H, J=3 Hz, ArH), 6.90 (d, 1H, J=8 Hz, ArH), 6.64 (dd, 1H, J=8, 3 Hz, ArH), 5.79 (br s, 1H, NH), 3.82 (s, 3H, OCH$_3$), 3.58 (m, 2H, CH$_2$), 2.95 (m, 2H, CH$_2$), 2.50-2.60 (m, 4H, CH$_2$); $^{13}$C NMR (125 MHz, CDCl$_3$) δ 202.31, 170.54, 158.31, 153.19, 133.90, 131.05, 129.64, 112.60, 112.04, 55.41, 48.10, 36.58, 34.03, 27.20; IR (neat film) 3256 (w, br), 3086 (w), 2927 (w), 1576 (s), 1512 (m), 1248 (m) cm$^{-1}$; HRMS (ESI) m/z: Calcd for C$_{14}$H$_{16}$NO$_2$ (MH$^+$) 230.1181; observed 230.1188.

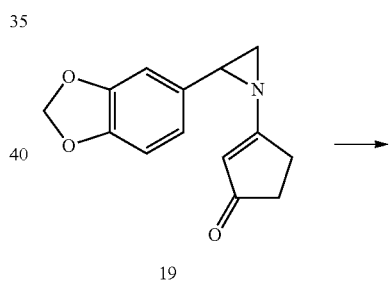

19

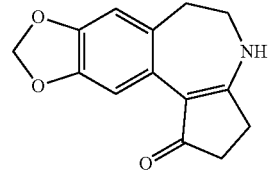

25

Tetracyclic benzazepine 25

Cesium carbonate (170 mg, 0.51 mmol, 4.0 equiv) was added to a stirred solution of aziridine 19 (31 mg, 0.13 mmol, 1.0 equiv) in 1,4-dioxane (19 mL) at 25° C. The reaction vessel was sealed under argon and heated to 100° C. via oil bath for 4 d. The reaction mixture was cooled to 25° C., gravity filtered, and concentrated by rotary evaporation. The residue was purified by silica gel column chromatography (10% methanol in chloroform) to afford 25 (21 mg, 68% yield) as a tan amorphous solid. $R_f$=0.43 (10% methanol in chloroform); $^1$H NMR (500 MHz, CDCl$_3$) δ 7.85 (s, 1H, ArH), 6.53 (s, 1H, ArH), 5.91 (s, 2H, OCH$_2$O), 5.37 (s, 1H, NH), 3.61 (br s, 2H, CH$_2$), 2.93 (m, 2H, CH$_2$), 2.56 (m, 4H, CH$_2$); $^{13}$C NMR (125 MHz, CDCl$_3$) δ 202.06, 169.13, 146.07, 145.29, 132.39, 126.19, 110.34, 108.83, 108.57, 100.79, 48.20, 37.00, 33.77, 27.06; IR (neat film) 3260 (w, br), 3074 (w), 2923 (w), 1557 (s), 1244 (m), 1038 (m) cm$^{-1}$; HRMS (EI) m/z: Calcd for C$_{14}$H$_{13}$NO$_3$ (M$^+$) 243.0895; observed 243.0895.

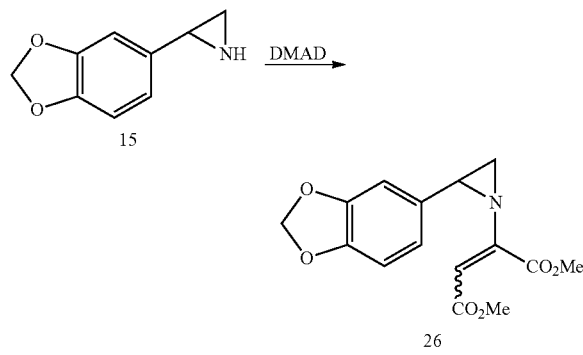

2-(2-Benzo[1,3]dioxol-5-yl-aziridin-1-yl)-but-2-enedioic acid dimethyl ester (26)

Dimethyl acetylene dicarboxylate (75 μL, 0.61 mmol, 1.0 equiv) was added via syringe to a stirred solution of aziridine 15 (100 mg, 0.61 mmol, 1.0 equiv) in tetrahydrofuran (1.0 mL) at 25° C. The resulting bright yellow solution was stirred at 25° C. for 2 d. The reaction mixture was concentrated by rotary evaporation. The residue was purified by silica gel column chromatography (1% triethylamine and 24% ethyl acetate in benzene) to afford 26 (110 mg, 57% yield, 3:1 E:Z mixture) as a yellow film. E-26: R$_f$=0.31 (1% triethylamine and 24% ethyl acetate in benzene); $^1$H NMR (500 MHz, C$_6$D$_6$) δ 6.64 (m, 1H, ArH), 6.52-6.54 (m, 2H, ArH), 5.30 (s, 1H, vinyl H), 5.22-5.25 (m, 2H, OCH$_2$O), 3.52 (s, 3H, OCH$_3$), 3.34 (s, 3H, OCH$_3$), 2.84 (dd, 1H, J=6, 3.5 Hz, ArCHN), 1.84 (d, 1H, J=6 Hz, CH$_2$N), 1.71 (d, 1H, J=3.5 Hz, CH$_2$N).

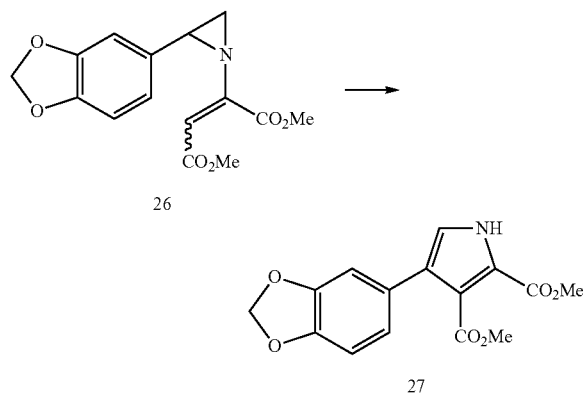

4-Benzo[1,3]dioxol-5-yl-1H-pyrrole-2,3-dicarboxylic acid dimethyl ester (27)

Cesium carbonate (110 mg, 0.30 mmol, 4.0 equiv) was added to a stirred solution of aziridine 26 (25 mg, 82 μmol, 1.0 equiv) in 1,4-dioxane (12 mL) at 25° C. The reaction vessel was sealed under argon and heated to 100° C. via oil bath for 20 h. The reaction mixture was cooled to 25° C., gravity filtered, and concentrated by rotary evaporation to afford 27 (23 mg, 92% yield) as a dark orange film. $^1$H NMR (500 MHz, CDCl$_3$) δ 10.22 (br d, 1H, J=11 Hz, NH), 7.43 (dd, 1H, J=14, 11 Hz, pyrrole H), 6.80 (d, 1H, J=1.5 Hz, ArH), 6.72 (d, 1H, J=8 Hz, ArH), 6.69 (dd, 1H, J=8, 1.5 Hz, ArH), 5.93 (s, 2H, OCH$_2$O), 3.89 (s, 3H, OCH$_3$), 3.73 (s, 3H, OCH$_3$); IR (neat film) 3348 (w, br), 2944 (w), 2890 (w), 1731 (m), 1651 (s), 1608 (s), 1503 (m), 1484 (m), 1444 (m) cm$^{-1}$; HRMS (ESI) m/z: Calcd for C$_{15}$H$_{14}$NO$_6$ (MH$^+$) 304.0821; observed 304.0815.

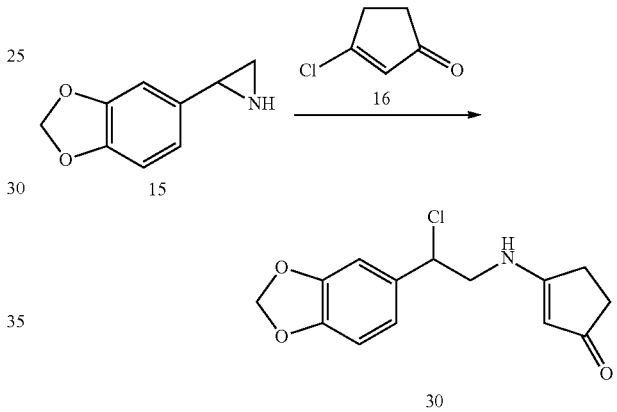

3-(2-Benzo[1,3]dioxol-5-yl-2-chloro-ethylamino)-cyclopent-2-enone (30)

A solution of chloroenone 16 (98 mg, 0.84 mmol, 1.2 equiv) in tetrahydrofuran (2.5 mL) at 25° C. was transferred via cannula to a stirred solution of aziridine 15 (110 mg, 0.70 mmol, 1.0 equiv) and triethylamine (0.20 mL, 1.4 mmol, 2.0 equiv) in tetrahydrofuran (2.5 mL) at 25° C. The reaction vessel was sealed under argon and heated to 60° C. via oil bath for 24 h. The reaction mixture was cooled to 25° C. and concentrated by rotary evaporation. The residue was purified by silica gel column chromatography (7% triethylamine in ethyl acetate) to afford 30 (120 mg, 64% yield) as a yellow film. R$_f$=0.13 (5% triethylamine in ethyl acetate); $^1$H NMR (500 MHz, C$_6$D$_6$) δ 6.64 (d, 1H, J=2 Hz, ArH), 6.47 (d, 1H, J=8 Hz, ArH), 6.31 (dd, 1H, J=8, 2 Hz, ArH), 5.24 (d, 1H, J=1.5 Hz, OCH$_2$O), 5.22 (d, 1H, J=1.5 Hz, OCH$_2$O), 4.99 (s, 1H, vinyl H), 4.51 (br s, 1H, CHCl), 3.92 (br s, 1H, NH), 2.93 (m, 2H, CH$_2$), 2.14 (t, 2H, J=5.5 Hz, CH$_2$), 1.62 (m, 2H, CH$_2$); IR (neat film) 3242 (w, br), 3061 (w), 2915 (w), 1565 (s), 1504 (m), 1490 (m), 1445 (m), 1251 (m), 1187 (w), 1038 (m) cm$^{-1}$; HRMS (EI) m/z: Calcd for C$_{14}$H$_{15}$NO$_3$Cl (MH$^+$) 280.0740; observed 280.0740.

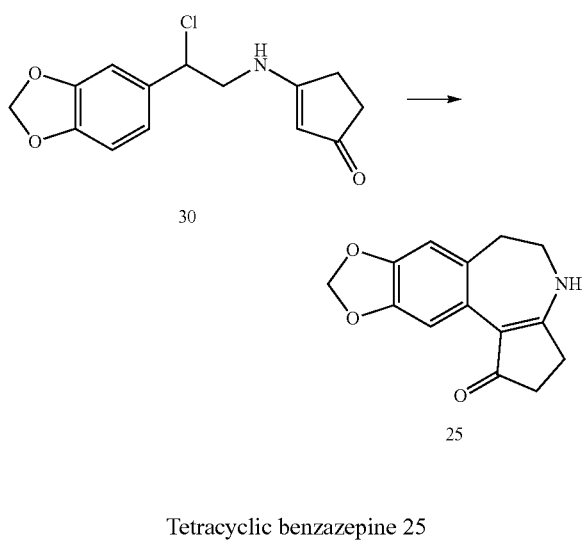

Tetracyclic benzazepine 25

Cesium carbonate (170 mg, 0.50 mmol, 4.0 equiv) was added to a stirred solution of chloride 30 (35 mg, 0.13 mmol, 1.0 equiv) in 1,4-dioxane (18 mL) at 25° C. The reaction vessel was sealed under argon and heated to 100° C. via oil bath for 4 d. The reaction mixture was cooled to 25° C., gravity filtered, and concentrated by rotary evaporation. The residue was purified by silica gel column chromatography (10% methanol in chloroform) to afford 25 (20 mg, 67% yield) as a tan amorphous solid. $R_f$=0.43 (10% methanol in chloroform); $^1$H NMR (500 MHz, CDCl$_3$) δ 7.85 (s, 1H, ArH), 6.53 (s, 1H, ArH), 5.91 (s, 2H, OCH$_2$O), 5.37 (s, 1H, NH), 3.61 (br s, 2H, CH$_2$), 2.93 (m, 2H, CH$_2$), 2.56 (m, 4H, CH$_2$); $^{13}$C NMR (125 MHz, CDCl$_3$) δ 202.06, 169.13, 146.07, 145.29, 132.39, 126.19, 110.34, 108.83, 108.57, 100.79, 48.20, 37.00, 33.77, 27.06; IR (neat film) 3260 (w, br), 3074 (w), 2923 (w), 1557 (s), 1244 (m), 1038 (m) cm$^{-1}$; HRMS (EI) m/z: Calcd for C$_{14}$H$_{13}$NO$_3$ (M$^+$) 243.0895; observed 243.0895.

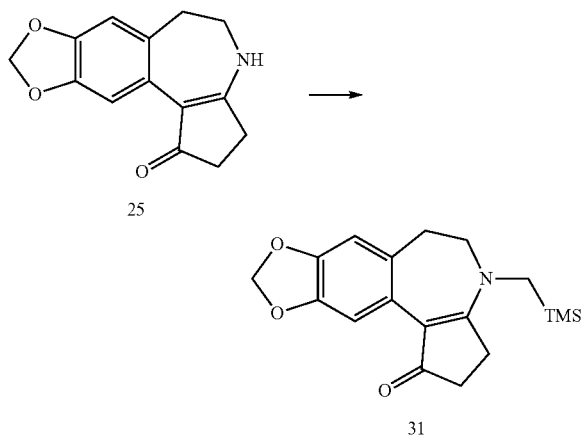

N-(Trimethylsilyl)methyl benzazepine 31

60% sodium hydride in mineral oil (39 mg, 0.96 mmol, 1.3 equiv) was added to a stirred solution of benzazepine 25 (180 mg, 0.74 mmol, 1.0 equiv) in tetrahydrofuran (9.3 mL) at 25° C. The resulting brown suspension was stirred at 25° C. for 1 h. (Iodomethyl)trimethylsilane (0.55 mL, 3.7 mmol, 5.0 equiv) was added via syringe at 25° C. The reaction vessel was sealed under argon and heated to 50° C. via oil bath for 30 m. The reaction mixture was cooled to 25° C. and approximately 50% of the solvent volume was removed by sweeping with nitrogen. The crude reaction mixture was loaded directly onto a column and purified by silica gel column chromatography (5% triethylamine in ethyl acetate) to afford 31 (151 mg, 62% yield) as an off-white amorphous solid. $R_f$=0.41 (5% triethylamine in ethyl acetate); $^1$H NMR (500 MHz, CDCl$_3$) δ 7.76 (s, 1H, ArH), 6.48 (s, 1H, ArH), 5.89 (s, 2H, OCH$_2$O), 3.56 (m, 2H, CH$_2$), 3.02 (br s, 2H, NCH$_2$Si), 2.91 (m, 2H, CH$_2$), 2.59 (m, 2H, CH$_2$), 2.49 (m, 2H, CH$_2$), 0.13 (s, 9H, Si(CH$_3$)$_3$); $^{13}$C NMR (125 MHz, CDCl$_3$) δ 200.86, 169.37, 146.18, 145.19, 132.71, 127.17, 110.46, 109.47, 108.06, 100.92, 57.78, 46.78, 36.22, 33.37, 28.08, −1.26; IR (neat film) 2953 (w, br), 1647 (w), 1556 (s), 1488 (m), 1445 (m), 1353 (w), 1248 (m), 1039 (m), 843 (m) cm$^{-1}$; HRMS (EI) m/z: Calcd for C$_{18}$H$_{23}$NO$_3$Si (MH$^+$) 330.1525; observed 330.1525.

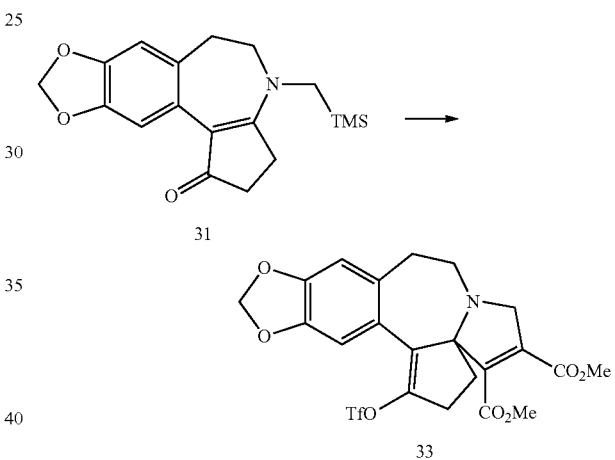

Pentacyclic enol trifluoromethanesulfonate 33

Trifluoromethanesulfonic anhydride (5.0 µL, 30 µmol, 1.1 equiv) was added to a stirred solution of vinylogous amide 31 (9.0 mg, 27 µmol, 1.0 equiv) in dichloromethane (0.40 mL) at 25° C. The resulting dark orange solution was stirred at 25° C. for 30 m. Dimethyl acetylenedicarboxylate (4.8 µL, 39 µmol, 1.4 equiv) and tetrabutylammonium triphenyldifluorosilicate (16 mg, 30 µmol, 1.1 equiv) were sequentially added at 25° C. The resulting dark purple mixture was stirred at 25° C. for 24 h. The crude reaction mixture was loaded directly onto a column and purified by silica gel column chromatography (50% hexane in ethyl acetate) to afford 33 (7.7 mg, 53% yield) as a colorless film. $R_f$=0.44 (50% hexane in ethyl acetate); $^1$H NMR (500 MHz, CDCl$_3$) δ 6.58 (s, 2H, ArH), 5.95 (d, 1H, J=1.5 Hz, OCH$_2$O), 5.91 (d, 1H, J=1.5 Hz, OCH$_2$O), 3.95 (s, 2H, NCH$_2$C), 3.76 (s, 3H, OCH$_3$), 3.70 (s, 3H, OCH$_3$), 3.54 (ddd, 1H, J=15, 11, 4 Hz, CH$_2$), 3.22 (ddd, 1H, J=16, 11, 5 Hz, CH$_2$), 3.03 (ddd, 1H, J=15, 5, 2 Hz, CH$_2$), 2.96 (m, 1H, CH$_2$), 2.77 (ddd, 1H, J=16, 10, 3 Hz, CH$_2$), 2.65 (m, 1H, CH$_2$), 2.54 (ddd, 1H, J=13, 9, 3 Hz, CH$_2$), 2.16 (ddd, 1H, J=13, 9, 6 Hz, CH$_2$).

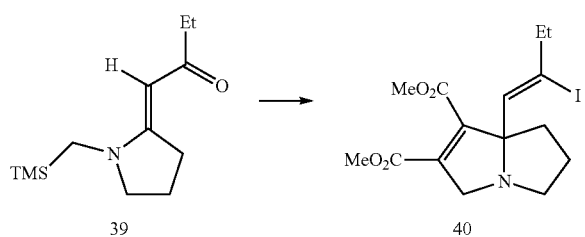 [SMILES: CCC(=O)/C=C1\CCCN1C[Si](C)(C)C ; CC/C(I)=C/C12CCCN1CC(C(=O)OC)=C2C(=O)OC]

7a-(2-Iodo-but-1-enyl)-5,6,7,7a-tetrahydro-3H-pyrrolizine-1,2-dicarboxylic acid dimethyl ester (40)

To a stirred solution of 1-(1-trimethylsilanylmethyl-pyrrolidi-2-ylidene)-butan-2-one (39) (49.6 mg, 0.220 mmol, 1.0 equiv) in dry dichloromethane (3 mL) at room temperature was added via syringe trifluoromethanesulfonic anhydride (41 µL, 0.24 mmol, 1.1 equiv). The resulting yellow solution was stirred for 15 minutes before the addition of dimethylacetylene dicarboxylate (135 µL, 1.10 mmol, 5.0 equiv) and tetrabutylammonium iodide (89.0 mg, 0.242 mmol, 1.1 equiv). The resulting dark amber solution was then stirred at room temperature for 10 minutes before the addition of tetrabutylammonium triphenyldifluorosilicate (131 mg, 0.242 mmol, 1.0 equiv). The resulting dark red solution was stirred at room temperature for 22 h and then concentrated in vacuo. Purification by silica gel flash chromatography (33% ethyl acetate in hexanes) provided 40 (46.6 mg, 52%, (Z)-isomer only) as a bright yellow oil. (Z)-isomer; $R_f$=0.41 (33% ethyl acetate in hexanes); $^1$H NMR (500 MHz, $C_6D_6$) δ 6.04 (s, 1H, vinyl H), 4.40 (d, 1H, J=16.8 Hz, $NCH_2$), 3.48 (d, 1H, J=16.8 Hz, $NCH_2$), 3.47 (s, 3H, $CO_2CH_3$), 3.31 (s, 3H, $CO_2CH_3$), 3.02 (dt, 1H, J=9.8, 5.7 Hz, $NCH_2CH_2CH_2$), 2.35 (qd, 2H, J=7.4, 1.1 Hz, $CH_2CH_3$), 2.26 (dt, 1H, J=10.6, 6.8 Hz, $NCH_2CH_2CH_2$), 2.21 (m, 1H, $NCH_2CH_2CH_2$), 2.05 (m, 1H, $NCH_2CH_2CH_2$), 1.55 (m, 1H, $NCH_2CH_2CH_2$), 1.44 (m, 1H, $NCH_2CH_2CH_2$), 0.92 (t, 3H, J=7.3 Hz, $CH_2CH_3$); FTIR (neat film, NaCl) 2967, 1722 (C=O), 1652, 1435, 1272, 1198, 1102 cm$^{-1}$; HRMS (FAB) m/z: Calcd for $C_{15}H_{21}N_1O_4I_1$ (M+H)$^+$ 406.0515; found 406.0517.

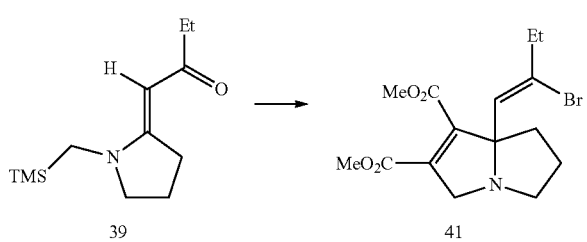 [SMILES: CCC(=O)/C=C1\CCCN1C[Si](C)(C)C ; CC/C(Br)=C/C12CCCN1CC(C(=O)OC)=C2C(=O)OC]

7a-(2-Bromo-but-1-enyl)-5,6,7,7a-tetrahydro-3H-pyrrolizine-1,2-dicarboxylic acid dimethyl ester (41)

To a stirred solution of 1-(1-trimethylsilanylmethyl-pyrrolidi-2-ylidene)-butan-2-one (39) (32.5 mg, 0.144 mmol, 1.0 equiv) in dry dichloromethane (2 mL) at room temperature was added via syringe trifluoromethanesulfonic anhydride (27 µL, 0.16 mmol, 1.1 equiv). The resulting yellow solution was stirred for 10 minutes before the addition of dimethylacetylene dicarboxylate (89 µL, 0.72 mmol, 5.0 equiv) and tetrabutylammonium bromide (102 mg, 0.317 mmol, 2.2 equiv). The resulting dark amber solution was then stirred at room temperature for 12 h before the addition of tetrabutylammonium triphenyldifluorosilicate (86.4 mg, 0.159 mmol, 1.0 equiv). The resulting dark red solution was stirred at room temperature for 1 h and then concentrated in vacuo. Purification by silica gel flash chromatography (50% ethyl acetate in hexanes) provided 41 (23.3 mg, 45%, (Z)-isomer only) as a bright yellow oil. (Z)-isomer; $R_f$=0.38 (50% ethyl acetate in hexanes); $^1$H NMR (500 MHz, $C_6D_6$) δ 6.06 (s, 1H, vinyl H), 4.32 (d, 1H, J=16.7 Hz, $NCH_2$), 3.52 (s, 3H, $CO_2CH_3$), 3.45 (d, 1H, J=16.7 Hz, $NCH_2$), 3.30 (s, 3H, $CO_2CH_3$), 2.96 (dt, 1H, J=9.7, 5.7 Hz, $NCH_2CH_2CH_2$), 2.43 (dt, 1H, J=13.0, 7.5 Hz, $NCH_2CH_2CH_2$), 2.23 (m, 4H, $NCH_2CH_2CH_2$ and $CH_2CH_3$), 1.54 (m, 1H, $NCH_2CH_2CH_2$), 1.45 (m, 1H, $NCH_2CH_2CH_2$), 0.92 (t, 3H, J=7.3 Hz, $CH_2CH_3$); FTIR (neat film, NaCl) 2950, 1721 (C=O), 1654, 1434, 1271, 1197, 1135 cm$^{-1}$; HRMS (FAB) m/z: Calcd for $C_{15}H_{21}N_1O_4Br_1$ (M+H)$^+$ 358.0654; found 358.0653.

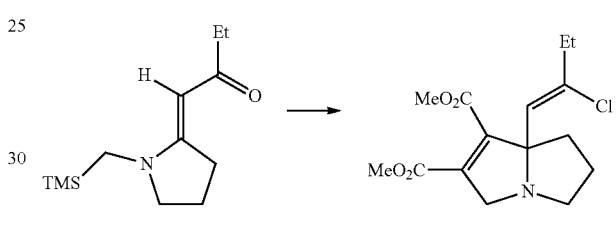

7a-(2-Chloro-but-1-enyl)-5,6,7,7a-tetrahydro-3H-pyrrolizine-1,2-dicarboxylic acid dimethyl ester (42)

To a stirred solution of 1-(1-trimethylsilanylmethyl-pyrrolidi-2-ylidene)-butan-2-one (39) (34.7 mg, 0.154 mmol, 1.0 equiv) in dry dichloromethane (2 mL) at room temperature was added via syringe trifluoromethanesulfonic anhydride (28 µL, 0.17 mmol, 1.1 equiv). The resulting yellow solution was stirred for 10 minutes before the addition of dimethylacetylene dicarboxylate (95 µL, 0.77 mmol, 5.0 equiv) and tetrabutylammonium chloride (94.2 mg, 0.339 mmol, 2.2 equiv). The resulting dark orange solution was then stirred at room temperature for 4 h before the addition of tetrabutylammonium triphenyldifluorosilicate (91.1 mg, 0.169 mmol, 1.0 equiv). The dark red solution was stirred at room temperature for 1 h and then concentrated in vacuo. Purification by silica gel flash chromatography (33% hexanes in ethyl acetate) provided 42 (25.1 mg, 52%, (Z)-isomer only) as a bright yellow oil. (Z)-isomer; $R_f$=0.42 (33% hexanes in ethyl acetate); $^1$H NMR (500 MHz, $C_6D_6$) δ 5.79 (s, 1H, vinyl H), 4.28 (d, 1H, J=16.7 Hz, $NCH_2$), 3.53 (s, 3H, $CO_2CH_3$), 3.44 (d, 1H, J=16.7 Hz, $NCH_2$), 3.29 (s, 3H, $CO_2CH_3$), 2.95 (dt, 1H, J=9.7, 5.7 Hz, $NCH_2CH_2CH_2$), 2.48 (dt, 1H, J=13.1, 7.5 Hz, $NCH_2CH_2CH_2$), 2.21 (m, 2H, $NCH_2CH_2CH_2$), 2.07 (q, 2H, J=7.3 Hz, $CH_2CH_3$), 1.53 (m, 1H, $NCH_2CH_2CH_2$), 1.45 (m, 1H, $NCH_2CH_2CH_2$), 0.91 (t, 3H, J=7.3 Hz, $CH_2CH_3$); FTIR (neat film, NaCl) 2951, 1722 (C=O), 1652, 1435, 1271, 1197, 1130, 1102 cm$^{-1}$; HRMS (FAB) m/z: Calcd for $C_{15}H_{21}N_1O_4Cl_1$ (M+H)$^+$ 314.1159; found 314.1159.

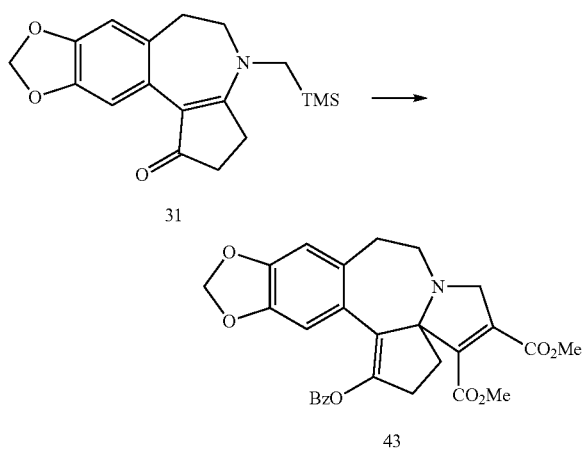

Pentacyclic enol benzoate 43

Trifluoromethanesulfonic anhydride (12 μL, 70 μmol, 1.1 equiv) was added to a stirred solution of vinylogous amide 31 (21 mg, 64 μmol, 1.0 equiv) in dichloromethane (0.50 mL) at 25° C. The resulting dark orange solution was stirred at 25° C. for 30 m. The solution was transferred via cannula to a stirred suspension of benzoic acid (8.6 mg, 70 μmol, 1.1 equiv) and cesium carbonate (25 mg, 76 μmol, 1.2 equiv) in dichloromethane (0.40 mL) at 25° C. The resulting dark brown mixture was stirred at 25° C. for 30 m. Dimethyl acetylenedicarboxylate (40 μL, 0.32 mmol, 5.0 equiv) and tetrabutylammonium triphenyldifluorosilicate (25 mg, 76 μmol, 1.2 equiv) were sequentially added at 25° C. The dark brown mixture was stirred at 25° C. for 24 h. The crude reaction mixture was loaded directly onto a column and purified by silica gel column chromatography (50% hexane in ethyl acetate) to afford 43 (8.0 mg, 64% yield) as a pale yellow film. $R_f$=0.32 (50% hexane in ethyl acetate); $^1$H NMR (500 MHz, CDCl$_3$) δ 8.01 (m, 2H, Ph), 7.57 (m, 1H, Ph), 7.44 (m, 2H, Ph), 6.62 (s, 1H, ArH), 6.54 (s, 1H, ArH), 5.90 (d, 1H, J=1.5 Hz, OCH$_2$O), 5.87 (d, 1H, J=1.5 Hz, OCH$_2$O), 3.98 (br d, 2H, J=2.8 Hz, NCH$_2$C), 3.80 (s, 3H, OCH$_3$), 3.75 (m, 1H, CH$_2$), 3.70 (s, 3H, OCH$_3$), 3.24 (ddd, 1H, J=15, 11, 5 Hz, CH$_2$), 3.03 (ddd, 1H, J=15, 5, 3 Hz, CH$_2$), 2.96 (m, 1H, CH$_2$), 2.77 (ddd, 1H, J=14, 10, 3 Hz, CH$_2$), 2.65 (m, 1H, CH$_2$), 2.58 (m, 1H, CH$_2$), 2.18 (m, 1H, CH$_2$); IR (neat film) 2949 (w, br), 1732 (s), 1484 (m), 1264 (s) cm$^{-1}$; HRMS (FAB) m/z: Calcd for C$_{28}$H$_{26}$NO$_8$ (MH$^+$) 504.1656; observed 504.1658.

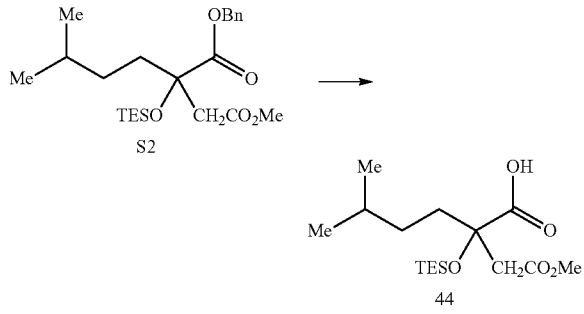

2-(3-Methyl-butyl)-2-triethylsilanyloxy-succinic acid 4-methyl ester (44)

10% Palladium on carbon (2 mg, ~10 wt. %) was added to a stirred solution of benzyl ester S2 (21 mg, 0.50 mmol, 1.0 equiv) in ethyl acetate (1.0 mL) at 25° C. The resulting black mixture was charged with an atmosphere of hydrogen (balloon) and stirred at 25° C. for 24 h. The crude reaction mixture was eluted through a short plug of celite (120 mL ethyl acetate) and the organic layer was concentrated by rotary evaporation to afford 44 (12 mg, 73% yield) as a colorless film. $R_f$=0.01 (17% ethyl acetate in hexane); $^1$H NMR (500 MHz, CDCl$_3$) δ 3.72 (br s, 1H, COOH), 3.66 (s, 3H, COOCH$_3$), 2.90 (d, 1H, J=6 Hz, CH$_3$OOCCH$_2$C), 2.69 (d, 1H, J=6 Hz, CH$_3$OOCCH$_2$C), 1.67 (m, 2H, CCH$_2$CH$_2$CH(CH$_3$)$_2$), 1.50 (hep, 1H, J=6.5 Hz, CCH$_2$CH$_2$CH(CH$_3$)$_2$), 1.40 (m, 2H, CCH$_2$CH$_2$CH(CH$_3$)$_2$), 0.99 (t, 9H, J=8 Hz, OSi(CH$_2$CH$_3$)$_3$), 0.80-0.90 (m, 12H, CCH$_2$CH$_2$CH(CH$_3$)$_2$, OSi(CH$_2$CH$_3$)$_3$); IR (neat film) 3507 (w), 2956 (s), 1744 (s), 1219 (s), 741 (s) cm$^{-1}$.

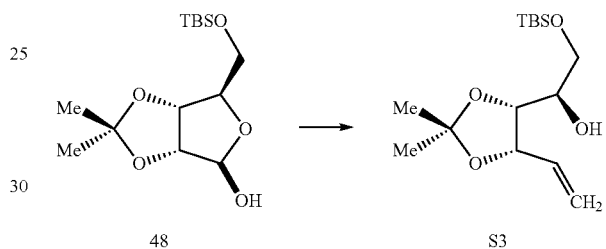

2-(tert-Butyl-dimethyl-silanyloxy)-1-(2,2-dimethyl-5-vinyl-[1,3]dioxolan-4-yl)-ethanol (S3)

Methyltriphenylphosphonium bromide (37 g, 100 mmol, 1.2 equiv) was added to a stirred solution of 95% potassium bis(trimethylsilyl)amide (18 g, 83 mmol, 1.0 equiv) in tetrahydrofuran (270 mL) at 0° C. The resulting yellow mixture was stirred at 0° C. for 2 h. A solution of hemiacetal 48 (26 g, 84 mmol, 1.0 equiv) in tetrahydrofuran (150 mL) was transferred via cannula to the reaction mixture at 0° C. The resulting off-white mixture was stirred at 0° C. for 30 min. The reaction vessel was equipped with a reflux condenser and heated to 60° C. via oil bath for 2 d. The reaction mixture was cooled to 25° C., diluted with diethyl ether (400 mL), washed with water (1×400 mL), and washed with a saturated solution of sodium chloride (1×400 mL). The organic layer was dried (magnesium sulfate), gravity filtered, and concentrated by rotary evaporation. The residue was purified by silica gel column chromatography (14% ethyl acetate in hexane) to afford S3 (19 g, 75% yield) as a colorless oil. $R_f$=0.35 (14% ethyl acetate in hexane); $^1$H NMR (500 MHz, C$_6$D$_6$) δ 6.20 (ddd, 1H, J=5, 10.5, 17 Hz, CHCH$_2$), 5.51 (ddd, 1H, J=1.5, 2, 17 Hz, CHCH$_2$), 5.19 (ddd, 1H, J=1.5, 2, 10.5 Hz, CHCH$_2$), 4.72 (m, 1H, CH(OR)), 4.10 (dd, 1H, J=6.5, 9 Hz, CH(OR)), 3.83 (m, 1H, CH(OH)), 3.72-3.77 (m, 2H, CH$_2$(OTBS)), 1.44 (s, 3H, CH$_3$), 1.27 (s, 3H, CH$_3$), 0.89 (s, 9H, C(CH$_3$)$_3$), 0.00 (s, 3H, SiCH$_3$), −0.01 (s, 3H, SiCH$_3$); $^{13}$C NMR (125 MHz, C$_6$D$_6$) δ 135.25, 116.57, 108.86, 78.97, 77.95, 70.30, 65.24, 28.07, 26.06, 25.60, 18.54, −5.28, −5.37; IR (neat film) 3505 (w), 2931 (m), 2858 (m) cm$^{-1}$; HRMS (ESI) m/z: Calcd for C$_{15}$H$_{30}$NaO$_4$Si (MNa$^+$) 325.1811; observed 325.1824.

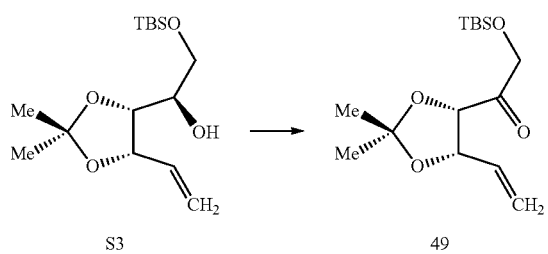

2-(tert-Butyl-dimethyl-silanyloxy)-1-(2,2-dimethyl-5-vinyl-[1,3]dioxolan-4-yl)-ethanone (49)

Dimethylsulfoxide (7.0 mL, 99 mmol, 30 equiv), triethylamine (2.8 mL, 20 mmol, 6.0 equiv), and sulfur trioxide-pyridine complex (3.2 g, 20 mmol, 6.0 equiv) were sequentially added to a stirred solution of alcohol S3 (1.0 g, 3.3 mmol, 1.0 equiv) in dichloromethane (185 mL) at 0° C. The resulting colorless solution was stirred at 0° C. for 15 min, warmed to 25° C., and stirred for 45 min. The reaction mixture was diluted with water (100 mL) and extracted with diethyl ether (3×80 mL). The combined organic layers were dried (magnesium sulfate), gravity filtered, and concentrated by rotary evaporation. The residue was purified by silica gel column chromatography (12.5% ethyl acetate in hexane) to afford 49 (870 mg, 88% yield) as a colorless oil. $R_f$=0.41 (12.5% ethyl acetate in hexane); $^1$H NMR (500 MHz, $C_6D_6$) δ 5.70 (ddd, 1H, J=5.5, 10.5, 17 Hz, CHCH$_2$), 5.51 (dt, 1H, J=1.5, 17 Hz, CHCH$_2$), 5.19 (dt, 1H, J=1.5, 10.5 Hz, CHCH$_2$), 4.50-4.56 (m, 3H, CH(OR), CH(OR), CH$_2$(OTBS)), 4.30 (d, 1H, J=19 Hz, CH$_2$(OTBS)), 1.47 (s, 3H, CH$_3$), 1.09 (s, 3H, CH$_3$), 0.96 (s, 9H, C(CH$_3$)$_3$), 0.05 (s, 3H, SiCH$_3$), 0.04 (s, 3H, SiCH$_3$); $^{13}$C NMR (125 MHz, $C_6D_6$) δ 205.42, 133.27, 117.84, 110.36, 82.21, 78.48, 69.07, 26.93, 26.01, 24.69, 18.60, −5.16, −5.21; IR (neat film) 2930 (m), 2858 (m), 1739 (m) cm$^{-1}$; HRMS (ESI) m/z: Calcd for $C_{15}H_{28}NaO_4Si$ (MNa$^+$) 323.1655; observed 323.1676.

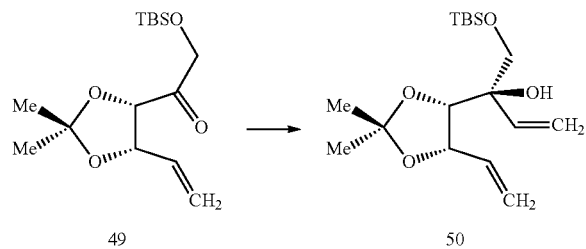

2-(tert-Butyl-dimethyl-silanyloxy)-2-(2,2-dimethyl-5-vinyl-[1,3]dioxolan-4-yl)-but-3-en-2-ol (50)

A 1 molar solution of vinyl bromide in tetrahydrofuran (26 mL, 26 mmol, 2.2 equiv) was added dropwise to a mixture of magnesium turnings (570 mg, 23 mmol, 2.0 equiv) in tetrahydrofuran at 25° C. The resulting mixture was stirred at 25° C. for 16 h (the mixture began to turn homogeneous brown and spontaneously reflux after 30 min). The solution of vinyl magnesium bromide in tetrahydrofuran was transferred via cannula to a stirred solution of ketone 49 (3.5 g, 12 mmol, 1.0 equiv) in tetrahydrofuran (35 mL) at −78° C. The resulting brown solution was stirred at −78° C. for 1.5 h, warmed to 25° C., and stirred for 30 min. The reaction mixture was cooled to −78° C., quenched with a saturated solution of ammonium chloride (20 mL), diluted with water (100 mL), and extracted with ethyl acetate (3×100 mL). The combined organic layers were dried (magnesium sulfate), gravity filtered, and concentrated by rotary evaporation. The residue was purified by passage through a plug of silica gel (dichloromethane) to afford 50 (3.5 g, 93% yield) as a colorless oil consisting of a 8:1 mixture of inseparable diastereomers. $R_f$=0.54 (12.5% ethyl acetate in hexane); $^1$H NMR (500 MHz, $C_6D_6$) δ 6.41 (ddd, 1H, J=5.5, 10.5, 17 Hz, CHCH$_2$), 6.27 (ddd, 1H, J=0.5, 12, 17.5 Hz, CHCH$_2$), 5.61 (dd, 1H, J=2, 17.5 Hz, CHCH$_2$), 5.37 (ddd, 1H, J=1.5, 2, 17 Hz, CHCH$_2$), 5.21 (ddd, 1H, J=0.5, 2, 12 Hz, CHCH$_2$), 5.10 (ddd, 1H, J=1.5, 2, 10.5 Hz, CHCH$_2$), 4.72 (m, 1H, CH(OR)), 4.41 (d, 1H, J=7 Hz, CH(OR)), 3.83 (d, 1H, J=10 Hz, CH$_2$(OTBS)), 3.44 (d, 1H, J=10 Hz, CH$_2$(OTBS)), 2.68 (d, 1H, J=0.6 Hz, OH), 1.48 (s, 3H, CH$_3$), 1.28 (s, 3H, CH$_3$), 0.89 (s, 9H, C(CH$_3$)$_3$), −0.01 (s, 3H, SiCH$_3$), −0.03 (s, 3H, SiCH$_3$); $^{13}$C NMR (125 MHz, $C_6D_6$) δ 138.56, 136.34, 116.35, 115.88, 108.30, 79.42, 78.55, 75.58, 68.99, 27.53, 26.00, 25.04, 18.51, −5.35, −5.45; IR (neat film) 3557 (w), 2955 (m), 2859 (m) cm$^{-1}$; HRMS (ESI) m/z: Calcd for $C_{17}H_{32}NaO_4Si$ (MNa$^+$) 351.1968; observed 351.1966.

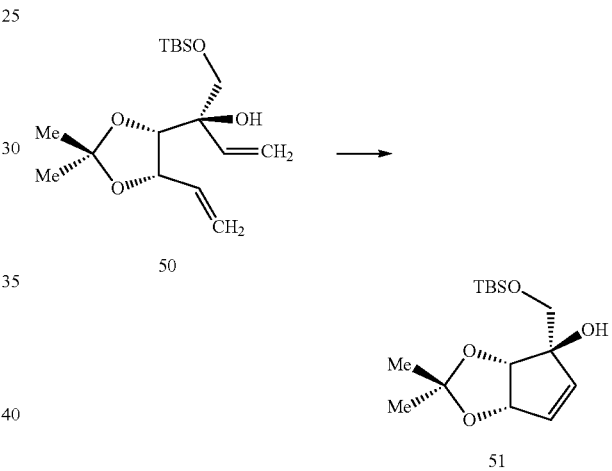

4-(tert-Butyl-dimethyl-silanyloxymethyl)-2,2-dimethyl-4,6adihydro-3aH-cyclopenta[1,3]-dioxol-4-61 (51)

A stirred solution of diene 50 (6:1 dr) (9.4 g, 29 mmol, 1.0 equiv) in dichloromethane (300 mL) was subjected to two freeze-pump-thaw cycles. Grubbs 2$^{nd}$ generation catalyst (490 mg, 0.57 mmol, 0.02 equiv) was added at 25° C. The resulting purple solution was subjected to one freeze-pump-thaw cycle. The purple solution was stirred at 25° C. for 24 h. The reaction mixture was concentrated by rotary evaporation. The residue was purified by silica gel column chromatography (12.5% ethyl acetate in hexane) to afford 51 (6.8 g, 95% yield based on 6:1 dr of 50) as a brown oil. $R_f$=0.23 (12.5% ethyl acetate in hexane); $^1$H NMR (500 MHz, $C_6D_6$) δ 5.80 (dd, 1H, J=2, 6 Hz, HCCH), 5.66 (d, 1H, J=6 Hz, HCCH), 5.19 (br d, 1H, J=6 Hz, CH(OR)), 4.55 (d, 1H, J=6 Hz, CH(OR)), 4.03 (d, 1H, J=10 Hz, CH$_2$(OTBS)), 3.69 (d, 1H, J=10 Hz, CH$_2$(OTBS)), 3.06 (s, 1H, OH), 1.36 (s, 3H, CH$_3$), 1.21 (s, 3H, CH$_3$), 0.91 (s, 9H, C(CH$_3$)$_3$), 0.03 (s, 3H, SiCH$_3$), 0.01 (s, 3H, SiCH$_3$); $^{13}$C NMR (125 MHz, $C_6D_6$) δ 135.48, 135.25, 112.07, 85.42, 85.16, 84.87, 65.77, 27.82, 26.13, 26.05, 18.58, −5.34; IR (neat film) 3541 (w), 2931 (m), 2858

(m) cm$^{-1}$; HRMS (ESI) m/z: Calcd for C$_{15}$H$_{28}$NaO$_4$Si (MNa$^+$) 323.1655; observed 323.1650.

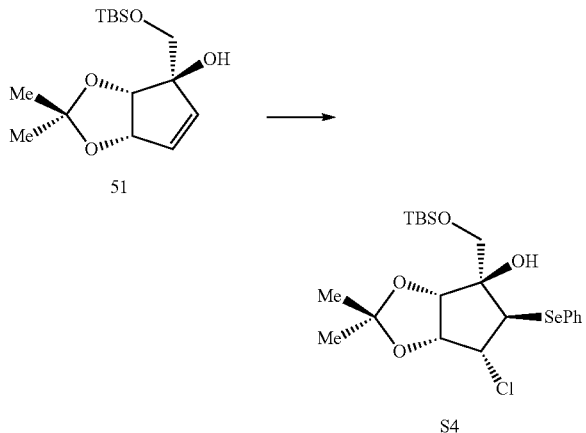

4-(tert-Butyl-dimethyl-silanyloxymethyl)-6-chloro-2,2-dimethyl-5-phenylselanyl-tetrahydro-cyclopenta[1,3]-dioxol-4-6l (S4)

Phenylselenenyl chloride (4.0 mg, 21 mmol, 1.1 equiv) was added to a stirred solution of alkene 51 (6.0 g, 20 mmol, 1.0 equiv) in acetonitrile (100 mL) at 0° C. The resulting orange solution was stirred at 0° C. for 1 h. The reaction mixture was concentrated by rotary evaporation to afford S4 (10 g, 99% yield) as an orange oil. R$_f$=0.36 (10% ethyl acetate in hexane); $^1$H NMR (500 MHz, C$_6$D$_6$) δ 7.48-7.51 (m, 2H, SePh), 6.90-6.96 (m, 3H, SePh), 4.95 (dt, 1H, J=1, 6 Hz, CH(OR)), 4.88 (dd, 1H, J=1, 2 Hz, CHCl), 4.43 (dd, 1H, J=2, 6 Hz, CH(OR)), 4.17 (d, 1H, J=10 Hz, CH$_2$(OTBS)), 4.00 (d, 1H, J=10 Hz, CH$_2$(OTBS)), 3.92 (m, 1H, CHSePh), 3.19 (s, 1H, OH), 1.56 (s, 3H, CH$_3$), 1.04 (s, 3H, CH$_3$), 0.88 (s, 9H, C(CH$_3$)$_3$), 0.02 (s, 3H, SiCH$_3$), 0.01 (s, 3H, SiCH$_3$); $^{13}$C NMR (125 MHz, C$_6$D$_6$) δ 132.79, 131.81, 129.48, 127.42, 112.09, 89.08, 85.72, 84.19, 69.35, 65.41, 56.79, 25.83, 25.77, 23.87, 18.30, -5.48, -5.62; IR (neat film) 3527 (w), 2930 (m), 2857 (m) cm$^{-1}$.

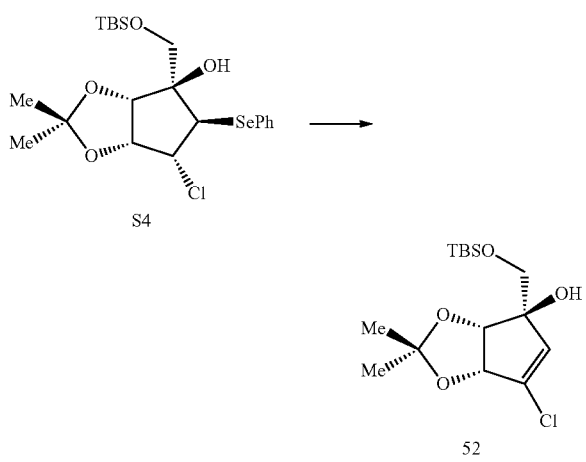

4-(tert-Butyl-dimethyl-silanyloxymethyl)-6-chloro-2,2-dimethyl-4,6a-dihydro-3aH-cyclopenta[1,3]-dioxol-4-6l (52)

70% meta-Chloroperoxybenzoic acid (6.4 g, 26 mmol, 1.3 equiv) was added to a stirred solution of selenide S4 (9.8 g, 20 mmol, 1.0 equiv) in dichloromethane (100 mL) at 0° C. The resulting orange mixture was stirred at 0° C. for 5 h. Dimethyl sulfide (19 mL, 260 mmol, 13 equiv) was added at 0° C. The resulting light brown mixture was stirred at 0° C. for 30 min Triethylamine (5.6 mL, 40 mmol, 2.0 equiv) was added at 0° C. The resulting brown solution was stirred at 0° C. for 10 min, warmed to 25° C., and stirred for 1 h. The reaction mixture was diluted with a saturated solution of sodium bicarbonate (400 mL), and extracted with ethyl acetate (3×300 mL). The combined organic layers were dried (magnesium sulfate), gravity filtered, and concentrated by rotary evaporation to afford 52 (6.7 g, 99% yield) as a brown oil. R$_f$=0.32 (12.5% ethyl acetate in hexane); $^1$H NMR (500 MHz, C$_6$D$_6$) δ 5.63 (br s, 1H, CHCCl), 4.96 (d, 1H, J=5 Hz, CH(OR)), 4.41 (dd, 1H, J=1.2, 5 Hz, CH(OR)), 3.88 (d, 1H, J=10 Hz, CH$_2$(OTBS)), 3.56 (d, 1H, J=10 Hz, CH$_2$(OTBS)), 3.15-3.35 (br s, 1H, OH), 1.32 (s, 3H, CH$_3$), 1.14 (s, 3H, CH$_3$), 0.87 (s, 9H, C(CH$_3$)$_3$), -0.02 (s, 3H, SiCH$_3$), -0.03 (s, 3H, SiCH$_3$); $^{13}$C NMR (125 MHz, C$_6$D$_6$) δ 140.02, 131.71, 113.01, 85.36, 85.10, 82.55, 65.35, 27.56, 26.28, 25.94, 18.47, -5.43, -5.48; IR (neat film) 3537 (w), 2931 (m), 2858 (m), 1715 (w), 1624 (w) cm$^{-1}$.

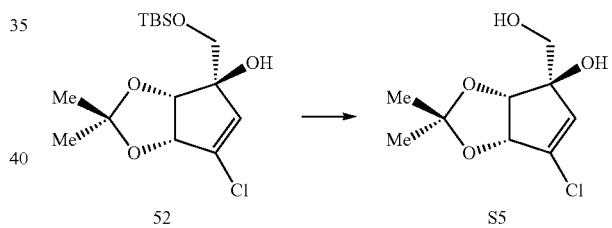

6-Chloro-4-hydroxymethyl-2,2-dimethyl-4,6a-dihydro-3aH-cyclopenta[1,3]-dioxol-4-6l (S5)

A 1 molar solution of tetrabutylammonium fluoride in tetrahydrofuran (27 mL, 27 mmol, 1.3 equiv) was added to a stirred solution of silyl ether 52 (6.7 g, 20 mmol, 1.0 equiv) in tetrahydrofuran (80 mL) at 25° C. The resulting brown solution was stirred at 25° C. for 3 h. The reaction mixture was concentrated by rotary evaporation. The residue was purified by silica gel column chromatography (25% hexane in ethyl acetate) to afford S5 (4.4 g, 99% yield) as a brown oil. R$_f$=0.44 (25% hexane in ethyl acetate); $^1$H NMR (500 MHz, C$_6$D$_6$) δ 5.37 (t, 1H, J=1 Hz, CHCCl), 4.79 (dd, 1H, J=0.5, 5.5 Hz, CH(OR)), 4.23 (dd, 1H, J=1, 5.5 Hz, CH(OR)), 3.64 (d, 1H, J=11 Hz, CH$_2$(OH)), 3.37 (d, 1H, J=11 Hz, CH$_2$(OH)), 1.23 (s, 3H, CH$_3$), 1.07 (d, 3H, J=0.6 Hz, CH$_3$); $^{13}$C NMR (125 MHz, C$_6$D$_6$) δ 139.51, 130.65, 113.46, 85.82, 85.33, 83.12, 65.29, 27.29, 26.08; IR (neat film) 3401 (m), 2989 (w), 2937 (w), 1624 (w) cm$^{-1}$; HRMS (ESI) m/z: Calcd for C$_9$H$_{13}$ClNaO$_4$ (MNa$^+$) 243.0400; observed 243.0412.

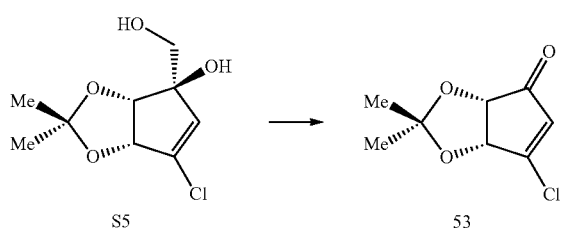

6-Chloro-2,2-Dimethyl-3a,6a-dihydro-cyclopenta[1,3]dioxol-4-one (53)

A 0.5 molar solution of sodium periodate in water (10 mL, 5.00 mmol, 1.1 equiv) was added to a stirred solution of diol S5 (1.0 g, 4.5 mmol, 1.0 equiv) in dichloromethane (23 µL) at 25° C. The resulting biphasic mixture was vigorously stirred at 25° C. for 30 min. The reaction mixture was diluted with water (50 mL) and extracted with dichloromethane (3×40 mL). The combined organic layers were dried (magnesium sulfate), gravity filtered, and concentrated by rotary evaporation. The residue was purified by silica gel column chromatography (20% ethyl acetate in hexane) to afford 53 (750 mg, 90% yield) as a white crystalline solid. $R_f$=0.35 (25% ethyl acetate in hexane); $^1$H NMR (500 MHz, $C_6D_6$) δ 5.54 (s, 1H, ClCCH), 4.21 (d, 1H, J=5.5 Hz, CH(OR)), 3.94 (d, 1H, J=5.5 Hz, CH(OR)); 1.19 (s, 3H, $CH_3$), 1.10 (d, 3H, J=0.3 Hz, $CH_3$); $^{13}$C NMR (125 MHz, $C_6D_6$) δ 196.82, 145.39, 131.16, 115.65, 81.01, 79.00, 27.30, 26.31; IR (neat film) 2987 (w), 2933 (w), 1722 (s), 1582 (s) cm$^{-1}$; HRMS (EI) m/z: Calcd for $C_8H_9ClO_3$ (M$^+$) 188.0240; observed 188.0242.

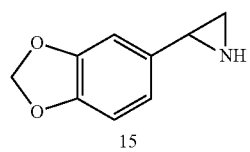

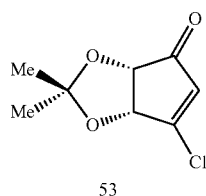

6-(2-Benzo[1,3]dioxol-5-yl-aziridin-1-yl)-2,2-Dimethyl-3a,6a-dihydro-cyclopenta[1,3]dioxol-4-one (54)

Triethylamine (0.4 mL, 3.0 mmol, 2.0 equiv) and β-chloroenone 53 (280 mg, 1.5 mmol, 1.0 equiv) were sequentially added to a stirred solution of aziridine 15 (360 mg, 2.2 mmol, 1.5 equiv) in tetrahydrofuran (10 mL) at 25° C. The resulting white mixture was stirred at 25° C. for 3 h. The crude reaction mixture was loaded directly onto a column and purified by silica gel column chromatography (1% triethylamine and 49% benzene in ethyl acetate) to afford 54 (400 mg, 85% yield) as a yellow foam. $R_f$=0.68 (1% triethylamine and 49% benzene in ethyl acetate); $^1$H NMR (500 MHz, $C_6D_6$) δ 6.55-6.70 (m, 3H, ArH), 5.24-5.28 (m, 2H, $OCH_2O$), 5.14-5.18 (m, 1H, NCCH), 4.50-4.56 (m, 1H, CH(OR)), 4.19-4.27 (m, 1H, CH(OR)), 2.46-3.18 (m, 1H, ArCHN), 1.84-2.17 (m, 1H, $CH_2N$), 1.63-1.78 (m, 1H, $CH_2N$), 1.28-1.32 (m, 3H, $CH_3$), 1.10-1.12 (m, 3H, $CH_3$); IR (neat film) 2989 (w), 1703 (m), 1586 (s) cm$^{-1}$; HRMS (ESI) m/z: Calcd for $C_{17}H_{18}NO_5$ (MO 316.1185; observed 316.1186.

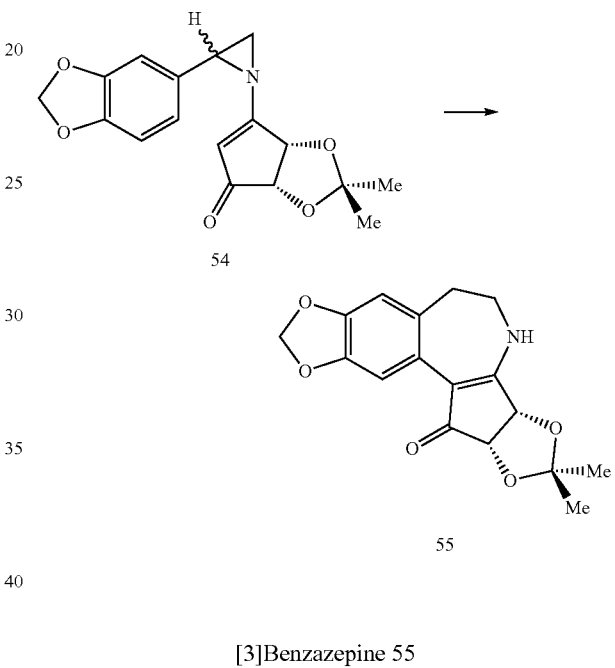

[3]Benzazepine 55

Cesium carbonate (3.2 g, 9.8 mmol, 4.0 equiv) was added to a stirred solution of aziridine 54 (770 mg, 2.4 mmol, 1.0 equiv) in 1,4-dioxane (350 mL) at 25° C. The reaction vessel was sealed under argon and heated to 100° C. via oil bath for 18 h. The reaction mixture was gravity filtered and concentrated by rotary evaporation. The residue was purified by passage through a plug of silica gel (ethyl acetate) to afford 55 (590 mg, 76% yield) as a tan foam. $R_f$=0.27 (50% ethyl acetate in benzene); $^1$H NMR (500 MHz, $CDCl_3$) δ 7.82 (br s, 1H, ArH), 6.54 (s, 1H, ArH), 5.93 (d, 1H, J=1.5 Hz, $OCH_2O$), 5.91 (d, 1H, J=1.5 Hz, $OCH_2O$), 5.77 (br s, 1H, NH), 4.97 (d, 1H, J=6 Hz, CH(OR)), 4.65 (d, 1H, J=6 Hz, CH(OR)), 3.80-3.85 (m, 1H, $ArCH_2CH_2N$), 3.60-3.65 (m, 1H, $ArCH_2CH_2N$), 2.95 (br t, 2H, J=4 Hz, $ArCH_2CH_2N$), 1.44 (s, 3H, $CH_3$), 1.43 (s, 3H, $CH_3$); $^{13}$C NMR (125 MHz, $C_6D_6$) δ 195.02, 165.26, 146.76, 146.28, 133.02, 126.24, 113.71, 109.55, 109.10, 109.00, 100.84, 78.98, 76.30, 47.65, 36.87, 27.89, 26.87; IR (neat film) 3266 (w), 2924 (s), 2855 (m), 1705 (w), 1585 (s) cm$^{-1}$; HRMS (ESI) m/z: Calcd for $C_{17}H_{18}NO_5$ (MH$^+$) 316.1185; observed 316.1189.

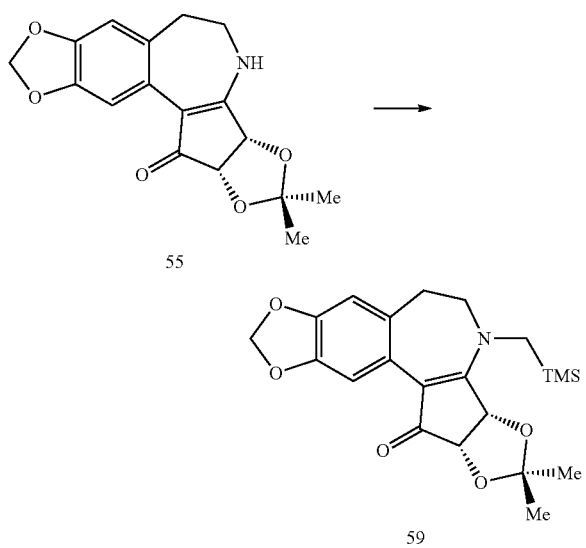

55

59

N-(trimethylsilyl)methyl vinylogous amide 59

Cesium carbonate (1.1 g, 3.5 mmol, 2.0 equiv) and (iodomethyl)trimethylsilane (1.3 mL, 8.7 mmol, 5.0 equiv) were sequentially added to a stirred solution of [3]benzazepine 55 (540 mg, 1.7 mmol, 1.0 equiv) in tetrahydrofuran (12 mL) at 25° C. The resulting brown mixture was stirred at 25° C. for 20 h. The reaction mixture was diluted with a saturated solution of sodium sulfate (50 mL) and extracted with ethyl acetate (3×50 mL). The combined organic layers were dried (magnesium sulfate), gravity filtered, and concentrated by rotary evaporation. The residue was purified by silica gel column chromatography (50% benzene in ethyl acetate) to afford 59 (490 mg, 75% yield) as a pale yellow film. $R_f$=0.55 (50% benzene in ethyl acetate); $^1$H NMR (500 MHz, CDCl$_3$) δ 7.73 (s, 1H, ArH), 6.49 (s, 1H, ArH), 5.92 (d, 1H, J=1.5 Hz, OCH$_2$O), 5.88 (d, 1H, J=1.5 Hz, OCH$_2$O), 5.10 (d, 1H, J=6 Hz, CH(OR)), 4.66 (d, 1H, J=6 Hz, CH(OR)), 3.55-3.65 (m, 2H, ArCH$_2$CH$_2$N), 3.20-3.40 (m, 2H, NCH$_2$SiMe$_3$), 2.85-3.00 (m, 2H, ArCH$_2$CH$_2$N), 1.44 (s, 3H, CH$_3$), 1.43 (s, 3H, CH$_3$), 0.14 (s, 9H, Si(CH$_3$)$_3$); $^{13}$C NMR (125 MHz, C$_6$D$_6$) δ 194.10, 164.04, 146.93, 146.24, 133.16, 127.00, 113.48, 110.62, 109.77, 108.22, 100.95, 78.78, 75.94, 57.48, 46.81, 35.82, 28.15, 26.84, −1.53; IR (neat film) 2924 (w), 1662 (w), 1567 (s) cm$^{-1}$; HRMS (ESI) m/z; Calcd for C$_2$H$_{28}$NO$_5$Si (MH$^+$) 402.1737; observed 402.1745.

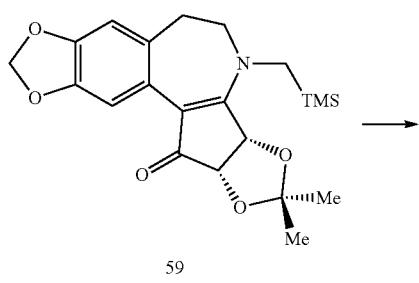

59

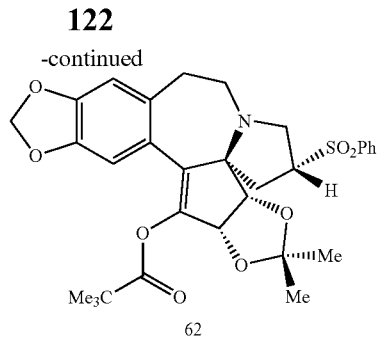

62

Hexacyclic sulfone 62

Pivaloyl chloride (62 µL, 0.50 mmol, 1.2 equiv) and silver trifluoromethanesulfonate (130 mg, 0.50 mmol, 1.2 equiv) were sequentially added to a stirred solution of vinylogous amide 59 (170 mg, 0.42 mmol, 1.0 equiv) in dichloromethane (5.6 mL) at 25° C. The resulting yellow mixture was stirred at 25° C. for 1 h, cooled to −45° C., and stirred for 15 min Phenyl vinyl sulfone (280 mg, 1.7 mmol, 4.0 equiv) and tetrabutylammonium triphenyldifluorosilicate (290 mg, 0.54 mmol, 1.3 equiv) were sequentially added at −45° C. The resulting tan mixture was stirred at −45° C. for 4 h, warmed to 25° C., and stirred for 16 h. The crude reaction mixture was loaded directly onto a column and purified by silica gel column chromatography (50% hexane in ethyl acetate) to afford 62 (190 mg, 77% yield) as a tan amorphous solid. $R_f$=0.43 (50% hexane in ethyl acetate); $^1$H NMR (500 MHz, C$_6$D$_6$) δ 7.04 (s, 1H, ArH), 6.80-6.85 (m, 3H, SO$_2$Ph), 6.70-6.75 (m, 2H, SO$_2$Ph), 6.45 (s, 1H, ArH), 5.71 (d, 1H, J=5.5 Hz, CH(OR)), 5.32 (d, 1H, J=1.4 Hz, OCH$_2$O), 5.24 (d, 1H, J=1.4 Hz, OCH$_2$O), 4.20 (d, 1H, J=5.5 Hz, CH(OR)), 3.80-3.85 (m, 1H, CH$_2$), 3.45-3.55 (m, 2H, CH$_2$), 3.20-3.35 (m, 2H, CH$_2$), 2.55-2.60 (m, 2H, CH$_2$), 2.22-2.32 (m, 2H, CH$_2$), 1.28 (s, 3H, CH$_3$), 1.20 (s, 3H, CH$_3$), 1.08 (s, 9H, C(CH$_3$)$_3$); $^{13}$C NMR (125 MHz, C$_6$D$_6$) δ 175.16, 148.43, 148.00, 146.23, 140.11, 133.69, 133.10, 129.12, 128.43, 123.26, 112.29, 110.61, 110.14, 101.18, 83.80, 80.59, 79.55, 63.46, 51.04, 50.97, 38.89, 32.39, 32.27, 30.96, 28.16, 26.99, 26.97; IR (neat film) 2981 (m), 2934 (m), 1751 (m), 1668 (w), 1568 (m) cm$^{-1}$; HRMS (ESI) m/z; Calcd for C$_{31}$H$_{36}$NO$_8$S (MH$^+$) 582.2162; observed 582.2159.

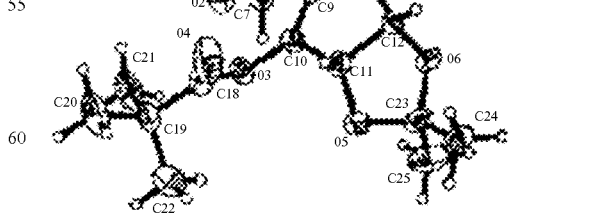

Note: this numbering system is for the X-ray crystal structure of 62 only and does not correspond to the numbering system of cephalotaxine (1).

Crystal Data and Structure Refinement for 62:

| | |
|---|---|
| Identification code | ga61fas |
| Empirical formula | C68 H84 N2 O16 S2 |
| Formula weight | 1249.49 |
| Temperature | 193(2) K |
| Wavelength | 0.71073 Å |
| Crystal system | Orthorhombic |
| Space group | P 21 21 21 |
| Unit cell dimensions | a = 10.4431(16) Å    a = 90°. |
| | b = 16.639(3) Å    b = 90°. |
| | c = 38.548(6) Å    g = 90°. |
| Volume | 6698.2(18) Å$^3$ |
| Z | 4 |
| Density (calculated) | 1.239 Mg/m$^3$ |
| Absorption coefficient | 0.147 mm$^{-1}$ |
| F(000) | 2664 |
| Crystal size | 0.40 × 0.08 × 0.06 mm$^3$ |
| Theta range for data collection | 1.33 to 25.70°. |
| Index ranges | −12 ≤ h ≤ 12, −20 ≤ k ≤ 20, −47 ≤ l ≤ 45 |
| Reflections collected | 32544 |
| Independent reflections | 12606 [R(int) = 0.1206] |
| Completeness to theta = 25.70° | 99.6 % |
| Absorption correction | Integration |
| Max. and min. transmission | 0.9940 and 0.9617 |
| Refinement method | Full-matrix least-squares on F$^2$ |
| Data/restraints/parameters | 12606/220/889 |
| Goodness-of-fit on F$^2$ | 0.932 |
| Final R indices [I > 2sigma(I)] | R1 = 0.0655, wR2 = 0.1174 |
| R indices (all data) | R1 = 0.1715, wR2 = 0.1546 |
| Absolute structure parameter | −0.03(11) |
| Largest diff. peak and hole | 0.233 and −0.275 e.Å−3 |

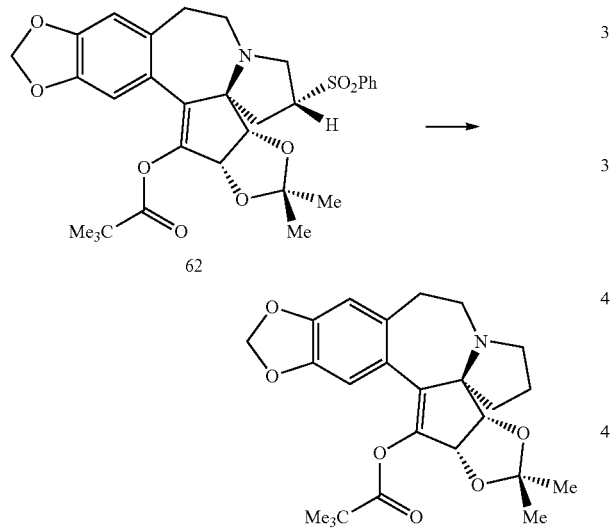

Hexacyclic pyrrolidine 65 tert-Butyl alcohol (50 μL, 0.52 mmol, 10 equiv) was added to hexacyclic sulfone 62 (14 mg, 24 mmol) at 25° C. The resulting tan mixture was stirred at 25° C. for 10 min, cooled to −78° C., and stirred for 10 min A 0.1 molar solution of samarium diiodide (2.6 mL, 0.26 mmol, 5.0 equiv) was added at −78° C. The resulting dark blue mixture was stirred at −78° C. for 10 min Hexamethyl phosphoric triamide (0.22 mL, 1.3 mmol, 25 equiv) was added at −78° C. The resulting purple mixture was stirred at −78° C. for 1 h, warmed to −45° C., and stirred for 2 h. The reaction mixture was warmed to 25° C., diluted with water (60 mL), and extracted with ethyl acetate (4×50 mL). The combined organic layers were dried (magnesium sulfate), gravity filtered, and concentrated by rotary evaporation. The residue was purified by silica gel column chromatography (50% benzene in ethyl acetate) to afford 65 (17 mg, 74% yield) as an off-white crystalline solid. R$_f$=0.39 (50% benzene in ethyl acetate); $^1$H NMR (500 MHz, C$_6$D$_6$) δ 7.03 (s, 1H, ArH), 6.45 (s, 1H, ArH), 5.72 (d, 1H, J=6 Hz, CH(OR)), 5.31 (d, 1H, J=1.5 Hz, OCH$_2$O), 5.26 (d, 1H, J=1.5 Hz, OCH$_2$O), 4.56 (d, 1H, J=6 Hz, CH(OR)), 3.70 (ddd, 1H, J=2, 12, 14 Hz, CH$_2$), 3.00 (ddd, 1H, J=3, 8, 11 Hz, CH$_2$), 2.82 (m, 1H, CH$_2$), 2.60-2.70 (m, 2H, CH$_2$), 2.50 (ddd, 1H, J=1.4, 6.6, 12 Hz, CH$_2$), 2.24 (ddd, 1H, J=1.7, 4, 18 Hz, CH$_2$), 1.78-1.88 (m, 1H, CH$_2$), 1.56-1.64 (m, 1H, CH$_2$), 1.51 (s, 3H, CH$_3$), 1.40-1.48 (m, 1H, CH$_2$), 1.30 (s, 3H, CH$_3$), 1.10 (s, 9H, C(CH$_3$)$_3$); $^{13}$C NMR (125 MHz, C$_6$D$_6$) δ 175.43, 147.62, 147.18, 145.95, 132.86, 130.44, 124.40, 111.97, 110.44, 110.25, 101.07, 86.00, 80.68, 78.90, 50.38, 48.51, 38.88, 32.07, 30.75, 28.28, 27.04, 26.85, 25.10; IR (neat film) 2930 (m), 1751 (m), 1485 (s) cm$^{-1}$; HRMS (ESI) m/z: Calcd for C$_{25}$H$_{32}$NO$_6$ (MH$^+$) 442.2230; observed 442.2231.

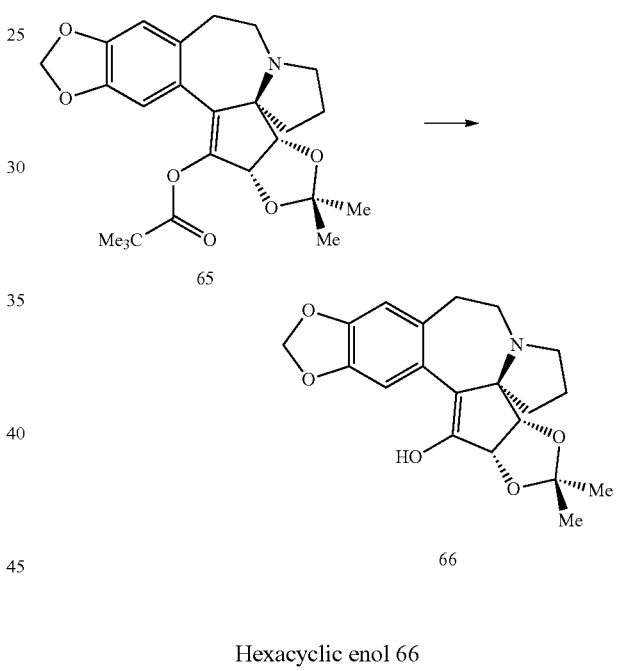

Hexacyclic enol 66

Schwartz's reagent (140 mg, 0.53 mmol, 3.0 equiv) was added to a stirred solution of enol-pivaloate 65 (78 mg, 0.18 μmol, 1.0 equiv) in tetrahydrofuran (0.33 mL) at 25° C. The reaction vessel was sealed under argon and heated to 40° C. via oil bath for 16 h. The reaction mixture was diluted with water (10 mL) and extracted with dichloromethane (3×10 mL). The crude reaction mixture was loaded directly onto a column and purified by silica gel column chromatography (10% methanol in chloroform) to afford 66 (63 mg, 99% yield) as a tan solid. R$_f$=0.34 (10% methanol in chloroform); $^1$H NMR (500 MHz, C$_6$D$_6$) δ 6.44 (br s, 2H, ArH), 5.32 (d, 2H, J=1.5 Hz, OCH$_2$O), 5.29 (br s, 2H, C(O)CH), 4.77 (br s, 1H, OH), 2.00-2.50 (m, 10H, CH$_2$), 1.35 (s, 3H, CH$_3$), 1.34 (s, 3H, CH$_3$); IR (neat film) 3417 (w), 2986 (m), 2935 (m), 2590 (w), 1720 (m), 1504 (m), 1485 (s) cm$^{-1}$; HRMS (ESI) m/z: Calcd for C$_{20}$H$_{24}$NO$_5$(MH$^+$) 358.1654; observed 358.1667.

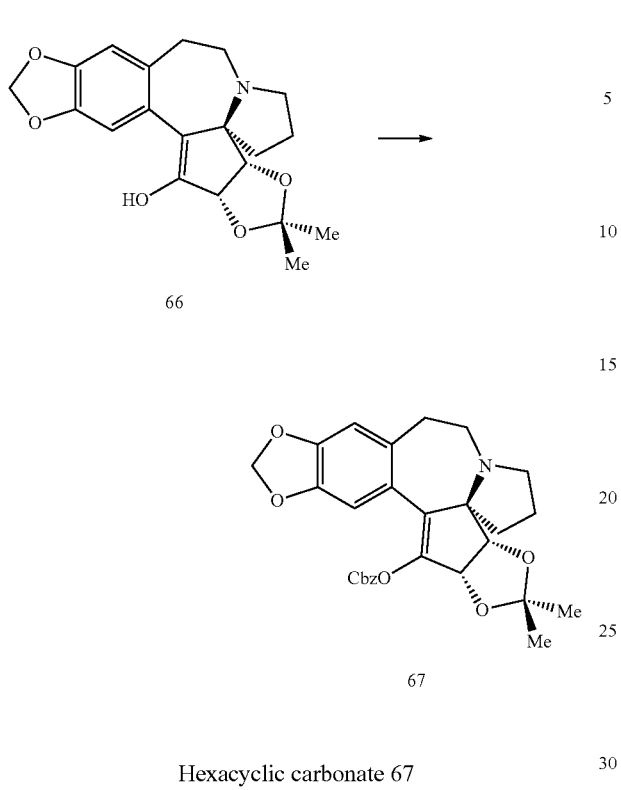

66

67

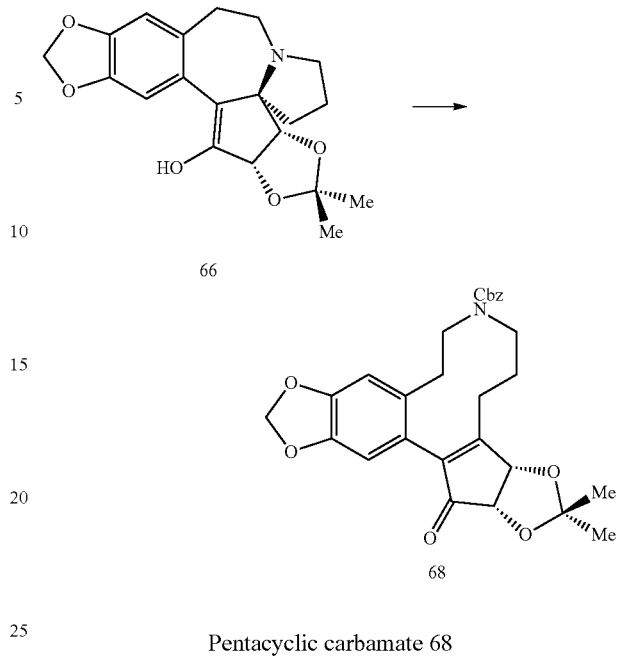

Pentacyclic carbamate 68

Hexacyclic carbonate 67

Potassium bis(trimethylsilyl)amide (63 mg, 0.30 mmol, 1.2 equiv) was added to a stirred solution of enol 66 (89 mg, 0.25 mmol, 1.0 equiv) in tetrahydrofuran (2.5 mL) at 0° C. The resulting orange solution was stirred at 0° C. for 15 min. Benzyl chloroformate (43 µL, 0.30 mmol, 1.2 equiv) was added at 0° C. The resulting yellow solution was stirred at 0° C. for 1 h. The reaction mixture was diluted with water (40 mL) and extracted with dichloromethane (2×40 mL). The combined organic layers were dried (magnesium sulfate), gravity filtered, and concentrated by rotary evaporation. The residue was purified by silica gel column chromatography (50% benzene in ethyl acetate) to afford 67 (110 mg, 86% yield) as a tan foam. $R_f$=0.34 (10% methanol in chloroform); $^1$H NMR (500 MHz, $C_6D_6$) δ 7.07 (s, 1H, ArH), 6.94-6.97 (m, 3H, Ph), 6.90-6.93 (m, 2H, Ph), 6.41 (s, 1H, ArH), 5.77 (d, 1H, J=6 Hz, C(O)CH), 5.24 (d, 1H, J=1.5 Hz, $OCH_2O$), 5.21 (d, 1H, J=1.5 Hz, $OCH_2O$), 4.76 (d, 1H, J=12 Hz, $OCH_2Ph$), 4.68 (d, 1H, J=12 Hz, $OCH_2Ph$), 4.56 (d, 1H, J=6 Hz, C(O)CH), 3.64 (m, 1H, $CH_2$), 2.98 (m, 1H, $CH_2$), 2.60-2.68 (m, 2H, $CH_2$), 2.46 (ddd, 1H, J=12, 6.5, 1.5 Hz, $CH_2$), 2.28 (ddd, 1H, J=17, 4, 1.5 Hz, $CH_2$), 1.76-1.84 (m, 1H, $CH_2$), 1.54-1.60 (m, 1H, $CH_2$), 1.48 (s, 3H, $CH_3$), 1.38-1.43 (m, 1H, $CH_2$), 1.30 (s, 3H, $CH_3$); $^{13}$C NMR (125 MHz, $C_6D_6$) δ 152.35, 147.79, 146.30, 146.12, 135.05, 132.45, 130.82, 128.40, 128.25, 128.16, 123.69, 112.04, 110.12, 109.95, 100.92, 85.70, 80.29, 78.70, 70.06, 50.21, 48.21, 31.85, 30.44, 28.10, 26.70, 24.88; IR (neat film) 2932 (w), 1762 (m), 1504 (m), 1485 (m) 1379 (m), 1222 (s) cm$^{-1}$; HRMS (ESI) m/z: Calcd for $C_{28}H_{30}NO_7$ (MH$^+$) 492.2022; observed 492.2032.

Triethylamine (5.0 µL, 36 µmol, 4.0 equiv) and benzyl chloroformate (5.0 µL, 36 µmol, 4.0 equiv) were sequentially added to a stirred solution of enol 66 (3.2 mg, 9.0 µmol, 1.0 equiv) in dichloromethane at 25° C. The resulting yellow solution was stirred at 25° C. for 18 h. The crude reaction mixture was loaded directly onto a column and purified by silica gel column chromatography (40% benzene in ethyl acetate) to afford 68 (2.2 mg, 50% yield) as a pale yellow film. $R_f$=0.76 (40% benzene in ethyl acetate); $^1$H NMR (500 MHz, $C_6D_6$) δ 7.07 (s, 1H, ArH), 6.94-6.98 (m, 3H, Ph), 6.90-6.94 (m, 2H, Ph), 6.41 (s, 1H, ArH), 5.77 (d, 1H, J=6 Hz, C(O)CH), 5.24 (d, 1H, J=1.5 Hz, $OCH_2O$), 5.21 (d, 1H, J=1.5 Hz, $OCH_2O$), 4.75 (d, 1H, J=12 Hz, $OCH_2Ph$), 4.68 (d, 1H, J=12 Hz, $OCH_2Ph$), 4.57 (d, 1H, J=6 Hz, C(O)CH), 3.65 (m, 1H, $CH_2$), 2.99 (m, 1H, $CH_2$), 2.82 (m, 1H, $CH_2$), 2.64 (m, 2H, $CH_2$), 2.47 (m, 1H, $CH_2$), 2.27 (m, 1H, $CH_2$), 1.80 (m, 1H, $CH_2$), 1.48 (s, 3H, $CH_3$), 1.40 (m, 1H, $CH_2$), 1.30 (s, 3H, $CH_3$).

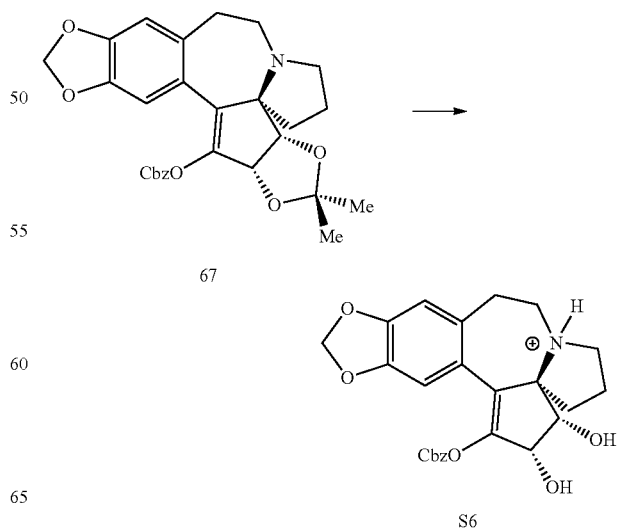

67

S6

Pentacyclic diol S6

A 33% solution of methanol in 2 molar hydrochloric acid (5 mL) was added to acetonide 67 (60 mg, 0.12 mmol, 1.0 equiv) at 25° C. The resulting cloudy white solution was stirred at 25° C. for 16 h. The reaction mixture was diluted with methanol and concentrated by rotary evaporation. This process was repeated four times. The residue was diluted with a 50% solution of methanol in toluene and concentrated by rotary evaporation. This process was repeated four times to afford S6 (60 mg, 99% yield) as a white film. $^1$H NMR (500 MHz, CD$_3$OD) δ 7.10-7.30 (m, 5H, Ph), 6.73 (s, 1H, ArH), 6.70 (s, 1H, ArH), 5.92 (d, 1H, J=1 Hz, OCH$_2$O), 5.90 (d, 1H, J=1 Hz, OCH$_2$O), 5.10 (d, 1H, J=12 Hz, OCH$_2$Ph), 5.06 (d, 1H, J=12 Hz, OCH$_2$Ph), 4.95 (d, 1H, J=6 Hz, CH(OH)), 4.40 (d, 1H, J=6 Hz, CH(OH)), 3.64-3.74 (m, 2H, CH$_2$), 3.10-3.32 (m, 4H, CH$_2$), 2.45 (m, 1H, CH$_2$), 2.00-2.10 (m, 2H, CH$_2$), 1.79 (m, 1H, CH$_2$); $^{13}$C NMR (125 MHz, CD$_3$OD) δ 152.46, 152.30, 150.03, 148.12, 136.05, 131.33, 129.77, 129.62, 129.44, 126.73, 122.58, 111.40, 110.48, 103.02, 85.29, 73.97, 71.79, 71.01, 53.31, 49.85, 30.55, 29.45, 23.00; IR (neat film) 3294 (s), 2957 (m), 2605 (m), 1766 (s), 1672 (w), 1621 (w), 1504 (s), 1487 (s), 1458 (s), 1380 (s), 1228 (s) cm$^{-1}$; HRMS (ESI) m/z: Calcd for C$_{25}$H$_{26}$NO$_7$ (MH$^+$) 452.1709; observed 452.1717.

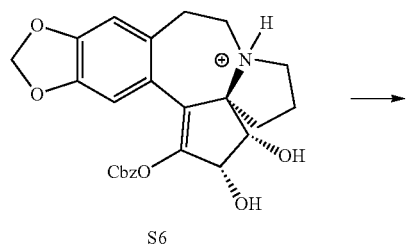

S6

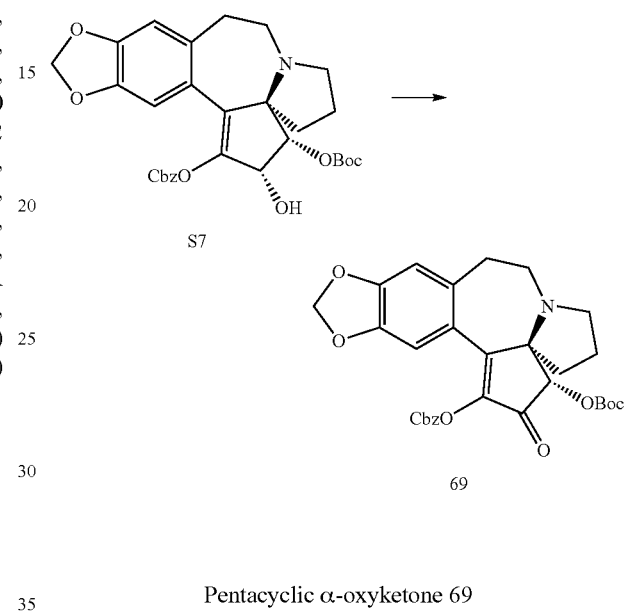

S7

Pentacyclic mono-carbonate S7

Ytterbium trifluoromethanesulfonate hydrate (87 mg, 0.12 mmol, 1.0 equiv) and di-tert-butyldicarbonate (0.11 mL, 0.48 mmol, 4.0 equiv) were sequentially added to a stirred solution of pentacyclic diol S6 (58 mg, 0.12 mmol, 1.0 equiv) in dichloromethane (3.0 mL) at 0° C. The resulting cloudy pale yellow solution was stirred at 0° C. for 2 d. The reaction mixture was diluted with water (50 mL) and extracted with ethyl acetate (3×40 mL). The combined organic layers were dried (magnesium sulfate), gravity filtered, and concentrated by rotary evaporation to afford crude S7 (70 mg) as a pale yellow foam. R$_f$=0.65 (10% methanol in chloroform); $^1$H NMR (500 MHz, CD$_3$OD) δ 7.30-7.35 (m, 3H, Ph), 7.26-7.30 (m, 2H, Ph), 6.65 (br s, 2H, ArH), 5.92 (s, 2H, OCH$_2$O), 5.13 (br s, 2H, OCH$_2$Ph), 4.85 (d, 1H, J=6 Hz, CH(OH)), 4.60 (d, 1H, J=6 Hz, CH(OBoc)), 3.42 (m, 1H, CH$_2$), 3.27 (m, 1H, CH$_2$), 2.99 (ddd, 1H, J=14.5, 5, 2 Hz, CH$_2$), 2.90 (m, 1H, CH$_2$), 2.72-2.80 (m, 2H, CH$_2$), 2.33 (dd, 1H, J=12.5, 7 Hz, CH$_2$), 1.60-1.80 (m, 4H, CH$_2$), 1.51 (s, 9H, OC(CH$_3$)$_3$); IR (neat film) 3520 (br, w) 2981 (m), 2933 (m), 1809 (m), 1743 (s), 1505 (m), 1487 (s), 1456 (m), 1372 (s), 1283 (s), 1225 (s) cm$^{-1}$; HRMS (ESI) m/z: Calcd for C$_{30}$H$_{34}$NO$_9$ (MH$^+$) 552.2234; observed 552.2216.

Pentacyclic α-oxyketone 69 ortho-Iodoxy benzoic acid (100 mg, 0.36 mmol, 3.0 equiv) was added to a stirred solution of crude mono-carbonate S7 (66 mg, 0.12 mmol, 1.0 equiv) in dimethylsulfoxide (3.0 mL) at 25° C. The resulting orange solution was stirred at 25° C. for 20 h. The reaction mixture was diluted with water (200 mL) and extracted with diethyl ether (5×40 mL). The combined organic layers were dried (magnesium sulfate), gravity filtered, and concentrated by rotary evaporation. The residue was purified by silica gel column chromatography (12.5% ethyl acetate in benzene) to afford 69 (33 mg, 50% yield from 67) as a pale yellow film. R$_f$=0.45 (12.5% ethyl acetate in benzene); $^1$H NMR (500 MHz, C$_6$D$_6$) δ 6.95-6.99 (m, 5H, Ph), 6.71 (s, 1H, ArH), 6.29 (s, 1H, ArH), 5.79 (s, 1H, CH(OBoc)), 5.17 (d, 1H, J=1.5 Hz, OCH$_2$O), 5.13 (d, 1H, J=1.5 Hz, OCH$_2$O), 4.81 (d, 1H, J=12 Hz, OCH$_2$Ph), 4.73 (d, 1H, J=12 Hz, OCH$_2$Ph), 3.09 (ddd, 1H, J=14.5, 11.5, 4.5 Hz, CH$_2$), 2.67 (ddd, 1H, J=17, 11, 6 Hz, CH$_2$), 2.60 (ddd, 1H, J=14.5, 8, 2 Hz, CH$_2$), 2.45-2.55 (m, 2H, CH$_2$), 2.36 (m, 1H, CH$_2$), 2.15 (dd, 1H, J=13, 7 Hz, CH$_2$), 1.86 (m, 1H, CH$_2$), 1.46 (m, 1H, CH$_2$), 1.32 (s, 9H, OC(CH$_3$)$_3$) 1.30 (m, 1H, CH$_2$); $^{13}$C NMR (125 MHz, C$_6$D$_6$) δ 191.35, 158.90, 153.68, 152.04, 149.30, 146.46, 142.65, 134.88, 132.69, 128.64, 128.58, 128.56, 121.72, 110.44, 110.07, 101.37, 82.49, 81.78, 73.31, 71.00, 48.45, 41.84, 34.29, 32.79, 27.62, 24.78; IR (neat film) 2978 (m), 2929 (m), 1753 (s), 1736 (s), 1692 (m), 1505 (m), 1485 (s) cm$^{-1}$; HRMS (ESI) m/z: Calcd for C$_{30}$H$_{32}$NO$_9$ (MH$^+$) 550.2077; observed 550.2080.

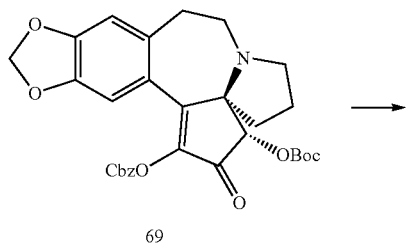

69

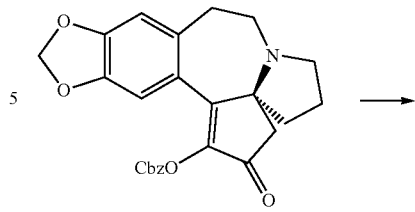

S8

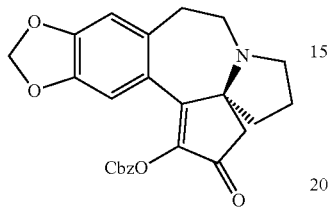

S8

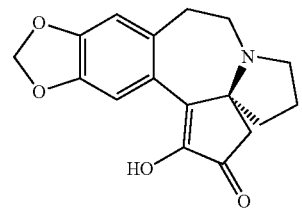

70

(+)-Demethylcephalotaxinone (70)

Pentacyclic enone S8

A stirred solution of α-oxyketone 69 (30 mg, 55 μmol, 1.0 equiv) in acetone (2.0 mL) was subjected to five freeze-pump-thaw cycles. A solution of water (1.0 mL) was subjected to 5 freeze-pump-thaw cycles, chromium(II) chloride (67 mg, 0.55 mmol, 10 equiv) was added, and the resulting blue/green solution was subjected to another five freeze-pump-thaw cycles. The aqueous chromium solution was transferred via cannula to the reaction mixture at 25° C. The resulting green solution was subjected to another 5 freeze-pump-thaw cycles. The green solution was stirred at 25° C. for 1 h. The reaction mixture was diluted with water (50 mL) and extracted with ethyl acetate (4×40 mL). The combined organic layers were dried (magnesium sulfate), gravity filtered, and concentrated by rotary evaporation. The residue was purified by silica gel column chromatography (50% benzene in ethyl acetate) to afford S8 (10 mg, 42% yield) as a colorless film. $R_f$=0.45 (12.5% ethyl acetate in benzene); $^1$H NMR (500 MHz, $C_6D_6$) δ 6.96-7.02 (m, 5H, Ph), 6.83 (s, 1H, ArH), 6.37 (s, 1H, ArH), 5.21 (d, 1H, J=1.5 Hz, $OCH_2O$), 5.16 (d, 1H, J=1.5 Hz, $OCH_2O$), 4.88 (d, 1H, J=12 Hz, $OCH_2Ph$), 4.77 (d, 1H, J=12 Hz, $OCH_2Ph$), 3.14 (ddd, 1H, J=15.5, 12, 4 Hz, $CH_2$), 2.80 (ddd, 1H, J=16.5, 11.5, 5.5 Hz, $CH_2$), 2.54-2.62 (m, 2H, $C(O)CH_2$, $CH_2$), 2.47-2.53 (m, 2H, $CH_2$), 2.37-2.45 (m, 2H, $C(O)CH_2$, $CH_2$), 1.55 (m, 1H, $CH_2$), 1.43 (m, 1H, $CH_2$), 1.23-1.29 (m, 2H, $CH_2$); $^{13}$C NMR (125 MHz, $C_6D_6$) δ 196.81, 161.39, 152.63, 149.13, 146.48, 145.12, 134.96, 132.54, 128.46, 128.31, 128.25, 122.90, 110.29, 109.39, 101.17, 70.58, 70.17, 51.35, 48.80, 42.97, 38.83, 32.44, 24.37; IR (neat film) 2924 (m), 1767 (s), 1718 (s), 1643 (w), 1504 (m), 1485 (s), 1382 (m), 1227 (s) cm$^{-1}$; HRMS (ESI) m/z: Calcd for $C_{25}H_{24}NO_6$ (MH$^+$) 434.1604; observed 434.1616.

10% Palladium on carbon (5 mg, ~33 wt. %) was added to a stirred solution of benzyl carbonate S8 (14 mg, 32 μmol, 1.0 equiv) in ethyl acetate (5.0 mL) at 25° C. The resulting black mixture was charged with an atmosphere of hydrogen (balloon) and stirred at 25° C. for 6 h. The crude reaction mixture was eluted through a short plug of celite (ethyl acetate followed by dichloromethane) and the organic layer was concentrated by rotary evaporation to afford (+)-70 (10 mg, 99% yield) as a colorless film. $R_f$=0.30 (10% methanol in chloroform); $^1$H NMR (500 MHz, $C_6D_6$) δ 7.04 (s, 1H, ArH), 6.42 (s, 1H, ArH), 5.27 (d, 1H, J=1.5 Hz, $OCH_2O$), 5.23 (d, 1H, J=1.5 Hz, $OCH_2O$), 2.83-2.97 (m, 2H, $CH_2$), 2.52-2.62 (m, 3H, $CH_2$), 2.43 (d, 1H, J=18 Hz, $C(O)CH_2$), 2.30-2.36 (m, 2H, $C(O)CH_2$, $CH_2$), 1.58 (m, 1H, $CH_2$), 1.48 (m, 1H, $CH_2$), 1.35 (m, 1H, $CH_2$), 1.19 (dd, 1H, J=12, 6 Hz, $CH_2$); $^{13}$C NMR (125 MHz, $C_6D_6$) δ 218.26, 161.31, 148.42, 148.02, 146.26, 132.65, 124.69, 110.51, 110.12, 101.18, 70.67, 51.28, 49.22, 44.37, 39.15, 32.75, 24.54; IR (neat film) 3386 (w, br) 2922 (m), 1702 (s), 1506 (m), 1484 (s) cm$^{-1}$; HRMS (ESI) m/z: Calcd for $C_{17}H_{18}NO_4$ (MH$^+$) 300.1236, observed 300.1246; $[α]^{23}_D$ 358.8 (c 0.39, CHCl$_3$).

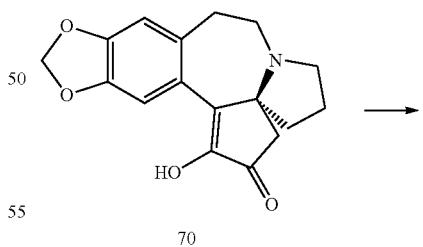

70

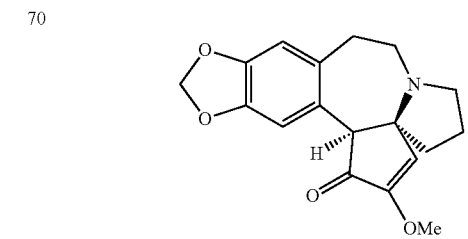

S9

(−)-Cephalotaxinone (S9)

Trimethyl orthoformate (33 µL, 0.30 mmol, 10 equiv) and tosylic acid monohydrate (12 mg, 60 µmol, 2.0 equiv) were sequentially added to a stirred solution of (+)-demethyl-cephalotaxinone (70) (9.0 mg, 30 µmol, 1.0 equiv) in dichloromethane (0.65 mL) at 0° C. The resulting dark orange solution was stirred at 0° C. for 30 min, warmed to 25° C., and stirred for 6.5 h. The reaction mixture was diluted with a saturated solution of sodium bicarbonate (30 mL) and extracted with dichloromethane (4×20 mL). The combined organic layers were dried (sodium sulfate), gravity filtered, and concentrated by rotary evaporation. The residue was purified by silica gel column chromatography (10% methanol in chloroform) to afford (−)-S9 (5.5 mg, 55% yield) as a pale yellow film. $R_f$=0.46 (10% methanol in chloroform); $^1$H NMR (500 MHz, $C_6D_6$) δ 6.58 (s, 1H, ArH), 6.47 (s, 1H, ArH), 5.76 (s, 1H, vinyl H), 5.34 (d, 1H, J=1.5 Hz, $OCH_2O$), 5.32 (d, 1H, J=1.5 Hz, $OCH_2O$), 3.16 (s, 3H, $OCH_3$), 2.71 (m, 1H, $CH_2$), 2.44-2.60 (m, 2H, $CH_2$), 2.28-2.40 (m, 2H, $CH_2$), 2.01 (dd, 1H, J=14, 7 Hz, $CH_2$), 1.72 (m, 1H, $CH_2$), 1.30-1.50 (m, 4H, $CH_2$); IR (neat film) 2928 (m), 1722 (s), 1624 (m), 1503 (m), 1486 (s), 1229 (s) $cm^{-1}$; HRMS (ESI) m/z: Calcd for $C_{18}H_{20}NO_4$ ($MH^+$) 314.1392; observed 314.1390.

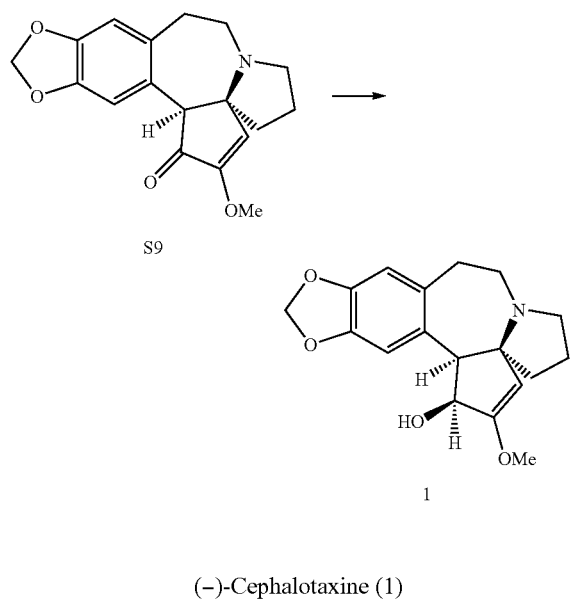

(−)-Cephalotaxine (1)

Sodium borohydride (27 mg, 0.70 mmol, 40 equiv) was added to a stirred solution of (−)-cephalotaxinone (S9) (5.5 mg, 18 µmol, 1.0 equiv) in methaol (0.65 mL) at −78° C. The resulting white mixture was stirred at −78° C. for 10 min, warmed to 25° C., and stirred for 1 h. The reaction mixture was diluted with water (30 mL) and extracted with dichloromethane (4×15 mL). The combined organic layers were dried (sodium sulfate), gravity filtered, and concentrated by rotary evaporation to afford (−)-1 (5.2 mg, 95% yield) as a pale yellow film. $R_f$=0.08 (10% methanol in chloroform); $^1$H NMR (500 MHz, $CDCl_3$) δ 6.68 (s, 1H, ArH), 6.65 (s, 1H, ArH), 5.90 (s, 2H, $OCH_2O$), 4.93 (s, 1H, vinyl H), 4.76 (d, 1H, J=9 Hz, CH(OH)), 3.73 (s, 3H, $OCH_3$), 3.68 (d, 1H, J=9 Hz, ArCHCH(OH)), 3.35 (m, 1H, $CH_2$), 3.08 (m, 1H, $CH_2$), 2.92 (ddd, 1H, J=12, 11, 7 Hz, $CH_2$), 2.54-2.62 (m, 2H, $CH_2$), 2.36 (dd, 1H, J=14, 7 Hz, $CH_2$), 2.00 (m, 1H, $CH_2$), 1.60-1.90 (m, 4H, $CH_2$); IR (neat film) 3411 (br, w), 2926 (m), 1651 (m), 1503 (m), 1486 (s), 1222 (s) $cm^{-1}$; HRMS (ESI) m/z: Calcd for $C_{18}H_{22}NO_4$ ($MH^+$) 316.1549; observed 316.1559.

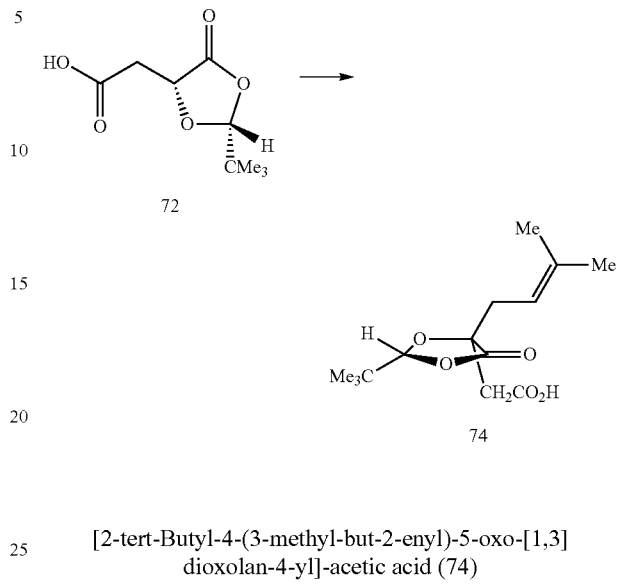

[2-tert-Butyl-4-(3-methyl-but-2-enyl)-5-oxo-[1,3]dioxolan-4-yl]-acetic acid (74)

A solution of LHMDS (413 mg, 2.47 mmol, 1.00 equiv) in THF (5 mL) at −78° C. was transferred via cannula to a stirred solution of acid 72 (500 mg, 2.47 mmol, 1.00 equiv) in THF (25 mL) at −78° C. The resulting solution was stirred at −78° C. for 15 minutes. A solution of LHMDS (496 mg, 2.96 mmol, 1.20 equiv) in THF (5 mL) at −78° C. was then added via cannula and the resulting solution was stirred for 20 min at −78° C. 3,3 dimethylallyl bromide (316 µL, 2.72 mmol, 1.10 equiv) was then added via syringe and the resulting solution was stirred at −78° C. for 19 h, at which time the reaction was quenched with 25 mL sat'd $NH_4Cl$, removed from the cold bath, and allowed to warm to RT. The solution was then poured into 75 mL 1N HCl, extracted with 3×75 mL $CH_2Cl_2$, the combined organic phases were dried over $MgSO_4$ and concentrated via rotary evaporation to yield an oily solid. Purification by silica gel column chromatography (19:1 MeOH:$CH_2Cl_2$) yielded 74 (438 mg, 66%) as a white powder. $R_f$=0.51 (19:1 $CH_2Cl_2$:MeOH); $^1$H NMR (400 MHz, $CDCl_3$) δ 5.16 (m, 2H, CH($CH_3$)$_3$; vinyl H), 2.83 (m, 2H, $CH_2$), 2.50 (d, 2H, J=7.7 Hz, $CH_2$), 1.74 (d, 3H, J=0.8 Hz, $CH_3$), 1.64 (d, 3H, J=0.8 Hz, $CH_3$), 0.93 (s, 9H, CH($CH_3$)$_3$; $^{13}$C NMR (100 mhz, $CDCl_3$) δ 174.91, 173.84, 137.96, 115.55, 108.42, 80.54, 39.44, 34.28, 32.40, 25.97, 23.60, 18.03; IR (neat film) 2973 (m), 2916 (m), 1800 (s), 1710 (s), 1181 (m), 1156 (m) $cm^{-1}$; HRMS (ESI) m/z calcd for $C_{14}H_{23}O_5$ ($M^+$) 271.1545; observed 271.1553; [α]p=−266° (c 2.98 $CHCl_3$).

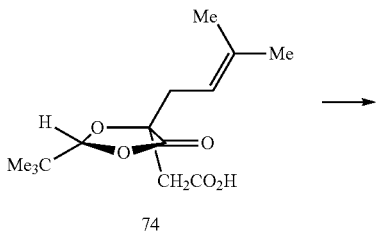

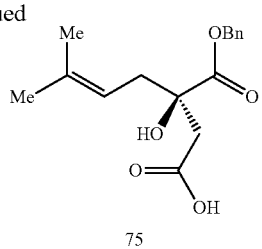

2-Hydroxy-2-(3-methyl-but-2-enyl)-succinic acid 1-benzyl ester (75)

A solution of dioxolanone 74 (120 mg, 0.444 mmol, 1.00 equiv) in THF (4.5 mL) was cooled to 0° C. and benzyl alcohol (69 µL, 0.67 mmol, 1.5 equiv) was added via syringe followed by a 60% dispersion of NaH in mineral oil (45 mg, 1.1 mmol, 2.5 equiv) which resulted in vigorous evolution of gas. The solution was allowed to stir at 0° C. for 30 min, at which time the reaction was quenched with 4.5 mL NaHCO$_3$, removed from the cold bath and allowed to warm to room temperature. The solution was then poured into H$_2$O (4.5 mL), washed with CH$_2$Cl$_2$ (1×6 mL), acidified to pH<5 with 1N HCl, and then extracted with Et$_2$O (4×6 mL). The combined ethereal phases were dried over MgSO$_4$ and solvent removal by rotary evaporation yielded a white solid which was purified by silica gel column chromatography (70:28:2 hex:EtOAc:HOAc) to yield 75 (114 mg, 88%) as a white solid. R$_f$=0.39 (60:38:2 EtOAc:Hex:HOAc); $^1$H NMR (500 MHz, CDCl$_3$) δ 7.35 (m, 5H, ArH), 5.20 (s, 2H, PhCH$_2$), 5.07 (m, 1H, vinyl H), 3.00 (d, 1H, J=16.7 Hz, C(O)CH$_2$), 2.76 (d, 1H, J=16.7 Hz, C(O)CH$_2$), 2.41 (m, 2H, CHCH$_2$), 1.67 (d, 3H, J=0.7 Hz, CH$_3$), 1.54 (d, 3H, J=0.7 Hz, CH$_3$); $^{13}$C NMR (100 MHz, CDCl$_3$) δ 176.43, 174.60, 136.79, 135.21, 128.71, 128.64, 128.61, 116.45, 75.41, 67.95, 42.69, 38.14, 26.06, 18.09; IR (neat film) 3483 (br m), 2968 (m), 1736 (s), 1498 (w), 1195 (s) cm$^{-1}$; HRMS (ESI) m/z calcd for C$_{16}$H$_{20}$O$_5$Na (M$^+$+Na$^+$) 315.1208; observed 315.1214; [α]$_D$=−18° (c 2.98, CHCl$_3$).

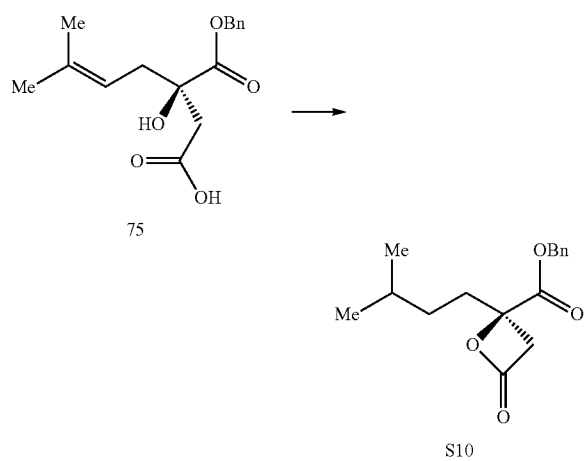

A solution of hydroxyester 75 (100 mg, 0.342 mmol, 1.00 equiv) and triethylamine (166 µL, 1.20 mmol, 3.50 equiv) in CH$_2$Cl$_2$ (14 mL) was added via syringe pump over 4 h to a solution of 2,4,6-trichlorobenzoyl chloride (80 µL, 0.51 mmol, 1.5 equiv) and N,N-dimethylaminopyridine (DMAP) (46 mg, 0.38 mmol, 1.1 equiv) in CH$_2$Cl$_2$ (3.4 mL). The solution was then allowed to stir for 1 h after complete addition after which time it was quenched with H$_2$O (10 mL). The phases were separated and the aqueous phase was extracted with CH$_2$Cl$_2$ (2×10 mL). The organic phases were combined, dried over Na$_2$SO$_4$, and the solvent was removed via rotary evaporation to yield a red solid which was purified by silica gel column chromatography (CH$_2$Cl$_2$) to yield S10 (47 mg, 50%) as a pale yellow oil. R$_f$=0.79 (60:38:2 Hex:EtOAc:HOAc); $^1$H NMR (500 MHz, CDCl$_3$) δ 7.37 (m, 5H, ArH), 5.25 (s, 2H, ArCH$_2$), 5.09 (m, 1H, vinyl H), 3.61 (d, 1H, J=16.4 Hz, C(O)CH$_2$), 3.36 (d, 1H, J=16.4 Hz, C(O)CH$_2$), 2.79 (m, 2H, CHCH$_2$), 1.70 (d, 3H, J=0.8 Hz, CH$_3$), 1.60 (d, 3H, J=0.8 Hz, CH$_3$); $^{13}$C NMR (100 MHz, CDCl$_3$) δ 169.21, 165.84, 138.67, 134.67, 128.68, 128.38, 114.24, 76.28, 67.84, 45.56, 33.43, 25.87, 17.99; IR (neat film) 2966 (m), 2914 (m), 1842 (s), 1737 (s), 1452 (m) 962 (m) cm$^{-1}$; HRMS (EI) m/z calcd for C$_{16}$H$_{18}$O$_4$ (M$^+$) 274.120509; observed 274.120646; [α]$_D$=+1.2° (c 2.92, CHCl$_3$).

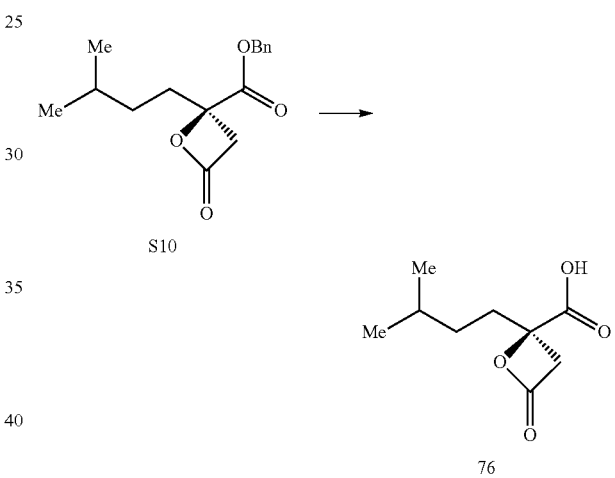

2-(3-Methyl-butyl)-4-oxo-oxetane-2-carboxylic acid (76)

To a solution of benzyl ester S10 (220 mg, 0.802 mmol, 1.00 equiv) in EtOAc (8 mL) was added Pd/C (10 wt % on C, 44 mg, 20% by weight). The resulting suspension was stirred under H$_2$ (1 atm) for 23 h, then filtered through a plug of celite. Solvent removal by rotary evaporation yielded an oil which showed alkene peaks by $^1$H NMR, so the residue was resubjected to the reaction conditions to yield carboxylic acid 76 (150 mg, >99%) as a clear, colorless oil. R$_f$=0.11 (60:38:2 hex:EtOAc:HOAc); $^1$H NMR (400 MHz, CDCl$_3$) δ 10.30 (br s, 1H, C(O)OH), 3.71 (d, 1H, J=16.6 Hz, C(O)CH$_2$), 3.45 (d, 1H, J=16.6 Hz, C(O)CH$_2$), 2.19 (ddd, 1H, J=14.2, 12.3, 4.8 Hz, CCH$_2$), 2.04 (ddd, 1H, J=14.2, 12.3, 4.8 Hz, CCH$_2$), 1.61 (septet, 1H, J=6.6 Hz (CH$_3$)$_2$CH), 1.40 (m, 1H, (CH$_3$)$_2$CHCH$_2$), 1.27 (m, 1H, (CH$_3$)$_2$CHCH$_2$), 0.92 (d, 6H, J=6.6 Hz (CH$_3$)$_2$); $^{13}$C NMR (400 MHz, CDCl$_3$) δ 174.96, 165.69, 76.43, 46.78, 33.17, 32.109, 27.89, 22.27, 22.20; IR (neat film) 3514 (br m), 3184 (br s), 2958 (s), 1828 (s), 1729 (s), 1408 (m), 1173 (s) cm$^{-1}$; [α]$_D$=22.1° (c 1.67, CHCl$_3$).

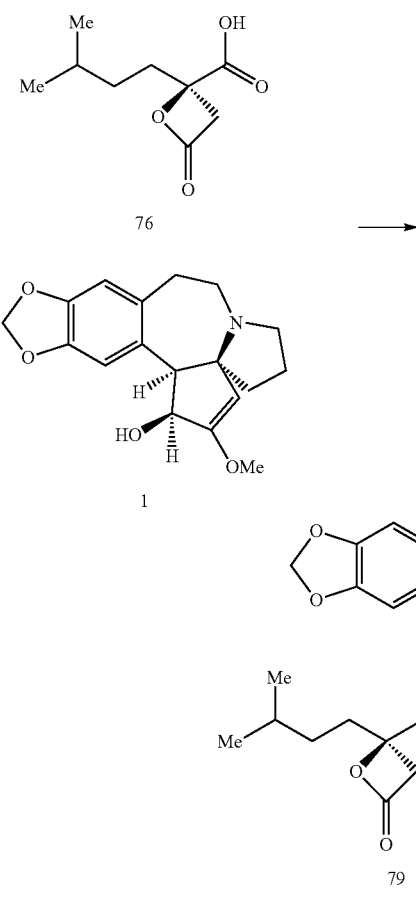

Deoxyharringtonine, β-lactone (I-3a)

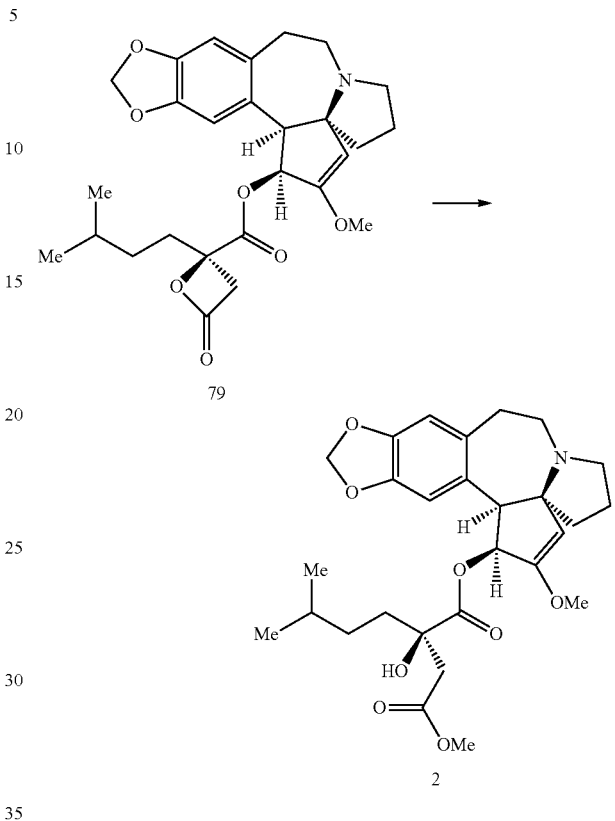

Deoxyharringtonine (2)

To a solution of β-lactone 76 (8.9 mg, 0.048 mmol, 1.5 equiv) and triethylamine (19.9 μL, 0.143 mmol, 4.50 equiv) in CH$_2$Cl$_2$ (320 μL) was added 2,4,6-trichlorobenzoyl chloride (8.2 μL, 0.052 mmol, 1.7 equiv) via syringe. The resulting dark purple solution was stirred at 23° C. for 1 h. This solution was then transferred via syringe to a solution of cephalotaxine (1) (10 mg, 0.032 mmol, 1.0 equiv) and N,N-dimethylaminopyridine (DMAP) in CH$_2$Cl$_2$ (320 μL). This solution was then stirred for 15 min, concentrated under a stream of N$_2$, and loaded directly onto a silica gel column that had been packed with 5% triethylamine in hexanes. The column was eluted with 1:1 hex:EtOAc to yield I-3a (12.4 mg, 81%) as an oil. R$_f$=0.39 (1:1 hex:EtOAc on plates pretreated with 5% TEA in pentane); $^1$H NMR (500 MHz, CDCl$_3$) δ 6.60 (app d, 2H, ArH), 5.91 (dd, 1H, J=9.6, 0.7 Hz, ArCHCH), 5.86 (dd, 2H, J=4.1, 1.4 Hz, OCH$_2$O), 5.08 (s, 1H, vinyl H), 3.81 (d, 1H, J=9.5 Hz, ArCHCH), 3.69 (s, 3H, OCH$_3$), 3.10 (m, 2H, CH$_2$), 2.98 (d, 1H, J=16.5 Hz, C(O)CH$_2$), 2.93 (m, 1H, CH$_2$), 2.73 (d, 1H, J=16.5 Hz, C(O)CH$_2$), 2.58 (m, 2H, CH$_2$), 2.35 (dd, 1H, J=14.3, 6.9, CH$_2$), 2.04 (m, 1H, CH$_2$), 1.88 (m, 2H, CH$_2$), 1.75 (m, 2H, CH$_2$), 1.62 (m, 1H, CH$_2$), 1.47 (septet, 1H, J=6.7 Hz, (CH$_3$)$_2$CH), 1.15 (m, 1H, CH$_2$), 1.02 (m, 1H, CH$_2$), 0.85 (dd, 6H, J=6.7, 1.2 Hz, (CH$_3$)$_2$CH); $^{13}$C (500 MHz, CDCl$_3$) δ 171.03, 168.57, 166.25, 113.17, 109.96, 109.91, 101.11, 76.53, 75.62, 65.63, 57.36, 54.05, 48.60, 46.31, 41.74, 33.21, 31.97, 27.91, 22.46, 22.14, 20.39; IR (neat film) 2958 (m), 1842 (s), 1750 (s), 1656 (m), 1504 (m), 1488 (s), 1037 (m) cm$^{-1}$; HRMS (EI) m/z calcd for C$_{27}$H$_{33}$NO$_7$ (M+) 483.225703; found 483.224659; [α]$_D$=−95° (c 2.77, CHCl$_3$).

To a solution of β-lactone I-3a (18 mg, 0.0372 mmol, 1.00 equiv) in MeOH (370 μL) was added a freshly prepared solution of 0.5M NaOMe in MeOH (82 μL, 0.0409 mmol, 1.10 equiv). After 15 min the solution was quenched with half sat'd NH$_4$Cl solution (300 μL) and partitioned between H$_2$O (10 mL) and CH$_2$Cl$_2$ (10 mL). The phases were separated and the aqueous phase was extracted with CH$_2$Cl$_2$ (2×10 mL), the combined organic phases were dried over MgSO$_4$, and concentrated by rotary evaporation to yield a yellow oil that was purified by silica gel column chromatography (70:28:2 benzene:hex:TEA) to yield deoxyharringtonine (2) (14.6 mg, 76%) as a clear, colorless oil. R$_f$=0.24 (9:1 benzene:EtOAc on plates pretreated with 5% TEA in pentane); $^1$H NMR (500 MHz, CDCl$_3$) δ 6.62 (s, 1H, ArH), 6.53 (s, 1H, ArH), 5.99 (dd, 1H, J=9.8, 0.7 Hz ArCHCH), 5.86 (dd, 2H, J=11.8, 1.5 Hz, OCH$_2$O), 5.04 (d, 1H, J=0.6 Hz, vinyl H), 3.77 (d, 1H, J=9.8 Hz, ArCHCH), 3.67 (s, 3H, OCH$_3$), 3.57 (s, 3H, OCH$_3$), 3.48 (s, 1H, OH), 3.12 (m, 2H, CH$_2$), 2.94 (td, 1H, J=11.1, 7.1 Hz, CH$_2$), 2.58 (m, 2H, CH$_2$), 2.37 (dd, 1H, J=14.3, 7 Hz, CH$_2$), 2.27 (d, 1H, J=16.6 Hz, C(O)CH$_2$), 2.04 (m, 1H, CH$_2$), 1.91 (m, 1H, CH$_2$), 1.88 (d, 1H, J=16.2 Hz, C(O)CH$_2$), 1.75 (m, 2H, CH$_2$), 1.42 (m, 3H, CH$_2$ & (CH$_3$)$_2$CH), 1.29 (m, 1H, CH$_2$), 0.97 (m, 1H, CH$_2$), 0.84 (d, 3H, J=7.0 Hz, (CH$_3$)$_2$CH), 0.83 (d, 3H, J=7.0 Hz, (CH$_3$)$_2$CH) $^{13}$C NMR (400 MHz, CDCl$_3$) δ 174.19, 170.57, 157.87, 146.75, 145.92, 133.43, 128.55, 128.46 (residual benzene), 112.75, 109.80, 100.94, 100.16, 74.83, 74.69, 70.70, 57.25, 55.98, 54.12, 51.63, 48.82, 43.54, 42.89, 36.87, 31.70, 31.48, 28.13, 22.83, 22.38, 20.42; IR (neat film) 3527 (w), 2955 (m), 1748 (s), 1653 (m), 1504 (m), 1488 (s), 1225 (s), 1036 (m), 754 (m); HRMS (ESI) calcd for $C_{28}H_{38}NO_8$ ($M^++H$) 516.2597; observed 516.2581; $[\alpha]_D=-110°$ (c 1.46, $CHCl_3$).

Lit $^1H$ NMR of 2 (100 MHz, $CDCl_3$) δ 6.59 (s, 1H, ArH), 6.50 (s, 1H, ArH), 5.96 (d, 1H, J=10 Hz ArCHCH), 5.82 (m, 2H, $OCH_2O$), 5.01 (s, 1H, vinyl H), 3.64 (s, 3H, $OCH_3$), 3.53 (s, 3H, $OCH_3$), 2.06 (q, 2H, J=16 Hz, $CH_2$), 0.82 (d, J=6 Hz, $(CH_3)_2CH$); $[\alpha]_D=-119°$ (c 0.6, $CHCl_3$) (Mikolajczak, K. L.; Powell, R. G.; Smith, C. R. Jr. Tetrahedron, 1972, 28, 1995).

Also, T. Ross Kelly and K. L. Mikolajczak compare deoxyharringtonine with its C2'-sidechain epimer: $^1H$ NMR of C2'-epi-2 Deoxyharringtonine: δ 6.59 (s, 1H, ArH), 6.50 (s, 1H, ArH), 5.97 (d, 1H, ArCHCH), 3.64 (s, 3H, $CH_3$), 3.53 (s, 3H, $CH_3$), 2.26 (d, 1H, $CH_2$), 1.86 (d, 1H, $CH_2$) Sidechain epimer: 6.56 (s, 2H, ArH), 5.86 (d, 1H, ArCHCH), 3.62 (s, 3H, $CH_3$) 3.60 (s, 3H, $CH_3$), 2.66 (d, 1H, $CH_2$), 2.46 (d, 1H, $CH_2$) The spectrum of our synthetic 1 clearly matches that of deoxyharringtonine and not its C2'-sidechain epimer (Mikolajczak, K. L.; Smith, C. R. Jr.; Weisleder, D.; Kelly, T. R.; McKenna, J. C.; Christenson, P. A. Tet. Lett, 1974, 283-286).

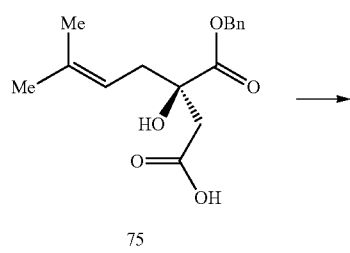

75

(R)-1-benzyl 4-methyl 2-hydroxy-2-(3-methylbut-2-enyl)succinate (77)

To a solution of acid 75 (175.2 mg, 0.599 mmol, 1.00 equiv) in 7:2 PhH:MeOH (6.0 mL) was added a 2.0 M solution of $TMSCHN_2$ (449 μL, 0.899 mmol, 1.50 equiv.). After the resulting gas evolution had subsided, the solvent was removed by rotary evaporation to yield methyl ester 77 (183.7 mg, 100%) as a clear, colorless oil. $R_f$=0.55 (2:1 hex:EtOAc); $^1H$ NMR (500 MHz, $CDCl_3$) δ 7.36 (m, 5H, aryl H), 5.23 (d, 1H, J=12.1 Hz, $PhCH_2$), 5.19 (d, 1H, J=12.1 Hz, $PhCH_2$), 5.08 (m, 1H, vinyl H), 3.68 (s, 1H, OH), 3.62 (s, 3H, $OCH_3$), 2.95 (d, 1H, J=16.2 Hz, $C(O)CH_2$), 2.72 (d, 1H, J=16.3 Hz, $C(O)CH_2$), 2.41 (m, 2H, $CHCH_2$), 1.67 (s, 3H, $C(CH_3)_2$), 1.54 (s, 3H, $C(CH_3)_2$); $^{13}C$ NMR (125 MHz, $CDCl_3$) δ 174.84, 171.43, 136.54, 135.46, 128.70, 128.66, 128.60, 116.75, 75.65, 67.79, 51.93, 42.81, 38.11, 26.06, 18.09; IR (neat film) 3514 (m), 3034 (w), 2955 (m), 1742 (s), 1498 (w), 1439 (s), 753 (m), 699 (m) $cm^{-1}$; LRMS (ESI) calc'd for $C_{17}H_{22}O_5Na$ ($M+Na^+$) 329.2; found 329.1.

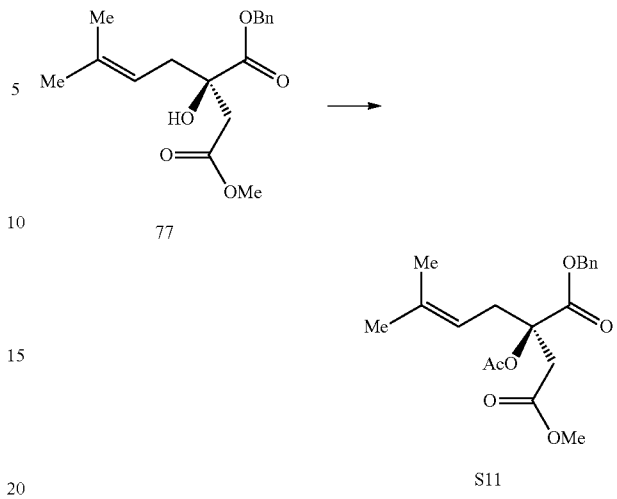

S11

(R)-1-benzyl 4-methyl 2-acetoxy-2-(3-methylbut-2-enyl)succinate (S11)

To a solution of tertiary alcohol 77 (33.0 mg, 0.109 mmol, 1.00 equiv) in dry pyridine (500 μL) at 0° C. was added acetic anhydride (114 μL, 1.09 mmol, 10.0 equiv) and N,N-dimethylaminopyridine (DMAP) (3.0 mg, 0.0246 mmol, 0.23 equiv). The solution was then stirred at 23° C. for 17 h at which time further DMAP (13.0 mg, 1.09 mmol, 1.00 equiv) and acetic anhydride (22 μL, 0.21 mmol, 1.9 equiv) were added. After 1 h the solution was diluted with $H_2O$ (10 mL) and extracted with $CH_2Cl_2$ (3×10 mL). The combined organic extracts were washed with 0.1M aqueous $CuSO_4$ soln, dried over $MgSO_4$, and concentrated by rotary evaporation to yield a dark red oil. Purification by silica gel column chromatography (5:1 hexanes:EtOAc) provided S11 (28.1 mg, 74%) as a colorless oil. $R_f$=0.32 (5:1 hexanes:EtOAc); $^1H$ NMR (500 MHz, $CDCl_3$) δ 7.35 (m, 5H, ArH), 5.14 (m, 2H, $ArCH_2$), 5.00 (tt, 1H, J=7.5, 1.3 Hz, vinyl H), 3.64 (s, 3H, $CO_2CH_3$), 3.27 (d, 1H, J=14.7 Hz, $C(O)CH_2$), 2.96 (d, 1H, J=14.7 Hz, $C(O)CH_2$), 2.80 (dd, 1H, J=14.6, 7.6 Hz, $CHCH_2$), 2.69 (dd, 1H, J=14.6, 7.6 Hz, $CHCH_2$), 2.06 (s, 3H, $C(O)CH_3$), 1.67 (s, 3H, $CCH_3$), 1.56 (s, 3H, $CCH_3$); $^{13}C$ NMR (125 MHz, $CDCl_3$) δ 170.34, 170.10, 169.79, 137.21, 135.45, 128.64, 128.50, 128.46, 115.89, 80.51, 67.48, 51.85, 37.41, 34.35, 26.11, 21.09, 18.00; IR (neat film) 3067 (w), 2955 (w), 1746 (s), 1441 (m), 1371 (m), 1227 (m); LRMS (ESI) calcd for $C_{19}H_{24}O_6Na$ ($M^++Na$) 371.16; observed 371.00.

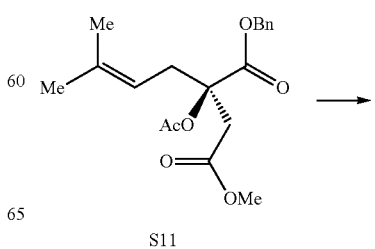

S11

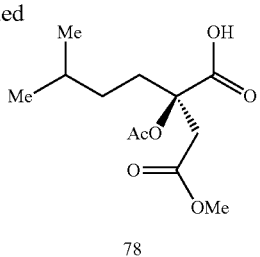

78

(R)-2-acetoxy-2-(2-methoxy-2-oxoethyl)-5-methyl-hex-4-enoic acid (78)

To a solution of benzyl ester S11 (28.0 mg, 0.0804 mmol, 1.00 equiv) in EtOAc (1.5 mL) was added 10% Pd/C (3.5 mg, 13 wt %). The resulting suspension was stirred under $H_2$ (1 atm) for 15 h and filtered through a plug of celite. Solvent removal by rotary evaporation yielded 78 (20.9 mg, 100%) as a clear, colorless oil. $^1$H NMR (500 MHz, CDCl$_3$) δ 10.34 (br s, 1H, CO$_2$H), 3.68 (s, 3H, CO$_2$CH$_3$), 3.29 (d, 1H, J=14.8 Hz, C(O)CH$_2$), 3.00 (d, 1H, J=14.8 Hz, C(O)CH$_2$), 2.09 (s, 3H, C(O)CH$_3$), 2.02 (m, 2H, CCH$_2$), 1.54 (septet, 1H, J=6.6 Hz, CH), 1.22 (m, 2H, CHCH$_2$), 0.89 (d, 6H, J=6.6 Hz, (CH$_3$)$_2$CH); $^{13}$C NMR (125 MHz, CDCl$_3$) δ 175.83, 170.18, 169.84, 80.49, 52.02, 37.55, 33.54, 31.89, 28.11, 22.55, 22.39, 21.08; IR (neat film) 3182 (v br m), 2958 (m), 2873 (m), 1746 (s), 1440 (m), 1370 (m), 1209 (s), 645 (w); LRMS (ESI) calcd for C$_{12}$H$_{20}$O$_6$Na (M$^+$+Na) 283.13; observed 283.01.

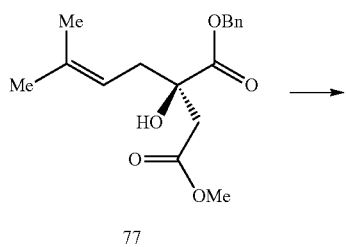

77

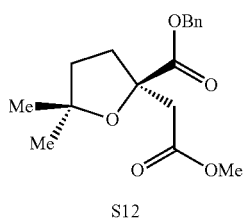

S12

(R)-benzyl 2-(2-methoxy-2-oxoethyl)-5,5-dimeth-yltetrahydrofuran-2-carboxylate (S12)

To a solution of alcohol 77 (183.6 mg, 0.599 mmol, 1.00 equiv) in 1:1 THF:H$_2$O (9.2 mL) was added Hg(OAc)$_2$ (382 mg, 1.199 mmol, 2.00 equiv). The resulting solution was stirred at 23° C. for 45 minutes. A 0.5M solution of NaBH$_4$ in 3M NaOH (1.2 mL, 0.599 mmol, 1.00 equiv) was then added by syringe, resulting in an immediate precipitation of Hg$^0$. After stirring for 5 minutes, the suspension was partitioned between 20 mL sat'd NH$_4$Cl soln. and 20 mL EtOAc. The phases were separated and the aqueous phase was extracted with 2×20 mL EtOAc. The combined organic phases were dried over MgSO$_4$ and solvent removal yielded a grey suspension that was purified by silica gel column chromatography (5:1 hex:EtOAc) to yield tetrahydrofuran S12 (141.6 mg, 77%) as a clear, colorless oil. R$_f$=0.58 (2:1 hex:EtOAc); $^1$H NMR (500 MHz, CDCl$_3$) δ 7.34 (m, 5H, aryl H), 5.21 (d, 1H, J=12.3 Hz, PhCH$_2$), 5.17 (d, 1H, J=12.3 Hz, PhCH$_2$), 3.59 (s, 3H, OCH$_3$), 2.91 (d, 1H, J=15.4 Hz, C(O)CH$_2$), 2.81 (d, 1H, J=15.4 Hz, C(O)CH$_2$), 2.41 (m, 1H, CH$_2$), 2.16 (m, 1H, CH$_2$), 1.85 (m, 1H, CH$_2$), 1.78 (m, 1H, CH$_2$), 1.30 (s, 3H, C(CH$_3$)$_2$), 1.24 (s, 3H, (CCH$_3$)$_2$); $^{13}$C NMR (125 MHz, CDCl$_3$) δ 173.70, 170.54, 135.93, 128.59, 128.43, 128.32, 84.26, 83.96, 67.10, 51.80, 43.93, 37.88, 35.58, 29.09, 28.33; IR (neat film) 3036 (w), 2973 (m), 1743 (s), 1500 (w), 1458 (m), 1440 (m), 701 (m) cm$^{-1}$; LRMS (ESI) calc'd for C$_{17}$H$_{22}$O$_5$Na (M+Na$^+$) 329.2; found 329.1.

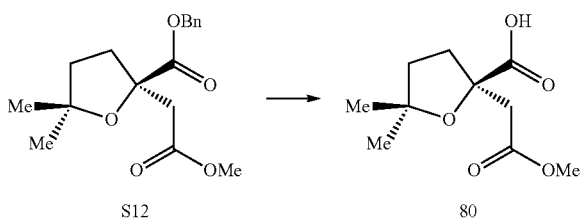

S12    80

(R)-2-(2-methoxy-2-oxoethyl)-5,5-dimethyltetrahy-drofuran-2-carboxylic acid (80)

To a solution of benzyl ester S12 (141.6 mg, 0.462 mmol, 1.00 equiv) in EtOAc (4.6 mL) was added 14.2 mg 10% Pd/C. The atmosphere in the vessel was replaced with H$_2$ under balloon pressure and the reaction was stirred at 23° C. for 2 hours, at which time it was filtered through a plug of celite and flushed with EtOAc. Solvent removal by rotary evaporation provided acid 80 (99.1 mg, 99%) as a white solid. R$_f$=0.07 (2:1 hex:EtOAc); $^1$H NMR (500 MHz, CDCl$_3$) δ 3.69 (s, 3H, OCH$_3$), 3.13 (d, 1H, J=15.9 Hz, C(O)CH$_2$), 2.67 (d, 1H, J=15.9 Hz, C(O)CH$_2$), 2.43 (m, 1H, CH$_2$), 2.22 (m, 1H, CH$_2$), 1.87 (m, 2H, CH$_2$), 1.39 (s, 3H, C(CH$_3$)$_2$), 1.31 (s, 3H, C(CH$_3$)$_2$); $^{13}$C NMR (125 MHz, CDCl$_3$) δ 175.72, 170.03, 85.91, 84.23, 52.08, 43.66, 37.67, 36.16, 28.69, 28.55; IR (neat film) ~3100-2800 (br m), 2983 (s), 1753 (s), 1733 (s), 1459 (w), 1370 (w), 1265 (s), 1192 (m), 1106 (m), 778 (w) cm$^{-1}$; LRMS (ESI) calc'd for C$_{10}$H$_{16}$O$_5$Na (M+Na$^+$) 239.1; found 239.0.

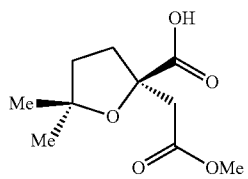

80

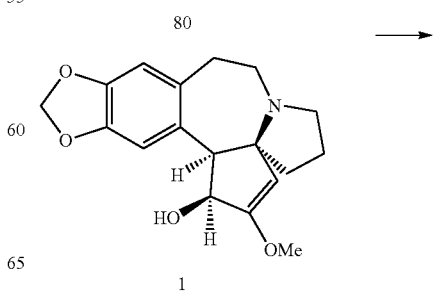

1

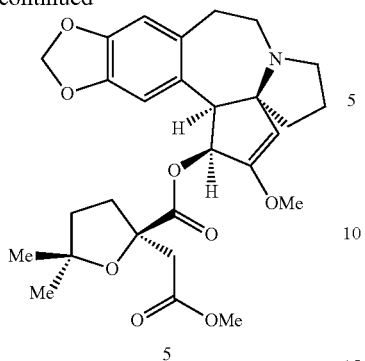

Anhydroharringtonine (5)

To a solution of acid 80 (13.7 mg, 0.0634 mmol, 2.00 equiv) and triethylamine (29.1 μL, 0.209 mmol, 6.6 equiv) in CH$_2$Cl$_2$ (320 μL) was added 2,4,6-trichlorobenzoyl chloride (10.9 μL, 0.0697 mmol, 2.20 equiv) via syringe. The resulting colorless solution was stirred at 23° C. for 1 h, then transferred via syringe to a solution of cephalotaxine (1) (10.0 mg, 0.0317 mmol, 1.00 equiv) and N,N-dimethylaminopyridine (DMAP) (4.4 mg, 0.0360 mmol, 1.14 equiv) in CH$_2$Cl$_2$ (320 μL). This solution was then stirred for 1 hour, then loaded directly onto a silica gel column. The column was eluted with 2% TEA in 9:1 toluene:EtOAc to yield 5 (16.1 mg, 99%) as a white solid. R$_f$=0.31 (2% TEA in 9:1 toluene:EtOAc on plates pretreated with 5% TEA in pentane); $^1$H NMR (500 MHz, CDCl$_3$) δ 6.58 (s, 1H, aryl H), 6.56 (s, 1H, aryl H), 5.87 (m, 3H, OCH$_2$O, arylCHCH), 5.02 (s, 1H, vinyl H), 3.80 (d, 1H, J=9.8 Hz, arylCHCH), 3.68 (s, 3H, OCH$_3$), 3.58 (s, 3H, OCH$_3$), 3.18-3.06 (m, 2H, CH$_2$), 2.93 (m, 1H, CH$_2$), 2.58 (m, 2H, CH$_2$), 2.33 (m, 1H, CH$_2$), 2.32 (d, 1H, J=15.1 Hz, C(O)CH$_2$), 2.26 (d, 1H, J=15.2 Hz, C(O)CH$_2$), 2.03 (m, 2H, CH$_2$), 1.87 (m, 2H, CH$_2$), 1.75 (m, 2H, CH$_2$), 1.65 (m, 2H, CH$_2$), 1.24 (s, 3H, C(CH$_3$)$_2$), 1.14 (s, 3H, C(CH$_3$)$_2$); $^{13}$C NMR (125 MHz, CDCl$_3$) δ 172.97, 170.33, 158.04, 146.81, 145.88, 133.37, 128.66, 113.23, 109.74, 100.89, 99.86, 84.03, 83.80, 74.61, 70.73, 57.33, 56.49, 54.14, 51.62, 48.95, 43.61, 42.63, 37.68, 34.92, 31.78, 28.96, 28.22, 20.49; IR (neat film) 2965 (m), 2880 (m), 2796 (w), 1740 (s), 1654 (s), 1503 (m), 1487 (s), 1223 (s), 1036 (s) cm$^{-1}$; LRMS (ESI) calc'd for C$_{28}$H$_{36}$NO$_8$ (M+Na$^+$) 514.2; found 514.2; [α]$_D$=−144° (c 1.08, CHCl$_3$).

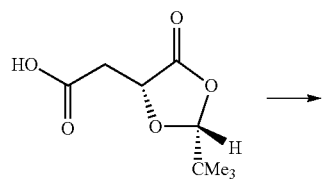

72

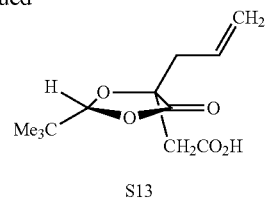

2-((2R,4R)-4-allyl-2-tert-butyl-5-oxo-1,3-dioxolan-4-yl)acetic acid (S13)

A solution of LHMDS (413 mg, 2.47 mmol, 1.00 equiv) in THF (5 mL) at −78° C. was transferred via cannula to a stirred solution of acid ent-72 (500 mg, 2.47 mmol, 1.00 equiv) in THF (25 mL) at −78° C. The resulting solution was stirred at −78° C. for 10 minutes. A solution of LHMDS (621 mg, 3.71 mmol, 1.50 equiv) in THF (7 mL) at −78° C. was then added via cannula and the resulting solution was stirred for 20 min at −78° C. allyl bromide (439 μL, 5.19 mmol, 2.10 equiv) was then added via syringe and the resulting solution was stirred at −78° C. for 21 h, at which time the reaction was partitioned between 75 mL 1 N HCl and 75 mL CH$_2$Cl$_2$, the phases were separated and the aqueous phase was extracted with 2×50 mL CH$_2$Cl$_2$. The combined organic phases were dried over MgSO$_4$ and concentrated via rotary evaporation to yield an oily solid. Purification by silica gel column chromatography (19:1 MeOH:CH$_2$Cl$_2$) yielded S13 (344 mg, 59%) as a clear, colorless oil. R$_f$=0.69 (60:38:2 EtOAc:Hex:HOAc); $^1$H NMR (500 MHz, CDCl$_3$) δ 5.77 (m, 1H, vinyl H), 5.22 (m, 3H, vinyl H; CH(CH$_3$)$_3$), 2.86 (d, 1H, J=16 Hz, CH$_2$), 2.81 (d, 1H, J=16.0 Hz, CH$_2$), 2.55 (m, 2H, CH$_2$), 0.92 (s, 9H, CH(CH$_3$)$_3$); $^{13}$C NMR (125 MHz, CDCl$_3$) δ 174.96, 173.49, 130.11, 121.34, 108.47, 79.90, 39.62, 38.18, 34.45, 23.66; IR (neat film) 3500-2500 (br s), 2966 (s), 1793 (s), 1718 (s), 1165 (m) cm$^{-1}$; LRMS (ESI) calcd. for C$_{12}$H$_{18}$O$_5$Na (M+Na$^+$) 265.1; observed 264.9.

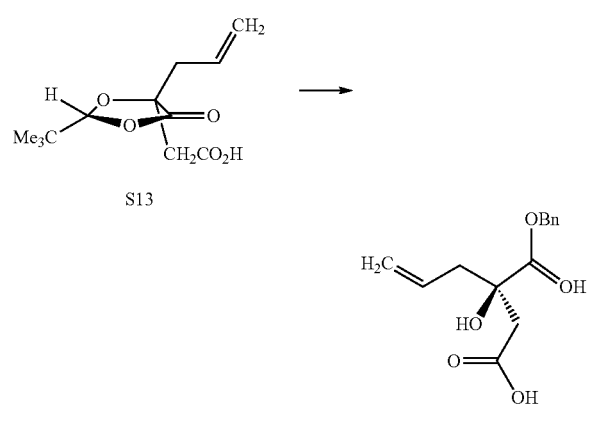

(R)-3-(benzyloxycarbonyl)-3-hydroxyhex-5-enoic acid (81)

A solution of dioxolanone S13 (1.10 g, 4.54 mmol, 1.00 equiv) in THF (45 mL) was cooled to 0° C. and benzyl alcohol (564 µL, 5.45 mmol, 1.20 equiv) was added via syringe followed by a 60% dispersion of NaH in mineral oil (454 mg, 11.35 mmol, 2.50 equiv) which resulted in vigorous evolution of gas. The solution was allowed to warm to 23° C. over 90 min, at which time the reaction was again cooled to 0° C., quenched with 45 mL 1 N HCl, poured into 45 mL EtOAc. The phases were separated and the aqueous phase was extracted with a further 3×45 mL EtOAc. The combined organic phases were dried over $MgSO_4$ and solvent removal by rotary evaporation yielded an oil which was purified by silica gel column chromatography (60:40:2 hex:EtOAc:HOAc) to yield 81 (1.02 g, 85%) as a clear, colorless oil. $R_f$=0.60 (38:60:2 hex:EtOAc:HOAc); $^1$H NMR (500 MHz, $CDCl_3$) δ 7.37 (m, 5H, arylH), 5.74 (m, 1H, vinylH), 5.22 (d, 1H, J=10.1 Hz, $PhCH_2$), 5.18 (d, 1H, J=10.1 Hz, $PhCH_2$), 5.11 (d, 1H, J=8.8 Hz, vinylH), 5.06 (d, 1H, J=17.1 Hz, vinyl H), 2.99 (d, 1H, J=16.6 Hz, $C(O)CH_2$), 2.76 (d, 1H, J=16.6 Hz, $C(O)CH_2$), 2.45 (d, 2H, J=7.2, $CHCH_2$); $^{13}$C NMR (125 MHz, $CDCl_3$) δ 176.19, 174.34, 135.14, 131.13, 128.74, 128.68, 120.01, 74.98, 68.08, 43.83, 42.74; IR (neat film) 3500-2500 (br m), 3077, 1737 (s), 1641 (w), 1219 (m) cm$^{-1}$; LRMS (ESI) calcd. for $C_{14}H_{16}O_5Na$ (M+Na$^+$) 287.1; observed 286.9.

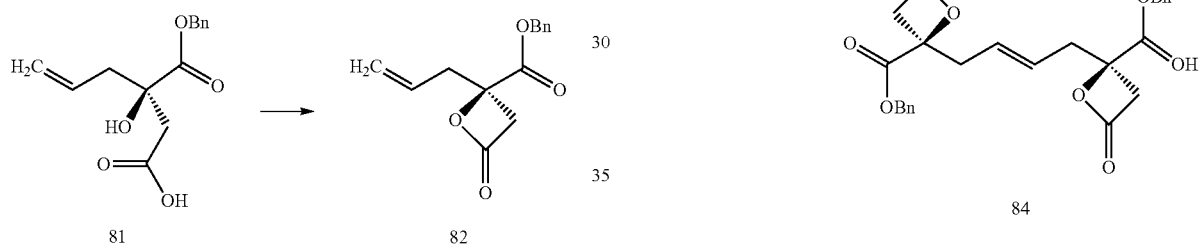

81    82

(R)-benzyl 2-allyl-4-oxooxetane-2-carboxylate (82).
A solution of hydroxyacid 81

(1.02 g, 3.86 mmol, 1.00 equiv) and triethylamine (519 µL, 17.37 mmol, 4.50 equiv) in $CH_2Cl_2$ (77 mL) was added via syringe pump over 4 h to a solution of 2,4,6-trichlorobenzoyl chloride (904 µL, 5.79 mmol, 1.50 equiv) and N,N-dimethylaminopyridine (DMAP) (519 mg, 4.25 mmol, 1.10 equiv) in $CH_2Cl_2$ (39 mL). The solution was then allowed to stir for 30 minutes after complete addition after which it was quenched with $H_2O$ (100 mL). The phases were separated and the aqueous phase was extracted with $CH_2Cl_2$ (2×100 mL). The organic phases were combined, dried over $MgSO_4$, and the solvent was removed via rotary evaporation to yield a black oil which was purified by silica gel column chromatography ($CH_2Cl_2$) to yield 82 (639 mg, 67%) as a yellow oil. $R_f$=0.52 ($CH_2Cl_2$); $^1$H NMR (500 MHz, $CDCl_3$) δ 7.38 (m, 5H, aryl H), 5.76 (m, 1H, vinyl H), 5.26 (s, 2H, $PhCH_2$), 5.22 (m, 2H, vinyl H), 3.65 (d, 1H, J=16.5 Hz, $C(O)CH_2$), 3.42 (d, 1H, J=16.5 Hz, $C(O)CH_2$), 2.89 (dd, 1H, J=14.6, 6.8 Hz, $CHCH_2$), 2.80 (dd, 1H, J=14.6, 6.8 Hz, $CHCH_2$); $^{13}$C NMR (125 MHz, $CDCl_3$) δ 169.03, 165.61, 134.75, 129.10, 128.95, 128.89, 128.59, 121.82, 75.65, 68.17, 45.86, 39.06; IR (neat film) 3034 (w), 1843 (s), 1741 (s), 1644 (w), 1456 (m) cm$^{-1}$; LRMS (ESI) calcd. for $C_{14}H_{14}O_4Na$ (M+Na$^+$) 269.1; observed 269.1.

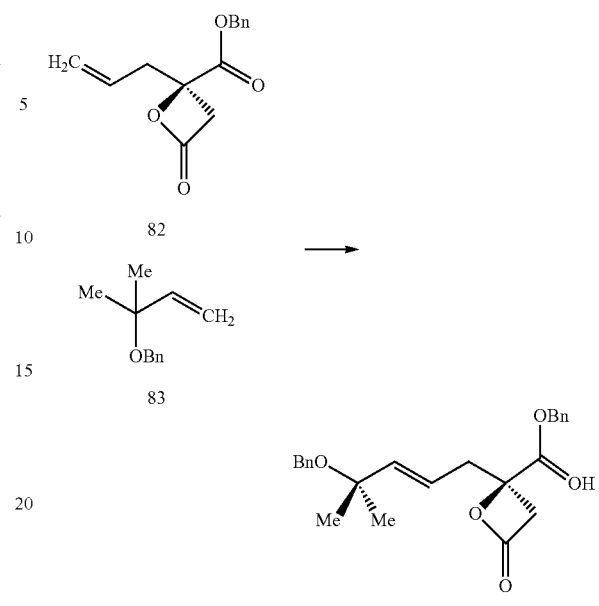

(R,E)-benzyl 2-(4-(benzyloxy)-4-methylpent-2-enyl)-4-oxooxetane-2-carboxylate (85)

A solution of alkene 82 (58.8 mg, 0.239 mmol, 1.00 equiv) in benzyl ether 83 (842 mg, 4.78 mmol, 20 equiv) was subjected to two freeze-pump-thaw cycles. Grubbs catalyst, 2$^{nd}$ generation (20.1 mg, 0.0237 mmol, 0.10 equiv) was then added and the resulting solution was subjected to one more freeze-pump-thaw cycle then allowed to stir at 23° C. for 16 h. Another portion of catalyst (10.3 mg, 0.0121 mmol, 0.051 equiv) was then added and the solution was again subjected to one freeze-pump-thaw cycle and allowed to stir at 23° C. for 8 h. A third portion of catalyst (10.2 mg, 0.0120 mmol, 0.050 equiv) was added and the solution was subjected to one freeze-pump-thaw cycle then allowed to stir at 23° C. for 25 h. The crude reaction mixture was then loaded directly onto a pH 7.0 buffered silica gel (10 wt % buffer) column which was eluted with a gradient eluant (1:1 hex:$CH_2Cl_2$ to $CH_2Cl_2$) to yield 85 (57.6 mg, 61%) as a yellow oil and 84 (11.5 mg 22%) as a yellow oil. Data for dimer 85: $R_f$=0.28 ($CH_2Cl_2$); $^1$H NMR (500 MHz, $CDCl_3$) δ 7.4-7.2 (m, 10H, arylH), 5.76 (d, 1H, J=15.9 Hz, $(CH_3)_2CH$), 5.57 (dt, 2H, J=15.8, 7.2 Hz, $CH_2CH$), 5.22 (s, 2H, $CO_2CH_2$), 4.31 (s, 2H, $COHCH_2$), 3.64 (d, 1H, J=16.4 Hz, $C(O)CH_2$), 3.37 (d, 1H, J=16.5 Hz, $C(O)CH_2$), 2.90 (dd, 1H, J=14.6, 7.0 Hz, $CCH_2$), 2.80 (dd, J=14.5, 7.3 Hz, $CCH_2$), 1.31 (d, 6H, J=2.8 Hz, $C(CH_3)_2$); $^{13}$C NMR (125 MHz, $CDCl_3$) δ 168.98, 165.50, 143.38, 139.56, 134.72, 128.97, 128.93, 128.56, 128.45, 127.41, 127.35, 120.22, 75.82, 75.30, 68.14, 65.11, 46.01, 37.90, 26.49, 26.41; IR (neat film) 3032 (m), 2976 (m), 1838 (s), 1743 (s), 1498 (m), 1455 (m), 1059 cm$^{-1}$; HRMS (ESI) calcd. for $C_{24}H_{26}O_5Na$ (M+Na$^+$) 417.1678; found 417.1673.

Data for dimer 84: $^1$H NMR (400 MHz, CDCl$_3$) δ 7.37 (m, 10H, aryl H), 5.54 (m, 2H, vinyl H), 5.24 (s, 4H, PhCH$_2$), 3.60 (d, 2H, J=16.5 Hz, C(O)CH$_2$), 3.32 (d, 2H, J=16.5 Hz, C(O)CH$_2$), 2.8 (m, 4H, CCH$_2$); $^{13}$C NMR (125 MHz, CDCl$_3$) δ 168.75, 165.28, 134.73, 128.98, 128.90, 128.67, 128.62, 127.87, 75.44, 68.22, 46.15, 38.05.

Recycling of Dimer 84

A solution of dimer 84 (36.5 mg, 0.0786 mmol, 1.00 equiv) in benzyl ether 83 (576 mg, 3.27 mmol, 41.6 equiv) was subjected to 2× freeze-pump-thaw cycles. Grubbs catalyst, 2$^{nd}$ generation (6.9 mg, 0.00818 mmol, 0.10 equiv) was added and the resulting solution was subjected to one more freeze-pump-thaw cycle then allowed to stir at 23° C. for 14 h. Another portion of catalyst (7.1 mg, 0.00836, 0.11 equiv) was added and the solution was subjected to one freeze-pump-thaw cycle then allowed to stir at 23° C. for 9.5 h. A third portion of catalyst (6.8 mg, 0.0080 mmol, 0.10 equiv) was added and the solution was subjected to one freeze-pump-thaw cycle then allowed to stir at 23° C. for 18.5 h. The crude reaction mixture was loaded directly onto a pH 7.0 buffered silica gel (10 wt % buffer) column which was eluted with a gradient eluant (1:1 hex:CH$_2$Cl$_2$ to CH$_2$Cl$_2$) to yield 85 (40.2 mg, 65%) as a colorless oil. Data are identical to that reported above.

left a brown oil that upon purification by silica gel column chromatography (4% HOAc in 1:1 hex:EtOAc) yielded acid 86 (34.4 mg, 85%) as a clear, colorless oil. R$_f$=0.17 (4% HOAc in 1:1 hex:EtOAc); $^1$H NMR (500 MHz, CDCl$_3$) δ 10.09 (br s, 1H, CO$_2$H), 7.33-7.23 (m, 5H, aryl H), 5.81 (d, 1H, J=15.9 Hz, (CH$_3$)$_2$CCH), 5.62 (m, 1H, CH$_2$CH), 4.35 (s, 2H, PhCH$_2$), 3.57 (d, 1H, J=16.6 Hz, C(O)CH$_2$), 3.36 (d, 1H, J=16.6, Hz, C(O)CH$_2$), 2.87 (dd, 1H, J=14.6, 7.1 Hz), 2.74 (dd, 1H, J=14.7, 7.3 Hz), 1.35 (s, 6H, (CH$_3$)$_2$); $^{13}$C NMR (125 MHz, CDCl$_3$) δ 173.48, 165.44, 143.27, 139.13, 128.48, 127.66, 127.53, 120.34, 75.85, 65.24, 46.06, 37.57, 26.51, 26.29; IR (neat film) 3500-2500 (br m), 3031 (w), 2977 (m), 1843 (s), 1745 (s), 1497 (w), 1453 (w), 1149 (m) cm$^{-1}$; LRMS (ESI) calc'd for $C_{17}H_{20}O_5Na$ 327.1; found 326.9.

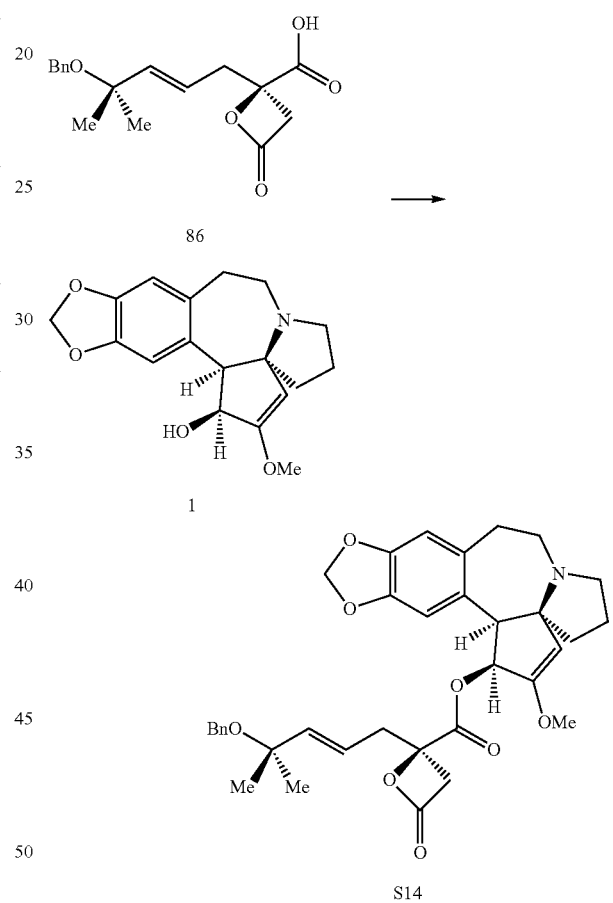

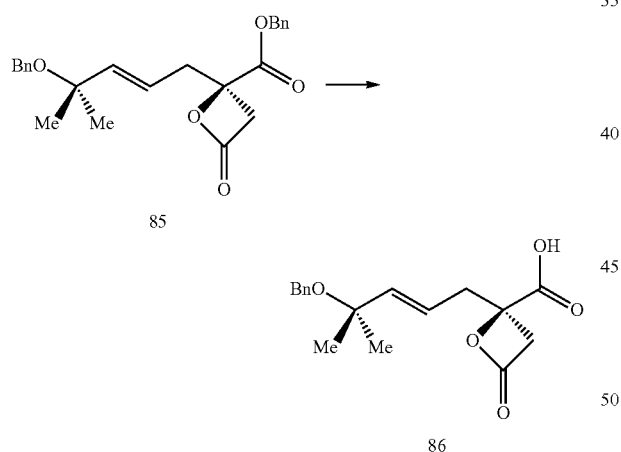

(R,E)-2-(4-(benzyloxy)-4-methylpent-2-enyl)-4-oxooxetane-2-carboxylic acid (86)

To a solution of benzyl ester 85 (52.8 mg, 0.134 mmol, 1.00 equiv.) were added TEA (3.0 µL, 0.0214 mmol, 0.16 equiv.), triethylsilane (32.1 µL, 0.201 mmol, 1.50 equiv.), and Pd(OAc)$_2$ (1.6 mg, 0.0071 mmol, 0.053 equiv.). The resulting black solution was stirred at 23° C. for 1 h then partitioned between 10 mL sat'd NH$_4$Cl solution and 10 mL CH$_2$Cl$_2$. The phases were separated and the aqueous phase was extracted with 2×10 mL CH$_2$Cl$_2$. The combined aqueous phases were dried over MgSO$_4$ and solvent removal by rotary evaporation (R,E)-2-(4-(benzyloxy)-4-methylpent-2-enyl)-4-oxooxetane-2-cephalotaxyl carboxylate S14

To a solution of β-lactone 86 (34.5 mg, 0.114 mmol, 2.00 equiv) and triethylamine (52.4 µL, 0.378 mmol, 6.6 equiv) in CH$_2$Cl$_2$ (570 µL) was added 2,4,6-trichlorobenzoyl chloride (19.6 µL, 0.126 mmol, 2.20 equiv) via syringe. The resulting dark purple solution was stirred at 23° C. for 1 h, then transferred via syringe to a solution of cephalotaxine (1) (18.0 mg, 0.0571 mmol, 1.00 equiv) and N,N-dimethylaminopyridine (DMAP) (7.8 mg, 0.063 mmol, 1.10 equiv) in CH$_2$Cl$_2$ (570 µL). This solution was then stirred for 25 minutes then loaded directly onto a pH 7.0 buffered silica gel column. The column was eluted with 1% TEA in 9:1 toluene:EtOAc to yield S14 (33.3 mg, 97%) as a light yellow oil. $R_f$=0.24 (1% TEA in 9:1 toluene:EtOAc on a TLC plate pretreated with 5% TEA in pentane); $^1$H NMR (500 MHz, CDCl$_3$) δ 7.32-7.22 (m, 5H, Aryl H), 6.60 (s, 1H, aryl H), 6.59 (s, 1H, aryl H), 5.86 (m, 3H, O(CH$_2$)O, arylCHCH), 5.71 (d, 1H, J=15.9 Hz, (CH$_3$)$_2$CCH), 5.47 (dt, 1H, J=15.8, 8.5 Hz, CH$_2$CH), 5.08 (s, 1H, CHCOCH$_3$), 4.31 (s, 2H PhCH$_2$), 3.80 (d, 1H, J=9.5 Hz, ArCHCH), 3.68 (s, 3H, OCH$_3$), 3.08 (m, 2H CH$_2$), 2.98 (d, 1H, J=16.4 Hz, C(O)CH$_2$), 2.94 (m, 1H, CH$_2$), 2.64 (d, 1H, J=16.5 Hz, C(O)CH$_2$), 2.59 (m, 3H, CH$_2$), 2.43-2.34 (m, 2H, CH$_2$), 2.02 (m, 1H, CH$_2$), 1.90 (m, 1H, CH$_2$), 1.75 (m, 2H, CH$_2$), 1.32 (s, 6H, C(CH$_3$)$_2$); $^{13}$C NMR (125 MHz, CDCl$_3$) δ 168.22, 165.58, 156.71, 147.19, 146.13, 143.19, 139.81, 133.73, 128.49, 128.01, 127.52, 127.37, 120.57, 113.50, 109.98, 101.39, 101.24, 75.95, 75.67, 75.41, 70.87, 65.17, 57.50, 56.66, 54.20, 48.74, 45.39, 43.72, 37.73, 31.70, 26.55, 26.39, 20.60; IR (neat film) 2972 (m), 2801 (w), 1842 (s), 1751 (s), 1654 (s), 1504 (s), 1223 (s) cm$^{-1}$; LRMS (ESI) calc'd for C$_{35}$H$_{40}$NO$_8$ 602.3; found 602.5; [α]$_D$=−88° (c 3.3, CHCl$_3$).

were separated and the aqueous phase was extracted with CH$_2$Cl$_2$ (2×10 mL), the combined organic phases were dried over MgSO$_4$, and concentrated by rotary evaporation to yield a yellow oil that was purified by silica gel column chromatography (1% TEA in 9:1 toluene:EtOAc) to yield I-5 (27.5 mg, 79%) as a clear, colorless oil. $R_f$=0.18 (9:1 toluene:EtOAc on plates pretreated with 5% TEA in pentane); $^1$H NMR (500 MHz, CDCl$_3$) δ 7.33-7.22 (m, 5H, aryl H), 6.61 (s, 1H, aryl H), 6.55 (s, 1H, aryl H), 5.94 (d, 1H, J=9.7 Hz, arylCHCH), 5.85 (app d, 2H, OCH$_2$O), 5.62 (d, 1H, (CH$_3$)$_2$CCH), 5.51 (m, 1H, CH$_2$CH), 5.05 (s, 1H, CHCOCH$_3$), 4.33 (s, 2H, PhCH$_2$), 3.77 (d, 1H, J=9.8 Hz, arylCHCH), 3.66 (s, 3H, OCH$_3$), 3.58 (s, 3H, OCH$_3$), 3.45 (s, 1H, OH), 3.12 (m, 2H, CH$_2$), 3.94 (m, 1H, CH$_2$), 2.59 (m, 2H, CH$_2$), 2.38 (dd, 1H, J=14.1, 6.9 Hz, CH$_2$), 2.29 (d, 1H, J=16.4 Hz), C(O)CH$_2$), 2.20 (m, 2H, CH$_2$), 2.01 (m, 1H, CH$_2$), 1.96 (d, 1H, J=16.4 Hz, C(O)CH$_2$), 1.90 (m, 1H, CH$_2$), 1.75 (m, 2H, CH$_2$), 1.33 (d, 6H, J=3.1, (CH$_3$)$_2$C); $^{13}$C NMR (125 MHz, CDCl$_3$) δ 173.72, 170.50, 146.98, 146.07, 141.16, 140.02, 128.44, 127.66, 127.29, 123.16, 113.06, 109.86, 101.05, 100.50, 75.47, 75.25, 74.61, 65.15, 57.49, 56.16, 54.15, 51.80, 48.81, 43.56, 41.92, 41.77, 31.63, 26.69, 26.52, 20.50; IR (neat film) 3527 (m), 2971 (s), 1749 (s), 1654 (s), 1504 (s), 1487 (s), 1363 (s), 1039 (s), 932 (m), 736 (s); LRMS (ESI) calcd for C$_{36}$H$_{44}$NO$_9$ (M$^+$+H) 634.29; found 634.08; [α]$_D$=−110° (c 1.5, CHCl$_3$).

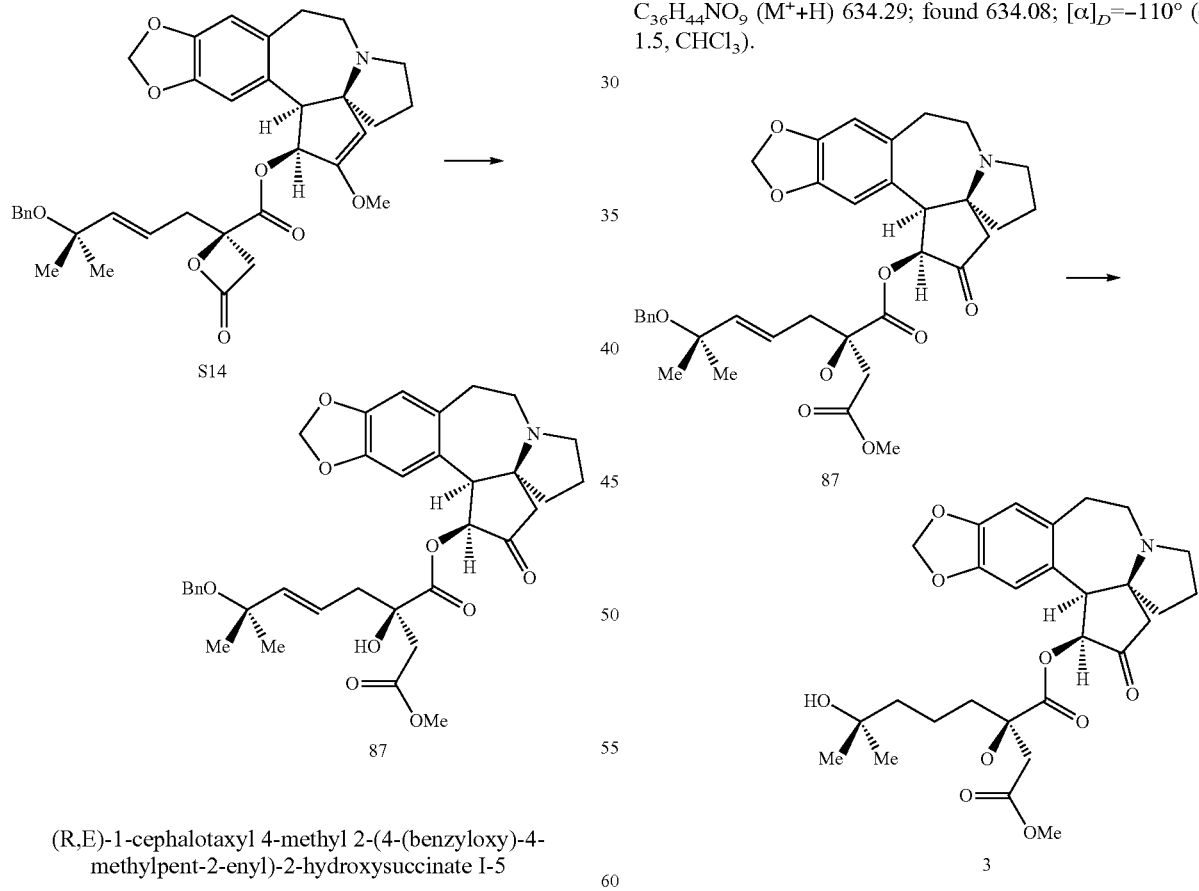

(R,E)-1-cephalotaxyl 4-methyl 2-(4-(benzyloxy)-4-methylpent-2-enyl)-2-hydroxysuccinate I-5

To a solution of β-lactone S14 (33.0 mg, 0.0548 mmol, 1.00 equiv) in MeOH (550 μL) was added a freshly prepared solution of 0.5M NaOMe in MeOH (121 μL, 0.0603 mmol, 1.10 equiv). After 10 min the solution was quenched with sat'd NH$_4$Cl solution (300 μL) and partitioned between sat'd NH$_4$Cl solution (10 mL) and CH$_2$Cl$_2$ (10 mL). The phases Homoharringtonine (3)

To a solution of allylic benzyl ether I-5 (12.6 mg, 0.0199 mmol, 1.00 equiv.) in MeOH (200 μL) was added 10% Pd/C (2.4 mg, 20% by wt). The atmosphere in the vessel was replaced with H₂ under balloon pressure and the suspension was stirred at 23° C. until LRMS (ESI) showed complete reduction of the alkene (26 h). Glacial acetic acid (20 μL) was added via syringe and the solution was stirred under H₂ at 23° C. for 21 h. Further 10% Pd/C (1.3 mg) and glacial acetic acid (20 μL) were added and the suspension was stirred under H₂ for 24 h then filtered through a plug of celite. The solvent was removed by rotary evaporation and the resulting film was purified by silica gel column chromatography (2% TEA in 1:1 toluene:EtOAc) to yield homoharringtonine (3) (8.5 mg, 79%) as a colorless film. $R_f$=0.25 (2% TEA in 1:1 toluene: EtOAc on TLC plates pretreated with 5% TEA in pentane); $^1$H NMR (500 MHz, CDCl₃) δ 6.62 (s, 1H, aryl H), 6.54 (s, 1H, aryl H), 6.00 (d, 1H, J=9.8 Hz, arylCHCH), 5.87 (app dd, 2H, J=2.9, 1.4, OCH₂O), 5.05 (s, 1H, CHCOCH₃), 3.77 (d, 1H, J=9.7 Hz, arylCHCH), 3.67 (s, 3H, OCH₃), 3.57 (s, 3H, OCH₃), 3.52 (s, 1H, OH), 3.10 (m, 2H, CH₂), 3.00 (m, 1H, CH₂), 2.60 (m, 2H, CH₂), 2.40 (dd, 1H, J=14.2, 6.9 CH₂), 2.26 (d, 1H, J=16.5 Hz, C(O)CH₂), 2.02 (m, 1H, CH₂), 1.90 (d, 1H, J=16.5 Hz, C(O)CH₂), 1.89 (m, 1H, CH₂), 1.75 (m, 2H, CH₂), 1.45-1.36 (m, 5H, CH₂), 1.27 (br s, 1H, CH₂), 1.19 (app d, 6H, (CH₃)₂C); $^{13}$C NMR (125 MHz, CDCl₃) δ 173.62, 170.38, 157.63, 146.86, 145.96, 141.06, 139.93, 133.44, 128.43, 128.33, 127.55, 127.18, 123.06, 112.95, 109.75, 100.94, 100.43, 75.37, 75.16, 74.51, 70.66, 65.05, 57.38, 56.11, 54.06, 51.69, 48.73, 43.50, 41.82, 41.67, 31.56, 26.59, 26.43, 20.42; IR (neat film) 3526 (br m), 2960 (s), 1744 (s), 1654 (s), 1503 (s), 1487 (s), 1366 (s), 1225 (s), 932 (m), 754 (s) cm⁻¹; LRMS (ESI) calcd for C₂₉H₄₀NO₉ (M⁺+H) 545.26; found 545.7; $[\alpha]_D$=−112° (c 0.75, CHCl₃).

Homodeoxyharringtonine (4)

To a solution of allylic benzyl ether I-5 (12.2 mg, 0.0192 mmol, 1.0 equiv) in glacial acetic acid (800 μL) was added degussa grade (E101 NE/W from Aldrich) Pd/C (10 wt % dry basis, 50% water, 25.3 mg, 62 mol %). The atmosphere in the vessel was replaced with H₂ (1 atm) and the suspension was stirred for 20 h at 23° C., filtered through a plug of celite, flushed with glacial acetic acid, and the solvent was removed by azeotrope with toluene. The crude product was purified by pH 7.0 buffered (10 wt %) silica gel column chromatography (2% TEA in 1:1 toluene:EtOAc) to yield homodeoxyharringtonine (4) (7.0 mg, 69%) as a colorless film as well as homoharringtonine (2.8 mg 27%) as a colorless film. $R_f$=0.66 (2% TEA in 1:1 toluene:EtOAc on TLC plates pretreated with 5% TEA in pentane); $^1$H NMR (500 MHz, CDCl₃) δ 6.62 (s, 1H, aryl H), 6.53 (s, 1H, aryl H), 5.99 (d, 1H, J=9.8 Hz, arylCHCH), 5.86 (dd, 2H, J=9.8, 1.5 Hz OCH₂O), 5.04 (s, 1H, CHCOCH₃), 3.77 (d, 1H, J=9.8 Hz, arylCHCH), 3.66 (s, 3H, OCH₃), 3.57 (s, 3H, OCH₃), 3.48 (s, 1H, OH), 3.11 (m, 2H, CH₂), 2.95 (m, 1H, CH₂), 2.59 (m, 2H, CH₂), 2.38 (dd, J=14.8, 6.9, 1H, CH₂), 2.31 (d, 1H, J=16.5 Hz, C(O)CH₂), 2.05 (m, 1H, CH₂), 1.91 (m, 1H, CH₂), 1.90 (d, 1H, J=16.5 Hz, C(O)CH₂), 1.75 (m, 2H, CH₂), 1.49 (m, 1H, CH₂), 1.38 (m, 3H, CH₂), 1.09 (m, 3H, CH₂), 0.85 (app t, 6H, J=6.4 Hz, CH(CH₃)₂); $^{13}$C NMR (125 MHz, CDCl₃) δ174.24, 170.61, 157.95, 146.82, 145.96, 133.48, 128.55, 112.81, 109.84, 100.96, 100.20, 74.84, 74.80, 70.75, 57.38, 56.00, 54.09, 51.63, 48.75, 43.53, 42.79, 39.16, 39.08, 31.49, 27.93, 22.81, 22.51, 20.71, 20.44; IR (neat film) 3529 (br w), 2953 (s), 1748 (s), 1654 (m), 1504 (m), 1487 (s), 1224 (s), 932 (m) cm⁻¹; LRMS (ESI) calcd for C₂₉H₄₀NO₈ (M⁺+H) 530.27; found 530.3; $[\alpha]_D$=−112° (c 0.7, CHCl₃).

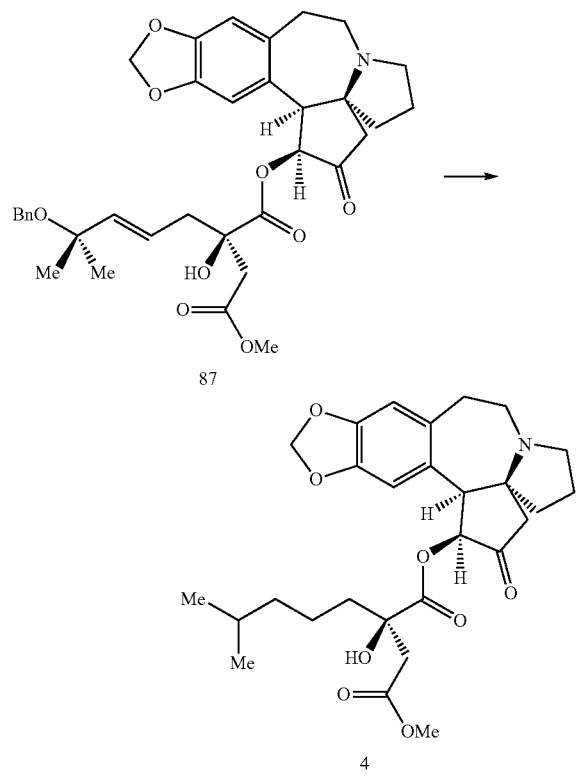

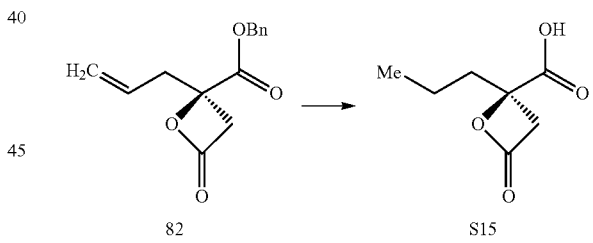

(R)-4-oxo-2-propyloxetane-2-carboxylic acid (S15)

To a solution of benzyl ester 82 (30.3 mg, 0.123 mmol, 1.0 equiv) in EtOAc (1.5 mL) was added 10% Pd/C (3.2 mg, 0.0030 mmol, 2.4 mol %). The atmosphere in the vessel was replaced with H₂ under balloon pressure and the mixture was stirred at 23° C. for 15 h. The suspension was then filtered through a plug of celite and flushed with EtOAc (25 mL). Solvent removal yielded carboxylic acid S15 (19.0 mg, 97%) as a yellow oil. $^1$H NMR (500 MHz, CDCl₃) δ 11.3 (br s, 1H, CO₂H), 3.73 (d, 1H, J=16.6 Hz, C(O)CH₂), 3.45 (d, 1H, J=16.5 Hz, C(O)CH₂), 2.20-2.15 (m, 1H, CCH₂), 2.06-2.00 (m, 1H, CCH₂), 1.57-1.50 (m, 1H, CCH₂CH₂), 1.48-1.44 (m, 1H, CCH₂CH₂), 1.01 (t, 3H, J=7.3 Hz, CH₃); $^{13}$C NMR (125 MHz, CDCl₃) δ 175.04, 165.78, 76.44, 47.07, 37.38, 17.20, 13.93; IR (neat film) 3500-3000 (br m), 2966 (m), 2878 (m), 1834 (s), 1736 (s), 1410 (w), 1143 (m), 960 (w) cm$^{-1}$.

16.82, 13.94; IR (neat film) 2961 (m), 1838 (s), 1743 (s), 1655 (s), 1487 (s), 1376 (w), 1037 (s), 731 (s) cm$^{-1}$; LRMS (ESI) (calcd for $C_{25}H_{30}NO_7$ (M$^+$+H) 455.19; found 455.96; [α]$_D$=−120° (c 1.13, CDCl$_3$).

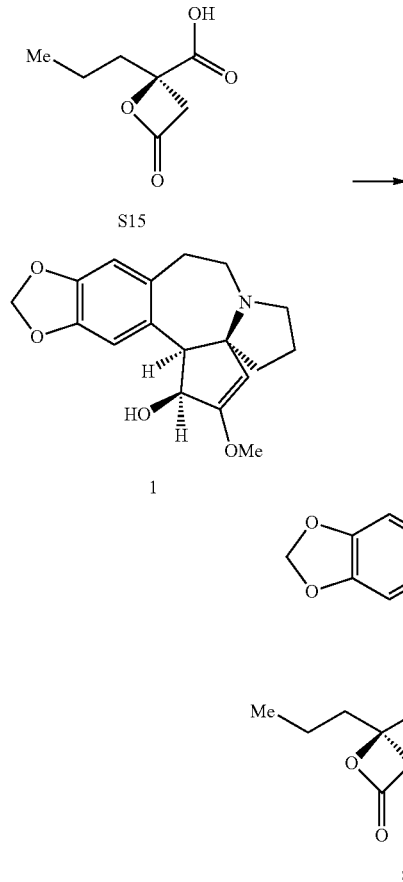

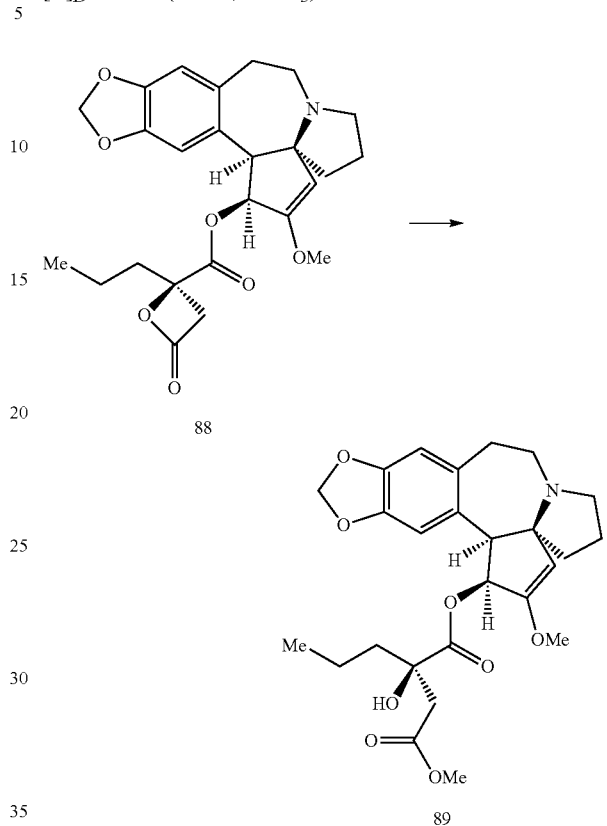

Bis(de-methyl)-deoxyharringtonine I-4

Beta-lactone I-1

To a solution of acid S15 (9.9 mg, 0.063 mmol, 2.0 equiv) and cephalotaxine (1) (9.9 mg, 0.031 mmol, 1.0 equiv) in CH$_2$Cl$_2$ (630 μL) were added triethylamine (29 μL, 0.21 mmol, 6.6 equiv) and 2,4,6-trichlorobenzoyl chloride (10.9 μL, 0.0697 mmol, 2.20 equiv) via syringe and N,N-dimethylaminopyridine (DMAP) (4.4 mg, 0.0360 mmol, 1.14 equiv) as a solid. The resulting dark purple solution was stirred at 23° C. for 15 m (TLC showed complete consumption of cephalotaxine after 5 m), then loaded directly onto a silica gel column The column was eluted with 2% TEA in 9:1 toluene:EtOAc to yield I-1 (11.7 mg, 81%) as a colorless oil. R$_f$=0.48 (2% TEA in 9:1 toluene:EtOAc on plates pretreated with 5% TEA in pentane); $^1$H NMR (500 MHz, CDCl$_3$) δ 6.61 (s, 1H, arylH), 6.59 (s, 1H, arylH), 5.90 (d, 1H, J=9.5 Hz, ArCHCH), 5.86 (dd, 2H, J=7.8, 1.5 Hz (OCH$_2$O), 5.08 (s, 1H, vinyl H), 3.81 (d, 1H, J=9.6 Hz, ArCHCH), 3.69 (s, 3H, OCH$_3$), 3.14-3.07 (m, 2H, CH$_2$), 3.02 (d, 1H, J=16.5 Hz, ArCHCH), 2.96-2.90 (m, 1H, CH$_2$), 2.85 (d, 1H, J=16.5 Hz, ArCHCH), 2.61-2.56 (m, 2H, CH$_2$), 2.36 (dd, 1H, J=14.3, 6.9 Hz, CH$_2$), 2.05-2.00 (m, 1H, CH$_2$), 1.92-1.88 (m, 1H, CH$_2$), 1.84-1.72 (m, 3H, CH$_2$), 1.64-1.58 (m, 1H, CH$_2$), 1.20-1.07 (m, 2H, CH$_2$), 0.86 (t, 3H, J=14.8 Hz, CH$_2$CH$_3$); $^{13}$C NMR (125 MHz, CDCl$_3$) δ168.62, 166.26, 156.79, 147.07, 145.99, 133.86, 127.89, 113.16, 110.02, 101.10, 76.48, 75.75, 70.85, 57.44, 56.43, 54.08, 48.63, 46.35, 43.61, 37.36, 31.55, 20.45, To a solution of β-lactone I-1 (9.5 mg, 0.021 mmol, 1.0 equiv) in MeOH (210 μL) was added a freshly prepared solution of 0.5M NaOMe in MeOH (4.2 μL, 0.0021 mmol, 0.1 equiv). After 15 min the solution was quenched with sat'd NH$_4$Cl solution (10 mL) and extracted with CH$_2$Cl$_2$ (3×10 mL). The combined organic phases were dried over MgSO$_4$ and concentrated by rotary evaporation to yield I-4 (9.5 mg, 93%) as a colorless oil without need for further purification. R$_f$=0.40 (2% TEA in 9:1 toluene:EtOAc on plates pretreated with 5% TEA in pentane); $^1$H NMR (500 MHz, CDCl$_3$) δ 6.62 (s, 1H, ArH), 6.54 (s, 1H, ArH), 5.98 (d, 1H, J=9.8 Hz, ArCHCH), 5.87 (d, 2H, J=5.7 Hz, OCH$_2$O), 5.04 (s, 1H, vinyl H), 3.77 (d, 1H, J=9.8 Hz, ArCHCH), 3.68 (s, 3H, OCH$_3$), 3.57 (s, 3H, OCH$_3$), 3.47 (s, 1H, OH), 3.17-3.07 (m, 2H, CH$_2$), 2.99-2.90 (m, 1H, CH$_2$), 2.63-2.56 (m, 2H, CH$_2$), 2.38 (dd, 1H, J=14.1, 6.8 Hz, CH$_2$), 2.29 (d, 1H, J=16.5 Hz, C(O)CH$_2$), 2.07-2.00 (m, 1H, CH$_2$), 2.00 (d, 1H, J=16.6, C(O)CH$_2$), 1.93-1.87 (m, 1H, CH$_2$), 1.80-1.71 (m, 2H, CH$_2$), 1.44-1.27 (m, 3H, CH$_2$), 1.14-1.05 (m, 1H, CH$_2$), 0.83 (t, 3H, J=7.2 Hz, CH$_2$CH$_3$); $^{13}$C NMR (100 MHz, CDCl$_3$) δ 174.15, 170.63, 157.89, 146.83, 145.96, 133.51, 128.44, 112.81, 109.83, 100.95, 100.21, 74.96, 74.85, 70.76, 57.33, 56.06, 54.10, 51.62, 48.77, 43.58, 42.75, 41.16, 31.52, 20.45, 16.29, 14.22; IR (neat film) 3525 (w), 2958 (m), 1747 (s), 1654 (m), 1503 (m), 1487 (s), 1225 (s), 1037 (s), 731 (w) cm$^{-1}$; LRMS (ESI) calcd for $C_{26}H_{34}NO_8$ (M$^+$+H) 488.22; found 487.84; [β]$_D$=−124° (c 0.95, CDCl$_3$).

General Procedures: Cytotoxicity Evaluations

Cell Line Panel.

The cell line panel used in this study included HL-60 (a human acute promyelocytic leukemia cell line), HL-60/RV+ (a P-glycoprotein over-expressing multidrug resistant HL-60 variant which was selected by continuous exposure to the vinca alkaloid vincristine), JURKAT (a human T cell leukemia cell line), ALL3 (acute lymphoblastic leukemia recently isolated from a patient treated at Memorial Sloan-Kettering Cancer Center (MSKCC) and characterized as Philadelphia chromosome positive (Ph+); provided by Dr. Mark Frattini, MSKCC), NCEB 1 (a Mantle cell lymphoma cell line), JEKO (a human B cell lymphoma), MOLT-3 (a human acute lymphoblastic T-cell line), SKNLP (a human neuroblastoma cell line), Y79 (a human retinoblastoma cell line isolated by explant culture of a primary tumor from the right eye immediately after enucleation), PC9, H1650, H1975, H2030, H3255 (all human non-small cell lung cancer cell lines derived from patients with pulmonary adenocarcinoma), TC71 (a sarcoma cell line obtained from tumor tissue of recurrent Ewing's sarcoma), HTB-15 (a human glioblastoma cell line), A431 (a human epithelial carcinoma cell line), HeLa (a human cervical adenocarcinoma cell line), and WD0082 (a human liposarcoma cell line isolated from a well-differentiated liposarcoma patient; provided by Dr. S. Singer, MSKCC). All of the cell lines were grown at 37° C. in a 5% $CO_2$ incubator using standard culture medium, which consisted of RPMI 1640 supplemented with 10% bovine calf serum, 2 mM glutamine, 100 IU/ml of penicillin, and 100 μg/ml of streptomycin or as recommended by the ATCC.

Proliferation Assay.

The assay used for the cytotoxicity evaluation is based on the dye resazurin and commercially sold as Alamar Blue (Serotec Ltd, USA). Cells were seeded at densities ranging from 250 to 20,000 cells in 45 μL of medium to compound containing plates and incubated for 72 hours at 37° C. in a 5% $CO_2$ incubator; at which time 5 μL of the Alamar Blue reagent was added and the cells were further incubated for another 24 hours, before the fluorescence intensity was read on the Amersham LEADseeker™ Multimodality Imaging System (GE, USA). The assays were performed on a fully automated linear track robotic platform (CRS F3 Robot System, Thermo Electron, Canada) using several integrated peripherals for plate handling, liquid dispensing, and fluorescence detection. Screening data files from the imaging system were loaded into the HTS Core Screening Data Management System, a custom built suite of modules for compound registration, plating, data management, and powered by ChemAxon Cheminformatic tools (ChemAxon, Hungary). Data analysis and curve fitting was performed on all the compounds tested, and the data summary exported as SD files for further analysis and reporting.

Dose Response Studies.

In each assay, the signal inhibition induced by the compounds was expressed as a percentage compared to high and low controls located on the same plate, as defined as % Inhibition=(high control average−read value)/(high control average−low control average)×100. The dose response was assessed in duplicate and using 12 point doubling dilutions with either 1, 10 or 100 μM compound concentration as the upper limit. The dose response curve for each set of data was fitted separately, and the two $IC_{50}$ values obtained were averaged.

What is claimed is:

1. A compound of formula (II-7):

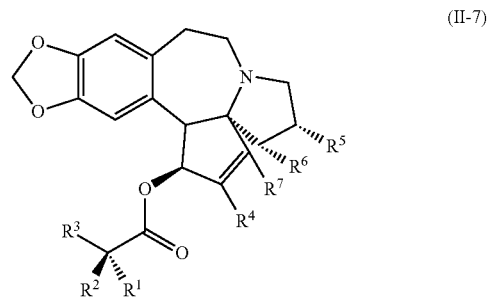

or a pharmaceutically acceptable salt thereof,
wherein:
$R^1$ is hydrogen, optionally substituted $C_{1-6}$ aliphatic, —$(CH_2)_nCO_2R^8$, —$(CH_2)_nCON(R^8)_2$, or —$(CH_2)_nCOSR^8$; wherein each $R^8$ is independently hydrogen, optionally substituted $C_{1-6}$ aliphatic, optionally substituted 6-10-membered aryl, or optionally substituted $C_{1-6}$ heteroaliphatic having 1-2 heteroatoms independently selected from nitrogen, oxygen, and sulfur; and n is an integer from 0-4;

$R^2$ is —$NR_2$ or —OR, wherein each instance of R is hydrogen;

$R^3$ is -T-$R^z$, wherein:

T is a bivalent $C_{1-12}$ saturated or unsaturated, straight or branched, hydrocarbon chain, wherein one or two methylene units of T are optionally and independently replaced by —O—, —S—, —N(R)—, —C(O)—, —C(O)O—, —OC(O)—, —N(R)C(O)—, —C(O)N(R)—, —S(O), —$S(O)_2$—, —$N(R)SO_2$—, or —$SO_2N(R)$—, wherein each R is independently hydrogen, optionally substituted acyl, optionally substituted arylalkyl, optionally substituted $C_{1-6}$ aliphatic, or optionally substituted $C_{1-6}$ heteroaliphatic having 1-2 heteroatoms independently selected from nitrogen, oxygen, and sulfur; and $R^z$ is —OR, —SR, or —$NR_2$, wherein each R is independently optionally substituted phenyl, optionally substituted arylalkyl, or optionally substituted $C_{1-6}$ aliphatic, or two R on the same nitrogen atom are taken with the nitrogen to form an optionally substituted 4-7-membered heterocyclic ring having 1-2 heteroatoms independently selected from nitrogen, oxygen, or sulfur;

$R^4$ is hydrogen or —OR, wherein R is hydrogen or an optionally substituted group selected from acyl, arylalkyl, $C_{1-6}$ aliphatic, or $C_{1-6}$ heteroaliphatic having 1-2 heteroatoms independently selected from nitrogen, oxygen, and sulfur; and $R^5$, $R^6$, and $R^7$ are each hydrogen.

2. The compound according to claim 1, wherein $R^1$ is —$(CH_2)_nCO_2R^8$.

3. The compound according to claim 1, wherein $R^2$ is —OR, wherein R is hydrogen.

4. The compound according to claim 1, wherein T is a bivalent $C_{1-12}$ saturated or unsaturated, straight or branched, hydrocarbon chain; and IV is —OR, wherein R is optionally substituted phenyl, optionally substituted arylalkyl, or optionally substituted $C_{1-6}$ aliphatic.

5. The compound according to claim 1, wherein T is selected from

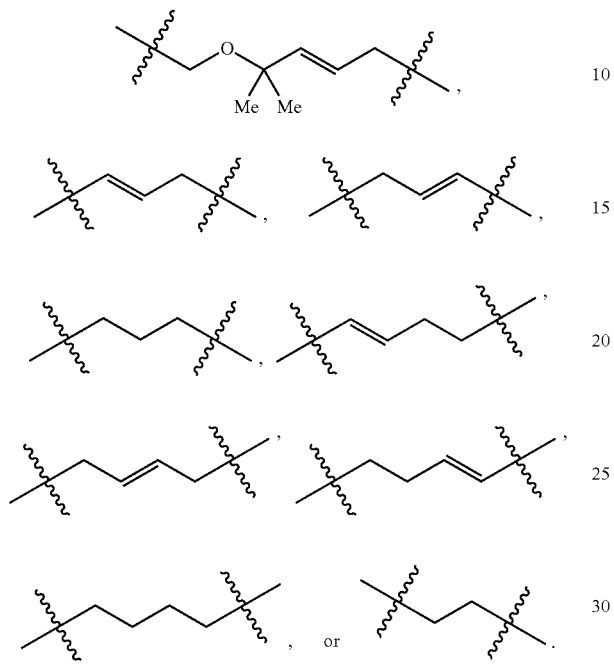

6. The compound according to claim 1, wherein $R^4$ is —OR, wherein R is $C_{1-6}$ aliphatic.

7. The compound of claim 1, wherein the compound is selected from:

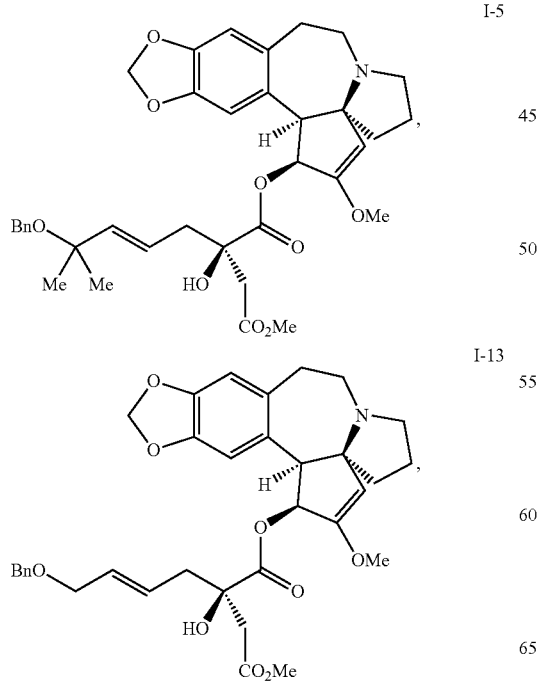

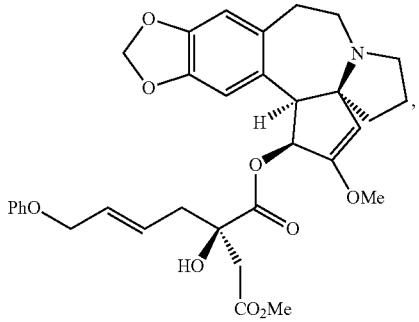

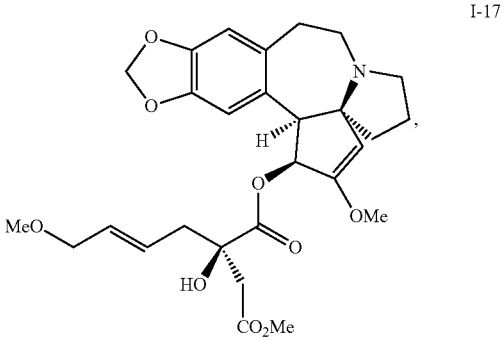

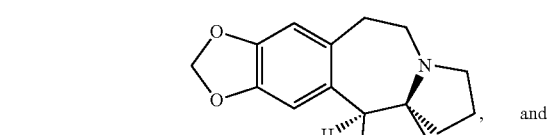

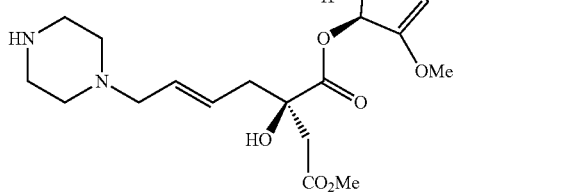

and pharmaceutically acceptable salts thereof.

8. A pharmaceutical composition comprising a compound of claim 1 or a pharmaceutically acceptable salt thereof, and a pharmaceutically acceptable excipient.

9. A method for treating cancer in a subject suffering therefrom comprising administering to the subject a therapeutically effective amount of a compound of claim 1, or a pharmaceutically acceptable salt thereof.

10. The method of claim 9, wherein the cancer is a multidrug resistant cancer.

11. The method of claim 9, wherein the cancer is a hematological malignancy.

12. The method of claim 11, wherein the hematological malignancy is acute lymphoblastic leukemia, acute myelogenous leukemia, chronic myelogenous leukemia, chronic lymphocytic leukemia, hairy cell leukemia, Hodgkin's lymphoma, non-Hodgkin's lymphoma, cutaneous T-cell lymphoma, peripheral T-cell lymphoma, Mantle cell lymphoma, B-cell lymphoma, acute lymphoblastic T cell leukemia, acute promyelocytic leukemia, or multiple myeloma.

13. The compound of claim 2, wherein n is 1, and $R^8$ is methyl.

14. The compound of claim 6, wherein $R^4$ is —OR, wherein R is methyl.

* * * * *

UNITED STATES PATENT AND TRADEMARK OFFICE
CERTIFICATE OF CORRECTION

PATENT NO. : 8,466,142 B2  
APPLICATION NO. : 12/920227  
DATED : June 18, 2013  
INVENTOR(S) : David Y. Gin et al.

Page 1 of 1

It is certified that error appears in the above-identified patent and that said Letters Patent is hereby corrected as shown below:

In Claim 1, at column 154, line 3, the chemical structure (II-7):

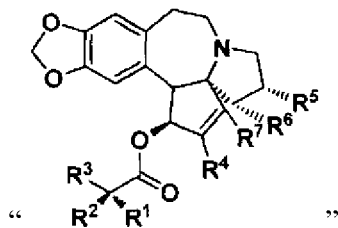

should be changed to:

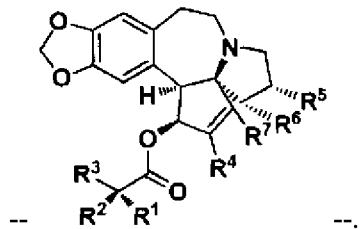

Signed and Sealed this  
Twenty-fourth Day of September, 2013

Teresa Stanek Rea  
*Deputy Director of the United States Patent and Trademark Office*